(12) United States Patent
Storici et al.

(10) Patent No.: US 10,787,703 B1
(45) Date of Patent: Sep. 29, 2020

(54) METHODS TO DETECT RIBONUCLEOTIDES IN DEOXYRIBONUCLEIC ACID

(71) Applicant: Georgia Tech Research Corporation, Atlanta, GA (US)

(72) Inventors: Francesca Storici, Atlanta, GA (US); Jay Hesselberth, Atlanta, GA (US); Kyung Duk Koh, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 610 days.

(21) Appl. No.: 15/402,217

(22) Filed: Jan. 9, 2017

Related U.S. Application Data

(60) Provisional application No. 62/276,274, filed on Jan. 8, 2016.

(51) Int. Cl.
| | | |
|---|---|---|
| C12Q 1/68 | (2018.01) | |
| C12Q 1/6855 | (2018.01) | |
| C12Q 1/6869 | (2018.01) | |
| C12Q 1/686 | (2018.01) | |
| C12Q 1/6806 | (2018.01) | |

(52) U.S. Cl.
CPC ......... *C12Q 1/6855* (2013.01); *C12Q 1/6806* (2013.01); *C12Q 1/686* (2013.01); *C12Q 1/6869* (2013.01)

(58) Field of Classification Search
None
See application file for complete search history.

(56) References Cited

U.S. PATENT DOCUMENTS

2012/0122702 A1* 5/2012 Leproust ................. C40B 20/02 506/2
2012/0151635 A1* 6/2012 Coruzzi ................ C07K 14/415 800/305
2012/0156730 A1* 6/2012 Zeiner ..................... C12P 19/34 435/91.3

OTHER PUBLICATIONS

Koh KD, Balachander S, Hesselberth JR, Storici F. Ribose-seq: global mapping of ribonucleotides embedded in genomic DNA. Nat Methods. Mar. 2015; 12(3):251-7, Epub Jan. 26, 2015. (Year: 2015).*
Genbank Accession No. AK230326—*Arabidopsis thaliana* mRNA for translation elongation factor EF-1 alpha, complete cds, clone: RAFL24-16-D10 (submitted by Jul. 7, 2006, retrieved from http://www.ncbi.nlm.nih.gov/nuccore/AK230326). (Year: 2006).*
Schutz K, Hesselberth JR, Fields S. Capture and sequence analysis of RNAs with terminal 2',3'-cyclic phosphates. RNA. Mar. 2010; 16(3):621-31. Epub Jan. 14, 2010. (Year: 2010).*
Kucuktas H, Liu ZJ. Library construction for next generation sequencing. Next Generation Sequencing and Whole Genome Selection in Aquaculture. Dec. 1, 2010; 57 pp. 1-11. (Year: 2010).*
Desai KK, Bingman CA, Phillips GN Jr, Raines RT. Structures of the noncanonical RNA ligase RtcB reveal the mechanism of histidine guanylylation. Biochemistry. Apr. 16, 2013; 52(15):2518-25. Epub Apr. 5, 2013. (Year: 2013).*
Das U, Shuman S. 2'-Phosphate cyclase activity of RtcA: a potential rationale for the operon organization of RtcA with an RNA repair ligase RtcB in *Escherichia coli* and other bacterial taxa. RNA. Oct. 2013; 19(10):1355-62. Epub Aug. 14, 2013. (Year: 2013).*
Das U, Shuman S. Mechanism of RNA 2',3'-cyclic phosphate end healing by T4 polynucleotide kinase-phosphatase. Nucleic Acids Res. Jan. 7, 2013; 41(1):355-65. (Year: 2013).*
Jinks-Robertson and Klein, "Ribonucleotides in DNA: hidden in plain sight," Nat. Str. and Mol. Bio. 22:3 (2015), pp. 176-178.
Koh, et al., "Ribose-seq: ribonucleotides in DNA," Protocol Exchange (2015), 1-13.
Koh, K. D., Balachander, S., Hesselberth, J. R. & Storici, F. Ribose-seq: global mapping of ribonucleotides embedded in genomic DNA. Nat. Methods 12, 251-257 (2015).
Williams, J. S. & Kunkel, T. A. Ribonucleotides in DNA: origins, repair and consequences. DNA Repair (Amst.) 19, 27-37 (2014).
Potenski, C. J. & Klein, H. L. How the misincorporation of ribonucleotides into genomic DNA can be both harmful and helpful to cells. Nucleic Acids Res. 42, 10226-10234 (2014).
Lujan, S. A., Williams, J. S., Clausen, A. R., Clark, A. B. & Kunkel, T. A. Ribonucleotides are signals for mismatch repair of leading-strand replication errors. Mol. Cell 50, 437-443 (2013).
Reijns, M. A. et al. Lagging-strand replication shapes the mutational landscape of the genome. Nature 518, 502-506 (2015).
Reijns, M. A. et al. Enzymatic removal of ribonucleotides from DNA is essential for mammalian genome integrity and development. Cell 149, 1008-1022 (2012).
Schutz, K., Hesselberth, J. R. & Fields, S. Capture and sequence analysis of RNAs with terminal 2',3'-cyclic phosphates. RNA 16, 621-631 (2010).

(Continued)

Primary Examiner — Gary Benzion
Assistant Examiner — Olayinka A Oyeyemi
(74) Attorney, Agent, or Firm — Thomas|Horstemeyer, LLP

(57) ABSTRACT

Genomic DNA contains embedded ribonucleotides (rNMPs) that are incorporated during DNA replication and repair, or formed during DNA damage. The modifications have been linked to genome instability and disease, but no method currently exists to profile their locations genome-wide. rNMP incorporation has been extensively studied in recent years; however, locating sites of rNMP incorporation in genomic DNA has not yet been possible. Disclosed herein is a unique method for mapping rNMPs in genomic DNA that exploits the unique ligation mechanism of *Arabidopsis thaliana* tRNA ligase (AtRNL), normally involved in tRNA maturation. As disclosed herein AtRNL captures 2',3'-cyclic phosphate or 2'-phosphate termini of DNA derived from alkaline cleavage of a DNA oligonucleotide (oligo) at an embedded rNMP, ligating the 2'-phosphate end to the 5'-phosphate terminus of the same DNA molecule and producing a ssDNA circle containing an embedded rNMP.

35 Claims, 91 Drawing Sheets
Specification includes a Sequence Listing.

(56) References Cited

OTHER PUBLICATIONS

Remus, B. S. & Shuman, S. Distinctive kinetics and substrate specificities of plant and fungal tRNA ligases. RNA 20, 462-473 (2014).

* cited by examiner

Supplementary Table 1. Results of 3' base bias for AtRNL ligation.

a

| Base | Circular | Dimer | Circular dimer |
|---|---|---|---|
| A | 48% (44–49) | 4.3% (1.8–7.1) | 1.5% (0.71–2.1) |
| G | 47% (44–48) | 4.0% (2.6–5.8) | 1.5% (0.88–2.3) |
| U | 47% (45–49) | 4.4% (2.1–5.1) | 1.5% (0.73–2.0) |
| C | 47% (44–49) | 4.5% (1.9–5.0) | 1.4% (0.59–1.8) | b

| P value | G | U | C |
|---|---|---|---|
| A | 0.4857 | 0.8857 | 1.0000 |
| G | – | 0.8857 | 0.6857 |
| U | – | – | 1.0000 | c

| Base | Circular | Dimer | Circular dimer |
|---|---|---|---|
| A | 27% (23–31) | 1.7% (1.5–2.3) | 0.53% (0.45–0.74) |
| G | 27% (24–28) | 1.9% (1.5–2.5) | 0.54% (0.39–1.1) |
| U | 29% (24–30) | 2.3% (1.3–2.7) | 0.64% (0.48–1.2) |
| C | 29% (25–32) | 1.8% (1.7–2.0) | 0.53% (0.47–0.80) | d

| P value | G | U | C |
|---|---|---|---|
| A | 1.0000 | 1.0000 | 0.6857 |
| G | – | 0.3429 | 0.2000 |
| U | – | – | 0.8857 |

FIG. 30

Supplementary Table 2. *S. cerevisiae* strains used in this study.

a

| Strain | Relevant genotype | Source |
|---|---|---|
| KK-100 | *MATα ade5-1 lys2-14A trp1-289 his7-2 leu2-3,112 ura3-52 rnh201Δ::hygMX4* | this study |
| KK-30 | *hoΔ hmlΔ::ADE1 MATa-inc hmrΔ::ADE1 ade1 leu2-3,112 lys5 trp1::hisG ura3-52 leu2::HOcs mataΔ::hisG rnh201Δ::hygMX4* | this study |
| KK-174 | KK-100 *rnh1Δ::kanMX4* | this study |
| KK-125 | KK-30 *rnh1Δ::kanMX4* | this study |
| KK-164 | KK-125 *ung1Δ::natMX4* | this study |
| KK-170 | KK-30 *pol2-M644G* | this study |
| KK-107 | KK-100 *pol2-4* | this study |
| KK-120 | KK-100 *pol3-5DV* | this study | b

| Strain | Relevant genotype | Source |
|---|---|---|
| FRO-767,768 | *hoΔ hmlΔ::ADE1 MATa-inc hmrΔ::ADE1 ade1 leu2-3,112 lys5 trp1::hisG ura3-52 ade3::GAL::HO leu2::HOcs mataΔ::hisG* | Storici et al., 2007[43] |
| FRO-984,985 | FRO-767,768 *rnh201Δ::kanMX4* | Storici et al., 2007[43] |
| KK-158,159 | FRO-767,768 *ung1Δ::hygMX4* | this study |

FIG. 31

Supplementary Table 3. Ribose-seq coverage for each library in this study.

| Ribose-seq library | Coverage (aligned reads/kb) | |
|---|---|---|
| | Nuclear | Mitochondrial |
| rnh201 (KK-100) | 0.449 | 19.5 |
| rnh201 (KK-100, EconoTaq) | 0.883 | 47.8 |
| rnh201 (KK-30) | 0.149 | 8.42 |
| rnh1 rnh201 (KK-174) | 0.149 | 9.92 |
| rnh1 rnh201 (KK-125) | 0.239 | 13.2 |
| rnh1 rnh201 ung1 (KK-164) | 0.269 | 42.2 |
| pol2-M644G rnh201 (KK-170) | 0.254 | 7.89 |
| pol2-4 rnh201 (KK-107) | 0.528 | 34.2 |
| pol3-5DV rnh201 (KK-120) | 0.510 | 33.9 |

FIG. 32

Supplementary Table 4. Absolute nucleotide frequencies of rNMPs and 3' flanking nucleotide.

| | Base | Position 0 | | Position +1 | |
|---|---|---|---|---|---|
| | | Nuclear | Mitochondrial | Nuclear | Mitochondrial |
| *rnh201* (KK-100) | A | 15.4% | 25.6% | 45.0% | 45.8% |
| | C | 44.0% | 36.8% | 22.4% | 15.3% |
| | G | 28.1% | 19.0% | 16.5% | 5.8% |
| | U/T | 12.5% | 18.7% | 16.1% | 33.1% |
| *rnh201* (KK-100, EconoTaq) | A | 23.2% | 38.2% | 43.3% | 43.5% |
| | C | 35.4% | 25.6% | 19.3% | 10.0% |
| | G | 22.7% | 14.5% | 13.5% | 6.2% |
| | U/T | 18.7% | 21.7% | 23.9% | 40.3% |
| *rnh201* (KK-30) | A | 20.4% | 35.7% | 47.5% | 47.8% |
| | C | 39.2% | 28.3% | 19.6% | 11.1% |
| | G | 27.5% | 24.1% | 14.4% | 7.2% |
| | U/T | 12.8% | 11.9% | 18.5% | 33.8% |
| *rnh1 rnh201* (KK-174) | A | 17.1% | 33.6% | 44.9% | 46.5% |
| | C | 40.2% | 27.0% | 22.0% | 11.8% |
| | G | 27.7% | 23.7% | 15.0% | 7.4% |
| | U/T | 15.1% | 15.7% | 18.2% | 34.2% |
| *rnh1 rnh201* (KK-125) | A | 20.1% | 35.4% | 45.2% | 44.3% |
| | C | 36.8% | 28.6% | 19.4% | 12.1% |
| | G | 29.7% | 20.9% | 15.0% | 5.9% |
| | U/T | 13.4% | 15.1% | 20.4% | 37.7% |
| *rnh1 rnh201 ung1* (KK-164) | A | 24.3% | 35.8% | 44.3% | 47.1% |
| | C | 35.3% | 30.2% | 19.4% | 13.2% |
| | G | 26.5% | 22.7% | 15.3% | 6.5% |
| | U/T | 14.0% | 11.3% | 21.0% | 33.2% |
| *pol2-M644G rnh201* (KK-170) | A | 19.5% | 38.9% | 52.2% | 47.2% |
| | C | 40.3% | 28.6% | 18.2% | 11.5% |
| | G | 26.5% | 21.5% | 13.0% | 6.6% |
| | U/T | 13.7% | 11.0% | 16.6% | 34.7% |
| *pol2-4 rnh201* (KK-107) | A | 14.9% | 21.9% | 42.5% | 46.2% |
| | C | 40.2% | 43.1% | 22.0% | 16.3% |
| | G | 23.6% | 16.3% | 16.4% | 6.4% |
| | U/T | 21.2% | 18.6% | 19.2% | 31.1% |
| *pol3-5DV rnh201* (KK-120) | A | 20.4% | 30.0% | 44.3% | 45.3% |
| | C | 37.1% | 33.1% | 19.4% | 14.6% |
| | G | 25.0% | 16.7% | 15.3% | 6.1% |
| | U/T | 17.5% | 20.3% | 21.0% | 34.0% |

FIG. 33

Supplementary Table 5. Results of rNMP bypass by Phusion DNA polymerase.

a

| Base | Bypass probability |
|---|---|
| C | 93% (93–93) |
| U | 93% (92–94) | b

| P value | U |
|---|---|
| C | 0.6857 |

FIG. 34

Supplementary Table 6. Results of DSB repair assay with rNMP-containing oligos.

a

| Oligo | WT | mh201 | ung1 |
|---|---|---|---|
| LEU2.D | 65% (55–75) | 63% (55–65) | 65% (55–70) |
| LEU2.rG | 30% (20–40) | 90% (75–100) | N/A |
| LEU2.dU | 5.0% (0–10) | N/A | 55% (45–60) |
| LEU2.rU | 33% (25–45) | 55% (45–65) | 33% (30–40) | b

| Oligo | mh201 | ung1 |
|---|---|---|
| LEU2.D | 0.5357 | 1.0000 |
| LEU2.rG | 0.0286 | N/A |
| LEU2.dU | N/A | 0.0294 |
| LEU2.rU | 0.0421 | 1.0000 |

FIG. 35

Supplementary Table 7. List of hotspots of rNMP incorporation within *S. cerevisiae* mitochondrial DNA, rDNA repeat, and *Ty1*.

| | | | | | | Number of rNMP reads | | | | | |
|---|---|---|---|---|---|---|---|---|---|---|---|
| Position | Strand | Gene | Base | rnh201 (KK-100) | rnh201 (KK-100, EconoTaq) | rnh201 (KK-30) | rnh1 rnh201 (KK-174) | rnh1 rnh201 (KK-125) | rnh1 rnh201 ung1 (KK-154) | pol2-M644G rnh201 (KK-170) | pol2-4 rnh201 (KK-107) | pol3-5DV rnh201 (KK-120) |
| Chr M 30,224 | W | COB | A | 30 | 136 | 17 | 24 | 34 | 2 | 20 | 10 | 22 |
| Chr XII* 453,839 | C | RDN25 | G | 97 | 45 | 18 | 30 | 22 | 1 | 25 | 12 | 10 |
| Chr IV^b 850,383 | C^b | Ty1 | A | 15 | 42 | 10 | 11 | 19 | 46 | 20 | 19 | 110 |
| Chr M 14,668 | W | COX1 | A | 7 | 49 | 5 | 10 | 14 | 33 | 12 | 8 | 38 |
| Chr M 14,739 | W | COX1 | A | 8 | 46 | 7 | 14 | 12 | 0 | 5 | 0 | 13 |
| Chr M 19,157 | W | COX1 | A | 15 | 73 | 4 | 5 | 22 | 28 | 5 | 7 | 27 |

FIG. 36

| SEQ ID NO: | Name | Length (nt) | Sequence (5'-3') with end modifications | Purification | Experiment |
|---|---|---|---|---|---|
| | Supplementary Table 8. Oligonucleotides used in this study. | | | | |
| 11 | Lig.47.D | 47 | CCCGAGTGTGATCATCTGGTCGCTGGGGAATGAGTCAGGCCACGGCG | PAGE | AtRNL ligation assay |
| 12 | Lig.47.R | 47 | CCCGAGTGTGATCATCTGGTCGCTGGGGAATrGAGTCAGGCCACGGCG | PAGE | AtRNL ligation assay |
| 13 | Lig.30.rA | 30 | NNNNNNNNNNNNNNNNNNNNNrANNNNNNNN | PAGE | AtRNL 3' base bias assay |
| 14 | Lig.30.rG | 30 | NNNNNNNNNNNNNNNNNNNNNrGNNNNNNNN | PAGE | AtRNL 3' base bias assay |
| 15 | Lig.30.rU | 30 | NNNNNNNNNNNNNNNNNNNNNrUNNNNNNNN | PAGE | AtRNL 3' base bias assay |
| 16 | Lig.30.rC | 30 | NNNNNNNNNNNNNNNNNNNNNrCNNNNNNNN | PAGE | AtRNL 3' base bias assay |
| 7 | Adaptor.L | 87 | P-NNNNNNNNAGATCGGAAGAGCGTCGTGTAGGGAAAG AGGGAGTTCAGACGTGTGCTCTTCCGATCTAGCCAGCGCAGACCGTGA GGT | PAGE | Ribose-seq library construction |
| 8 | Adaptor.S | 20 | P-CCTCACGGTCTGCGCTGGCT-Am | Desalted | Ribose-seq library construction |
| 9 | PCR.1.Index1 | 63 | CAAGCAGAAGACGGCATACGAGATCGTGATGTGACTGGAGTTCAGACGT GTGCTCTTCCGATC | Desalted | Ribose-seq library construction |
| 17 | PCR.1.Index2 | 63 | CAAGCAGAAGACGGCATACGAGATACATCGGTGACTGGAGTTCAGACGT GTGCTCTTCCGATC | Desalted | Ribose-seq library construction |
| 18 | PCR.1.Index3 | 63 | CAAGCAGAAGACGGCATACGAGATGCCTAAGTGACTGGAGTTCAGACGT GTGCTCTTCCGATC | Desalted | Ribose-seq library construction |
| 19 | PCR.1.Index4 | 63 | CAAGCAGAAGACGGCATACGAGATTGGTCAGTGACTGGAGTTCAGACGT GTGCTCTTCCGATC | Desalted | Ribose-seq library construction |
| 10 | PCR.2 | 58 | AATGATACGGCGACCACCGAGATCTACACTCTTTCCCTACACGACGCTC TTCCGATCT | Desalted | Ribose-seq library construction |
| 20 | ByTemp.rC | 46 | NNNNNNNNrCNNNNNNNNAGATCGGAAGAGCGTCGTGTAGGGAAAGAG | PAGE | Polymerase bypass assay |
| 21 | ByTemp.rU | 46 | NNNNNNNNrUNNNNNNNNAGATCGGAAGAGCGTCGTGTAGGGAAAGAG | PAGE | Polymerase bypass assay |
| 22 | ByPrim | 30 | CTCTTTCCCTACACGACGCTCTTCCGATCT | PAGE | Polymerase bypass assay |
| 23 | LEU2.D | 60 | TTAGGTGCTGTGGGTGGTCCTAAATGGGGATCCGGTAGTGTTAGGCCTG AACAAGGTTTA | Desalted | leu2 DSB repair assay |
| 24 | LEU2.rG | 60 | TTAGGTGCTGTGGGTGGTCCTAAATGGGGATCCGGTAGTrGTTAGGCCT GAACAAGGTTTA | Desalted | leu2 DSB repair assay |
| 25 | LEU2.dU | 60 | TTAGGTGCTGTGGGTGGTCCTAAATGGGGATCCGGTAGTGUTAGGCCT GAACAAGGTTTA | Desalted | leu2 DSB repair assay |
| 26 | LEU2.rU | 60 | TTAGGTGCTGTGGGTGGTCCTAAATGGGGATCCGGTAGTGrUTAGGCCT GAACAAGGTTTA | Desalted | leu2 DSB repair assay |
| 27 | LEU2.3 | 20 | ATGTCTGCCCCTAAGAAGAT | Desalted | leu2 DSB repair assay |
| 28 | LEU2.6 | 20 | TGCCAAAGAATAAGGTCAAC | Desalted | leu2 DSB repair assay |

FIG. 37

- Alignment.sh
    1. Obtain reverse complement of raw reads
    2. Trim UMI from 3' ends of the reversed reads
    3. Align UMI trimmed reads to reference genome
    4. Remove PCR duplicates from the mapped reads

- Nucleotide-Frequencies.sh
  - Determine coordinates of rNMPs
  - Determine coordinates of +/- 100 upstream/downstream dNTPs
  - Calculate raw and normalized nucleotide (rNMP and dNTPs) frequencies
  - Final output: Tab-delimited datasets containing nucleotide frequencies

- Nucleotide-Frequency-Plot.R
  - Plot nucleotide frequencies for each library using ggplot in R

- Nucleotide-Frequency-Plot.sh
  - Generate all plots from dataset files at once
  - Allows user to specify title and output filename

FIG. 42B

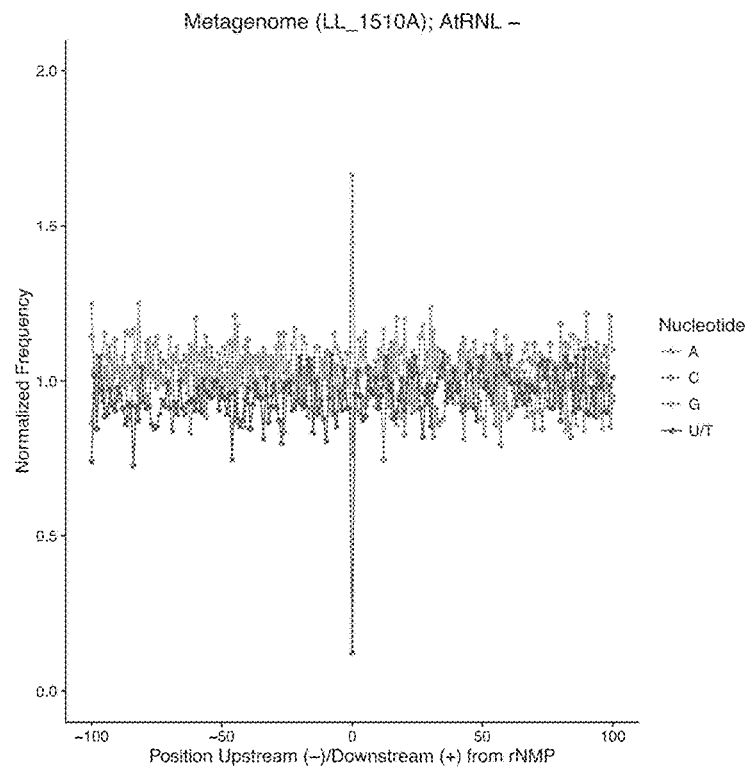
FIG. 54AWW
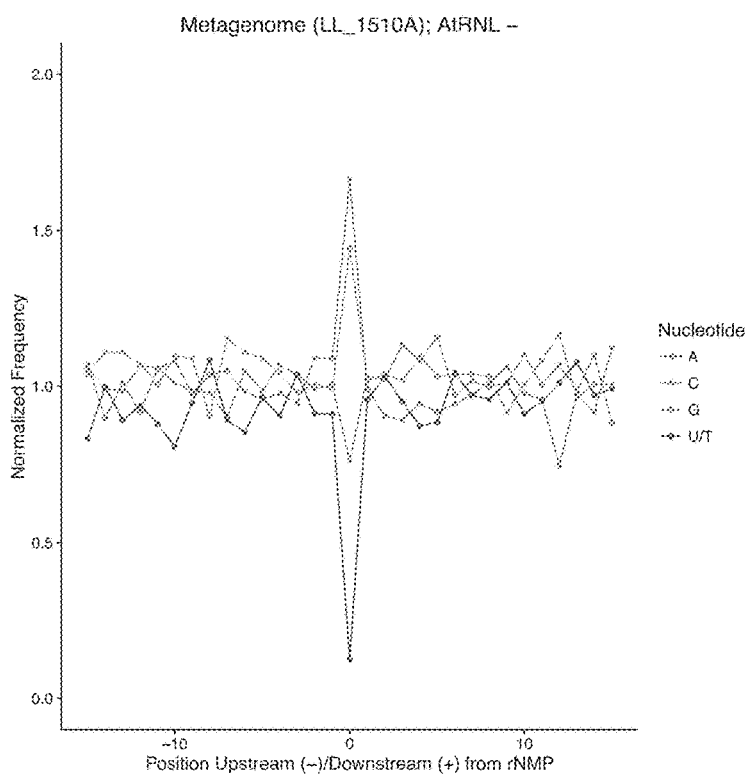
FIG. 54A XX

METHODS TO DETECT RIBONUCLEOTIDES IN DEOXYRIBONUCLEIC ACID

CROSS-REFERENCE TO RELATED APPLICATIONS

This application claims the benefit of and priority to U.S. Provisional Patent Application No. 62/276,274, filed on Jan. 8, 2016, entitled "METHOD TO CAPTURE AND MAP RIBONUCLEOTIDES INCORPORATED IN DNA VIA SELF-LIGATION BY *ARABIDOPSIS THALIANA* TRNA LIGASE," the contents of which is incorporated by reference herein in its entirety.

STATEMENT REGARDING FEDERALLY SPONSORED RESEARCH OR DEVELOPMENT

This invention was made with government support under grant numbers MCB-1021763 awarded by the National Science Foundation and 1R01ES026243-01 awarded by the National Institutes of Health. The government has certain rights in the invention.

SEQUENCE LISTING

This application contains a sequence listing filed in electronic form as an ASCII.txt file entitled 62021-1330_ST25.txt, created on Jan. 9, 2017. The content of the sequence listing is incorporated herein in its entirety.

BACKGROUND

Genomic deoxy ribonucleic acid (DNA) contains embedded ribonucleotides. This modification of DNA is the most abundant modification of DNA known to date. Although the scope and function of these embedded ribonucleotides remains to be fully-understood, they have been linked to genome instability and disease. As such, there remains a need for improved techniques and methods for analyzing these embedded ribonucleotides.

SUMMARY

Provided herein are embodiments of a method of detecting a ribonucleotide in a molecule of deoxyribonucleic acid (DNA), where the method can contain the steps of ligating a first adaptor to a fragment of genomic DNA, wherein the adaptor includes a first primer-binding sequence; a first annealing sequence, wherein the first annealing sequence is coupled to the first-primer binding sequence; and a unique molecular identifier (UMI) sequence, wherein the UMI sequence is coupled to the first primer-binding sequence; cleaving the fragment of genomic DNA via an alkali treatment; ligating the cleaved fragment of genomic DNA using an *Arabidopsis thaliana* tRNA ligase (AtRNL) to produce a circular single stranded DNA fragment; amplifying the circular single stranded DNA fragment using polymerase chain reaction (PCR) to produce a PCR product using a first primer that is capable of specifically binding the first primer-binding sequence and a second primer that is capable of specifically binding the second primer sequence; and sequencing the PCR product. Embodiments of the method can further include the step of removing a 2'-phosphate from the circular single stranded DNA fragment prior to amplifying the circular single stranded DNA fragment. The AtRNL can have an amino acid sequence that is 90-100% identical to SEQ ID NO: 1 or SEQ ID NO: 2. The AtRNL can have blunt-end ligase activity. The molecule of DNA can be obtained from a cell. The cell can be a eukaryotic cell or a prokaryotic cell. Some embodiments can include the step of ligating a second adaptor to the cleaved fragment of genomic DNA on the end opposite of where the first adaptor is ligated, wherein the second adaptor comprises a second annealing sequence and wherein the second annealing sequence is identical to the first annealing sequence. The fragment of genomic DNA can have blunt ends. In some embodiments, the method can further include the step of fragmenting genomic DNA prior to the step of ligating the adaptor to the fragment of genomic DNA. In some embodiments, the method can further include the step of dA-tailing the fragment of genomic DNA prior to the step of ligating the adaptor to the fragment of genomic DNA. In some embodiments, the method can further include the step of removing a linear single stranded DNA after the step of ligating the cleaved fragment of genomic DNA. The adaptor can further include a second primer-binding sequence.

Also provided herein are embodiments of a method of detecting a ribonucleotide in a molecule of deoxyribonucleic acid (DNA), where the method can include the steps of ligating an adaptor to a fragment of genomic DNA, wherein the adaptor can contain a first primer-binding sequence; a second primer-binding sequence, wherein the second primer-binding sequence is coupled to the first primer binding sequence; a first annealing sequence, wherein the first annealing sequence is coupled to the first-primer binding sequence; and a unique molecular identifier (UMI) sequence, wherein the UMI sequence is coupled to the first primer-binding sequence; cleaving the fragment of genomic DNA via an alkali treatment; ligating the cleaved fragment of genomic DNA using an *Arabidopsis thaliana* tRNA ligase (AtRNL) to produce a circular single stranded DNA fragment; amplifying the circular single stranded DNA fragment using polymerase chain reaction (PCR) to produce a PCR product, using a first primer that is capable of specifically binding the first primer-binding sequence and a second primer that is capable of specifically binding the second primer sequence; and sequencing the PCR product. In some embodiments, the method can further include the step of removing a 2'-phosphate from the circular single stranded DNA fragment prior to amplifying the circular single stranded DNA fragment. The fragment of genomic DNA can have blunt ends. In some embodiments, the method can further include the step of fragmenting genomic DNA prior to the step of ligating the adaptor to the fragment of genomic DNA. In some embodiments, the method can further include the step of dA-tailing the fragment of genomic DNA prior to the step of ligating the adaptor to the fragment of genomic DNA. In some embodiments, the method can further include the step of removing a linear single stranded DNA after the step of ligating the cleaved fragment of genomic DNA. In some embodiments, the method can further include the step of ligating a second adaptor to the cleaved fragment of genomic DNA on the end opposite of where the first adaptor is ligated, wherein the second adaptor comprises a second annealing sequence and wherein the second annealing sequence is identical to the first annealing sequence.

Also provided herein are embodiments of a method of detecting a ribonucleotide in a molecule of deoxyribonucleic acid (DNA), where the method can contain the steps of ligating an adaptor to a fragment of genomic DNA, wherein the adaptor can contain a first primer-binding sequence; a first annealing sequence, wherein the first annealing sequence is coupled to the first-primer binding sequence;

and a unique molecular identifier (UMI) sequence, wherein the UMI sequence is coupled to the first primer-binding sequence; cleaving the fragment of genomic DNA via an alkali treatment; ligating the cleaved fragment of genomic DNA using a ligase capable of coupling a 2',3'-cyclic phosphate to a 5'-phosphate to produce a circular single stranded DNA fragment; amplifying the circular single stranded DNA fragment using polymerase chain reaction (PCR) to produce a PCR product; and sequencing the PCR product using a first primer that is capable of specifically binding the first primer-binding sequence. The ligase can be an *Arabidopsis thaliana* tRNA ligase (AtRNL). The AtRNL can have an amino acid sequence that is 90-100% identical to SEQ ID NO: 1 or SEQ ID NO: 2. The ligase can be an RtcB ligase. The RtcB ligase can have an amino acid sequence that is 90-100% identical to SEQ ID NO: 3. In some embodiments, the method can further include the step of removing a 2'-phosphate from the circular single stranded DNA fragment prior to amplifying the circular single stranded DNA fragment. The fragment of genomic DNA can have blunt ends. In some embodiments, the method can further include the step of fragmenting genomic DNA prior to the step of ligating the adaptor to the fragment of genomic DNA. In some embodiments, the method can further include the step of dA-tailing the fragment of genomic DNA prior to the step of ligating the adaptor to the fragment of genomic DNA. In some embodiments, the method can further include the step of removing a linear single stranded DNA after the step of ligating the cleaved fragment of genomic DNA. The adaptor can further contain a second primer-binding sequence. In some embodiments, the method can further include the step of sequencing the PCR product using a second primer that is capable of specifically binding the second primer-binding sequence, wherein the step of sequencing the PCR product using the second primer is performed simultaneously or sequentially with the step of sequencing the PCR product using the first primer that is capable of specifically binding the first primer-binding sequence. The ligase can have blunt-end ligase activity. The molecule of DNA can be obtained from a cell. The cell can be a eukaryotic cell or a prokaryotic cell. In some embodiments, the method can further include the step of ligating a second adaptor to the cleaved fragment of genomic DNA on the end opposite of where the first adaptor is ligated, wherein the second adaptor comprises a second annealing sequence and wherein the second annealing sequence is identical to the first annealing sequence.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 30 for more statistics. First left lane, ss DNA ladder. No 3' base bias was observed for AtRNL ligation (see FIG. 30). Self-ligation was preferred to dimerization with a shorter 22-nt substrate; however, with the shorter substrate, lower levels of linear dimers, which are not resistant to T5 exonuclease, and circular dimers were observed. Increasing the length of the ss DNA substrate from 22 nt to 32 nt eliminated dimerization (FIG. 2).

FIG. 28A shows a diagram and sequence of the chromosomal leu2 region targeted by DNA-control LEU2.D, rGMP-containing LEU2.rG, dUMP containing LEU2.dU, and rUMP-containing LEU2.rU oligos (FIG. 37). StuI recognition sequence is underlined in turquoise. Position of either rGMP, dUMP, or rUMP was selected so that it is about 4-5 nt upstream of the G-T mispair. Both RNase H2-initiated excision repair (RER) and base excision repair (BER) remove a short ss DNA region downstream of the damage during the repair 13,27. FIG. 28B shows the oligos were transformed to either RNase H2- and uracil DNA N-glycosylase-proficient wild-type (VVT; FRO-767,768), RNase H2-deficient (rnh201; FRO-984, 985), or DNA N-glycosylase-deficient (ung1; KK-158,159) *S. cerevisiae* cells (see FIG. 31). Median percentages of StuI-cut Leu+ transformants from four independent transformations are shown with ranges as bars. For each transformation, 20 Leu+ transformants were selected for analysis. Mann-Whitney U-test was implemented for statistical analysis against the VVT. P values of less than 0.05 are marked as asterisk. See FIG. 35 for more statistics.

FIG. 30 shows a table demonstrating the results of 3' base bias for AtRNL ligation.

FIG. 31 shows a table demonstrating *S. cerevisiae* strains used.

FIG. 32 shows a table demonstrating Ribose-seq coverage for each library generated.

FIG. 33 shows a table demonstrating absolute nucleotide frequencies of rNMPs and 3'flanking nucleotide.

FIG. 34 shows a table demonstrating the results of rNMP bypass by Phusion DNA polymerase.

FIG. 35 shows a table demonstrating the results of DSB repair assay with rNMP-containing oligos.

FIG. 36 shows a table demonstrating a list of hotspots of rNMP incorporation within *S. cerevisiae* mitochondrial DNA, rDNA repeat, and Ty1.

FIG. 37 shows a table of oligonucleotides used.

FIGS. 42A-42B shows details of various steps in an embodiment of a computational analysis of libraries generated by ribose-seq.

DETAILED DESCRIPTION

Figure 1:
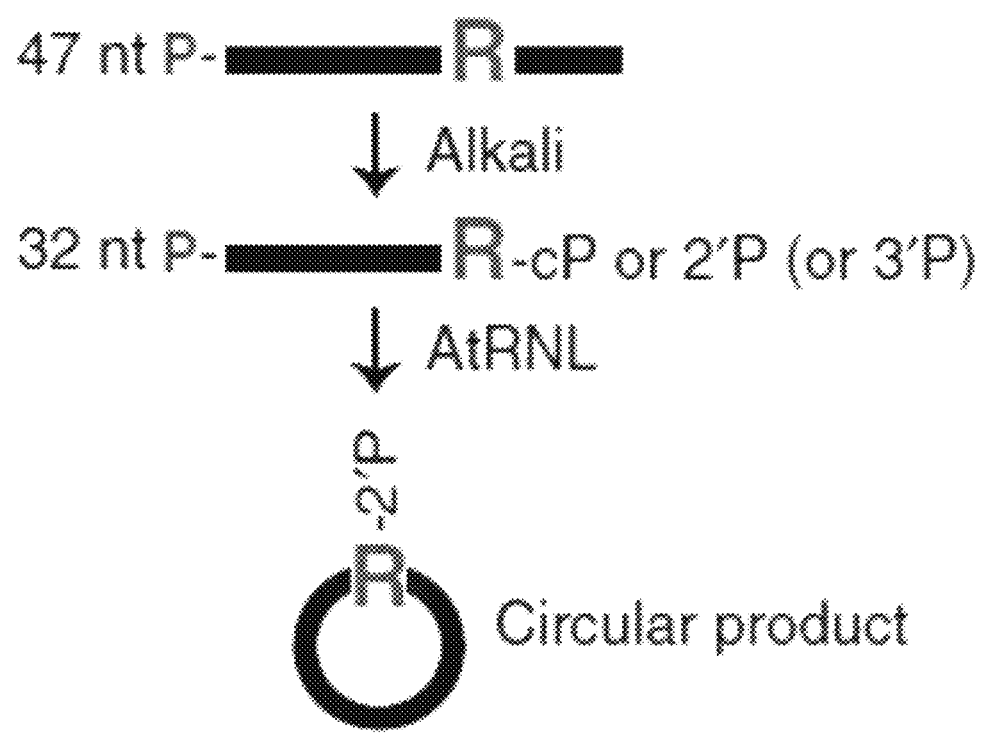
FIG. 1 shows a schematic demonstrating that AtRNL captures of 2',3'-cyclic phosphate (cP) or 2'-phosphate (2'P) DNA termini, and does not capture 3'-phosphate (3'P) DNA termini (indicated in parentheses), generated by alkaline cleavage of a single rGMP in a 5'-radiolabeled 47-nt ssDNA oligonucleotide (see FIG. 37). R designates rGMP or rGMP-bearing oligonucleotide. D designates DNA-only control oligonucleotide. P in bold indicates the 5' radiolabel.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, As used herein, "about," "approximately," and the like, when used in connection with a numerical variable, can generally refers to the value of the variable and to all values of the variable that are within the experimental error (e.g., within the 95% confidence interval for the mean) or within +/−10% of the indicated value, whichever is greater.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

As used herein, "concentrated" can refer to a molecule or population thereof, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" can refer to an alternative subject or sample used in an experiment for comparison purpose and included to minimize or distinguish the effect of variables other than an independent variable.

As used herein, "culturing" can refer to maintaining cells under conditions in which they can proliferate and avoid senescence as a group of cells. "Culturing" can also include conditions in which the cells also or alternatively differentiate.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" can include nucleic acids/polynucleotides that are made of DNA.

As used herein, "identity," "identical to", can refer to the relationship between two or more nucleotide or polypeptide sequences, as determined by comparing the sequences. In the art, "identity" also refers to the degree of sequence relatedness between nucleotide or polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein. As used herein, "nucleic acid sequence" and "oligonucleotide" also encompasses a nucleic acid and polynucleotide as defined above.

As used herein, "operatively linked" can indicate that the regulatory sequences useful for expression of the coding sequences of a nucleic acid are placed in the nucleic acid molecule in the appropriate positions relative to the coding sequence so as to effect expression of the coding sequence. This same term can be applied to the arrangement of coding sequences and/or transcription control elements (e.g. promoters, enhancers, and termination elements), and/or selectable markers in an expression vector. "Operatively linked" can also refer to an indirect attachment (i.e. not a direct fusion) of two or more polynucleotide sequences or polypeptides to each other via a linking molecule (also referred to herein as a linker).

As used herein "peptide" refers to chains of at least 2 amino acids that are short, relative to a protein or polypeptide.

As used herein, "positive control" can refer to a "control" that is designed to produce the desired result, provided that all reagents are functioning properly and that the experiment is properly conducted.

As used herein, "protein" as used herein can refer to a molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs.

As used herein, "purified" or "purify" can be used in reference to a nucleic acid sequence, peptide, or polypeptide that has increased purity relative to the natural environment.

As used herein, "separated" can refer to the state of being physically divided from the original source or population such that the separated compound, agent, particle, or molecule can no longer be considered part of the original source or population.

As used herein "specifically cleave" can refer to the ability of an enzyme, such as a protease, to cleave a particular substrate with a higher efficiency, rate, and/or amount as compared to all other molecules or compounds. In some instances, the term "specifically cleave" can refer to the ability of one enzyme to cleave a particular substrate or class of substrates (e.g. those sharing a particular structural feature) to the substantial exclusion of all other substrates.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%.

Most preferably, the object species is purified to essential homogeneity (contaminant species cannot be detected in the composition by conventional detection methods) wherein the composition consists essentially of a single species.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

Unless otherwise defined herein, all technical and scientific terms used herein have the same meaning as commonly understood by one of ordinary skill in the art.

Discussion

Genomic DNA contains embedded ribonucleotides (rNMPs) that are incorporated during DNA replication and repair or formed during DNA damage. The modifications have been linked to genome instability and disease, but no method currently exists to profile their locations genome wide. Despite abundant evidence for the frequent incorporation of rNMPs in DNA and correlation to disease, a comprehensive and detailed picture of rNMP incorporation throughout a genome is lacking. This is primarily due to the lack of techniques for detecting and quantitating the incorporation of rNMPs in DNA.

Figure 56:
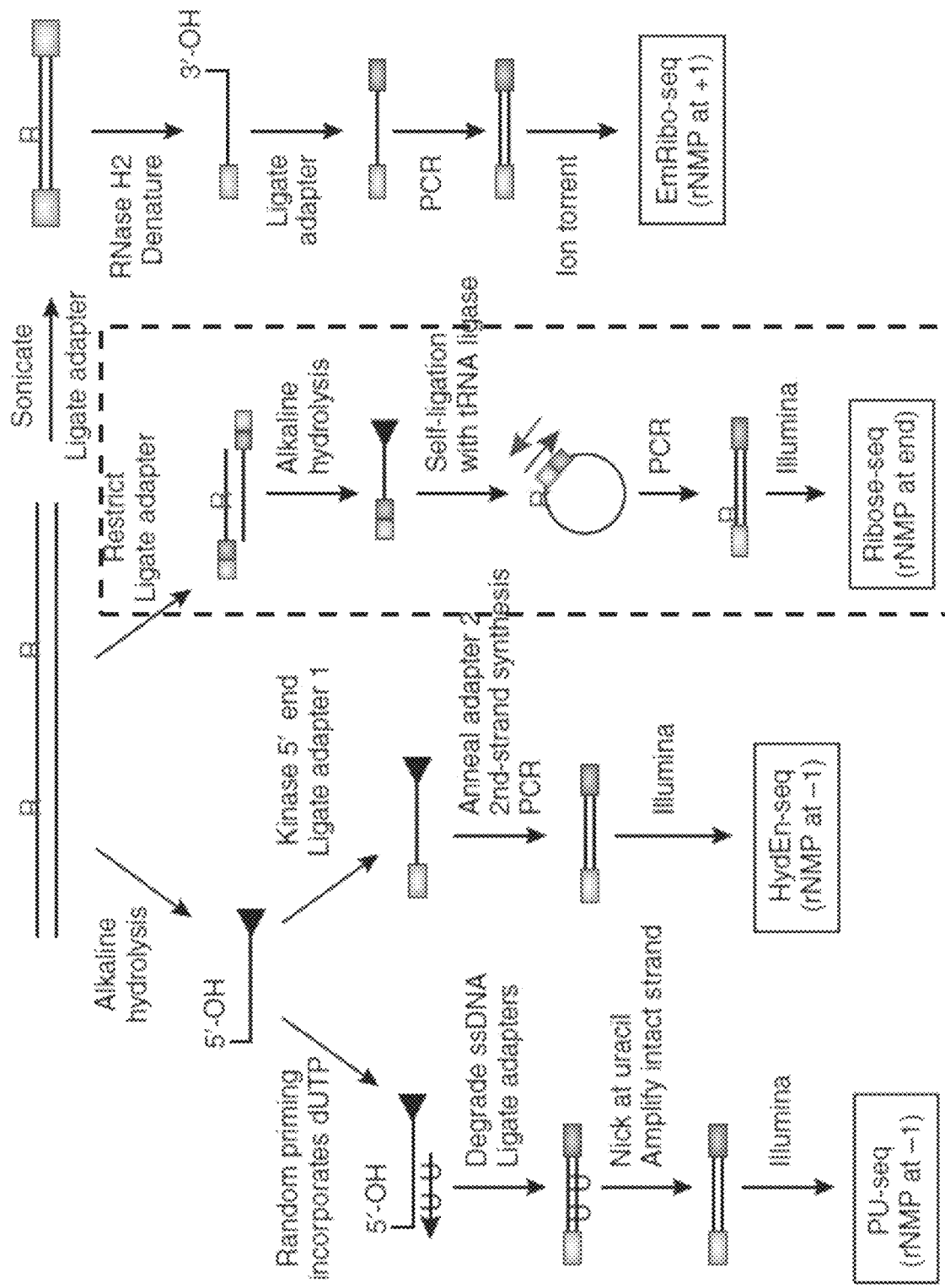
FIG. 56 shows a comparison of the embodiments of a method for determining rNMPs embedded in DNA as provided herein (method within the dashed line) as compared to other methods developed in parallel, which was adapted from Jinks-Robertson and Klein. Nat. Struct. And Mol. Biol., 2015. 22(3): 176-178.

Some techniques have been developed to detect rNMPs embedded in DNA (Jinks-Roberston and Klein. Nat. Struct. And Mol. Biol., 2015. 22(3): 176-178). As shown in FIG. 56 none of the existing methods are capable of directly attaching a sequencing adaptor to the embedded rNMP DNA. Stated differently, all currently available methods capture the nucleotides downstream or upstream of rNMP positions of the rNMP as opposed to directly capturing the rNMP. As such these current methods can be less efficient and can have a higher rate of error in determining the positions of embedded rNMPs that a method that relies upon direct attachment of a sequencing adaptor to the embedded rNMP.

Wth that said, described herein are methods of detecting and/or determining the position of rNMPs embedded in DNA that use a ligase capable of circular single stranded (ss) DNA that can result in a sequencing adaptor being directly attached to the rNMP. The methods provided herein can be used to map or profile rNMPs in genomic DNA. ther compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Methods of Determining rNMPs in DNA

Provided herein are embodiments of a method that can determine the location of one or more rNMPs in genomic DNA. The method can, in some embodiments, include the step of ligating an adaptor to a fragment of genomic DNA, wherein the adaptor can contain a first primer-binding sequence, an annealing sequence, wherein the annealing sequence can be coupled to the first-primer binding sequence, and a unique molecular identifier (UMI) sequence, wherein the UMI sequence ca be coupled to the first primer-binding sequence, the step of cleaving the fragment of genomic DNA via an alkali treatment, the step of ligating the cleaved fragment of genomic DNA using a ligase capable of coupling a 2',3'-cyclic phosphate to a 5'-OH to produce a circular single stranded DNA fragment, the step of amplifying the circular single stranded DNA fragment using polymerase chain reaction (PCR) to produce a PCR product; and the step of sequencing the PCR product using a first primer that is capable of specifically binding the first primer-binding sequence. Wth this in mind, embodiments of the method are described in greater detail.

DNA Extraction and Fragmentation:

DNA, such as genomic DNA, can be isolated from a cell using a suitable method. Any DNA can be used. DNA from any type of cell or population thereof can be used. In some embodiments, the cell is a cancer cell. In some embodiments, the cell is a stem cell, such as an induced pluripotent stem cell. Suitable genomic DNA extraction methods will be appreciated by one of ordinary skill in the art. The DNA can be nuclear genomic DNA. The DNA can be mitochondrial genomic DNA. The DNA can be fragmented by a suitable method. The cell can be eukaryotic or prokaryotic. The cell can be from a plant or an animal. The cell can be a human cell. Suitable methods include, but are not limited to, chemical fragmentation, enzymatic fragmentation, and/or mechanical fragmentation. Non-limiting examples of suitable fragmentation techniques can include, but are not limited to, restriction enzyme digestion with one or more restriction enzymes, sonication, acoustic shearing, and hydrodynamic shearing. In some embodiments, restriction enzymes that produced blunt ended fragments can be used. The fragment size can range from about 50 bp to about 3000 bp or more. In some embodiments the average fragment size produced can range from about 200 base pairs (bp) to about 1500 bp. In some embodiments, the amount of DNA that can be fragmented can range from about 1 µg or less to 20 µg or more. The reaction can be scaled as needed. In some embodiments, the amount of DNA that can be fragment can be about 10 µg.

DNA Blunting and dA-Tailing:

The fragmented DNA can be blunted, which is the removal of 3' or 5' overhangs on the end(s) of the DNA fragments. Several techniques can be suitable for blunting of the fragmented DNA. Terminal unpaired nucleotides can be removed from DNA ends using an enzyme having exonuclease activity, which removes the overhang one base at a time. DNA fragments with 5' overhangs can be blunted by filing in a recessed 3' terminus with a DNA polymerase in the presence of dNTPs. Many suitable enzymes are commercially available and include, but are not limited to DNA Polymerase I (Klenow) Fragment, T4 DNA Polymerase, and Mung Bean Nuclease. Exemplary and non-limiting DNA blunting reaction protocols are provided elsewhere herein and others will be appreciated by those of ordinary skill in the art. Prior to blunting, the DNA can be purified.

The fragmented DNA can be dA-tailed, which can refer to the process of incorporating a non-templated dAMP on the 3' end of a blunt DNA fragment (See e.g. Clark et al., (1987) J. Mol. Biol. 198:123-127. Prior to dA-tailing, the DNA can be purified using a suitable technique. dA-tailing can be performed using a suitable enzyme, including but not limited to, Taq DNA polymerase and Klenow exo-enzyme. Klenow exo– is capable of adding the 3'-dA via its DNA polymerase activity but contains mutations that abolish it's ability to degrade 3' dA. The amount of fragmented DNA in a single reaction can range from about 1 µg to about 5 µg. Reaction conditions and techniques will be appreciated by one of ordinary skill in the art. In some embodiments, 500 units of Klenow Fragment exo– (a unit is defined as the amount of Klenow Fragment exo– that catalyzes the incorporation of 10 nmol of dNTP into acid soluble material in 30 minutes at 37° C.) for about 1 µg to about 5 µg DNA can be used.

Adaptor Ligation:

A sequencing adaptor can be attached (ligated) to the DNA fragment. The sequencing adaptor can be a polynucleotide. In some embodiments, adaptor ligation can occur after the step of dA-tailing. The sequencing adaptor can contain a single nucleotide 3' T tail and can be ligated to a 5' end of a DNA fragment. The sequencing adaptor can contain a binding-sequence that can bind a first primer. The sequencing adaptor can contain a binding-sequence for a second primer. In some embodiments, the sequencing adaptor can contain a first binding-sequence that can bind a first primer and a second binding sequence that can bind a second primer, where the first binding-sequence can be operatively linked to the second binding-sequence. In some embodiments, the first binding-sequence can be directly attached to a terminus of the second binding-sequence. The first binding sequence and the second binding sequence, in some embodiments, can range from about 20 bp to about 40 bp. The exact number of base pairs can be determined based on the sequencing primers used. Suitable sequencing primers can be designed using commercially and publically available software, including but not limited to, the Primer3 program, Primer3Plus program, PrimerQuest tool, Primer-BLAST program, and the PrimerDesigner tool. Others will be appreciated by those of ordinary skill in the art.

Figure 38A:
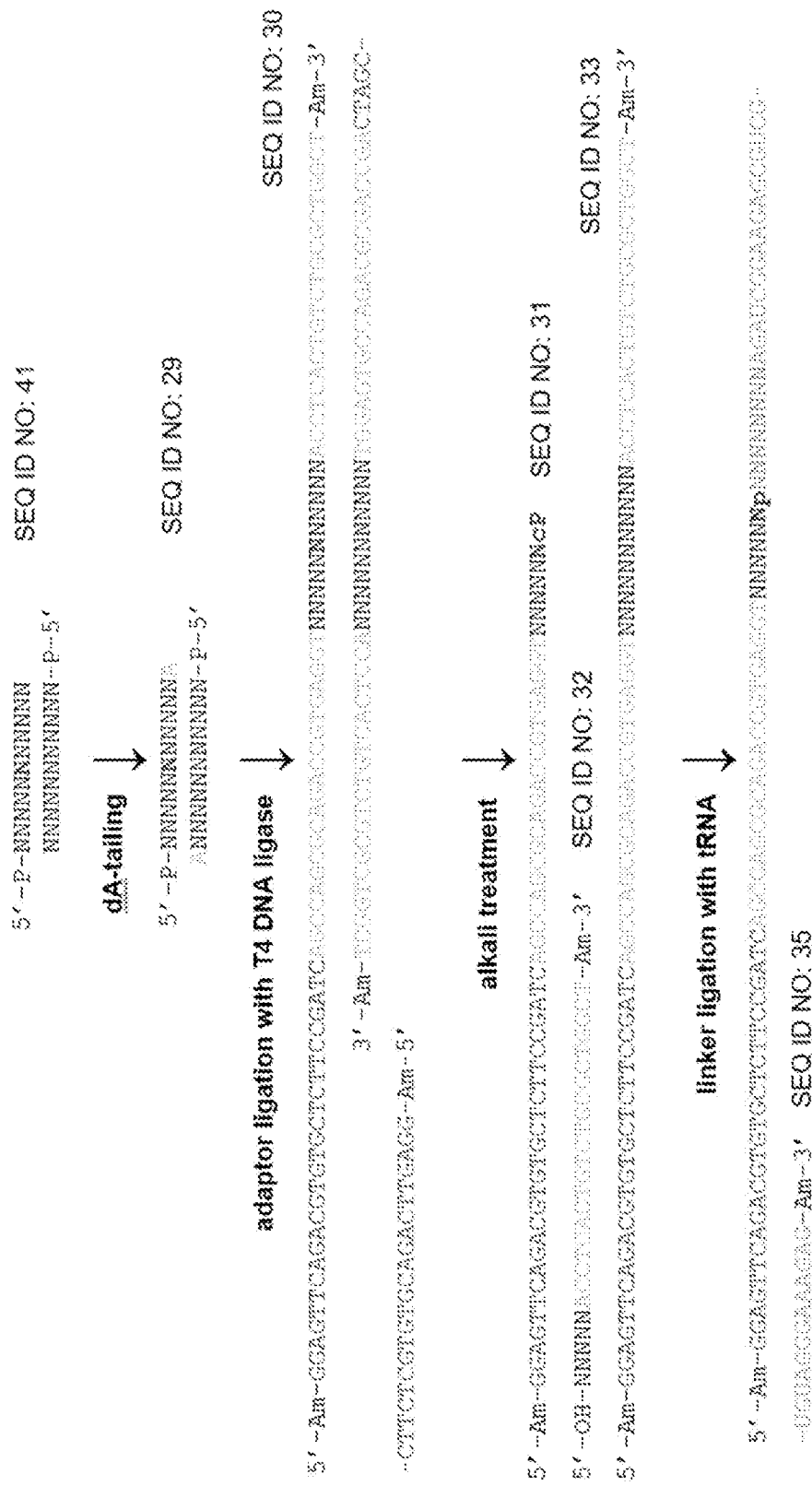
FIGS. 38A and 38B show steps in an embodiment of a method of detecting rNMPs in DNA with exemplary nucleotide sequences shown.
Figure 38B:
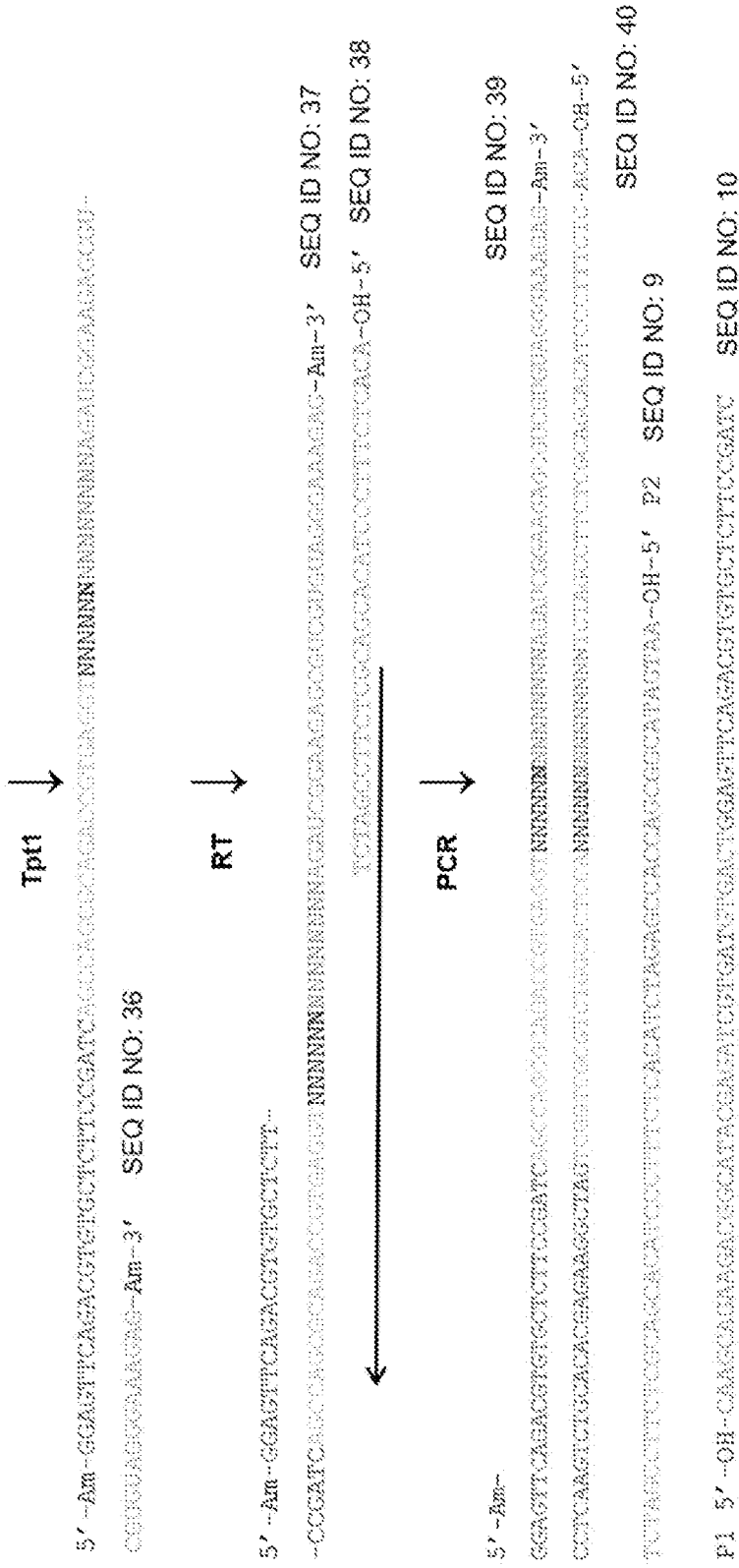
Figure 39A:
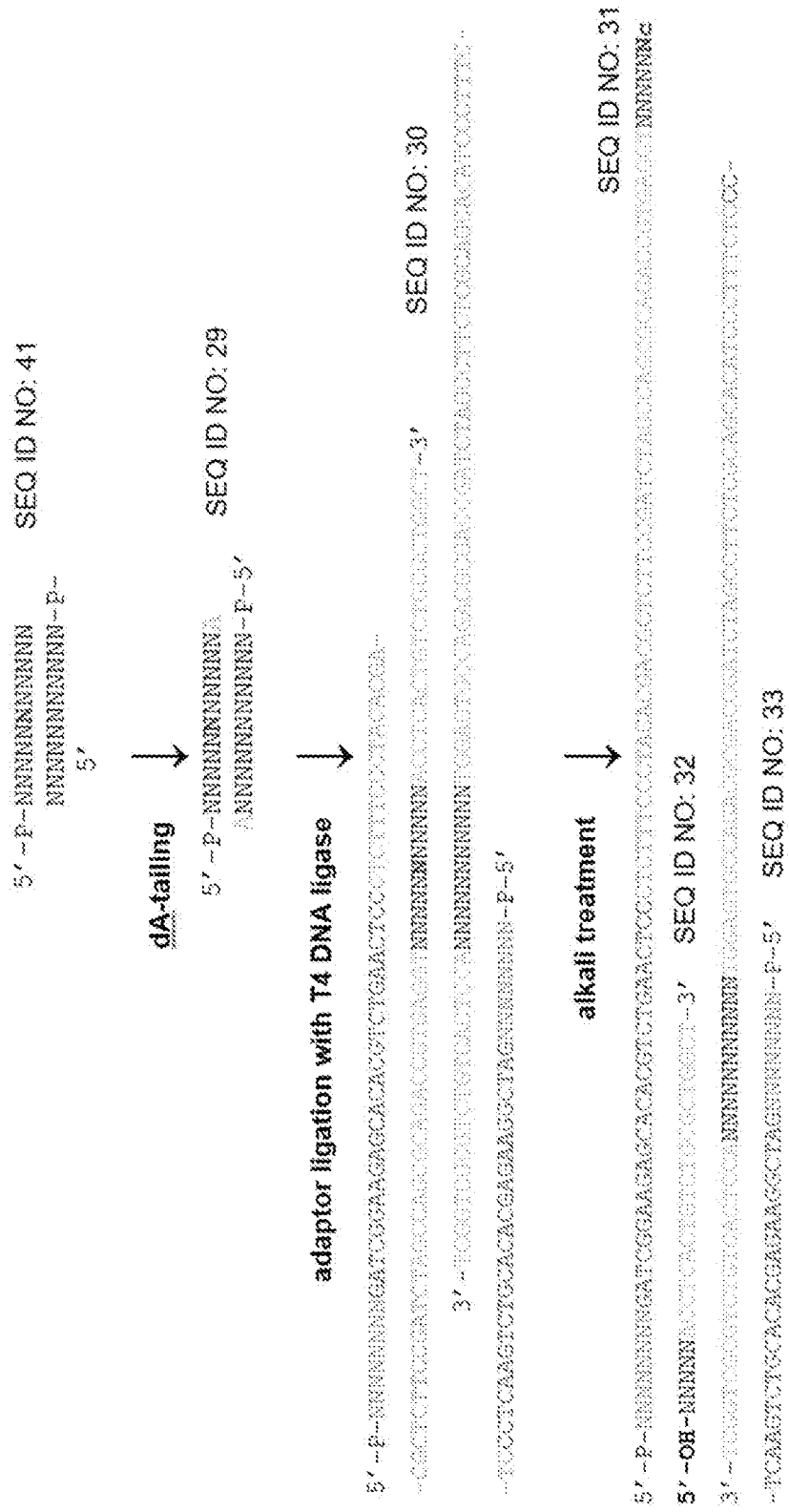
FIGS. 39A and 39B show steps in an embodiment of a method of detecting rNMPs in DNA with exemplary nucleotide sequences shown
Figure 39B:
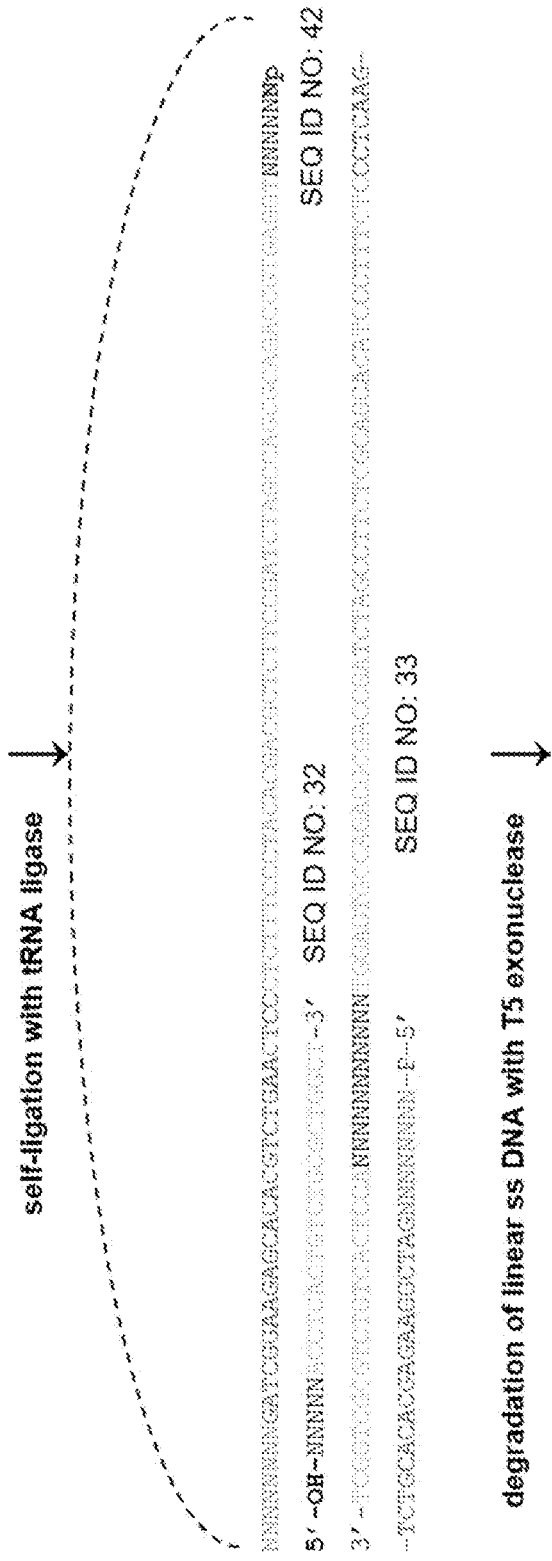
Figure 40:
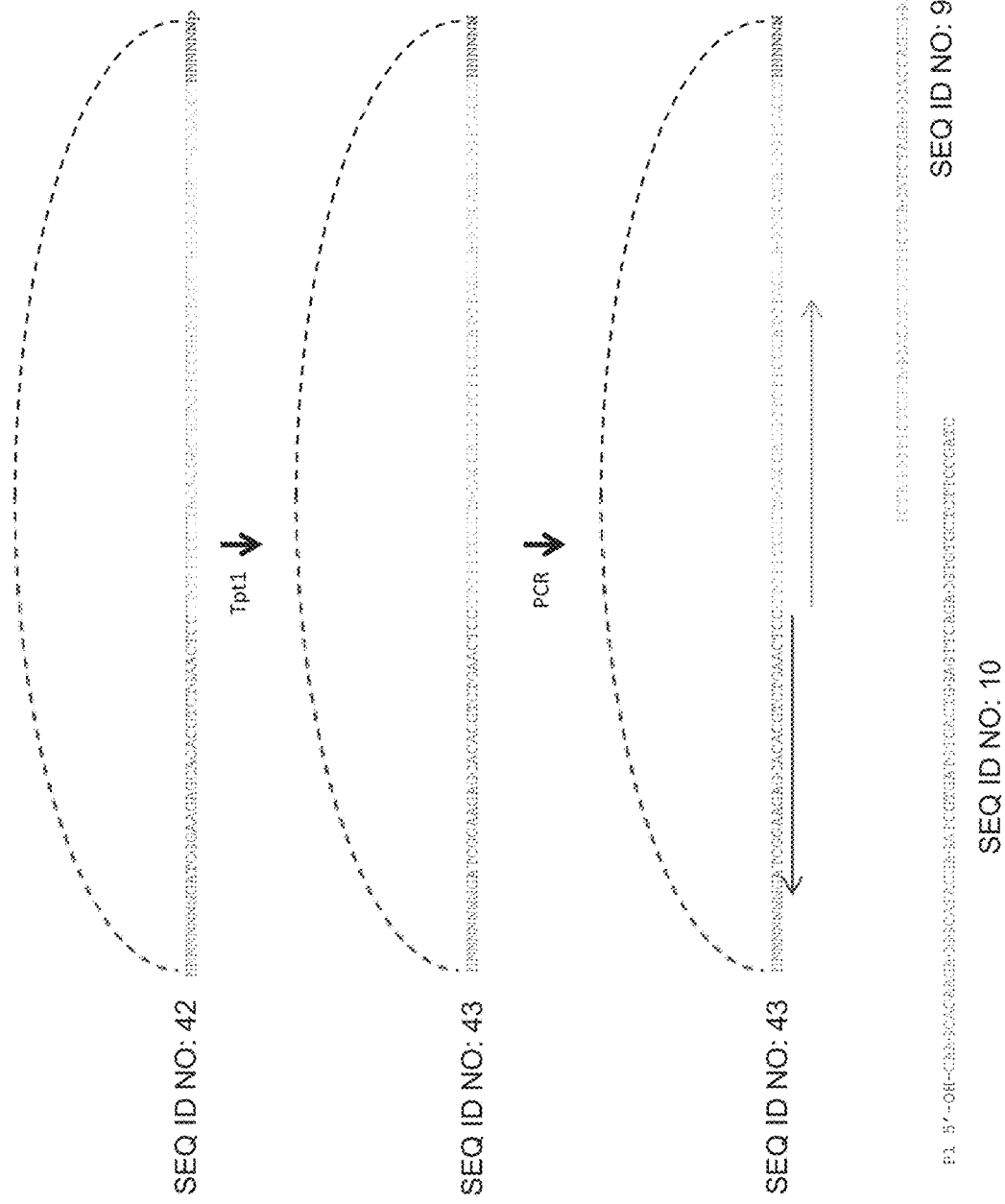
FIG. 40 is a continuation of FIG. 39 and shows steps in an embodiment of a method of detecting rNMPs in DNA with exemplary nucleotide sequences shown.
Figure 55:
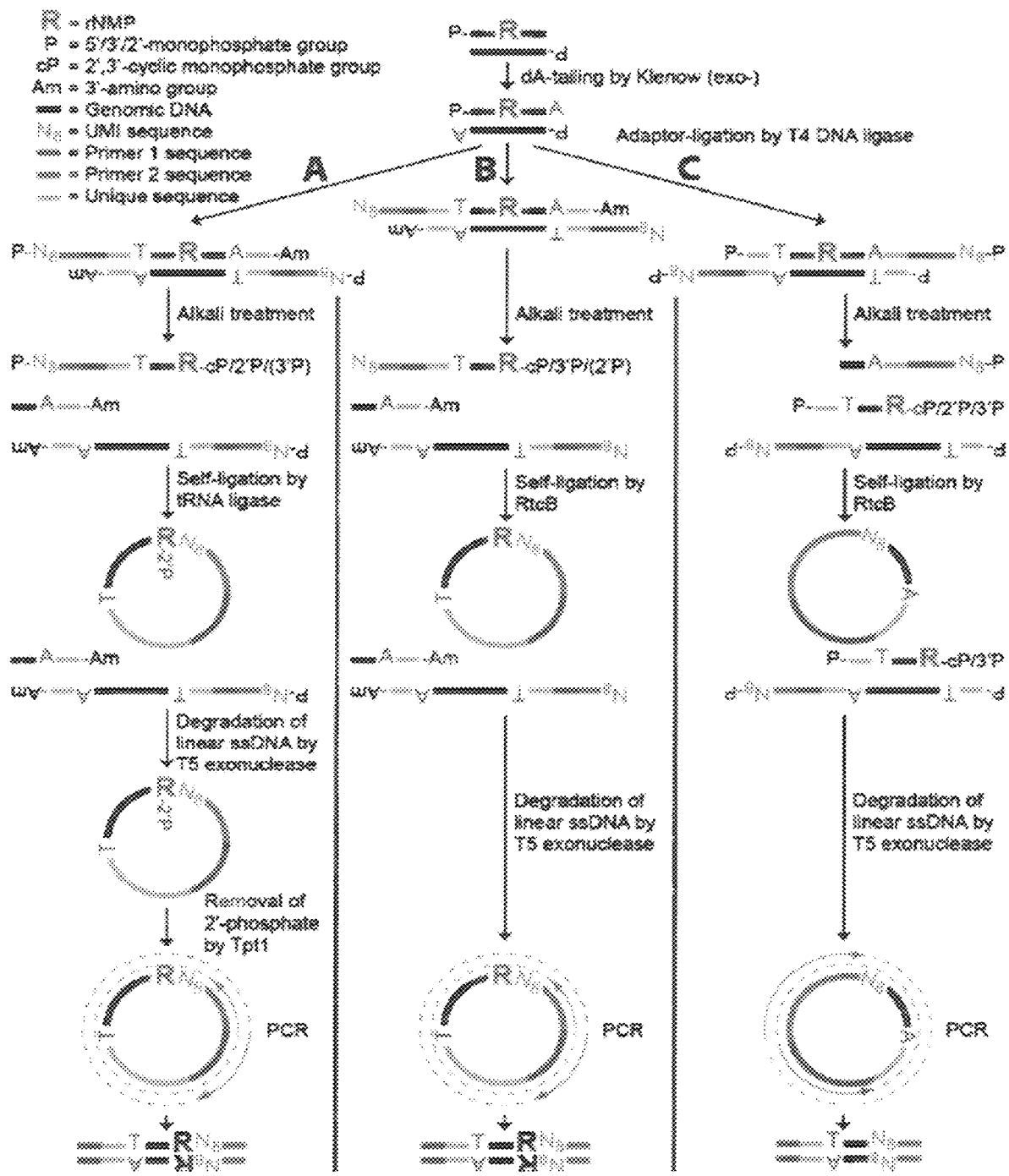
FIG. 55 shows embodiments of a method for determining rNMPs embedded in DNA as provided herein. Path A is the ribose-seq approach showing that cyclic phosphate or 2' phosphate ends of the ribonucleotide terminating ends are captured. In path B, a variant in which cyclic phosphate or 3' phosphate ends of the ribonucleotide terminating ends are captured. In path C, a process is shown to capture the nucleotide sequence downstream from the ribonucleotide.

The sequencing adaptor can further contain an annealing polynucleotide sequence that can serve as a molecular barcode. See e.g. FIGS. 3, 38 and 55, yellow portion. The annealing sequence is preferred (as compared to unique sequence). The function of this sequence to anneal with the short sequence (see FIG. 3 or 55 and also see FIG. 38, which provides the actual sequence 20 nt before the T-A pair of this yellow region of the adaptor) that is complementary to it to create a double-stranded part that is used to ligate the adaptor to the dsDNA fragments. The annealing sequence, in some embodiments can range from about 18 to about 40 nucleotides (nt) long.

The sequencing adaptor can further include a unique molecular identifier (UMI). The UMI can be positioned at a terminus of the adaptor. In some embodiments, the UMI is present at the 5' end of the sequencing adaptor. The UMI is used to eliminate PCR duplicates via computational analysis, and after the pink primer sequence, the UMI are the first nucleotides that are sequenced, so, for example if the UMI is 8 nt long then to determine which nucleotide is the embedded ribonucleotide, one would count 8 nt of the UMI and then the next nt in the read is the nucleotide opposite (or complementary) to the ribonucleotide. This feature will be explained in further detail below. The UMI can also be used to identify repeated sequencing reads and thus aid in removing noise in an analysis due to differences in PCR and/or sequencing efficiency of different DNA fragments. During sequencing, sequence reads having different unique sequences represent different original molecules, while sequence reads having the same barcode are the result of PCR duplication from one original molecule. The unique polynucleotide (molecular barcode) in the sequencing adaptor can range from about 5 nucleotides to about 20 nucleotides.

In some embodiments, the UMI contains 8 consecutive random nucleotides (e.g. NNNNNNNN, SEQ ID NO: 6). In other embodiments, the UMI is composed of known sequence of 3-5 nucleotides flanked on each terminus by 4 random nucleotides. The known portion can be used to identify different libraries that the fragment originated from in a multiplexed downstream reaction (e.g. during sequencing). For example, a UMI having a sequence of NNNNCGTNNNN (SEQ ID NO: 4) can be used to tag fragments that will be used to generate a first library and a UMI having a sequence of NNNNGACNNNN (SEQ ID NO: 5) can be used to tag fragments used generate a second library. This can be useful for examining conditions to generate a library insofar as the same starting DNA fragment pool can be used, subjected to different conditions, and be distinguishable from each other when sequenced. The known portion can be any nucleotides and is known and predetermined prior to tagging the fragments with the adaptor. The UMI can be any 5-20 nucleotides. In some embodiments the UMI can contain 8 random nucleotides (total excluding the known portion where included).

A ligation adaptor can also be attached to the DNA fragment. The ligation adaptor can be composed of the annealing sequence. The ligation adaptor can contain a single nucleotide 5' A tail and can be attached to the 3' end of a DNA fragment.

In some embodiments, the sequencing adaptor can be annealed to the ligation adaptor prior to ligating the adaptors to the DNA fragment(s). In other embodiments, they can be ligated sequentially or simultaneously and then annealed.

Alkali Treatment

Figure 22:
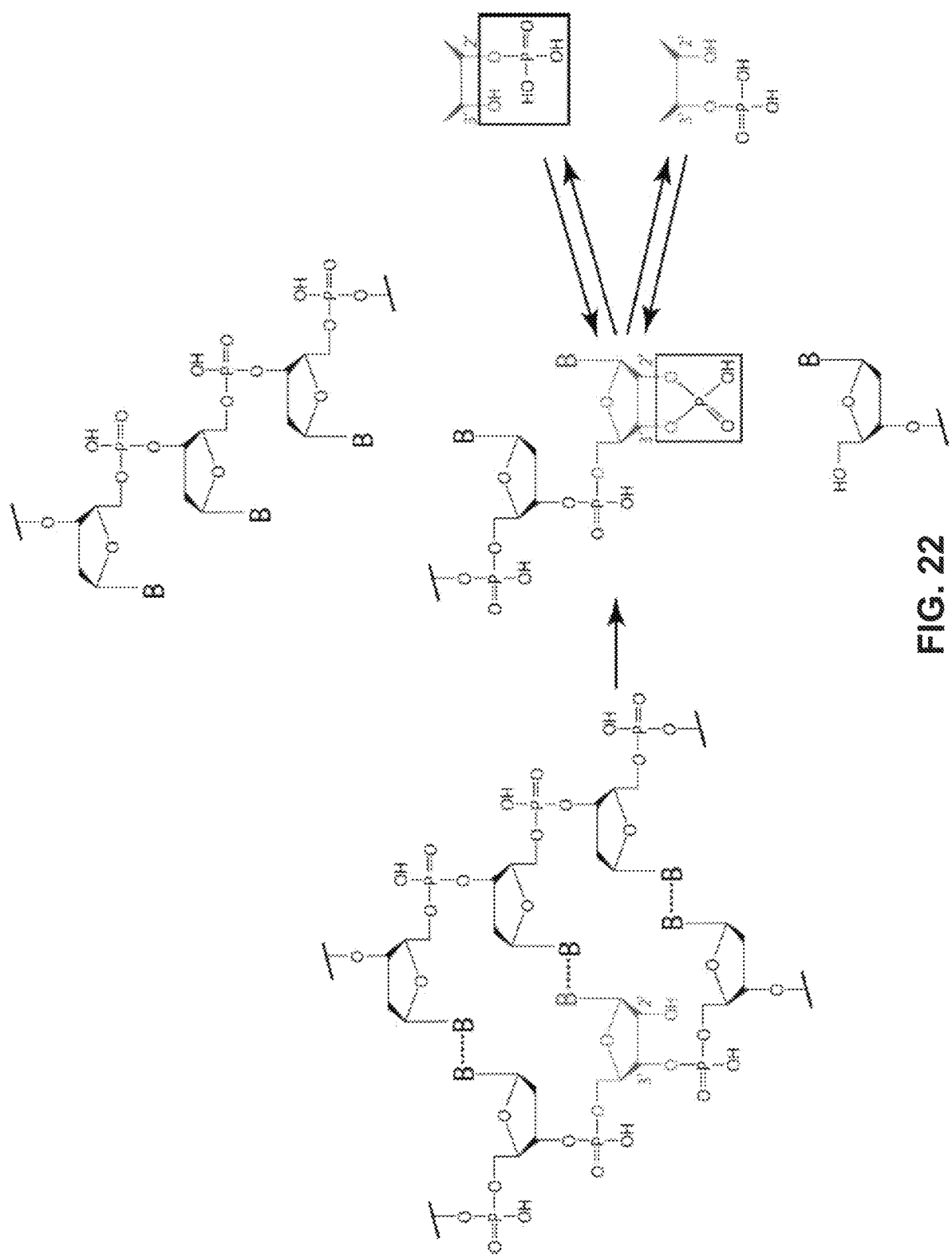
FIG. 22 shows a schematic demonstrating the mechanism of alkaline cleavage of ribonucleotides in DNA. The ribonucleoside embedded in double-stranded DNA is in red. During alkaline treatment, DNA strands are denatured, and cleavage occurs at the rNMP site, generating a 2',3'-cyclic phosphate end and an opposite 5'-hydroxyl end. The 2',3'-cyclic phosphate is in equilibrium with 2'-phosphate and 3'-phosphate forms. Boxes in black indicate the 2',3'-cyclic phosphate and 2'-phosphate DNA termini, which are substrates of AtRNL.

After adaptor ligation the adaptor-modified DNA fragments can undergo alkali treatment. Ribonucleotides, as opposed to deoxy ribonucleotides, contain a 2'-OH on the ribose portion of the nucleotide. Alkali treatment cleaves the hydrogen bonding between base-pairs and specifically cleaves at ribonucleotides contained in the DNA (see e.g. FIG. 22). Upon cleavage, a cyclic phosphate is formed at the 2' and 3' position of the embedded rNMP. This cyclic phosphate is not formed at any cleavage that may occur at a deoxy ribonucleotide by alkali treatment because deoxy ribonucleotides lack the 2'-OH. The cyclic phosphate form of the embedded ribonucleotide can exist at equilibrium with a phosphate group present at the 2' position on the ribose or the 3' position on the ribose (see FIG. 22). In some embodiments, the adaptor-modified DNA fragment(s) can be incubated in a solution containing NaOH for an amount of time. The NaOH can range from about 0.01 M NaOH to 1 M NaOH or more. In some embodiments, the concentration of NaOH is about 0.3M. The incubation in the alkaline solution can occur for about 10 min to 6 hours or more. In some embodiments, the adaptor-modified DNA fragment(s) are incubated in the alkaline solution for about 2 hours. The incubation in the alkaline solution can occur at about 50-60° C. or greater. In some embodiments, the incubation in the alkaline solution can occur at about 55° C. After incubation, the solution can be neutralized and the alkali-treated DNA can be purified.

Self-Ligation and Removal of Linear ssDNA

The ssDNA produced from alkali treatment of the adaptor modified DNA fragment(s) can then undergo a ligation reaction using a DNA ligase that is capable of coupling a 2',3'-cyclic phosphate to a 5'-phosphate (see FIG. 3) to produce a circular single stranded DNA fragment. In some embodiments, the ligase can be a tRNA ligase. In some embodiments, the tRNA ligase is *Arabidopsis thaliana* tRNA ligase (AtRNL) or variant thereof. AtRNL is normally involved in tRNA maturation. AtRNL or variant thereof can convert 2',3'-cyclic phosphate ends of RNA to 2'-phosphate and ligates these to 5'-phosphate ends of RNA or DNA (Schutz, K., Hesselberth, J. R. & Fields, S. Capture and sequence analysis of RNAs with terminal 2',3'-cyclic phosphates. RNA 16, 621-631 (2010) and Remus, B. S. & Shuman, S. Distinctive kinetics and substrate specificities of plant and fungal tRNA ligases. RNA 20, 462-473 (2014)). In other embodiments, the ligase can be a RtcB ligase or suitable variant thereof. RtcB ligase or variant thereof can ligate 3' phosphate ends of a ribonucleotide or deoxyribonucleotide to 5'-OH ends of a polynucleotide. (Chakravarty et al., PNAS, 2012. 109 (16):6072-6077). The ssDNA products produced from alkali treatment can be incubated with the DNA ligase for about 15 minutes to about 2 hours or more. In some embodiments, the ssDNA products produced from alkali treatment can be incubated with the DNA ligase for about 1 hour. The ssDNA products produced from alkali treatment can be incubated with the DNA ligase at about 25 to about 37° C. In some embodiments, the ssDNA products produced from alkali treatment can be incubated with the DNA ligase at about 30° C. Self-ligation can occur between the UMI of the sequencing adaptor and the now exposed ribonucleotide. The reaction can produce a cyclic single-stranded polynucleotide.

Any linear single stranded products remaining can be removed by degrading them with a suitable nuclease. Suitable nucleases can be those that are specific for linear DNA, such as linear ssDNA. Suitable nucleases include, but are not limited to, T5 exonuclease, [[T7 exonuclease and other exonucleases. The remaining circular ssDNA can be optionally purified.

Optionally, 2'-phosphates at the ligation junction can be removed by incubating the circular DNA with an amount of Tpt1, which is a tRNA 2'-phosphotransferase enzyme. In some embodiments, the circular DNA can be reacted in a solution containing at least Tpt1 at about about 30° C. for about 1 hr. One of skill in the art will be capable of modifying the reaction conditions as necessary.

Polymerase Chain Reaction (PCR) Amplification and Sequencing

In preparation for sequencing, the resulting circular DNA products can be amplified using PCR with a first primer that can bind the first binding-sequence and a second primer that can bind the second binding-sequence. The resulting product is a double stranded linear DNA (the ribonucleotide has been converted to a deoxy ribonucleotide during PCR due to the incorporation of dNTPs in the reaction. The PCR reaction can begin by an initial heating to about 95° C. to about 100° C. In some embodiments, the initial heating step can be conducted at about 98° C. This can be followed by about 26-32 cycles of the following steps: incubating at about 98° C. for about 10 s, incubating at about 65° C. for about 20 s, and incubating at about 72° C. for about 30 s. These cycles can be followed by a final extension conducted at about 72° C. for about 5-10 min. Optionally, the reaction can then be kept at 4° C.

The resulting products can be used as templates for sequencing. Any sequencing method can be used. Preferably, a next generation sequencing method can be used. Suitable next generation sequencing methods include but are not limited to 454 pyrosequencing, Illumina sequencing, Solexa sequencing, and SOLiD sequencing. Alternatively, the Sanger method of sequencing can be used.

Generating an Embedded rNMP Profile

After sequencing, the location of the second binding sequence and thus the UMI can be identified from the sequence. The location corresponding to the rNMP will be the nucleotide after that last nucleotide of the UMI. By aligning the sequence reads to a reference sequence and knowing which position in the read corresponds to the rNMP, the embedded ribonucleotides within a sample of DNA can be determined. Collectively, the profile of embedded rNMPs of a sample of DNA can be obtained. The profiles obtained can be used to, inter alia, identify biomarkers for diseases, provide a better understanding of DNA function and stability, and provide targets for therapeutics.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Ribose-Seq: Global Mapping of Ribonucleotides Embedded in Genomic DNA Abundant ribonucleotide incorporation in DNA during replication and repair has profound consequences for genome stability, but the global distribution of ribonucleotide incorporation is unknown. We developed ribose-seq, a method for capturing unique products generated by alkaline cleavage of DNA at embedded ribonucleotides. High-throughput sequencing of these fragments in DNA from the yeast *Saccharomyces cerevisiae* revealed widespread ribonucleotide distribution, with a strong preference for cytidine and guanosine, and identified hotspots of ribonucleotide incorporation in nuclear and mitochondrial DNA. Ribonucleotides were primarily incorporated on the newly synthesized leading strand of nuclear DNA and were present upstream of (G+C)-rich tracts in the mitochondrial genome. Ribose-seq is a powerful tool for the systematic profiling of ribonucleotide incorporation in genomic DNA.

Genomic DNA contains embedded ribonucleotides (rNMPs) that are incorporated during DNA replication and repair or formed during DNA damage (reviewed in ref. 1). The modifications have been linked to genome instability and disease, but no method currently exists to profile their locations genome wide.

rNMPs were initially found at specific DNA loci in mouse and human mitochondrial DNA[2] and the mating type locus of fission yeast[3], but they have since been detected in a variety of cell types[4]. Many DNA polymerases can incorporate rNMPs into DNA, including the human replicative DNA polymerase (Pol) δ[5] and mitochondrial Pol γ[6], budding yeast nuclear replicative Pol α, δ and ε[7], Escherichia coli polymerase V[8], and the polymerase components of bacterial nonhomologous end joining ligases[9]. rNMP incorporation could also be a consequence of incomplete maturation of Okazaki fragments during lagging strand synthesis in DNA replication[10]. Moreover, generation of hydroxyl radicals during oxidative stress can modify DNA deoxyribose sugars to ribose, forming rNMPs in DNA both in vitro and in vivo[11].

RNase H type 2 (RNase H2 or HII) cleaves single rNMPs or longer rNMP tracts incorporated in DNA[12] and initiates ribonucleotide excision repair, the main rNMP repair mechanism in bacterial DNA and in eukaryotic nuclear DNA (ref. 13 and references therein). By contrast, RNase H1 (or HI) recognizes only rNMP tracts longer than four nucleotides. Inactivation of RNase H2 leads to the accumulation of high amounts of rNMPs in genomic DNA, enabling >1 million rNMPs to be quantified per mouse embryonic fibroblast genome and suggesting that rNMPs are the most common noncanonical nucleotides in dividing mouse cells[14]. Similar measurements on genomic DNA derived from RNase H2-deficient (rnh201Δ) budding yeast estimated a few thousand rNMPs incorporated per genome per cell cycle[15,16], and RNase HII-null Bacillus subtilis cells have high levels of incorporated rNMPs[17]. Embedded rNMPs in DNA have highly reactive 2'-hydroxyl groups, altering its properties, structure and function[18,19] and leading to genome instability[16,20-22]. In humans, mutations in any of the three subunits of RNase H2 are associated with Aicardi-Goutieres syndrome, a neurological disorder[23].

Despite abundant evidence for the frequent incorporation of rNMPs in DNA, a comprehensive and detailed picture of rNMP incorporation throughout a genome is lacking. Here we introduce ribose-seq: a technique for mapping rNMPs in genomic DNA.

Results

Ribose-Seq Strategy to Capture rNMPs in DNA

Figure 2:
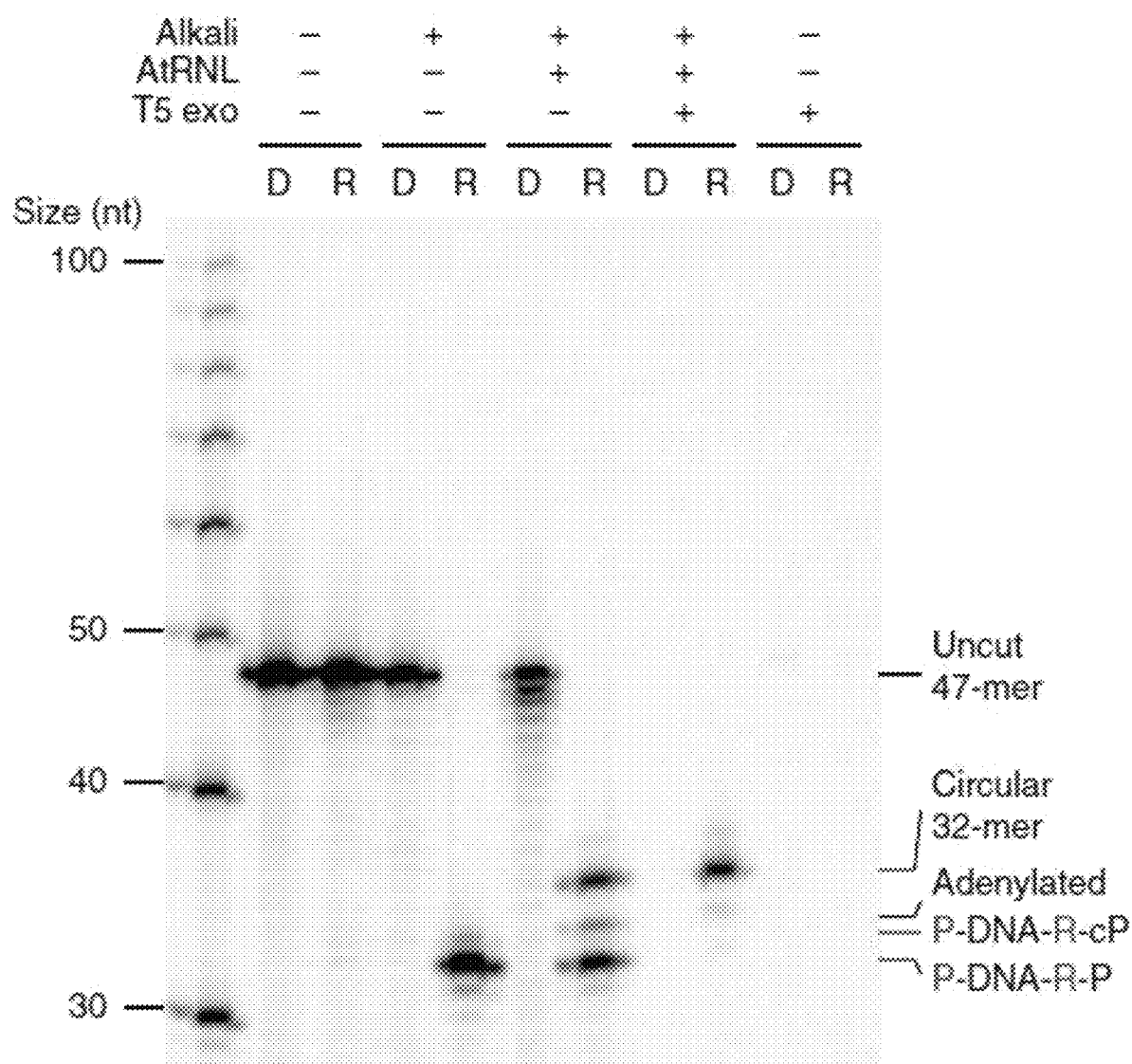
FIG. 2 shows an image of a gel demonstrating the effect of T5 exonuclease treatment on the ligation product. T5 exonuclease treatment confirms the presence of circular ligation product. Left lane, ssDNA ladder. Ligation efficiency was about 50% due to the mixture of 2'-phosphate and 3'-phosphate ends generated upon alkaline cleavage.
Figure 23A:
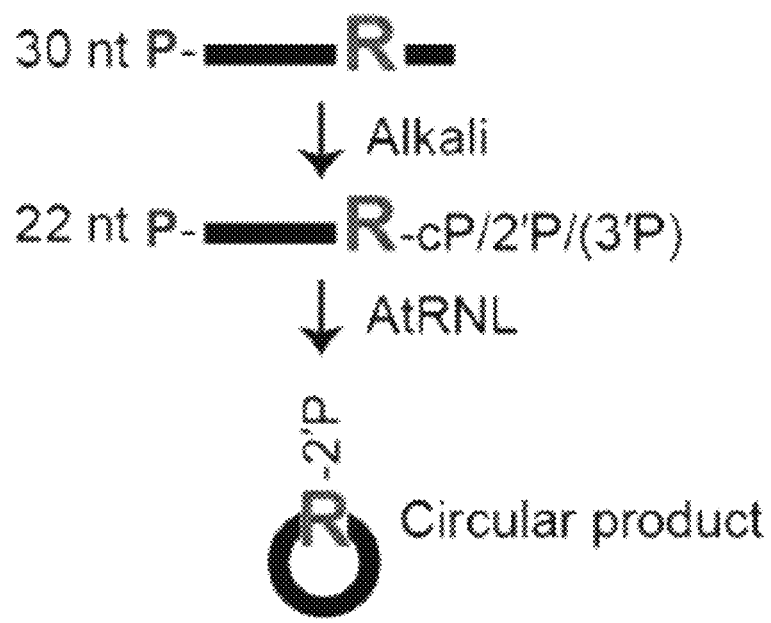
FIG. 23A shows a schematic demonstrating a 3' base bias for AtRNL ligation.
Figure 23B:
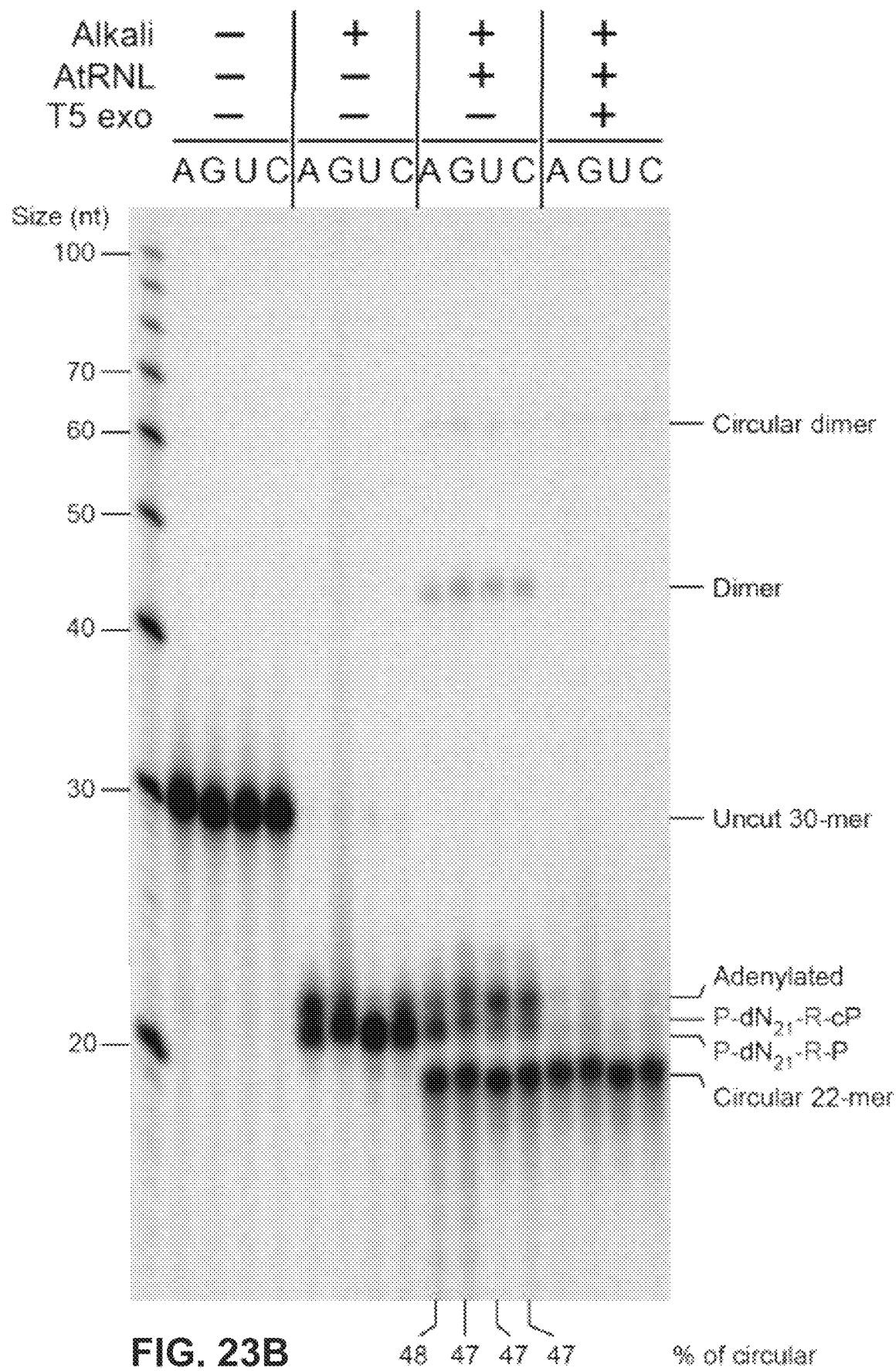
FIG. 23B shows a image demonstrating Hot 5'-radiolabeled 30-nt DNA oligo with a single rNMP (either A, G, U, or C) in the 22nd position was mixed with cold equimolar 30-nt DNA oligos with rNMPs of 3 other bases in the 22nd positions. 5'-radiolabel is indicated by 'P' in purple. The mixture was treated with 0.3M NaOH for 2 hr at 55° C. and neutralized. 100 nM of alkali-cleaved products (25 nM of each base) were then incubated with 1 μM AtRNL in appropriate buffer (see Methods) for 1 hr at 30° C. The resulting products were treated with T5 exonuclease for 2 hr at 37° C. Aliquots were withdrawn after appropriate steps and quenched. The products were analyzed by urea-PAGE. The circular 22-mer migrates faster than the unligated, linear 22-mer. Only circular products were resistant to T5 exonuclease while all linear substrates/products were degraded. Median percentages of circular 22-mer formation from four independent reactions are displayed.

Ribose-seq captures rNMP-terminated single-stranded DNA (ssDNA) fragments generated by alkaline cleavage of rNMPs in DNA (FIGS. 1-3 and FIG. 22). We exploited the distinctive ligation mechanism of Arabidopsis thaliana tRNA ligase (AtRNL), normally involved in tRNA maturation. AtRNL converts 2',3'-cyclic phosphate ends of RNA to 2'-phosphate and ligates these to 5'-phosphate ends of RNA (24,25) or DNA (25). We demonstrated that AtRNL captures 2',3'-cyclic phosphate or 2'-phosphate termini of DNA derived from alkaline cleavage of a DNA oligonucleotide at an embedded rNMP, ligating the 2'-phosphate end to the 5'-phosphate terminus of the same DNA molecule and producing a ssDNA circle containing an embedded rNMP. Self-ligation was strongly preferred over dimerization, as linear dimers were not detected (FIGS. 1-2). Further, these ssDNA circles are resistant to T5 exonuclease, enabling their enrichment relative to unligated linear DNA upon exonuclease treatment (FIGS. 1-2). We did not observe any bias for the 3' rNMP substrate of AtRNL: the ligase captured an embedded rAMP, rCMP, rGMP or rUMP with equal efficiency ($0.49 \leq P \leq 1.0$) (FIGS. 23A-23B and FIG. 30), nor was any bias observed in a previous study[26]. These data indicate that self-ligation is favored for AtRNL on 2'-phosphate-terminated ssDNA fragments as small as 22 nt (FIGS. 1-2 and FIGS. 23A-23B), thus facilitating library construction and high-throughput DNA sequencing.

The ribose-seq methodology was applied to identify rNMPs embedded in nuclear and mitochondrial DNA of RNase H2-deficient budding yeast (strain KK-100, FIG. 31)[1]. Genomic DNA was extracted from cells grown to stationary phase, and a mixture of three blunt-end restriction enzymes was used to fragment the DNA. Application of our rNMP-capture scheme (FIG. 3) yielded a library of DNA molecules (FIG. 24A) with an average size of ~350 bp, each of which maps to a single site of rNMP incorporation and its upstream sequence. In control experiments, we found that exclusion of either AtRNL (FIG. 24A) or alkali treatment (FIG. 24B) prevented library formation, validating that captured molecules derive from rNMPs embedded in DNA.

Spectrum of rNMPs in S. cerevisiae Genome

Figure 4:
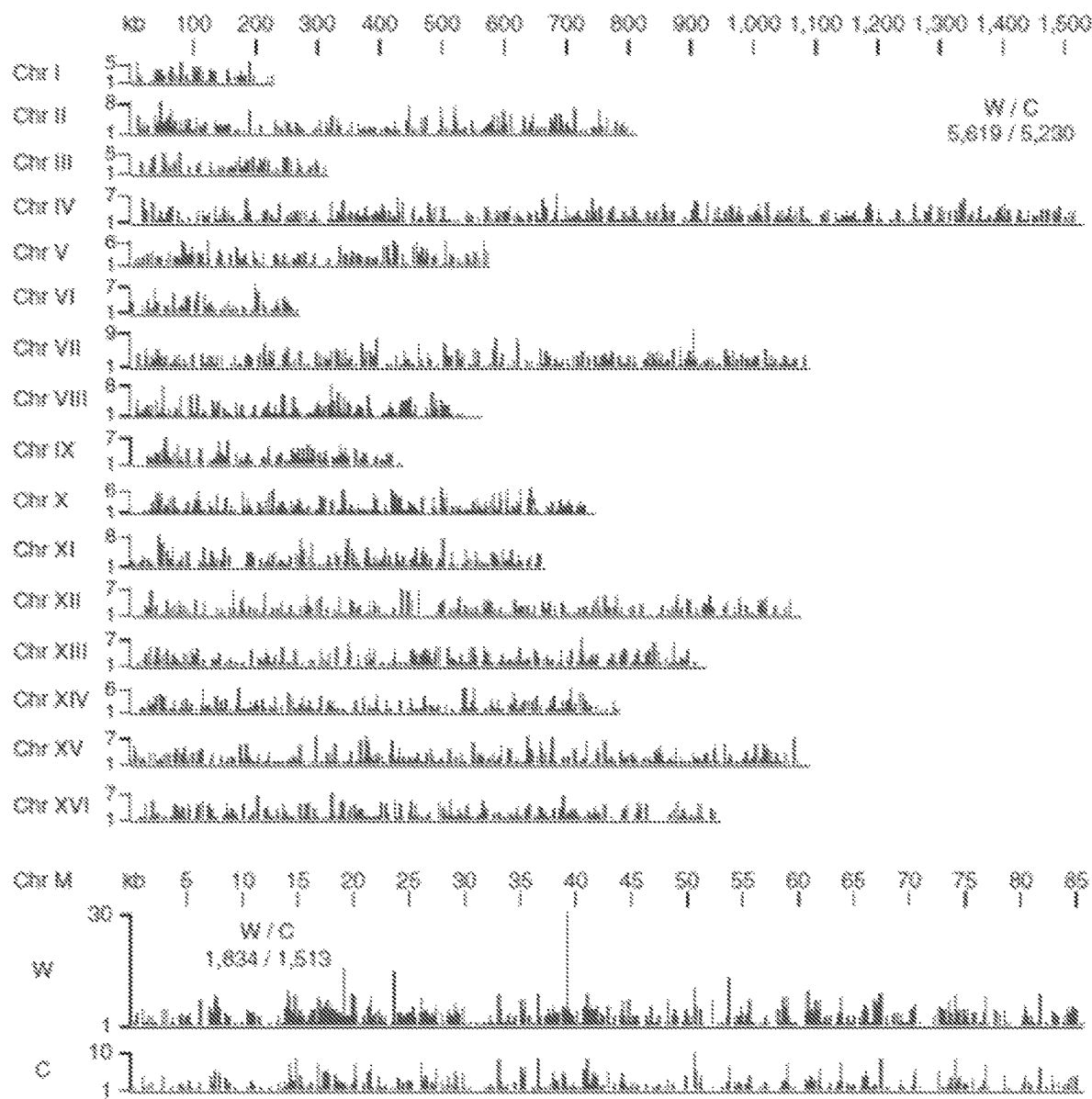
FIG. 4 shows a Ribose-seq map of rNMPs in genomic DNA from rnh201Δ (KK-100) cells. The data, as peaks of rNMP reads, are shown for the individual nuclear chromosomes (Chr I-XVI) and the two strands of mitochondrial DNA (Chr M). The height of each peak corresponds to the number of reads. A comparison of nuclear and mitochondrial rNMP reads for Watson (W) and Crick (C) strands is also displayed. Raw sequencing reads are available at NCBI GE039 under accession code GSE61464.
Figure 5A:
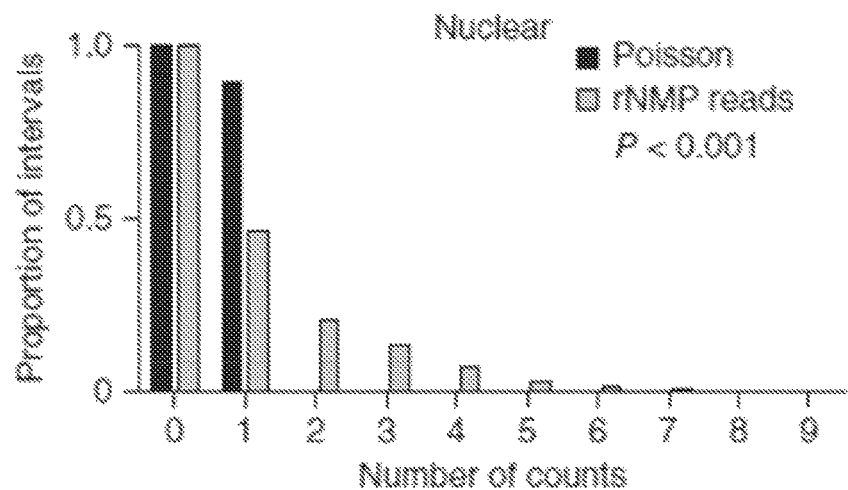
FIGS. 5A-5B show graphs demonstrating the proportion of 2.5-kb windows containing an observed number of rNMPs was calculated for nuclear (FIG. 5A) and mitochondrial (FIG. 5B) genomes and compared to random expectation based on Poisson frequencies. The P values calculated from a chi-squared goodness-of-fit test are shown (n=10,847 and 3,347 aligned rNMP sites for nuclear and mitochondrial, respectively).
Figure 5B:
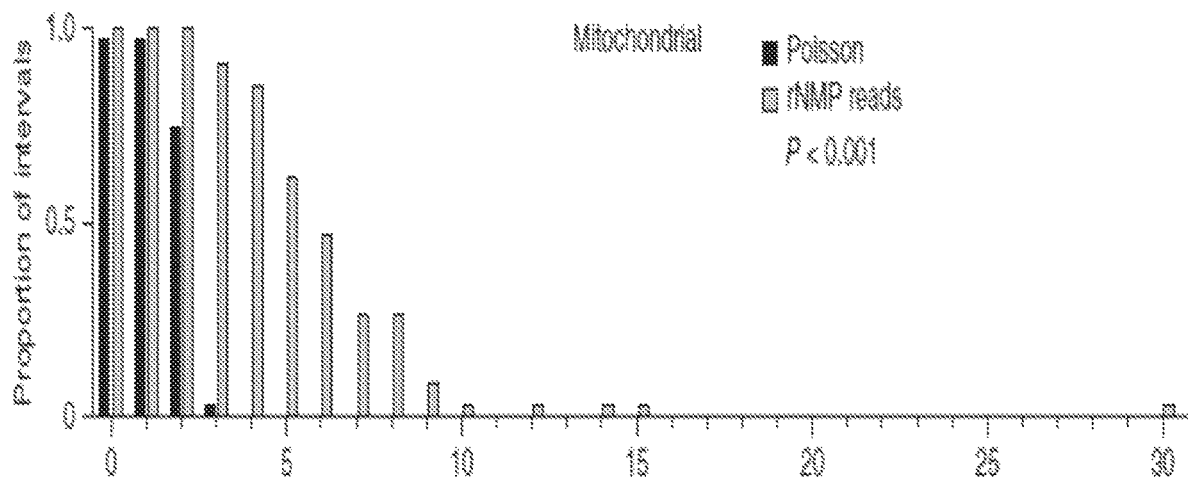
Figure 6:
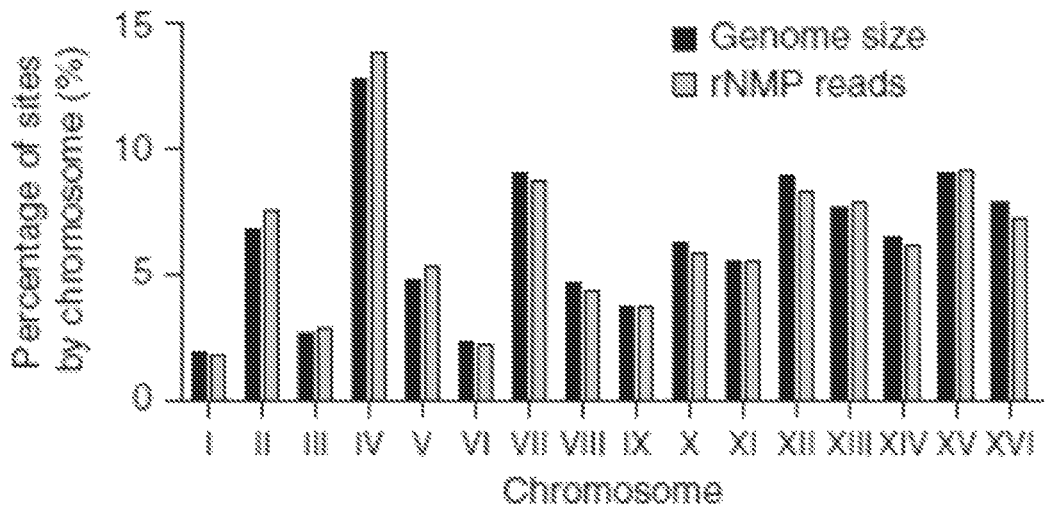
FIG. 6 shows a graph demonstrating the chromosomal distribution of rNMPs compared to the size of each nuclear chromosome.

A ribose-seq library prepared from rnh201Δ cells (KK-100) was sequenced to a depth of ~2 million reads, which were mapped to the yeast S. cerevisiae genome, allowing us to define rNMP locations along yeast nuclear and mitochondrial DNA with single-nucleotide resolution. This analysis uncovered widespread rNMP incorporation with a coverage of 0.449 and 19.5 rNMP reads per kilobase in the nuclear and mitochondrial genome, respectively (FIG. 32 and FIG. 4). While broadly scattered, the rNMP sites in the nuclear and mitochondrial DNA were not randomly distributed (FIGS. 5A-5B). We found no major Watson/Crick strand bias in ribonucleotide distribution throughout the genome (FIG. 4), and the number of rNMPs identified per nuclear chromosome was proportional to chromosome size (FIG. 6).

Figure 7:
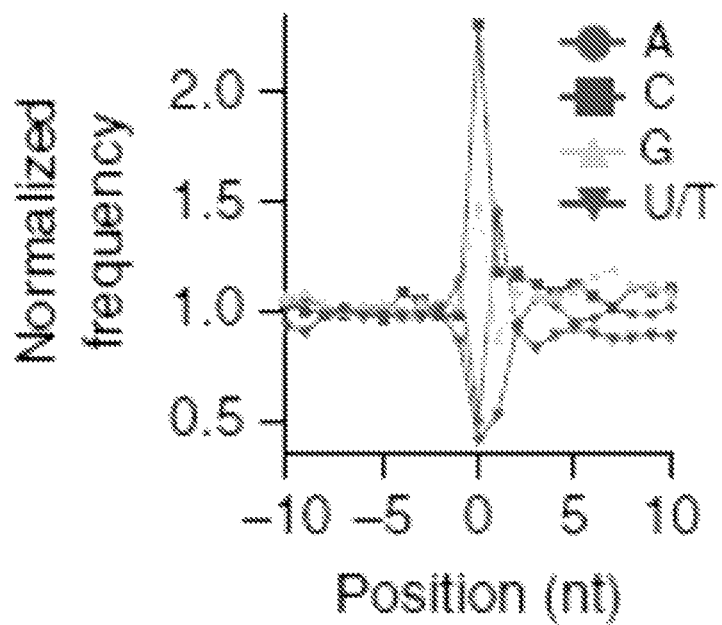
FIG. 7 shows a graph demonstrating the normalized nucleotide frequencies for the nuclear genome relative to mapped positions of sequences from the ribose-seq library of rnh201Δ (KK-100) cells. Position 0 is the rNMP.
Figure 8:
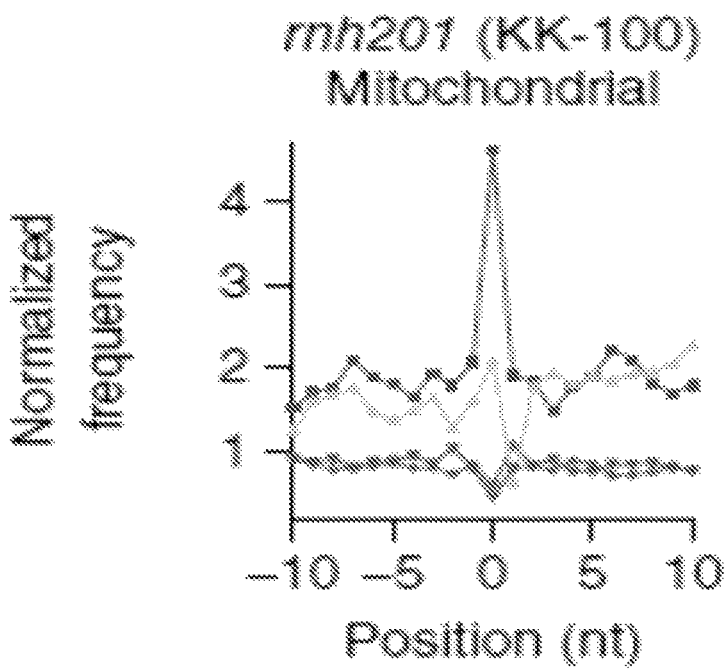
FIG. 8 shows a graph demonstrating the normalized nucleotide frequencies for the mitochondrial genome relative to mapped positions of sequences from the ribose-seq library of rnh201Δ (KK-100) cells. Position 0 is the rNMP.

The identity and relative frequencies of incorporated rNMPs was determined, the reverse complement of the 5' base of each read, as well as flanking bases for the nuclear and mitochondrial genomes in rnh201Δ cells. At the site of rNMP incorporation, we found that rCMP and rGMP were incorporated more frequently than expected from the G+C content, while rAMP and in particular rUMP were incorporated less frequently than expected from the A+T content in both nuclear and mitochondrial genomes, indicating a strong bias in the rNMP spectrum considering the (A+T)-rich nature of these genomes in yeast (62% and 83%, respectively) (FIGS. 7-8). Examining the absolute composition of the genomic rNMPs, we found 44% rC, 28.1% rG, 15.4% rA and 12.5% rU in the nuclear genome and 36.8% rC, 25.6% rA, 19% rG and 18.7% rU in the mitochondrial genome (FIG. 33). The difference in the base composition between nuclear and mitochondrial rNMPs is likely to be due to the higher A+T content of the mitochondrial genome.

Figure 25:
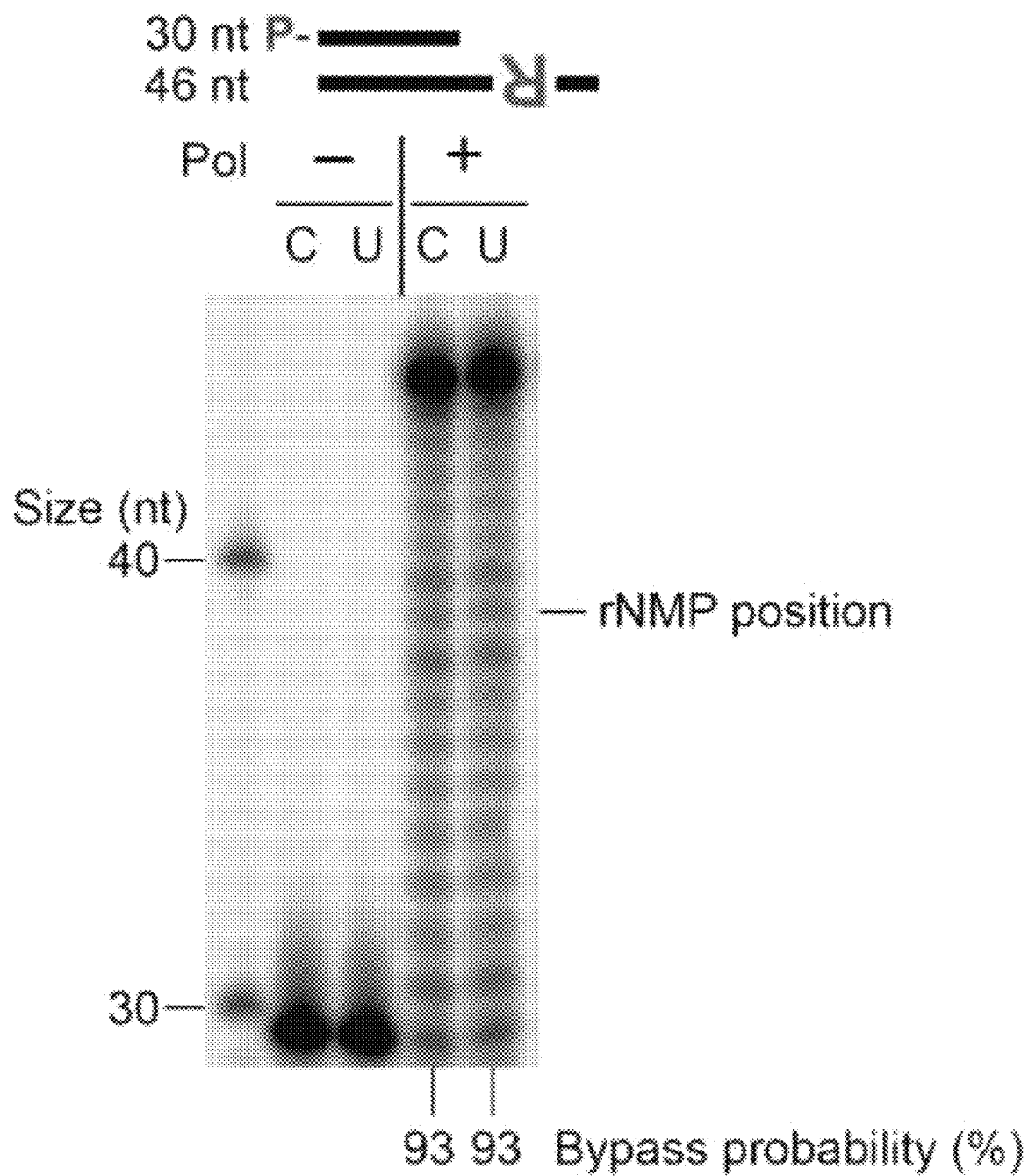
FIG. 25 shows a schematic and an image demonstrating bypass of a single rNMP by Phusion DNA polymerase. 5'-radiolabeled 30-nt primer, ByPrim (FIG. 37), was annealed to the 46-nt template oligo containing either rCMP (ByTemp.rC) or rUMP (ByTemp.rU) in the 8th position. 100 nM of annealed substrate was incubated with 0.2 units of Phusion High-Fidelity DNA Polymerase (NEB) and 2 mM dNTPs in appropriate buffer (see Methods) for 30 sec at 72° C. The reactions were quenched and analyzed by urea-PAGE. Median bypass probabilities from four independent reactions are shown. See FIG. 34 for more statistics. First left lane, ss DNA ladder. The primer extension assay showed no significant difference between bypass efficiency over rUMP and rCMP by Phusion DNA polymerase (FIG. 34).
Figure 26A:
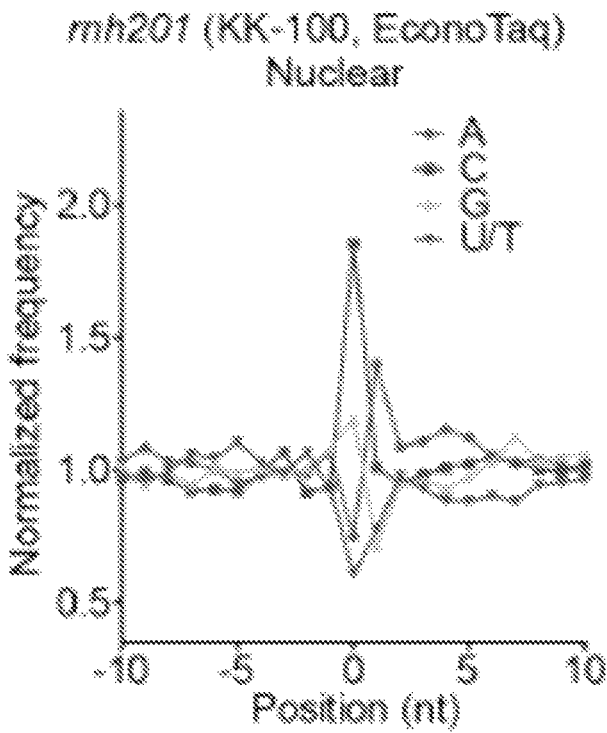
FIGS. 26A-26N shows graphs demonstrating the normalized frequency of nucleotides surrounding the rNMP sites. Normalized frequency of nucleotides relative to (FIG. 26A) nuclear and (FIG. 26B) mitochondrial mapped positions of sequences from ribose-seq library, PCR-amplified with EconoTaq DNA Polymerase (Lucigen), of genomic DNA from S. cerevisiae rnh201Δ (KK-100) cells. Position 0 corresponds to the rNMP. Negative and positive numbers (from -10 to -1 and 1 to 10) correspond to upstream and downstream positions from the rNMP, respectively. Frequencies were normalized to either nuclear or mitochondrial genomic mononucleotide frequencies. Normalized frequency of nucleotides relative to (FIG. 26C) nuclear and (FIG. 26D) mitochondrial mapped positions of sequences from ribose-seq library of genomic DNA from S. cerevisiae rnh201Δ (KK-30) cells. Normalized frequency of nucleotides relative to (FIG. 26E) nuclear and (FIG. 26F) mitochondrial mapped positions of sequences from ribose-seq library of genomic DNA from S. cerevisiae rnh1Δ rnh201Δ (KK-174) cells. Normalized frequency of nucleotides relative to (FIG. 26G) nuclear and (FIG. 26H) mitochondrial mapped positions of sequences from ribose-seq library of genomic DNA from S. cerevisiae rnh1Δ rnh201Δ (KK-125) cells. Normalized frequency of nucleotides relative to (FIG. 26I) nuclear and (FIG. 26J) mitochondrial mapped positions of sequences from ribose-seq library of genomic DNA from S. cerevisiae rnh1Δ rnh201Δ ung1Δ (KK-164) cells. Normalized frequency of nucleotides relative to (FIG. 26K) nuclear and (FIG. 26L) mitochondrial mapped positions of sequences from ribose-seq library of genomic DNA from S. cerevisiae pol2-M644G rnh201Δ (KK-170) cells. Normalized frequency of nucleotides relative to (FIG. 26M) nuclear and (FIG. 26N) mitochondrial mapped positions of sequences from ribose-seq library of genomic DNA from S. cerevisiae pol3-5DV rnh201Δ (KK-120) cells.
Figure 26B:
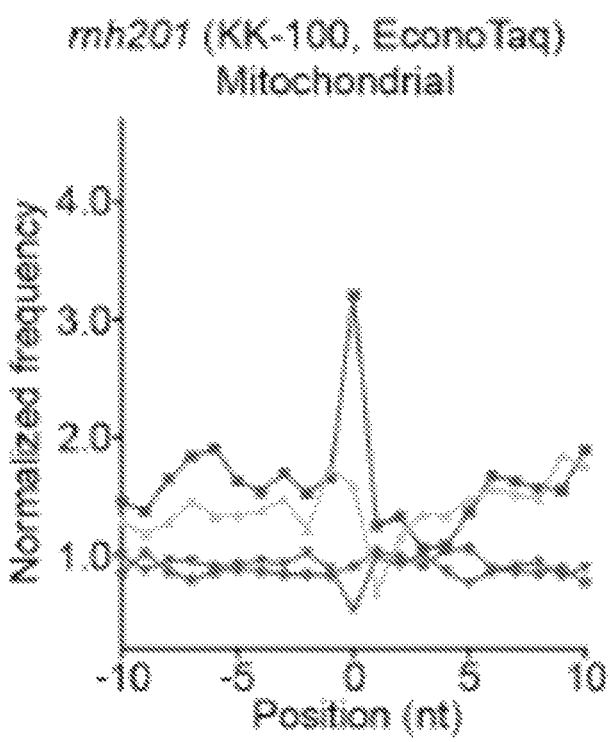
Figure 26C:
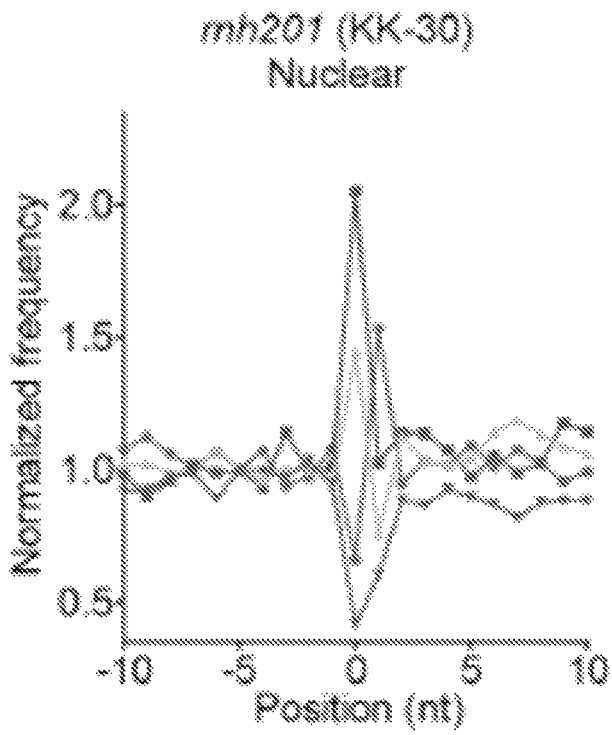
Figure 26D:
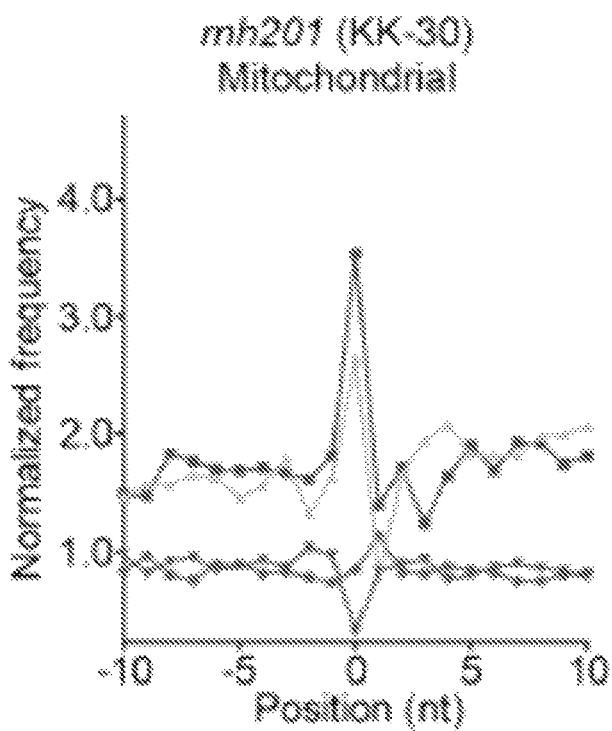
Figure 26E:
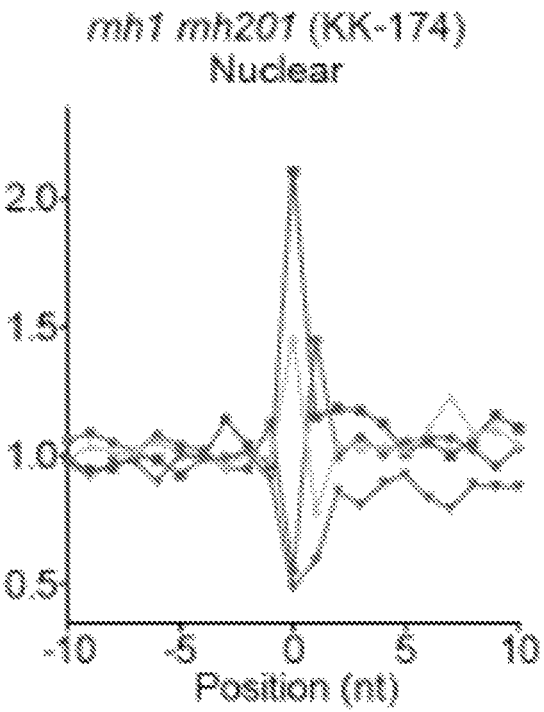
Figure 26F:
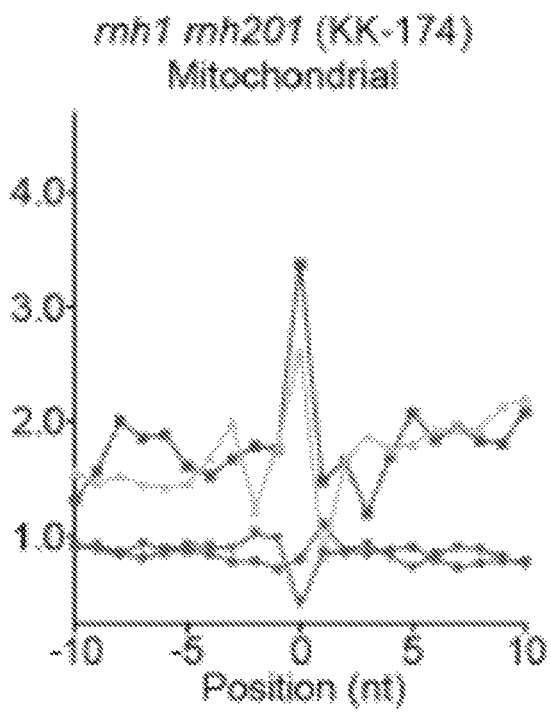
Figure 26G:
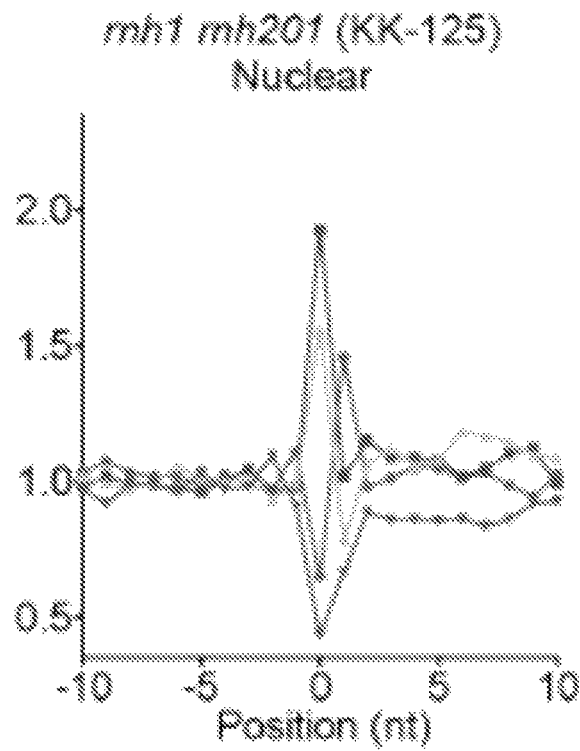
Figure 26H:
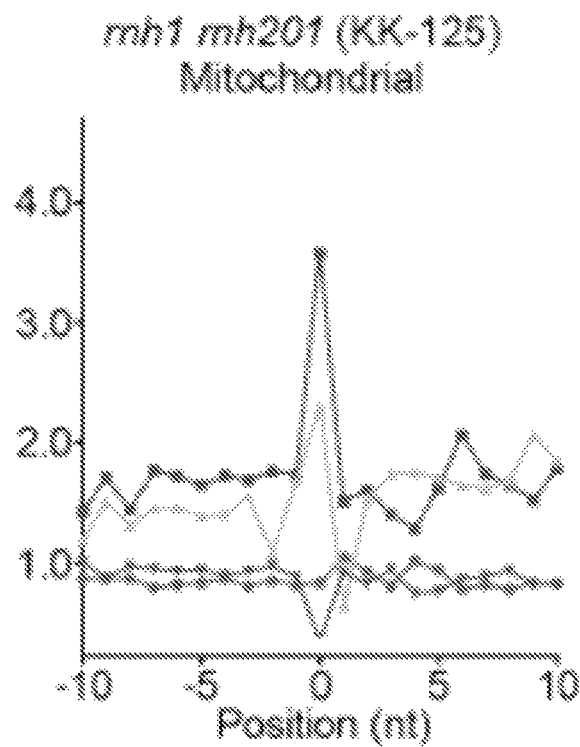
Figure 26I:
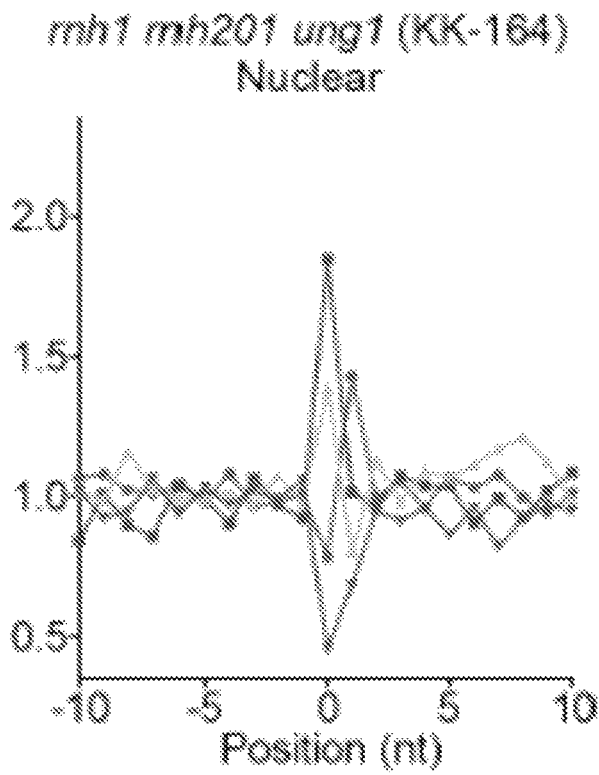
Figure 26J:
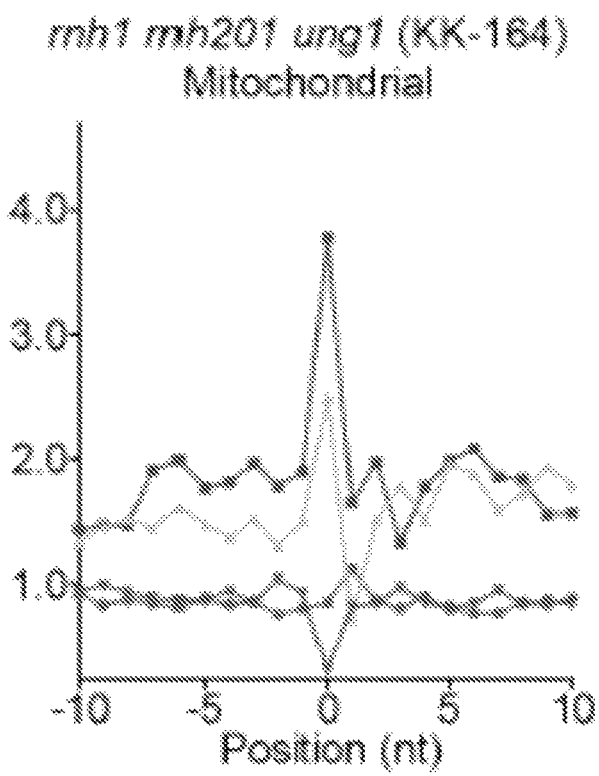
Figure 26K:
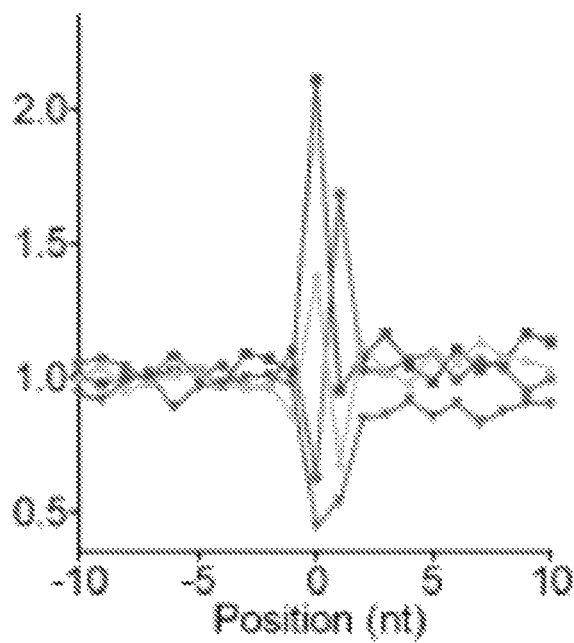
Figure 26L:
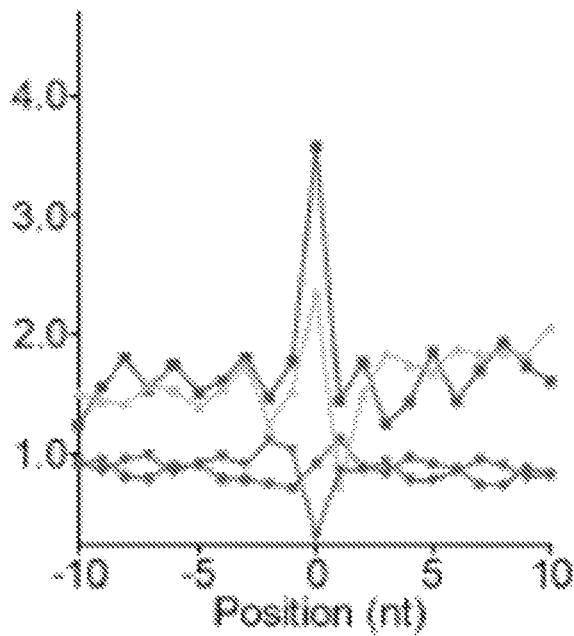
Figure 26M:
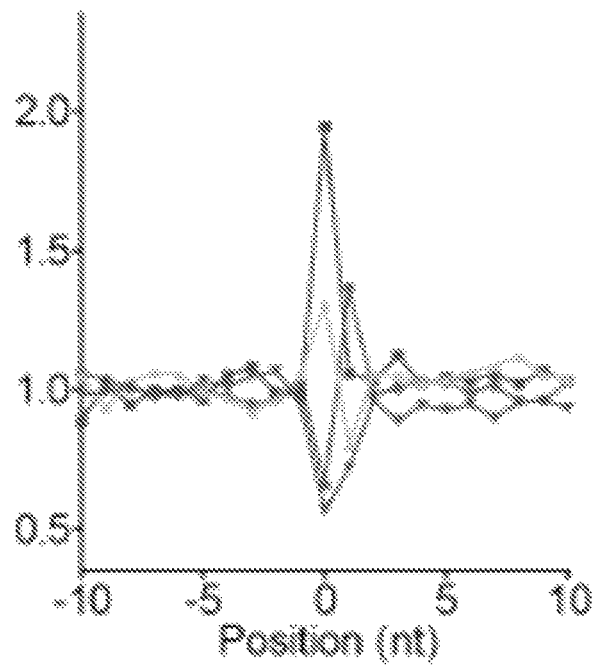
Figure 26N:
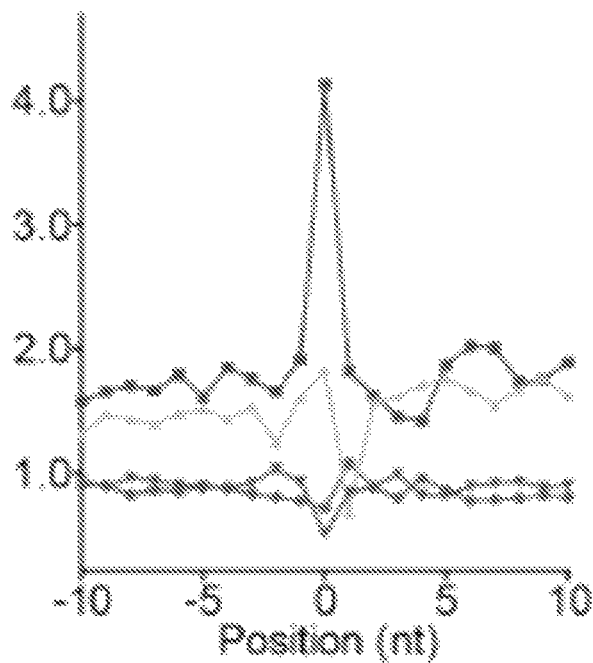
Figure 27A:
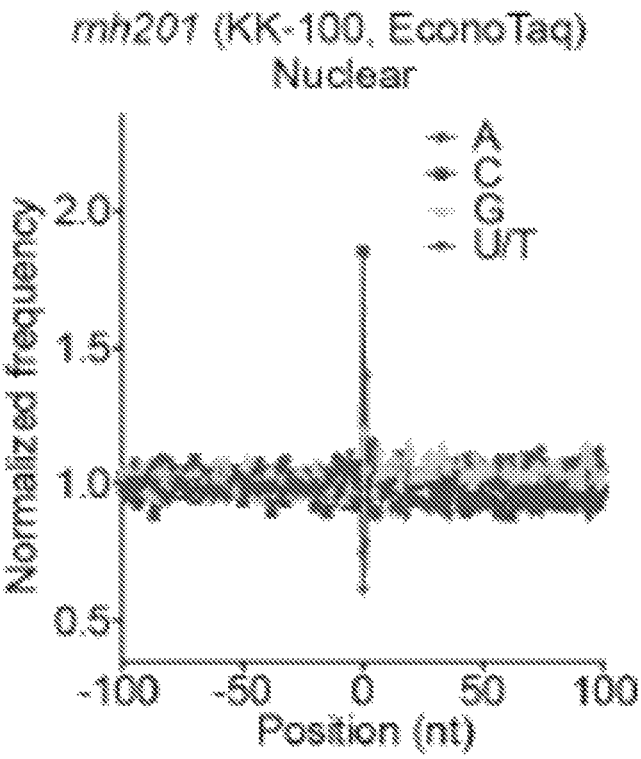
FIGS. 27A-27P show graphs demonstrating zoom-outs of normalized frequency of nucleotides surrounding the rNMP sites. Normalized frequency of nucleotides relative to (FIG. 27A) nuclear and (FIG. 27B) mitochondrial mapped positions of sequences from ribose-seq library, PCR-amplified with EconoTaq DNA Polymerase (Lucigen), of genomic DNA from *S. cerevisiae* rnh201Δ (KK-100) cells. Position 0 corresponds to the rNMP. Negative and positive numbers (from −100 to −1 and 1 to 100) correspond to upstream and downstream positions from the rNMP, respectively. Frequencies were normalized to either nuclear or mitochondrial genomic mononucleotide frequencies. Normalized frequency of nucleotides relative to (FIG. 27C) nuclear and (FIG. 27D) mitochondrial mapped positions of sequences from ribose-seq library of genomic DNA from *S. cerevisiae* rnh201Δ (KK-30) cells. Normalized frequency of nucleotides relative to (FIG. 27E) nuclear and (FIG. 27F) mitochondrial mapped positions of sequences from ribose-seq library of genomic DNA from *S. cerevisiae* rnh1Δ rnh201Δ (KK-174) cells. Normalized frequency of nucleotides relative to (FIG. 27G) nuclear and (FIG. 27H) mitochondrial mapped positions of sequences from ribose-seq library of genomic DNA from *S. cerevisiae* rnh1Δ rnh201Δ (KK-125) cells. Normalized frequency of nucleotides relative to (FIG. 27I) nuclear and (FIG. 27J) mitochondrial mapped positions of sequences from ribose-seq library of genomic DNA from *S. cerevisiae* rnh1Δ rnh201Δ ung1Δ (KK-164) cells. Normalized frequency of nucleotides relative to (FIG. 27K) nuclear and (FIG. 27L) mitochondrial mapped positions of sequences from ribose-seq library of genomic DNA from *S. cerevisiae* pol2-M644G rnh201Δ (KK-170) cells. Normalized frequency of nucleotides relative to (FIG. 27M) nuclear and (FIG. 27N) mitochondrial mapped positions of sequences from ribose-seq library of genomic DNA from *S. cerevisiae* pol2-4 rnh201Δ (KK-107) cells. Normalized frequency of nucleotides relative to (FIG. 27O) nuclear and (FIG. 27P) mitochondrial mapped positions of sequences from ribose-seq library of genomic DNA from *S. cerevisiae* pol3-5DV rnh201Δ (KK-120) cells.
Figure 27B:
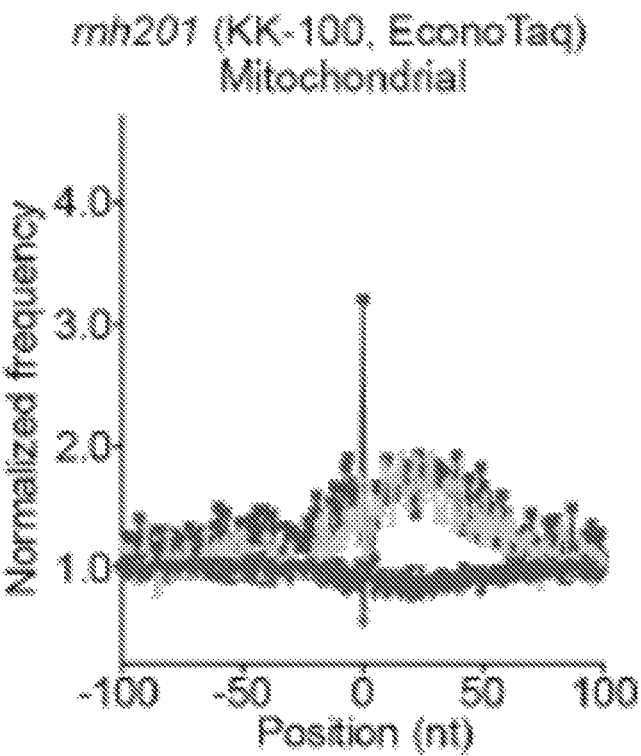
Figure 27C:
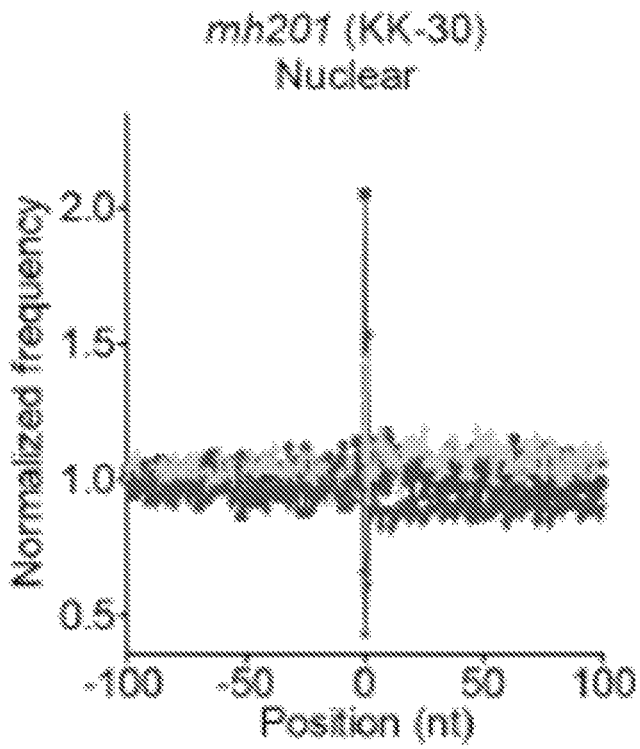
Figure 27D:
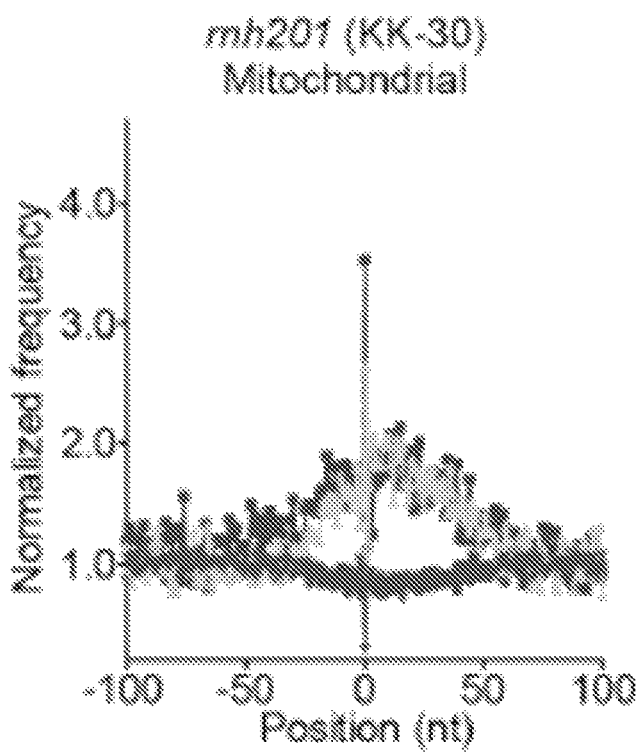
Figure 27E:
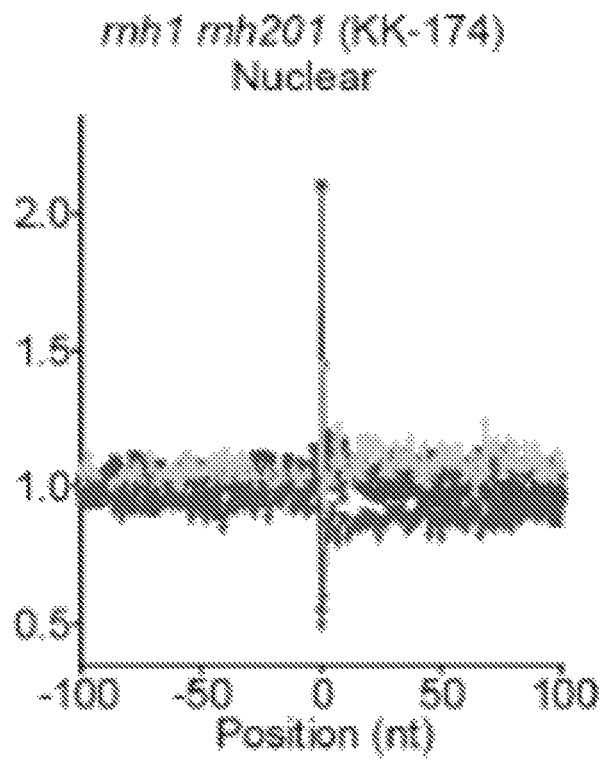
Figure 27F:
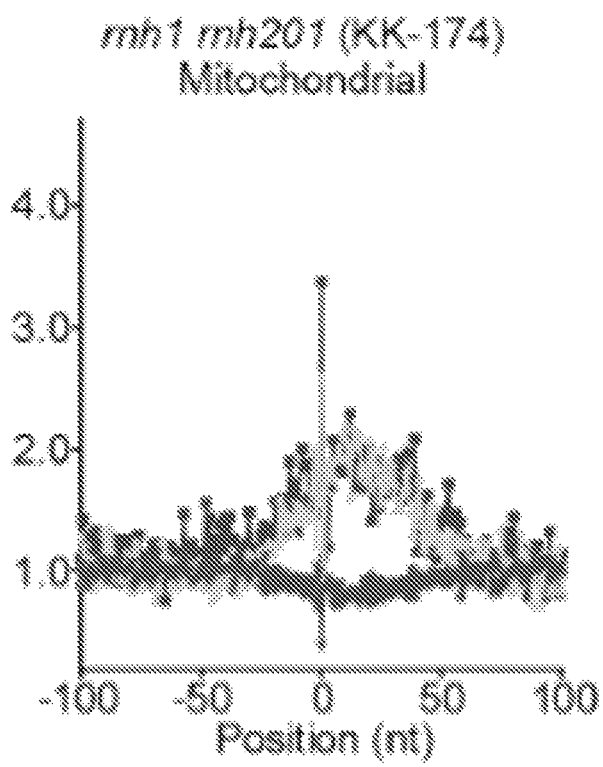
Figure 27G:
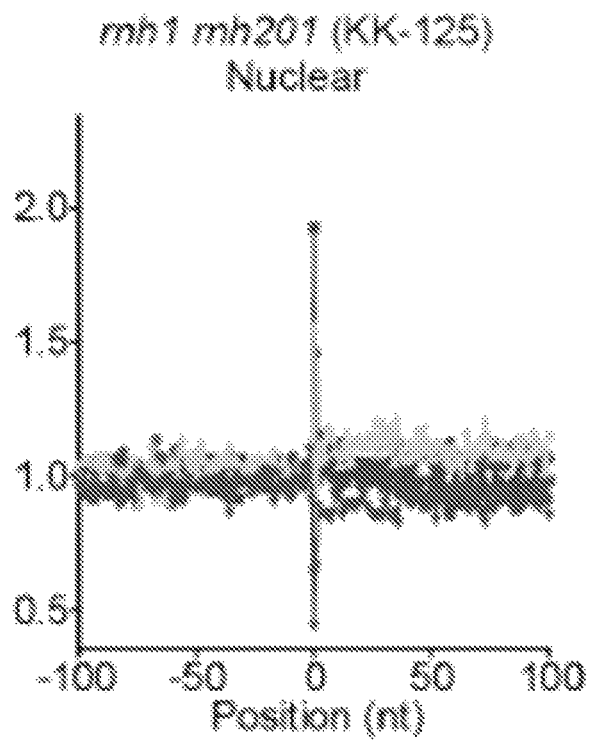
Figure 27H:
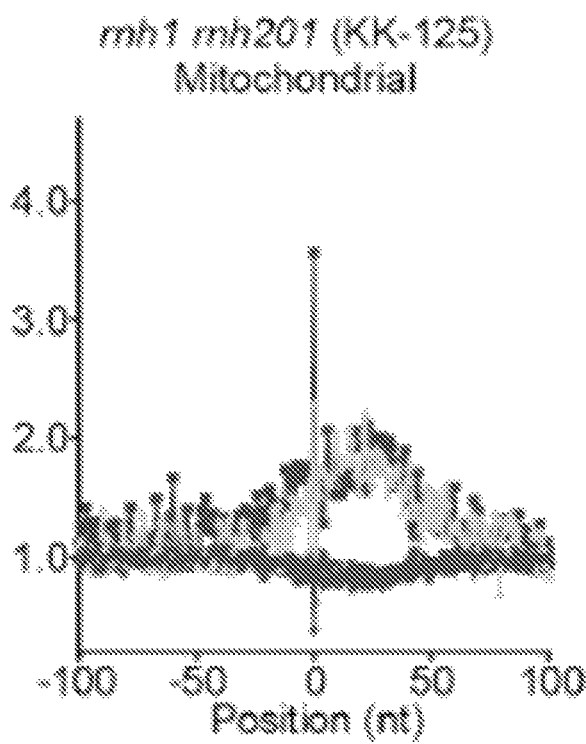
Figure 27I:
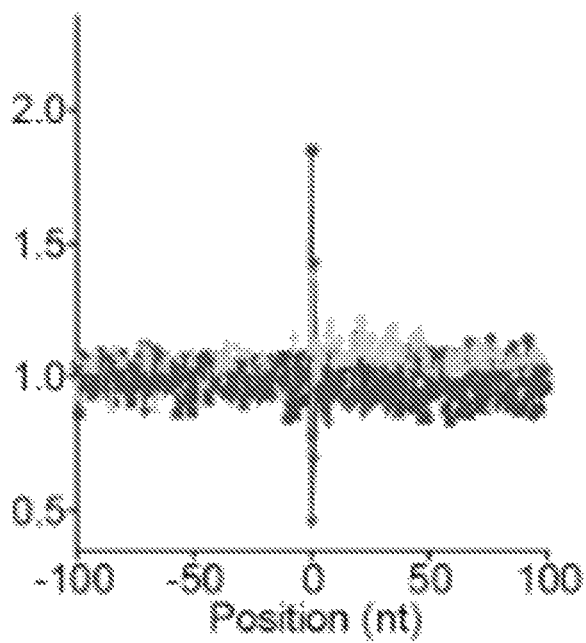
Figure 27J:
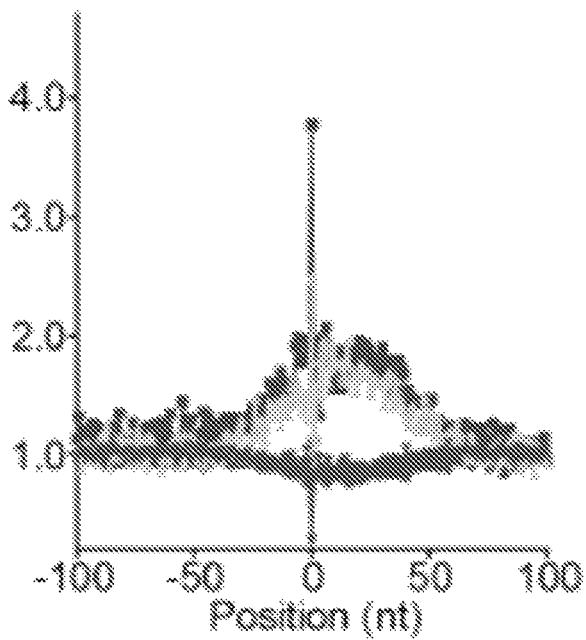
Figure 27K:
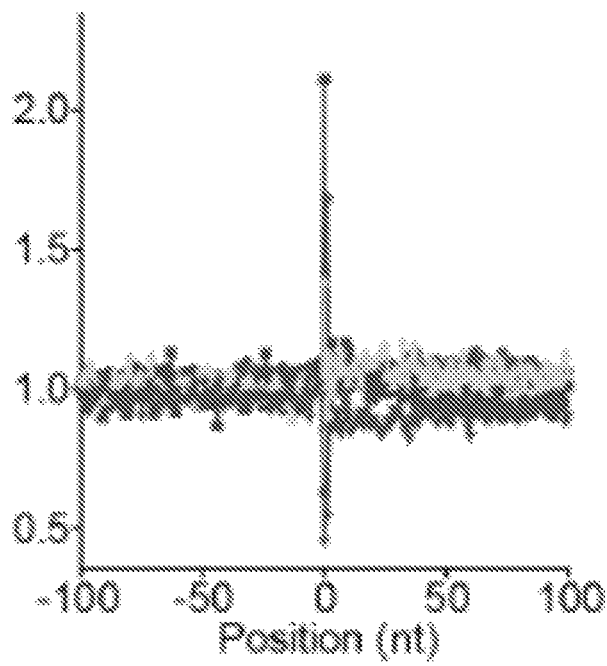
Figure 27L:
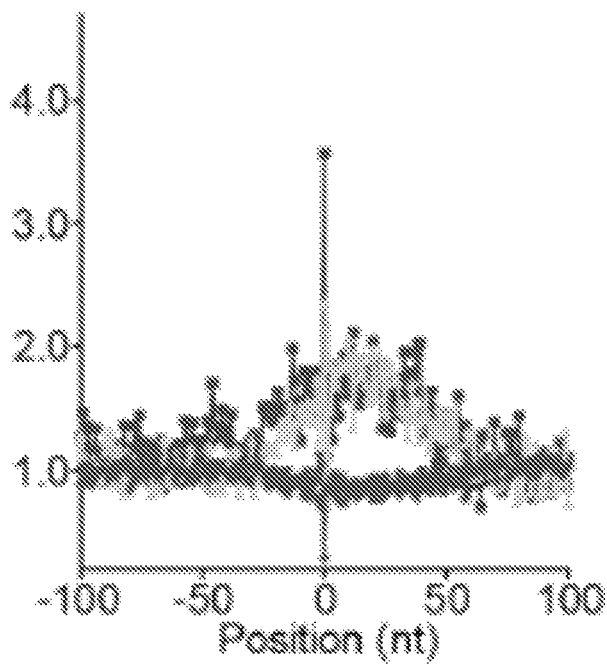
Figure 27M:
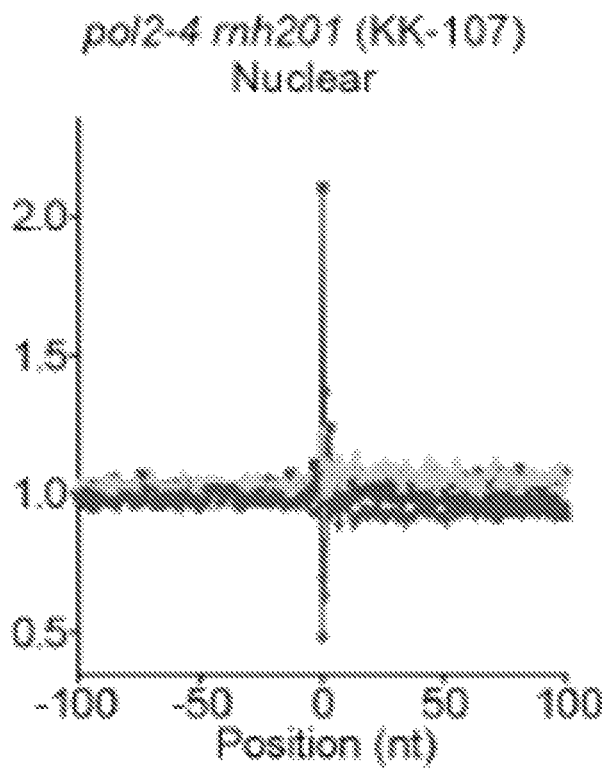
Figure 27N:
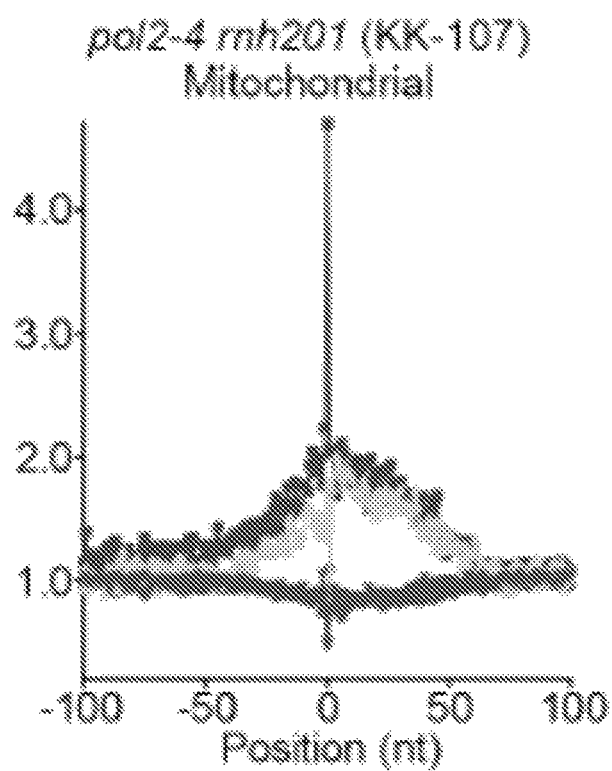
Figure 27O:
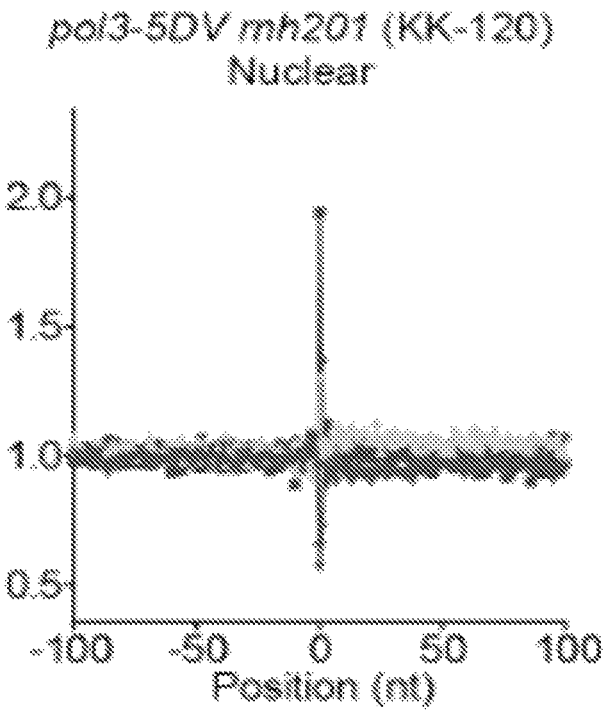
Figure 27P:
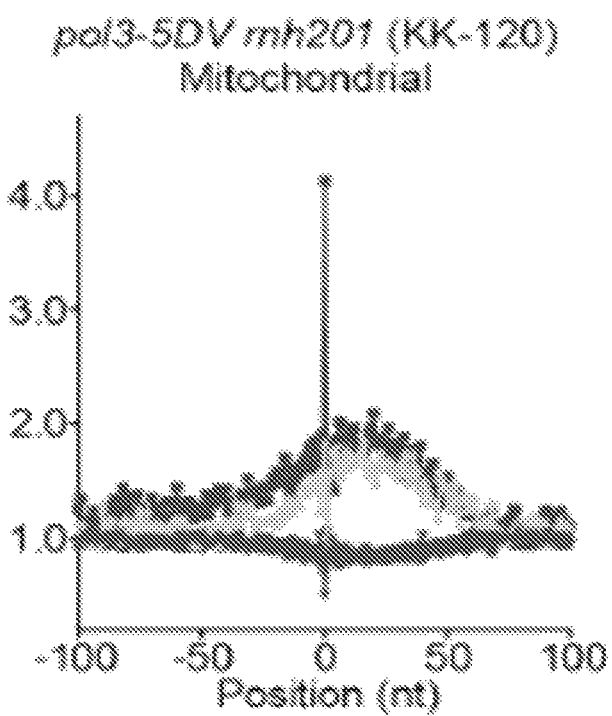

The high level of rCMP and low level of rUMP observed both for nuclear and mitochondrial DNA in the rnh201Δ library are not attributable to differential bypass by the Pfu-based DNA polymerase used for PCR (FIG. 25 and FIG. 34), as we also observed similar rNMP patterns using a Taq-based DNA polymerase (FIGS. 26A-26B and FIGS. 27A-27B). Similarly, the nucleotide frequency derived from a ribose-seq library constructed from another rnh201Δ strain (KK-30, FIG. 31) was comparable to that obtained from strain KK-100 both for nuclear and mitochondrial sites (FIGS. 26C-26D and FIGS. 27C-27D). Additional deletion of the gene encoding RNase H1 (rnh1Δ), generating rnh1Δ rnh201Δ strains KK-174 and KK-125, did not affect the nucleotide frequency of rNMP incorporation (FIGS. 26E-26H and FIGS. 27E-27H). While some variation in the absolute rNMP counts were found among these different libraries in the mitochondrial DNA (FIG. 33), the high level of rCMP and low level of rUMP remained constant, as well as a preferred rNMP incorporation in (G+C)-rich regions of the mitochondrial DNA. These data support a model in which rNMPs in yeast genomic DNA are present as single, di- or tri-nucleotides, which are not substrates of RNase H1 (ref. 14), and indicate that RNase H1 has only a minor impact on the distribution of genomic rNMPs.

To test whether the low frequency of rUMP incorporation was a consequence of removal by the uracil N-glycosylase, Ung1, we deleted the UNG1 gene in the RNases H-defective background (rnh201Δ rnh1Δ ung1Δ, strain KK-164) and mapped rNMP sites in these cells. Ung1 repairs dUMP from nuclear and mitochondrial DNA27. Although Ung1 does not act on uracil in RNA (for example, ribosomal RNA)[28], it is not known whether Ung1 can act on rUMP embedded in a DNA duplex. We found that the level of rUMP incorporation in the chromosomal and mitochondrial genomes of an rnh1Δ rnh201Δ ung1Δ strain was similar to that in an rnh1Δ rnh201Δ strain, demonstrating that Ung1 does not target rUMP in DNA (FIGS. 26I-26J, FIGS. 27I-27J, and FIG. 33).

Figure 28B:
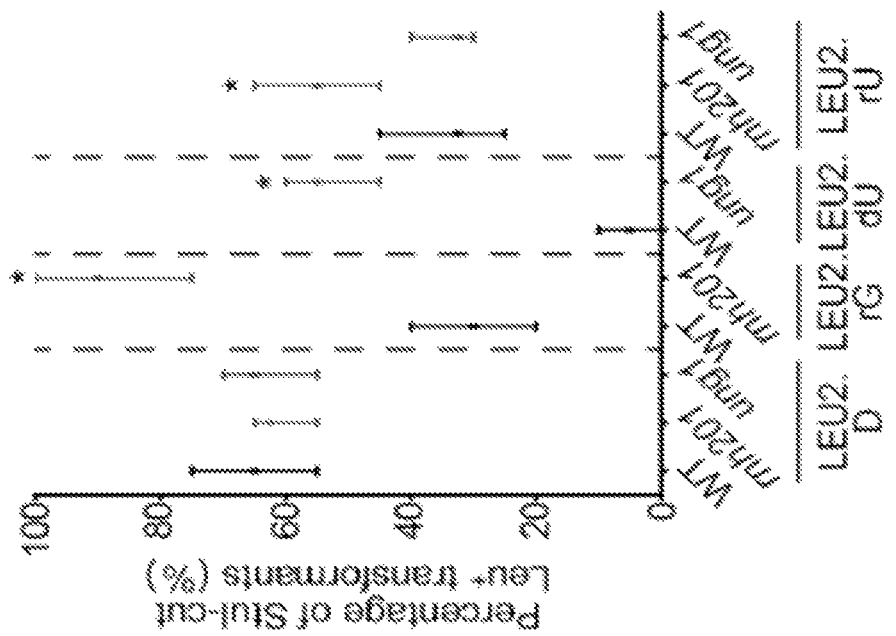
FIGS. 28A-28B demonstrate targeting of rGMP and rUMP by RNase H2 and uracil DNA N-glycosylase during DSB repair in *S. cerevisiae* cells.
Figure 28A:
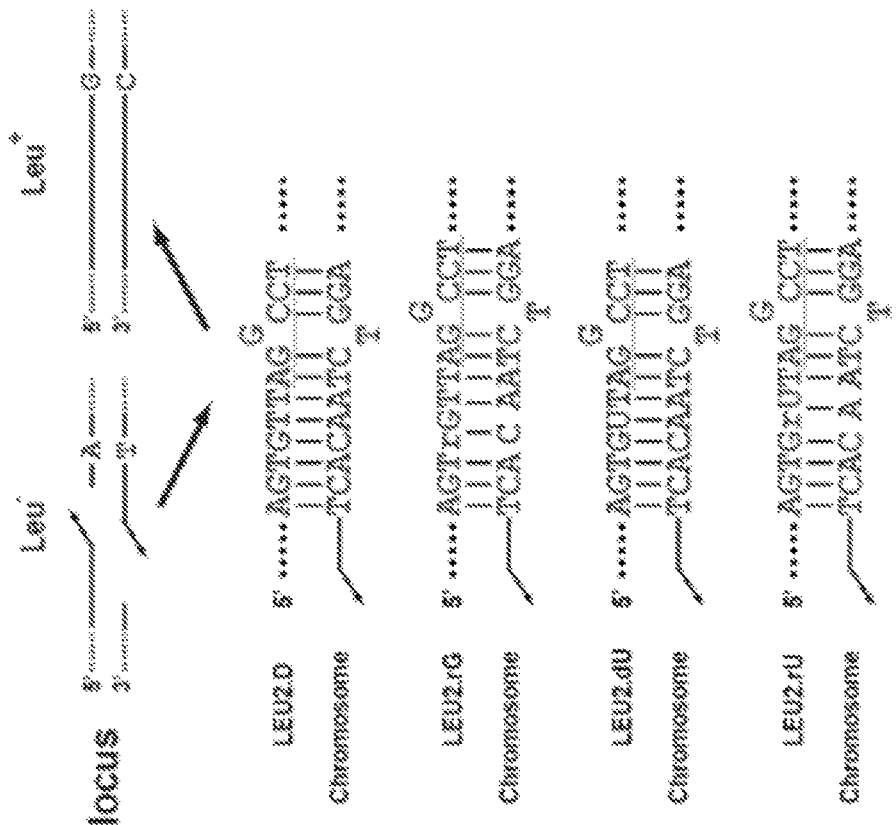
Figure 29A:
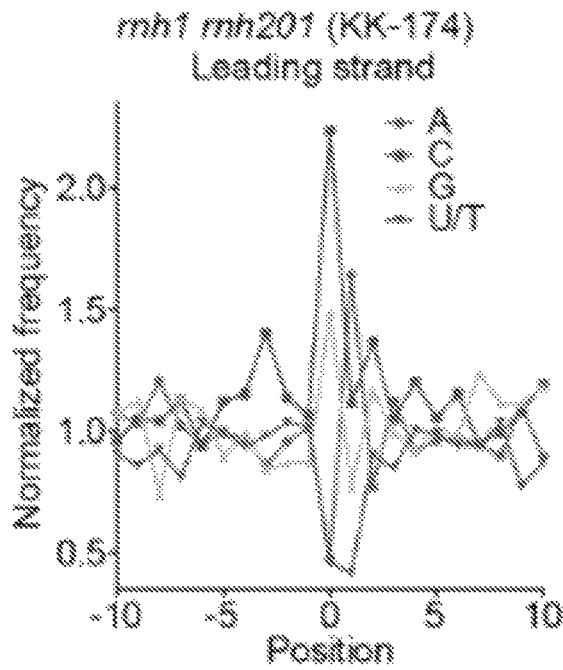
FIGS. 29A-29D show graphs demonstrating the normalized frequency of nucleotides surrounding the rNMP sites on leading and lagging strands. Normalized frequency of nucleotides relative to mapped positions of sequences in (a) leading and (b) lagging strands from ribose-seq library of genomic DNA from *S. cerevisiae* rnh1Δ rnh201Δ (KK-174) cells. Position 0 corresponds to the rNMP. Negative and positive numbers (from −10 to −1 and 1 to 10) correspond to upstream and downstream positions from the rNMP, respectively. ARSs with Trep of no longer than 25 min were selected with flanking size of 10 kb. Frequencies were normalized to genomic mononucleotide frequencies of either leading or lagging strand of the selected ARSs and flanking size. Normalized frequency of nucleotides relative to mapped positions of sequences in (c) leading and (d) lagging strands from ribose-seq library of genomic DNA from *S. cerevisiae* pol3-5DV rnh201Δ (KK-120) cells.
Figure 29B:
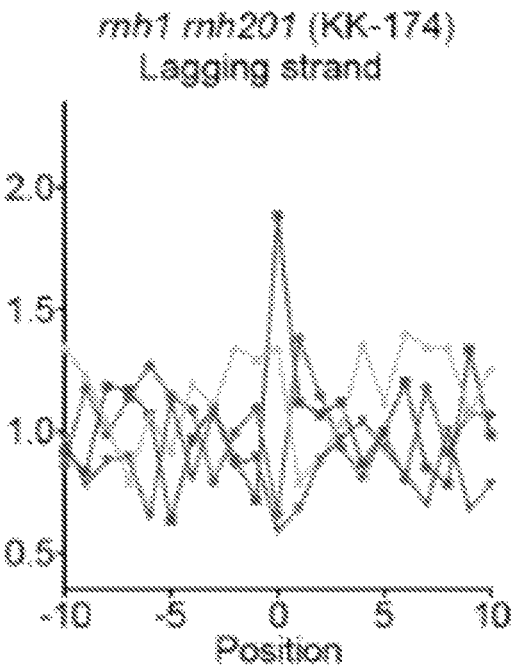
Figure 29C:
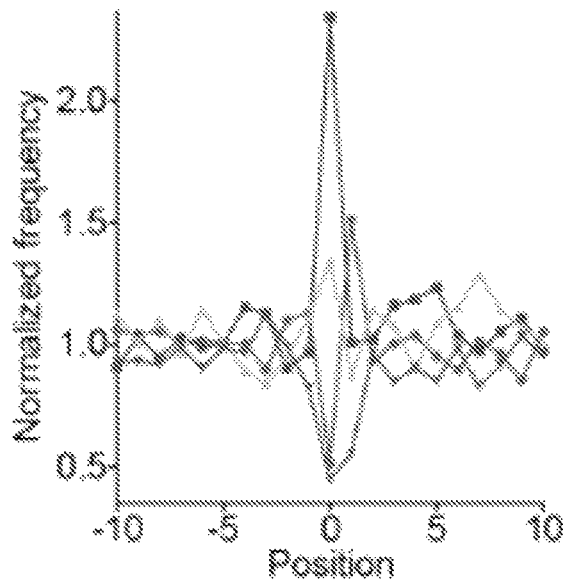
Figure 29D:
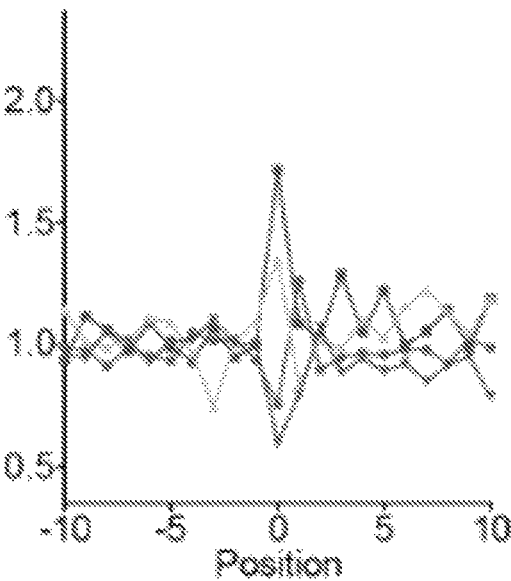

Using a yeast assay of chromosomal double-strand break repair (DSB), in which DNA oligonucleotides carrying embedded rGMP, rUMP or deoxyribonucleotides only are templates for DSB repair (FIG. 28A), we demonstrated that Ung1 targets uracil from a dUMP but not an rUMP embedded in DNA, while RNase H2 targets only rNMPs (rGMP and rUMP in this experiment) but not dNMPs (FIG. 28B and FIG. 35). We attribute rNMP incorporation frequencies to the levels of corresponding dNTPs. dCTP and dGTP are typically the least abundant dNTPs7,29 and therefore might be depleted faster than dTTP and dATP, increasing the probability of rCMP and rGMP incorporation over rUMP and rAMP. These results are also consistent with the finding that rCMP and rGMP are the most frequently incorporated rNMPs by DNA polymerases in vitro under physiological dNTP and rNTP concentrations 5,30. This ability of DNA polymerases to incorporate rNMPs into genomic DNA could serve as a mechanism for continuing replication under conditions in which one or more dNTP pools are depleted. In the presence of hydroxyurea, a known ribonucleotide reductase inhibitor, higher levels of rNMPs are found incorporated in genomic DNA14. However, extensive rNMP incorporation would also result in increased breaks and genomic instability.

Pattern of Sequences Flanking rNMPs in *S. cerevisiae* DNA

Downstream of incorporated rNMPs, we found that the +1 position was most frequently dA and least frequently dG both in the nuclear and in the mitochondrial genomes, with 42-52% dA and 6-16% dG among all four deoxyribonucleotides (dA, dC, dG and dT) (FIG. 33). At the +1 position, dT was also frequent (31-40%) in the mitochondrial genome. In mitochondrial DNA, the high level of dA or dT at the +1 position 3' from the rNMP could reflect the high A+T content in the mitochondrial genome. It is also possible that the dA in +1 position influences rNMP incorporation by DNA polymerases. Alternatively, we speculate that dA in the +1 position might stabilize incorporated rNMPs, possibly by affecting base stacking and preventing its repair by mechanisms other than ribonucleotide excision repair. It will be useful to determine the nearest-neighbor thermodynamic parameters for single rNMPs in DNA duplex and, in particular, the stability trend for the base pair 3' of the rNMP sites. We recently showed that single rGMPs embedded in a short DNA duplex have a marked effect on the elastic properties of DNA by altering the DNA structure at the site encompassing the rNMP and the nucleotide 3' to it18. Thus, it is reasonable to think that the +1 position 3' from the rNMP is prone to altered structure, and it is the most critical site for signaling the presence of an rNMP in DNA because it is the closest nucleotide to the 2'-OH group of the rNMP.

Figure 9:
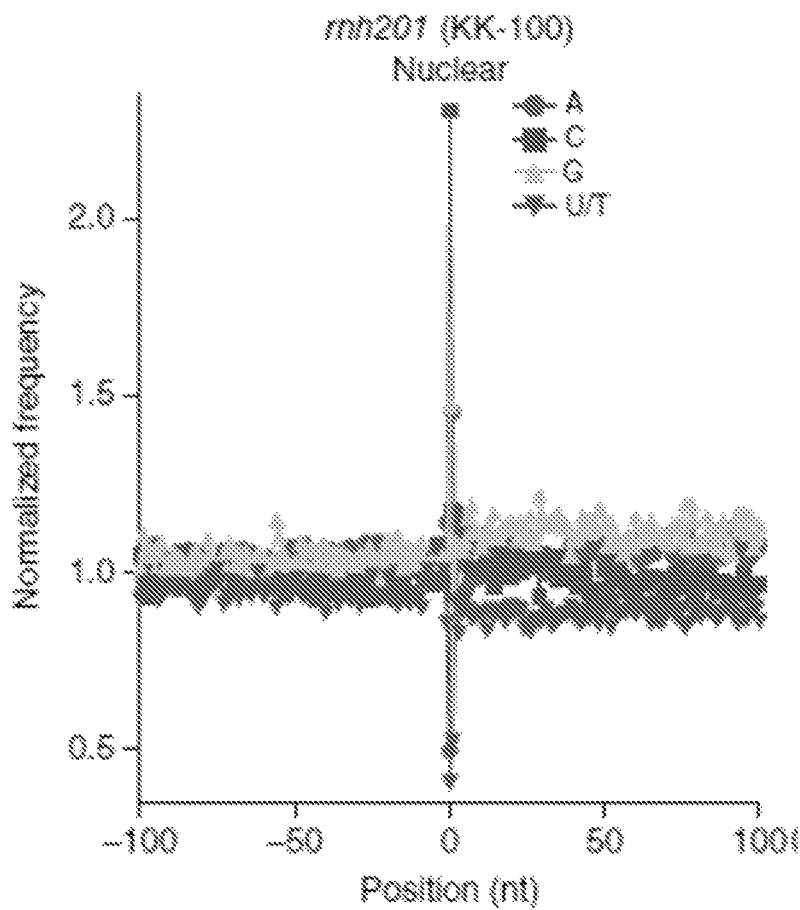
FIG. 9 shows a zoomed-out graph of the data presented in FIG. 7.
Figure 10:
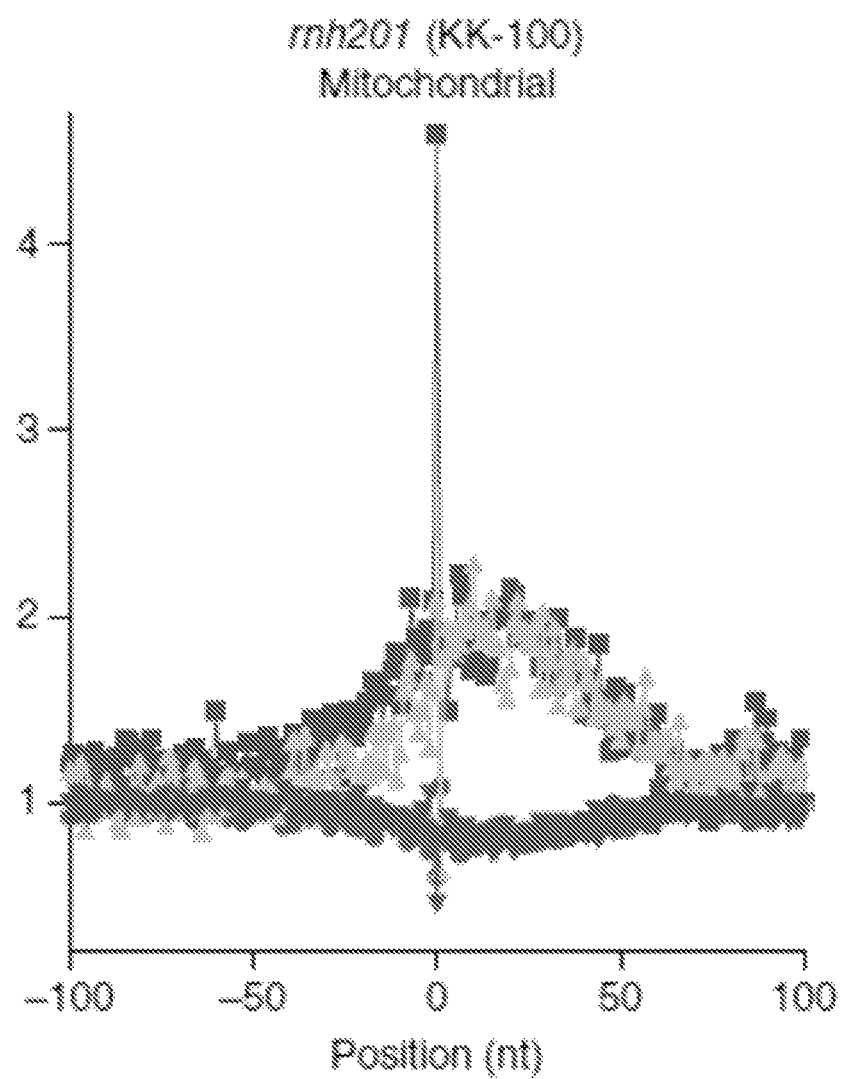
FIG. 10 shows a zoomed-out graph of the data presented in FIG. 8.

Sites of rNMP incorporation were flanked by sequence contexts that differed between the nuclear and mitochondrial DNA genomes. While nucleotide frequencies up- and downstream of rNMP sites in the nuclear genome were largely similar to background frequencies (FIG. 9), rNMP sites in mitochondrial DNA were primarily upstream of (G+C)-rich regions, concentrated in areas in which G+C content was 1.7 to 1.8 times that of the background (FIG. 10). Notably, mitochondrial G+C tracts have been shown to have recombinogenic properties 31, and mitochondrial DNA recombination has been suggested to initiate mitochondrial DNA replication in yeast (ref. 32 and references therein). Thus, it is possible that the presence of rNMP sites in yeast mitochondrial G+C clusters influences these recombination events in mitochondrial DNA. rNMP incorporation by replicative DNA polymerases We next analyzed rNMP incorporation in the newly synthesized leading and lagging strands of yeast nuclear DNA. We selected 154 to 271 early-firing yeast autonomously replicating sequences (ARSs) (activated in the first 25 or 30 min, respectively) on the basis of replication timing 33. We examined the type and abundance of rNMPs incorporated in regions 5 or 10 kb upstream and downstream from selected ARSs. This analysis was conducted using all our ribose-seq libraries, including a library derived from yeast RNase H2-deficient cells containing the low-fidelity Pol ε mutant (rnh201Δ pol2-M644G, FIG. 31). Because yeast Pol ε is mainly responsible for leading strand synthesis during DNA replication, yeast cells containing the pol2-M644G mutation, which leads to increased rNMP incorporation, would be predicted to contain more rNMPs on the newly synthesized leading strand than on the lagging strand[15].

Figure 11:
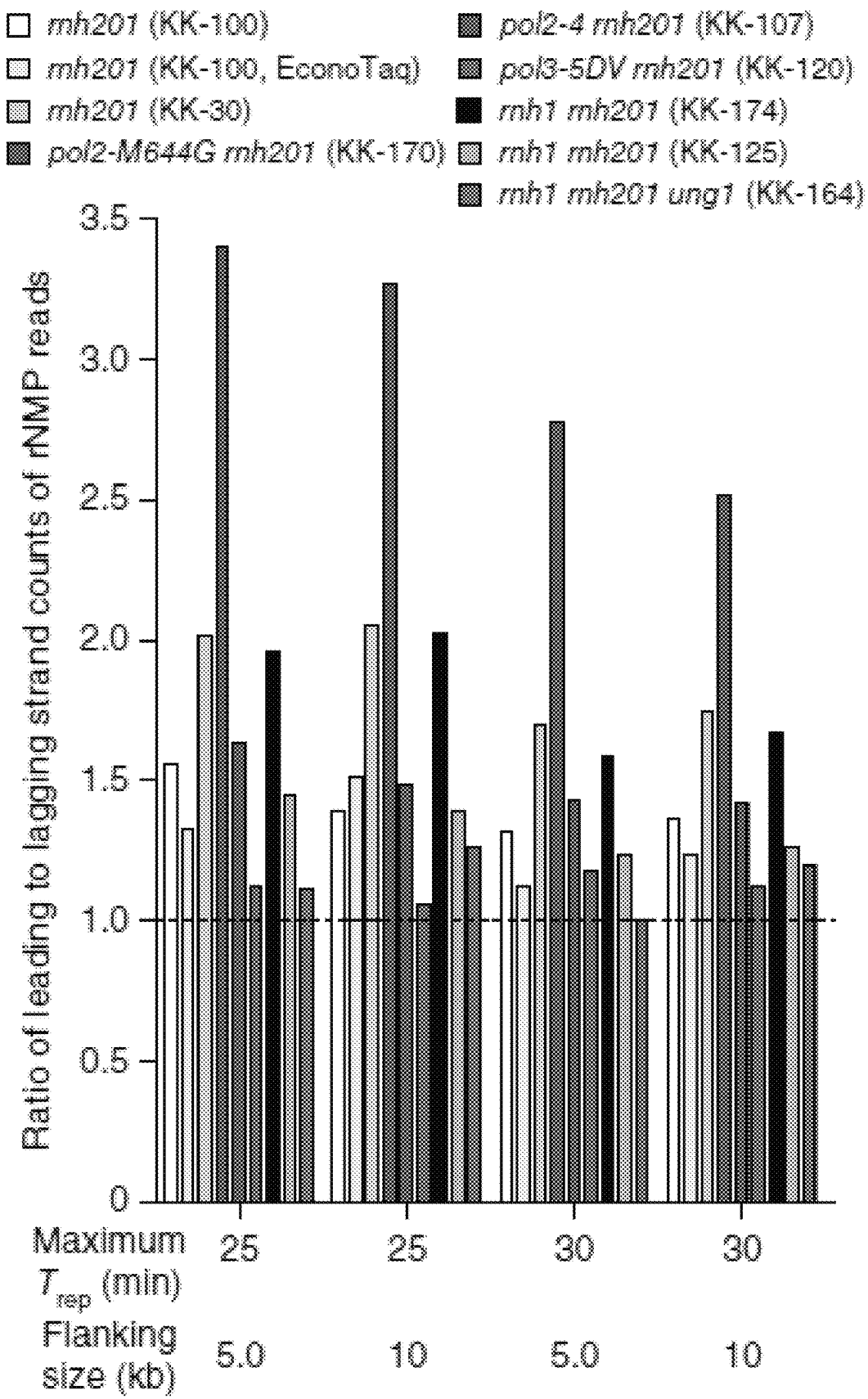
FIG. 11 shows a graph demonstrating the Ratios of rNMPs on newly synthesized leading to lagging strand for all ribose-seq libraries. Early-firing ARSs selected by their replication timing (Trep) were investigated for two different flanking sizes. EconoTaq indicates the library constructed using a Taq-based DNA polymerase. All other libraries were constructed with a Pfu-based DNA polymerase.
Figure 12:
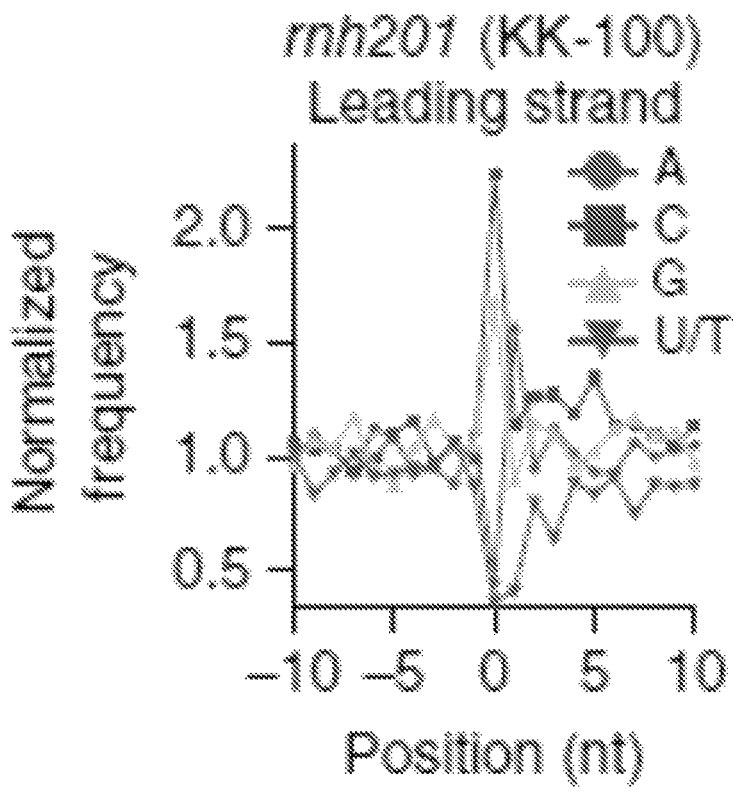
FIG. 12 shows a graph demonstrating normalized nucleotide frequencies relative to mapped sequence positions in leading strands from the rnh201Δ (KK-100) library. ARSs with a Trep of no longer than 25 min were selected with flanking size of 10 kb.
Figure 13:
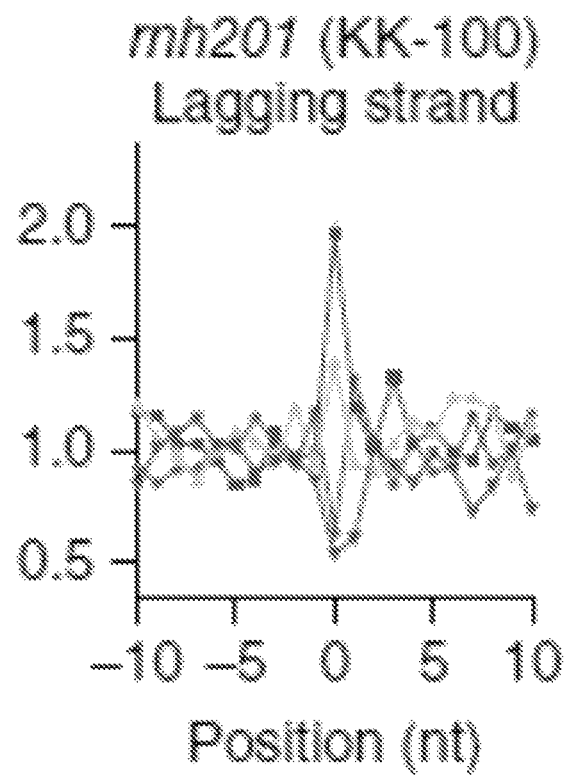
FIG. 13 shows a graph demonstrating normalized nucleotide frequencies relative to mapped sequence positions in lagging strands from the rnh201Δ (KK-100) library. ARSs with a Trep of no longer than 25 min were selected with flanking size of 10 kb.
Figure 14:
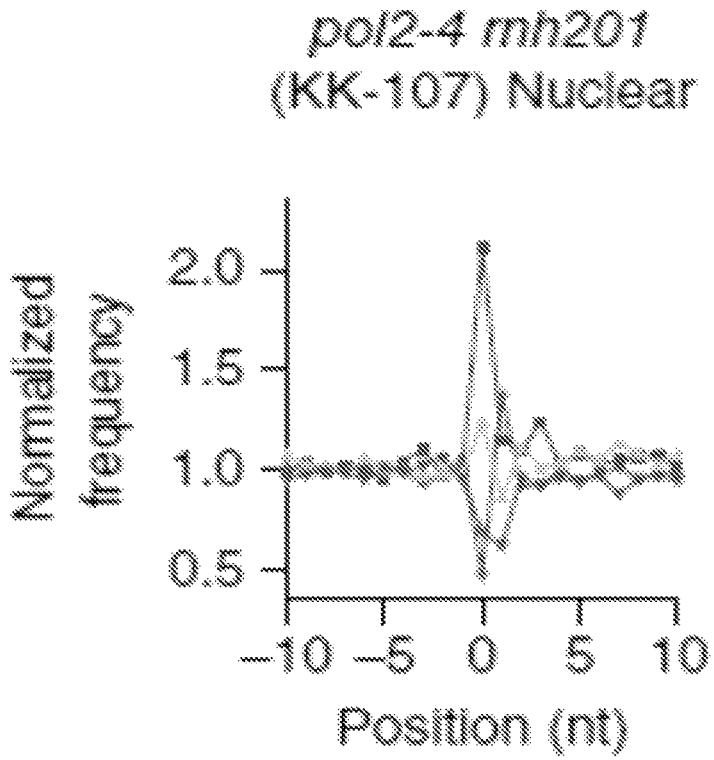
FIG. 14 shows a graph demonstrating the normalized frequencies relative to mapped sequence positions from a pol2-4 rnh201Δ (KK-107) library. Reads were mapped to the nuclear genome.
Figure 15:
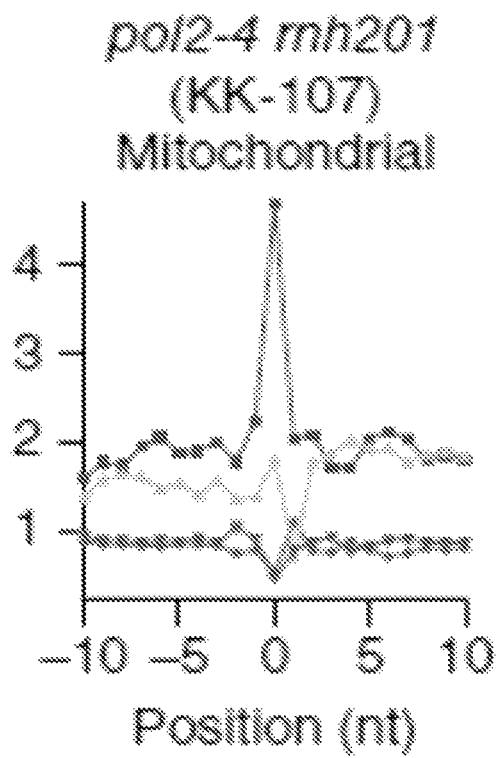
FIG. 15 shows a graph demonstrating the normalized frequencies relative to mapped sequence positions from a pol2-4 rnh201Δ (KK-107) library. Reads were mapped to the mitochondrial genome.
Figure 16:
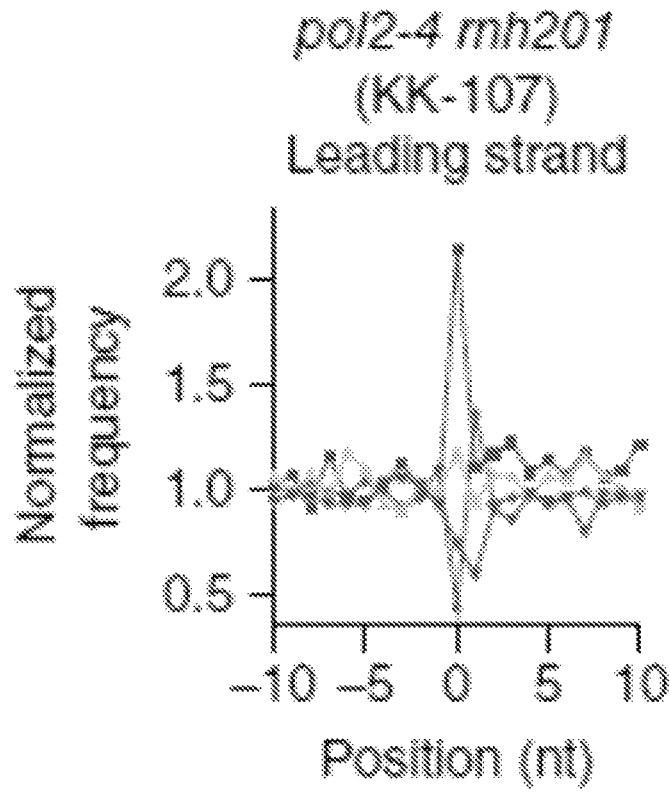
FIG. 16 shows a graph demonstrating the normalized frequencies relative to mapped sequence positions from a pol2-4 rnh201Δ (KK-107) library. Reads were mapped to the leading strand.
Figure 17:
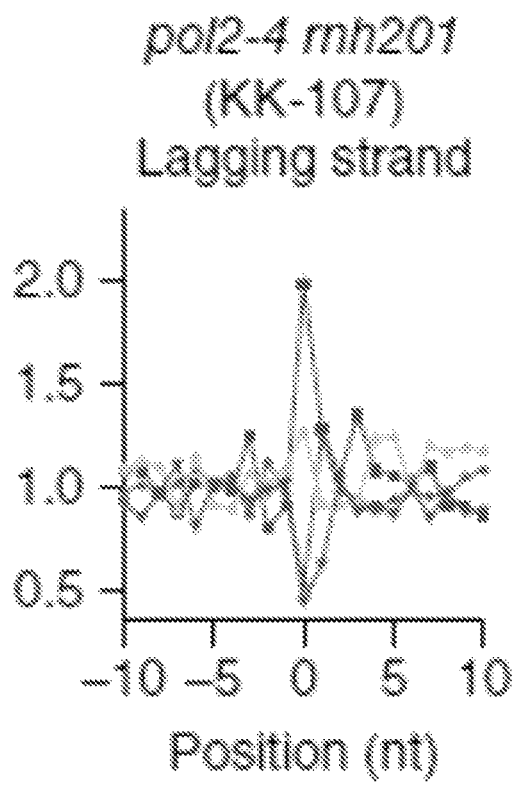
FIG. 17 shows a graph demonstrating the normalized frequencies relative to mapped sequence positions from a pol2-4 rnh201Δ (KK-107) library. Reads were mapped to the lagging strand.

Higher rNMP incorporation on the newly synthesized leading strand of DNA replication (FIG. 11) was observed, consistent with previous observations that the leading strand DNA Pol ε incorporates more rNMPs than the lagging strand Pol δ7. As expected, analysis of rNMPs from rnh201Δ pol2-M644G cells revealed a stronger bias toward rNMP incorporation on the newly synthesized leading strand as compared to that in all other libraries (FIG. 11). However, the increase in rNMP incorporation by the low fidelity Pol ε mutant did not change the overall rNMP spectrum, which had similar patterns of rNMP incorporation to those of libraries derived from wild-type Pol ε strains (FIGS. 26K-26L and FIGS. 27K-27L). Furthermore, it was examined whether the spectrum of rNMP incorporation was different between the newly synthesized leading and the lagging strand upon DNA replication. Cells containing either rnh201Δ or rnh1Δ rnh201Δ mutations had similar spectra of rNMP incorporation on the leading and the lagging strand (FIGS. 12-13 and FIGS. 29A-29B). In contrast, mapping of rNMPs in yeast cells carrying a mutant allele of DNA Pol ε that is defective in proofreading activity (pol2-4, FIG. 31)

showed a lower frequency of rA versus rU in the nuclear but not in the mitochondrial genome (FIGS. 14-15, FIGS. 27M-27N and FIG. 33), and it showed a bias for lower rA than rU only on the newly synthesized leading strand (FIGS. 14-15), which was not observed in libraries derived from wild-type nor low-fidelity mutant Pol ε strains. The rNMP spectra for a strain with proofreading-defective DNA Pol δ (pol3-5DV, FIG. 31) were not different from those containing the wild-type Pol δ (FIGS. 26M-26N, FIGS. 27O-27P, FIGS. 29C-29D, and FIG. 33). These results suggest that DNA Pol ε can proofread rNMPs, particularly rUMP, in DNA and that this activity is superior to that of DNA Pol δ, as is consistent with previous biochemical studies[6,30].

Hotspots of rNMP Incorporation in the *S. cerevisiae* Genome

Figure 18:
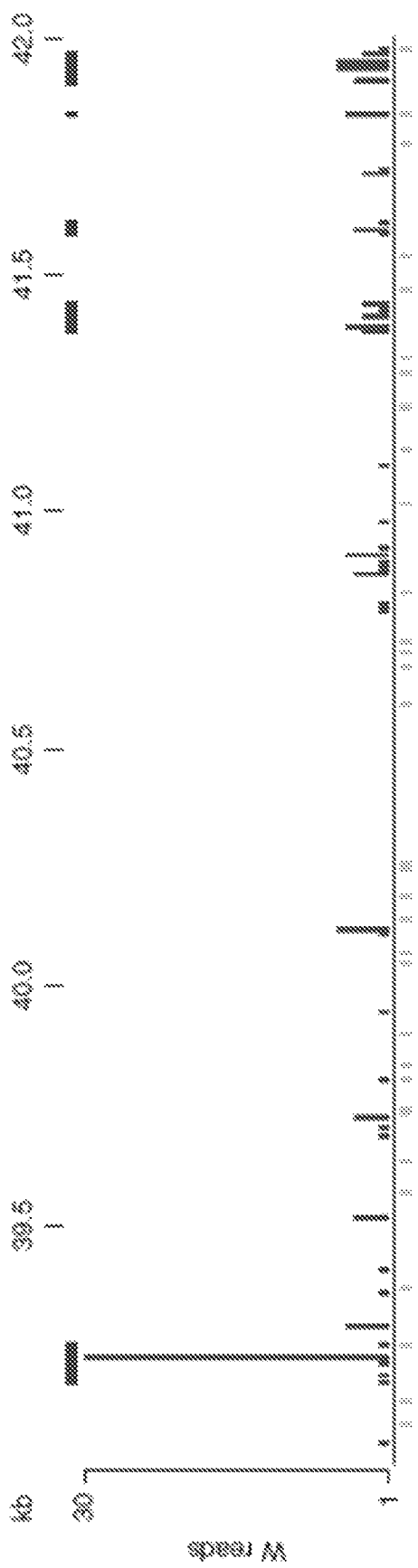
FIG. 18 shows a Ribose-seq map of rNMPs in a 3-kb window (39001-42000) of mitochondrial DNA showing enriched regions of rNMP incorporation. Enriched regions with q-value <0.001 are shown in blue above the plot. Positions of restriction sites used for genomic fragmentation are displayed below the plot.
Figure 19:
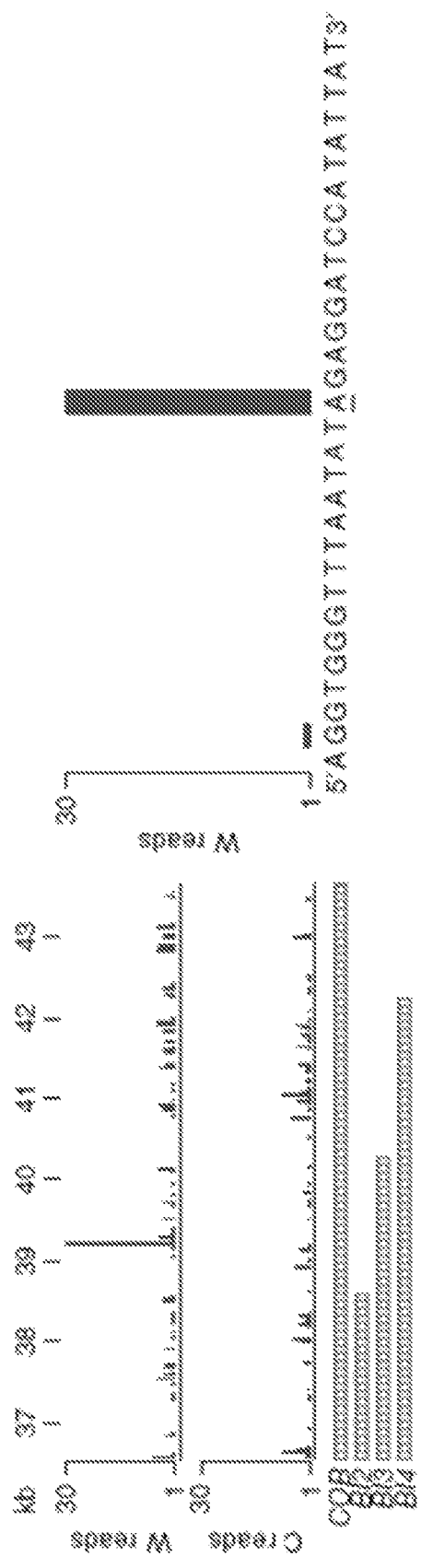
FIG. 19 shows a map of rNMPs in the COB mitochondrial locus (left). Zoom-in map (right) with sequence at the hotspot site (underlined).
Figures 20, 21:
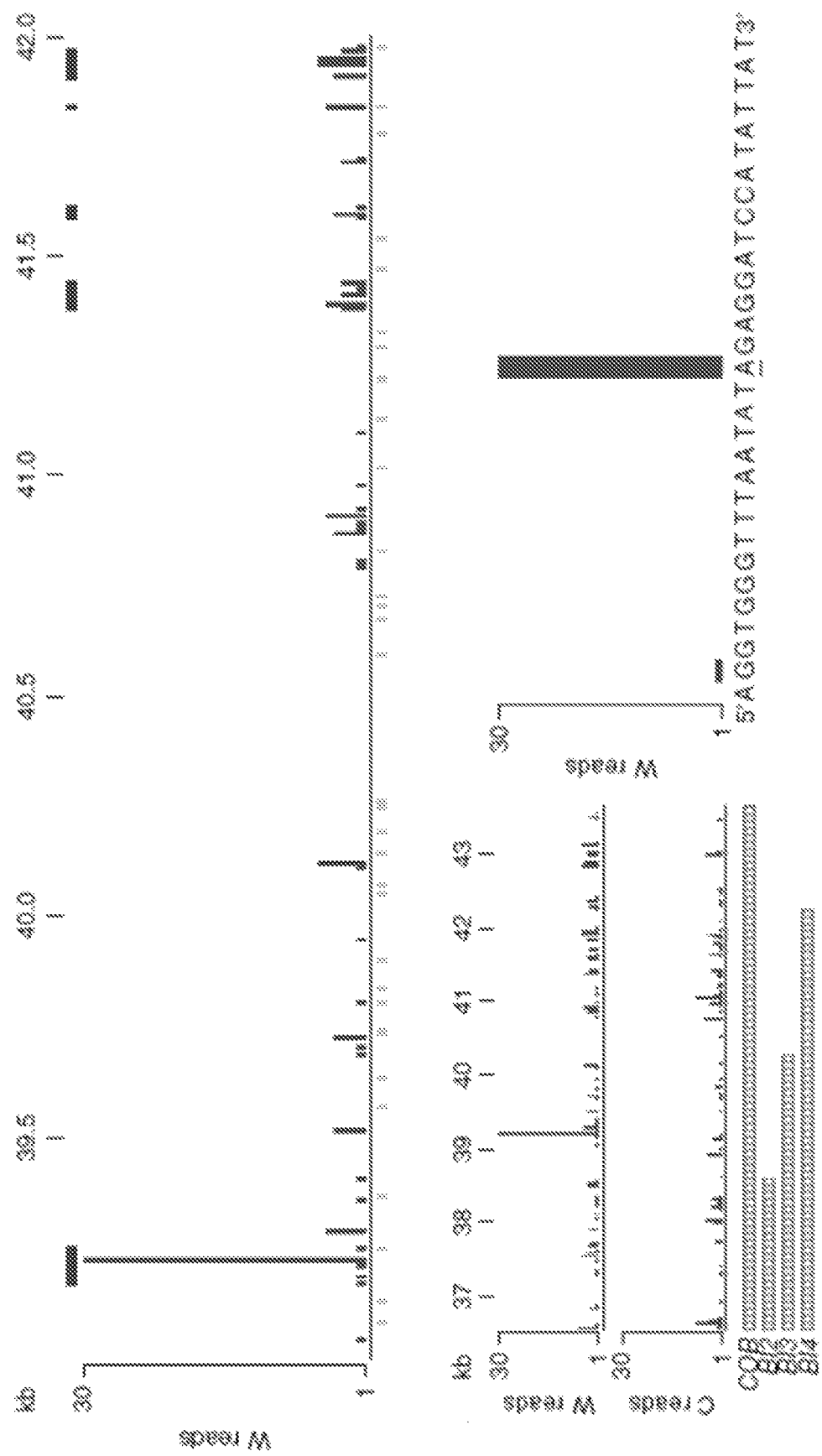
FIG. 20 shows a map of map of rNMPs in the first of two rDNA repeat loci on Chr XII, based on alignment data from the two loci of the reference genome (left). Zoom-in map (right) of the rDNA hotspot.
FIG. 21 shows a Map of rNMPs in the Ty1 locus YDRCTy1-1 on Chr IV based on multiple-alignment data from several Ty1 loci (left). Zoom-in map (right) of the Ty1 hotspot. Results are shown for rnh201Δ (KK-100) cells. W, Watson strand; C, Crick strand.

Two types of analysis were performed to determine potential hotspots of rNMP incorporation in the *S. cerevisiae* genome. We identified enriched regions of rNMP incorporation in genomic DNA from ribose-seq data (see Online Methods). Several regions of notable rNMP incorporation in mitochondrial DNA for each ribose-seq library in this study was observed (FIG. 18 displays a few regions). Because this analysis excludes all reads aligning to more than one position in the genome, we performed a second analysis with respect to specific loci to identify single-nucleotide hotspots that were reproducibly present in multiple ribose-seq libraries (see Online Methods). We identified hotspots of rNMP incorporation in sequences present in multiple copies per yeast cell: the mitochondrial genome (~80 copies)[34], the ribosomal DNA (rDNA) repeats (about 140) clustered on chromosome X1135 and the yeast retrotransposon (Ty), of which there are about 30 copies encoded on multiple chromosomes[36]. In mitochondrial DNA, we found a marked hotspot at an rAMP on the Watson strand in the cytochrome oxidase B gene (COB) and the overlapping maturase B13 and B14 genes (FIG. 19 and FIG. 36), in addition to several other hotspots (FIG. 36). In the rDNA locus, the strongest hotspot was found in gene RDN37-1 and the overlapping RDN25-1 at an rGMP (FIG. 20 and FIG. 36). In the yeast Ty1 sequence, we found a hotspot at an rAMP in the coding sequence of TY1A-1 (FIG. 21 and FIG. 36).

The occurrence of such hotspots indicates that there are preferred sites for rNMP incorporation in the mitochondrial genome, rDNA and Ty1 sequences. In addition to the recombinogenic properties of mitochondrial G+C clusters discussed above, yeast rDNA and Ty are also active in recombination[36,37]. Frequent rNMP incorporation could trigger recombination, as do rNMPs embedded in the mating type locus of *Schizosaccharomyces pombe*[3]. The rNMPs detected in Ty DNA could originate from cDNA rather than genomic DNA. Because rnh201Δ rnh1Δ cells have abundant Ty cDNA[38], if rNMPs are incorporated in Ty1 during the process of reverse transcription, which forms the cDNA, we would expect a different rNMP pattern in Ty1 DNA in rnh201Δ rnh1Δ than in rnh201Δ cells. Although we did not observe major differences in the rNMP spectra derived from rnh201Δ single mutant versus rnh201Δ rnh1Δ cells at the Ty1 locus or in general (FIG. 11, FIGS. 26A-27P, and FIG. 36), it would be of interest to conduct in vitro tests to determine whether Ty reverse transcriptase incorporates rNMPs frequently opposite RNA and/or DNA, and whether it has a particular bias for rNMP incorporation.

Discussion rNMP incorporation has been extensively studied in recent years; however, locating sites of rNMP incorporation in genomic DNA has not yet been possible. Alkaline cleavage of rNMPs and AtRNL ligation exclude Okazaki fragments and DNA abasic sites, allowing the construction of ribose-seq libraries containing stably incorporated rNMP sites. Ribose-seq enabled us to determine the widespread but nonrandom distribution of rNMPs in budding yeast genomic nuclear and mitochondrial DNA, with several hotspots.

These findings both validated the approach and uncovered new aspects of rNMP incorporation in the yeast genome. The observed strand bias incorporation on the newly synthesized leading strand in wild-type and low-fidelity Pol ε strains, and the specific rNMP pattern in yeast containing proofreading deficient Pol ε, provide strong support for the in vitro results obtained for these forms of Pol ε. rCMP and rGMP were more abundant than rAMP and rUMP, and there was frequently a dA downstream of the rNMPs. We also found that RNase H1 did not contribute substantially to rNMP incorporation, and Ung1 did not remove genomic uracil. It is possible that the paucity of rUMP in DNA reflects inherent cleavage bias in other rNMP removal pathways, such as topoisomerase-mediated rNMP cleavage[22]. It would be of interest to determine the rNMP spectrum in cells with defects in alternative rNMP removal pathways, either in RNase H2 wild-type or null cells growing under normal and/or stressed conditions. Ribose-seq, together with HydEn-seq[40], emRiboSeq[41] and Pu-seq[42] which were developed in parallel and capture the nucleotides downstream or upstream of rNMP positions, should allow us to better understand the impact of rNMPs on the structure and function of DNA and chromatin, and specific rNMP signatures may represent new biomarkers for human diseases such as Aicardi-Goutieres syndrome, cancer and other degenerative disorders.

Methods

Yeast Strain Construction.

Yeast strains used in this study are presented in FIG. 31. Isogenic yeast haploid strains KK-100, KK-174, KK-107 and KK-120 were derived from E134 (MATα ade5-1 lys2-14A trpl-289 his7-2 leu2-3,112 ura3-52)[43]. KK-100 was made from E134 by deletion and replacement of RNH201 via transformation with a PCR product containing the hygMX4 cassette flanked by 50 nt of sequence homologous to regions upstream and downstream of the RNH201 ORF. KK-174 was constructed from KK-100 by deletion and replacement of RNH1 via transformation with a PCR product containing the kanMX4. KK-107 was generated by introducing the pol2-4 mutation into KK-100 via integration-excision using plasmid YlpJB1 (ref. 44). KK-120 was made by introducing the pol3-5DV mutation into KK-100 via integration-excision using plasmid p170-5DV[45].

Isogenic yeast haploid strains KK-30, KK-125, KK-164 and KK-170 were derived from FRO-767,768 (hoΔ hmlΔøADE1 MATa-inc hmrΔøADE1 ade1 leu2-3,112 lys5 trpløhisG ura3-52 ade3øGALøHO leu2øHOcs mataΔøhisG)[46]. KK-30 was made from FRO-768 by reversion of ade3øGALøHO to intact ADE3 via transformation with a PCR product containing ADE3, followed by replacement of RNH201 with the hygMX4. KK-125 was constructed from KK-30 by replacement of RNH1 with the kanMX4 cassette. KK-164 was generated from KK-125 by replacement of UNG1 with the natMX4 cassette. KK-170 was made by introducing the pol2-M644G mutation into KK-30 via integration-excision using plasmid p173-M644G[47].

Isogenic yeast haploid strains KK-158 and KK-159 were derived from FRO-767 and FRO-768 (ref. 46). KK-158 and KK-159 were constructed from FRO-767 and FRO-768 by replacement of UNG1 with the hygMX4 cassette.

AtRNL Ligation Assay.

Ribonucleotide (rNMP)-containing DNA oligonucleotide Lig.47.R (see FIG. 37) and its DNA-only control, Lig.47.D, were 5' end-labeled with [γ-$^{32}$P]ATP (PerkinElmer) by T4 polynucleotide kinase (New England Biolabs). Alkali treatment was carried out in 0.3 M NaOH for 2 h at 55° C. The resulting solution was neutralized and diluted. 100 nM of alkali-treated 5'-radiolabeled products were incubated in 50 mM Tris-HCl, pH 7.5, 40 mM NaCl, 5 mM MgCl$_2$, 1 mM DTT, 30 µM ATP (Sigma-Aldrich) and 1 µM AtRNL[24] for 1 h at 30° C. After dilution, the ligated products and remaining substrates were treated with T5 exonuclease (NEB) for 2 h at 37° C. Aliquots were withdrawn after appropriate steps and quenched with 90% formamide. The products were analyzed by 15% (wt/vol) polyacrylamide, 8 M urea gel electrophoresis (urea-PAGE). 20-100 Oligonucleotide Length Standard (Integrated Device Technology) was used as a ladder. After electrophoresis, gels were exposed to a phosphor screen overnight. Images were taken with Typhoon Trio+(GE Healthcare) and obtained with ImageQuant (GE Healthcare). Band intensities were quantified by Multi Gauge V3.0 (Fujifilm).

3' Base Bias for AtRNL Ligation Assay.

rAMP, rGMP, rUMP and rCMP-containing DNA oligonucleotides (Lig.30.rA, Lig.30.rG, Lig.30.rU and Lig.30.rC, respectively; see FIG. 37) were 5' end-labeled with either hot [γ-32P]ATP (PerkinElmer) or cold ATP (Sigma-Aldrich) by T4 polynucleotide kinase (NEB). Each of the hot rNMP-containing 5'-radiolabeled DNA oligonucleotides was mixed with the other three cold DNA oligonucleotides at equimolar ratios. The mixtures were treated with 0.3 M NaOH for 2 h at 55° C., neutralized, and diluted. 100 nM alkali-cleaved products (25 nM of each base) was then incubated in 50 mM Tris-HCl, pH 7.5, 40 mM NaCl, 5 mM MgCl2, 1 mM DTT, 30 µM ATP (Sigma-Aldrich) and either 1 µM or 200 nM AtRNL24 for 1 h at 30° C. After dilution, the resulting products were treated with T5 exonuclease for 2 h at 37° C. Aliquots were withdrawn after appropriate steps, quenched, and analyzed by urea-PAGE.

rNMP Bypass Assay.

A DNA primer oligonucleotide, ByPrim (see FIG. 37), was 5' end-labeled with [γ-$^{32}$P] ATP (PerkinElmer) by T4 polynucleotide kinase (NEB). The 5'-radiolabeled primer was annealed to either rCMP- or rUMP-containing template oligonucleotide (ByTemp.rC or ByTemp.rU, respectively). 100 nM annealed substrates was incubated in HF buffer, 2 mM dNTPs and 0.2 units of Phusion High-Fidelity DNA Polymerase (NEB) for 30 s at 72° C. The reactions were quenched and analyzed by urea-PAGE. Bypass probability was calculated as the band intensity at the +1 position plus all longer products divided by the intensity at the −1 position (preceding the rNMP) plus all longer products, as described by Kokoska et al.[48].

Double-Stranded Break Repair Assay with rNMP-Containing Oligonucleotides.

Transformations with rNMP-containing DNA oligonucleotides LEU2.rG and LEU2. rU (see FIG. 37) and DNA-only oligonucleotides LEU2.D and LEU2.dU were done as described by Storici et al.[46]. Cells from each oligonucleotide transformation were plated to selective Leu− medium. For each transformation, 20 Leu+ transformants were selected. Colony PCR was performed on those transformants, amplifying with primers LEU2.3 and LEU2.6 a 900-bp region in LEU2 locus where a new StuI restriction site is expected. The resulting PCR products were treated with StuI (NEB) and analyzed by agarose gel electrophoresis to confirm the presence of the StuI restriction site.

Ribose-Seq Library Construction to Map rNMPs in DNA.

Genomic DNA from *S. cerevisiae* cells grown in liquid rich medium containing yeast extract, peptone and 2% (wt/vol) dextrose (YPD) for 2 d to stationary phase was extracted following the protocol "Preparation of Yeast Samples" in the Qiagen Genomic DNA Handbook. Genomic-tip 500/G (Qiagen), Genomic DNA Buffer Set (Qiagen), proteinase K (Qiagen), RNase A (Qiagen) and lyticase (Sigma-Aldrich) were used to extract genomic DNA from *S. cerevisiae* cells. Extracted genomic DNA was digested with SspI, DraI and EcoRV (NEB) overnight at 37° C. to create a population of 500- to 3,000-bp genomic fragments with an average size of about 1.5 kb. Assuming that rNMPs, if present, could be located in any position of each genomic fragment, an average of 1.5 kb allows a reasonable window for rNMP capture. Following confirmation of digestion by Experion Automated Electrophoresis System (Bio-Rad), the fragments were tailed with dATP (Sigma-Aldrich) by exo-Klenow fragment (NEB) for 30 min at 37° C. The resulting products were purified by spin column (Qiagen) and then ligated to preannealed double-stranded adaptors (Adaptor.L:Adaptor.S; see FIG. 37) that contain single dT overhangs and a randomized 8-base unique molecular identifier (UMI) by T4 DNA ligase (NEB) overnight at 15° C. The products were purified using AMPure XP beads (Beckman Coulter). All subsequent purifications were done using AM Pure XP beads. The adaptor-ligated DNA fragments were incubated in 0.3 M NaOH for 2 h at 55° C. to expose 2',3'-cyclic phosphate and 2'-phosphate termini of DNA at rNMP sites, followed by neutralization and purification. The resulting single-stranded (ss) fragments were incubated in 50 mM Tris-HCl, pH 7.5, 40 mM NaCl, 5 mM MgCl2, 1 mM DTT, 30 µM ATP (Sigma-Aldrich) and 1 µM AtRNL (24) for 1 h at 30° C., followed by purification. The products and remaining fragments of DNA were treated with T5 exonuclease (NEB) for 2 h at 37° C. to degrade the background of unligated, linear ssDNA, leaving self-ligated ssDNA circles intact. Treatment with 1 µM Tpt1 (ref. 24) in 20 mM Tris-HCl, pH 7.5, 5 mM MgCl2, 0.1 mM DTT, 0.4% Triton X-100 and 10 mM NAD+(Sigma-Aldrich) for 1 h at 30° C. was used to remove the 2' phosphate remaining at the ligation junction. After purification and resuspension, the libraries were PCR-amplified with one of the barcoded primers, PCR.1.Index1-4, and PCR.2 (see FIG. 37) using either Phusion High-Fidelity DNA Polymerase (NEB) or EconoTaq DNA Polymerase (Lucigen), confirmed by 6% PAGE, purified and pooled for analysis by Illumina sequencing. 100-bp DNA Ladder (NEB) was used as a size standard. SYBR Gold Nucleic Acid Gel Stain (Life Technologies) was used to stain PAGE gels for visualization under ultraviolet light. Ribose-seq does not capture RNA primers of Okazaki fragments because the 5'-most rNMP is a 5'-triphosphate (49), and the T4 DNA ligase used to attach the sequencing adaptors absolutely requires a 5'-monophosphate (50). Moreover, the rest of the primers are reduced to single nucleotides upon alkali treatment, and they will have no adaptor sequence ligated on. Ribose-seq also does not detect rNMP positions derived from residual RNA molecules or RNA:DNA hybrids not embedded in DNA (such as cDNA) nor DNA abasic sites, which could have been ligated to the adaptor sequence by T4 DNA ligase. Following alkali treatment, RNA stretches are reduced to single nucleotides that are removed in subsequent purification steps; even if the 5'-most rNMP is captured, the rNMP-containing single-stranded circle would not have any sequence to be aligned to the reference genome. Abasic sites undergo both β- and δ-eliminations to yield 5'-phosphate and 3'-phosphate ends (51, 52), which cannot be ligated by AtRNL. Because of the nature of alkaline hydrolysis within a stretch of rNMPs embedded in DNA, the ribose-seq method captures only the 5'-most rNMP of the stretch of two or more rNMPs. Moreover, ribose-seq does not require rNMPs to be present at the same location from cell to cell, and it can identify incorporated rNMPs with single-base precision.

DNA Sequencing.

Indexed sequencing libraries were mixed at equimolar concentrations and normalized to 10 nM. Libraries were sequenced on an Illumina MiSeq and 50-cycle single-end reads were collected. Raw sequencing reads are available at NCBI GEO[39] under accession code GSE61464.

Code Availability.

Software and pipelines are available in Github.

Sequence Alignment and Processing.

Reads were aligned to the *S. cerevisiae* genome (sacCer2) with bowtie using two different settings to report uniquely aligning and multiple aligning reads ("–m 1" and "—all," respectively). Aligned reads in BAM format were processed to remove PCR duplicates using umitools (https://github.com/brwnyumitools/), which filters reads that contain duplicate UMIs and reports reads with unique UMIs. Reads in this study had an eight-base UMI incorporated during ligation, corresponding to the first eight cycles of raw FASTQ sequence. Following UMI removal, read depths at each 5' position were calculated with BEDTools[53,54].

Nucleotide Frequencies.

Nucleotide frequencies for mapped rNMP positions (that is, the 5' position of each aligned read) were calculated and normalized to genome frequencies (nuclear and mitochondrial genomes in sacCer2). The identity of the rNMP base is the reverse complement of the 5' base of each read. Nucleotide frequencies of downstream sequences of incorporated rNMPs, including the +1 position, cannot be affected by our approach of capturing rNMPs in DNA because the rNMPs and their upstream sequences are captured, sequenced and aligned to the reference genome.

Replication Correlations.

The density and identity of rNMPs present on leading and lagging strands were calculated relative to annotated origins of replication[55] and were further categorized by replication timing[33]. Data were filtered for specified replication timings (for example, 25 min after release into S phase) and distances relative to the middle of each ARS annotation (for example, 5.0 kb up- and downstream of each ARS).

Determination of Hotspots of rNMP Incorporation in Genomic DNA.

Two different analyses were conducted to identify hotspots of rNMP incorporation in genomic DNA. Peak calling was performed with macs2 (version 2.1.0.20140616) 56 with specific parameters (—keep-dup all—nomodel—s 25—extsize 5—call-summits). Peaks of length greater than 1,000 were filtered from further analysis, and remaining peaks with a q-value less than 0.001 were selected. A second analysis involved finding positions of rNMPs within the locus of interest with ribose-seq signal greater than the mean plus 3 s.d. for each library from rnh201Δ (KK-100), rnh201Δ (KK-100, EconoTaq), rnh201Δ (KK-30), rnh1Δ rnh201Δ (KK-174) and rnh1Δ rnh201Δ (KK-125) cells.

Data Presentation and Statistics.

Graphs were made using GraphPad Prism 5 (GraphPad Software). A nonparametric two-tailed Mann-Whitney U-test57 was implemented for statistical analysis of AtRNL ligation efficiencies, rNMP bypass probabilities and the percentages of StuI-cut Leu+ transformants in the DSB repair assay. A chi-squared goodness-of-fit test55 was used for statistical comparison of the distribution of rNMP reads to the expected Poisson distribution.

References for Example 1

1. Williams, J. S. & Kunkel, T. A. Ribonucleotides in DNA: origins, repair and consequences. DNA Repair (Amst.) 19, 27-37 (2014).
2. Grossman, L. I., Watson, R. & Vinograd, J. The presence of ribonucleotides in mature closed-circular mitochondrial DNA. Proc. Natl. Acad. Sci. USA 70, 3339-3343 (1973).
3. Vengrova, S. & Dalgaard, J. Z. The wild-type *Schizosaccharomyces pombe* mat1 imprint consists of two ribonucleotides. EMBO Rep. 7, 59-65 (2006).
4. Potenski, C. J. & Klein, H. L. How the misincorporation of ribonucleotides into genomic DNA can be both harmful and helpful to cells. Nucleic Acids Res. 42, 10226-10234 (2014).
5. Clausen, A. R., Zhang, S., Burgers, P. M., Lee, M. Y. & Kunkel, T. A. Ribonucleotide incorporation, proofreading and bypass by human DNA polymerase delta. DNA Repair (Amst.) 12, 121-127 (2013).
6. Kasiviswanathan, R. & Copeland, W. C. Ribonucleotide discrimination and reverse transcription by the human mitochondrial DNA polymeraseJ. Biol. Chem. 286, 31490-31500 (2011).
7. Nick McElhinny, S. A. et al. Abundant ribonucleotide incorporation into DNA by yeast replicative polymerases. Proc. Natl. Acad. Sci. USA 107, 4949-4954 (2010).
8. McDonald, J. P., Vaisman, A., Kuban, W., Goodman, M. F. & Woodgate, R. Mechanisms employed by *Escherichia coli* to prevent ribonucleotide incorporation into genomic DNA by pol V. PLoS Genet. 8, e1003030 (2012).
9. Zhu, H. & Shuman, S. Bacterial nonhomologous end joining ligases preferentially seal breaks with a 3'-OH monoribonucleotide. J. Biol. Chem. 283, 8331-8339 (2008).
10. Rumbaugh, J. A., Murante, R. S., Shi, S. & Bambara, R. A. Creation and removal of embedded ribonucleotides in chromosomal DNA during mammalian Okazaki fragment processing. J. Biol. Chem. 272, 22591-22599 (1997).
11. Randerath, K. et al. Formation of ribonucleotides in DNA modified by oxidative damage in vitro and in vivo. Characterization by 32P-postlabeling. Mutat. Res. 275, 355-366 (1992).
12. Cerritelli, S. M. & Crouch, R. J. Ribonuclease H: the enzymes in eukaryotes. FEBS J. 276, 1494-1505 (2009).
13. Sparks, J. L. et al. RNase H2-initiated ribonucleotide excision repair. Mol. Cell 47, 980-986 (2012).
14. Reijns, M. A. et al. Enzymatic removal of ribonucleotides from DNA is essential for mammalian genome integrity and development. Cell 149, 1008-1022 (2012).
15. Lujan, S. A., Williams, J. S., Clausen, A. R., Clark, A. B. & Kunkel, T. A. Ribonucleotides are signals for mismatch repair of leading-strand replication errors. Mol. Cell 50, 437-443 (2013).

16. Williams, J. S. et al. Topoisomerase 1-mediated removal of ribonucleotides from nascent leading-strand DNA. Mol. Cell 49, 1010-1015 (2013).
17. Yao, N.Y., Schroeder, J. W., Yurieva, O., Simmons, L. A. & O'Donnell, M. E. Cost of rNTP/dNTP pool imbalance at the replication fork. Proc. Natl. Acad. Sci. USA 110, 12942-12947 (2013).
18. Chiu, H. C. et al. RNA intrusions change DNA elastic properties and structure. Nanoscale 6, 10009-10017 (2014).
19. Caldecott, K. W. Molecular biology. Ribose—an internal threat to DNA. Science 343, 260-261 (2014).
20. Kim, N. et al. Mutagenic processing of ribonucleotides in DNA by yeast topoisomerase I. Science 332, 1561-1564 (2011).
21. Potenski, C. J., Niu, H., Sung, P. & Klein, H. L. Avoidance of ribonucleotide-induced mutations by RNase H2 and Srs2-Exo1 mechanisms. Nature 511, 251-254 (2014).
22. Cho, J. E., Kim, N., Li, Y. C. & Jinks-Robertson, S. Two distinct mechanisms of Topoisomerase 1-dependent mutagenesis in yeast. DNA Repair (Amst.) 12, 205-211 (2013).
23. Crow, Y. J. et al. Mutations in genes encoding ribonuclease H2 subunits cause Aicardi-Goutieres syndrome and mimic congenital viral brain infection. Nat. Genet. 38, 910-916 (2006).
24. Schutz, K., Hesselberth, J. R. & Fields, S. Capture and sequence analysis of RNAs with terminal 2',3'-cyclic phosphates. RNA 16, 621-631 (2010).
25. Remus, B. S. & Shuman, S. Distinctive kinetics and substrate specificities of plant and fungal tRNA ligases. RNA 20, 462-473 (2014).
26. Cooper, D. A., Jha, B. K., Silverman, R. H., Hesselberth, J. R. & Barton, D. J. Ribonuclease L and metal-ion-independent endoribonuclease cleavage sites in host and viral RNAs. Nucleic Acids Res. 42, 5202-5216 (2014).
27. Krokan, H. E., Drablos, F. & Slupphaug, G. Uracil in DNA—occurrence, consequences and repair. Oncogene 21, 8935-8948 (2002).
28. Lindahl, T., Ljungquist, S., Siegert, W., Nyberg, B. & Sperens, B. DNA N-glycosidases: properties of uracil-DNA glycosidase from Escherichia coli. J. Biol. Chem. 252, 3286-3294 (1977).
29. Fasullo, M., Tsaponina, O., Sun, M. & Chabes, A. Elevated dNTP levels suppress hyper-recombination in Saccharomyces cerevisiae S-phase checkpoint mutants. Nucleic Acids Res. 38, 1195-1203 (2010).
30. Williams, J. S. et al. Proofreading of ribonucleotides inserted into DNA by yeast DNA polymerase varepsilon. DNA Repair (Amst.) 11, 649-656 (2012).
31. Foury, F., Roganti, T., Lecrenier, N. & Purnelle, B. The complete sequence of the mitochondrial genome of Saccharomyces cerevisiae. FEBS Lett. 440, 325-331 (1998).
32. Gerhold, J. M., Aun, A., Sedman, T., Joers, P. & Sedman, J. Strand invasion structures in the inverted repeat of Candida albicans mitochondrial DNA reveal a role for homologous recombination in replication. Mol. Cell 39, 851-861 (2010).
33. Yabuki, N., Terashima, H. & Kitada, K. Mapping of early firing origins on a replication profile of budding yeast. Genes Cells 7, 781-789 (2002).
34. Moraes, C. T. What regulates mitochondrial DNA copy number in animal cells? Trends Genet. 17, 199-205 (2001).
35. Szostak, J. W. & Wu, R. Unequal crossing over in the ribosomal DNA of Saccharomyces cerevisiae. Nature 284, 426-430 (1980).
36. Hani, J. & Feldmann, H. tRNA genes and retroelements in the yeast genome. Nucleic Acids Res. 26, 689-696 (1998).
37. Mieczkowski, P. A., Lemoine, F. J. & Petes, T. D. Recombination between retrotransposons as a source of chromosome rearrangements in the yeast Saccharomyces cerevisiae. DNA Repair (Amst.) 5, 1010-1020 (2006).
38. El Hage, A., Webb, S., Kerr, A. & Tollervey, D. Genome-wide distribution of RNA-DNA hybrids identifies RNase H targets in tRNA genes, retrotransposons and mitochondria. PLoS Genet. 10, e1004716 (2014).
39. Barrett, T. et al. NCBI GEO: archive for functional genomics data sets—update. Nucleic Acids Res. 41, D991-D995 (2013).
40. Clausen, A. R. et al. Tracking replication enzymology in vivo by genome-wide mapping of ribonucleotide incorporation. Nat. Struct. Molec. Biol. doi:10.1038/nsmb.2957 (26 Jan. 2015).
41. Reijns, M. A. M. et al. Lagging strand replication shapes the mutational landscape of the genome. Nature doi:10.1038/nature14183 (26 Jan. 2015).
42. Daigaku, Y. et al. A global profile of replicative polymerase usage. Nat. Struct. Mol. Biol. (in the press).
43. Clark, A. B. et al. Functional analysis of human MutSα and MutSβ complexes in yeast. Nucleic Acids Res. 27, 736-742 (1999).
44. Morrison, A., Bell, J. B., Kunkel, T. A. & Sugino, A. Eukaryotic DNA polymerase amino acid sequence required for 3'→5' exonuclease activity. Proc. Natl. Acad. Sci. USA 88, 9473-9477 (1991).
45. Jin, Y. H. et al. The 3'→5' exonuclease of DNA polymerase δ can substitute for the 5' flap endonuclease Rad27/Fen1 in processing Okazaki fragments and preventing genome instability. Proc. Natl. Acad. Sci. USA 98, 5122-5127 (2001).
46. Storici, F., Bebenek, K., Kunkel, T. A., Gordenin, D. A. & Resnick, M. A. RNA-templated DNA repair. Nature 447, 338-341 (2007).
47. Pursell, Z. F., lsoz, I., Lundstrom, E. B., Johansson, E. & Kunkel, T. A. Yeast DNA polymerase c participates in leading-strand DNA replication. Science 317, 127-130 (2007).
48. Kokoska, R. J., McCulloch, d. & Kunkel, T. A. The efficiency and specificity of apurinic/apyrimidinic site bypass by human DNA polymerase q and Sulfolobus solfataricus Dpo4. J. Biol. Chem. 278, 50537-50545 (2003).
49. Kuchta, R. D. & Stengel, G. Mechanism and evolution of DNA primases. Biochim. Biophys. Acta 1804, 1180-1189 (2010).
50. Smith, C. W. J. RNA-Protein Interactions: A Practical Approach 1st edn. (Oxford Univ. Press, New York, 1998).
51. Lhomme, J., Constant, J. F. & Demeunynck, M. Abasic DNA structure, reactivity, and recognition. Biopolymers 52, 65-83 (1999).
52. Bailly, V. & Verly, W. G. Possible roles of [3-elimination and 6-elimination reactions in the repair of DNA containing AP (apurinic/apyrimidinic) sites in mammalian cells. Biochem. J. 253, 553-559 (1988).
53. Quinlan, A. R. & Hall, I. M. BEDTools: a flexible suite of utilities for comparing genomic features. Bioinformatics 26, 841-842 (2010).

54. Dale, R. K., Pedersen, B. S. & Quinlan, A. R. Pybedtools: a flexible Python library for manipulating genomic data sets and annotations. Bioinformatics 27, 3423-3424 (2011).
55. Siow, C. C., Nieduszynska, S. R., Muller, C. A. & Nieduszynski, C. A. OriDB, the DNA replication origin database updated and extended. Nucleic Acids Res. 40, D682-D686 (2012).
56. Zhang, Y. et al. Model-based analysis of ChIP-Seq (MACS). Genome Biol. 9, R137 (2008).
57. Sokal, R. R. & Rohlf, F. J. Biometry: The Principles and Practice of Statistics in Biological Research 3rd edn. (W.H. Freeman, New York, 1995).

Example 2

Introduction

Ribonucleotides, also known as ribonucleoside 5'-monophosphates (rNMPs), which are normally monomers of RNA, have been found to be the most abundant non-canonical nucleotides incorporated into DNA (2,3). Sources of ribonucleotide incorporation into DNA include incomplete Okazaki fragment maturation, oxidative damage, and numerous DNA polymerases. Quantitative measures of rNMPs in DNA following alkali treatment of yeast genomic DNA derived from RNase H2-deficient cells estimated about 2,000 rNMPs per genome (4,5) while similar measurement conducted for genomic DNA derived from RNase H2-deficient embryonic fibroblasts revealed the presence of more than one million rNMPs in the mouse genome (6). Ribonuclease H type 2 (RNase H2) is a major protein factor involved in repair of rNMPs in DNA and initiates ribonucleotide excision repair (2,3). If not removed, rNMPs have been shown to have both positive roles, such as acting as strand discrimination signal during MMR, and negative consequences, including replication stress and genome instability (2,3). Despite the numerous studies showing the presence of rNMPs in DNA, information about the distribution and identity of these rNMPs in genomic DNA was unknown till very recently. We developed ribose-seq to capture rNMPs in genomic DNA along with their upstream DNA sequence for library construction, next-generation sequencing, and analysis (1). Implementation of ribose-seq to genomic DNA from RNase H2-deficient yeast *Saccharomyces cerevisiae* cells revealed widespread but non-random distribution of rNMPs in yeast genome, with specific base preferences, neighboring DNA sequence preferences, bias of leading and lagging strand, and hotspots. Ribose-seq allows us to explore rNMP incorporation into DNA potentially in any cell type of any organism and opens up a new direction to better comprehend the impact of rNMPs on genome integrity.

Figure 3A:
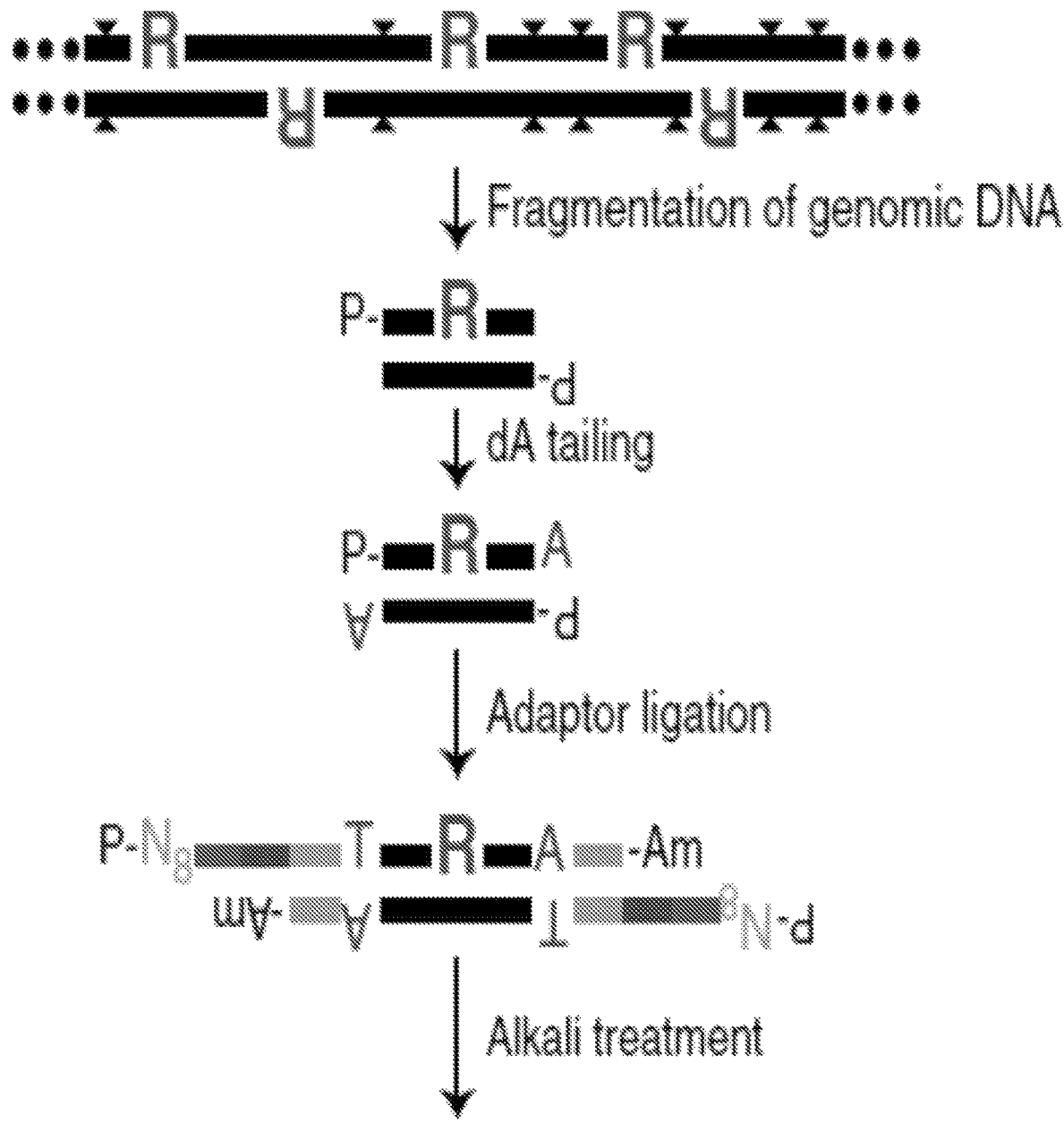
FIGS. 3A to 3C show a schematic of the ribose-seq protocol. Genomic DNA is fragmented, dA-tailed and ligated to a molecular barcode-containing sequencing adaptor. Alkali treatment denatures the DNA and cleaves at rNMP sites, exposing 2',3'-cyclic phosphate and 2'-phosphate termini, which are self-ligated to 5'-phosphate ends by AtRNL. Linear, unligated fragments are degraded by T5 exonuclease and the remaining rNMP-captured, circular DNA molecules, upon removal of the 2'-phosphate at the ligation junction by the 2'-phosphotransferase Tpt1, are PCR-amplified and sequenced. UMI, unique molecular identifier. R in black indicates the rNMP converted to a dNMP during PCR. Sequencing results, which go 5' to 3', will read after the pink primer sequence the 8 nt of the UMI and then there will be the nucleotide opposite to the ribonucleotide. The position of the ribonucleotide is the complement of this one.
Figure 3B:
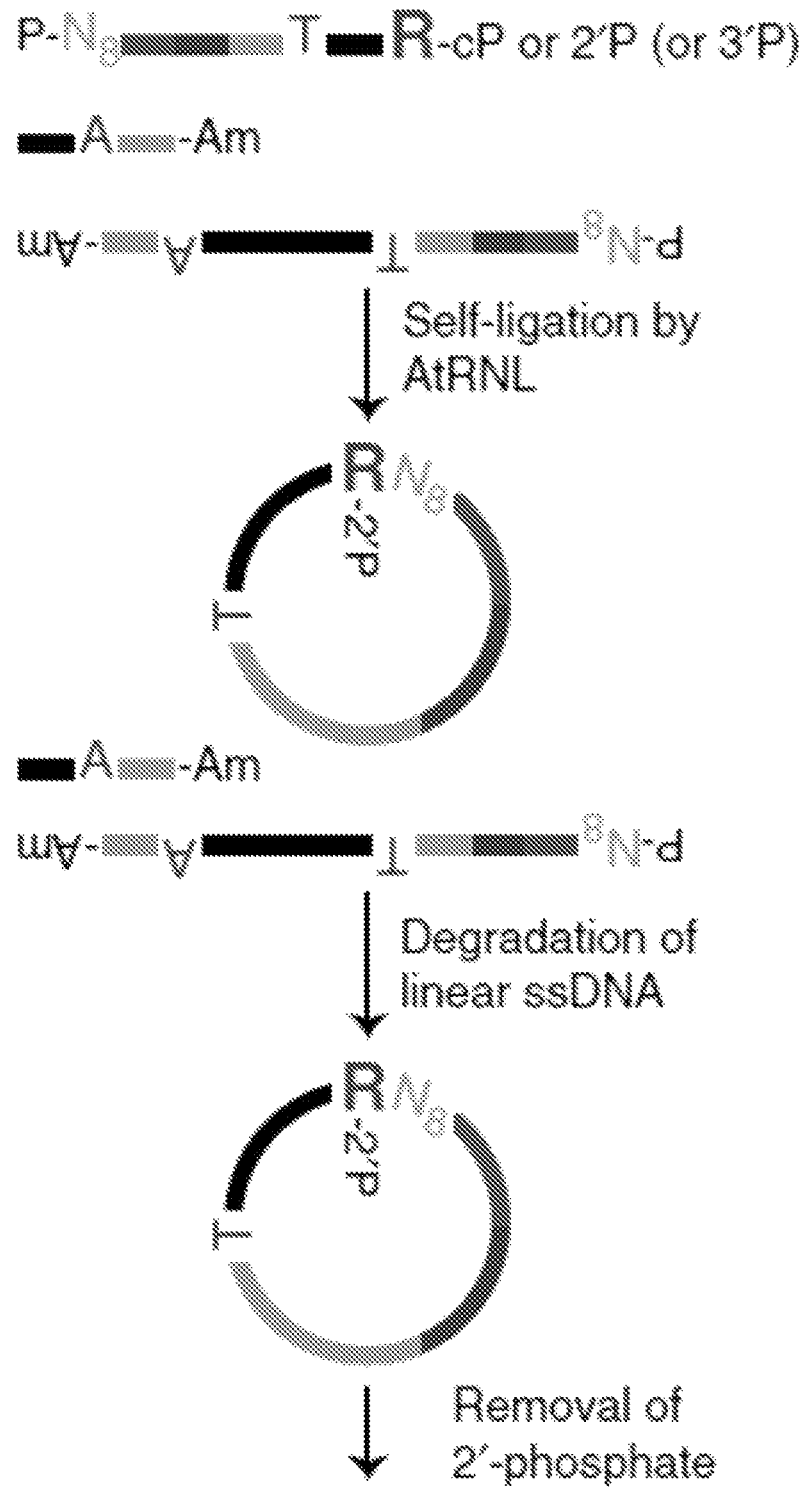
Figure 3C:
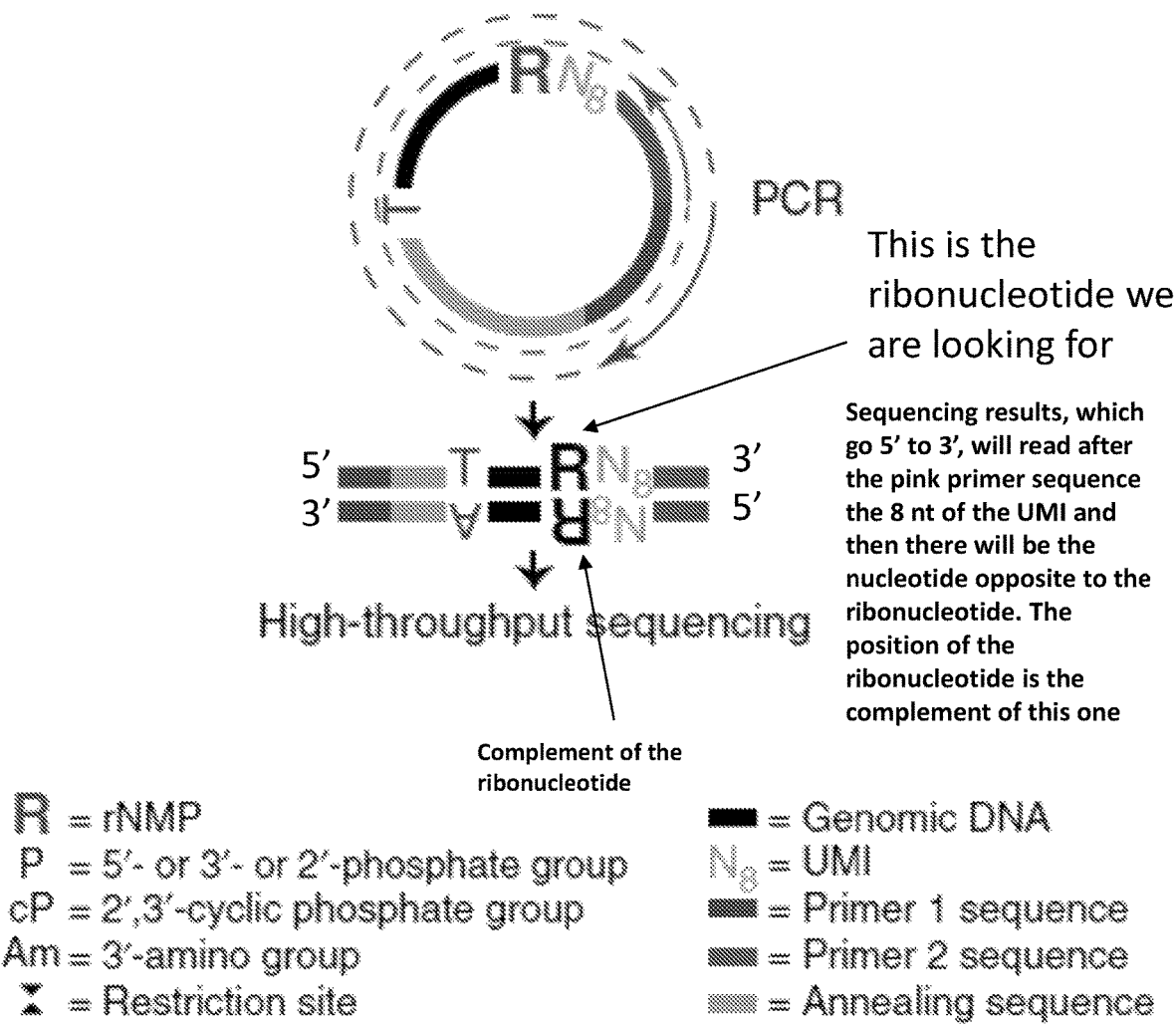

This example demonstrates embodiments of the steps of ribose-seq library construction as shown in FIG. 3. Ribose-seq employs the unique capacity of *Arabidopsis thaliana* tRNA ligase (AtRNL) to ligate 2',3'-cyclic monophosphate or 2'-monophosphate termini of DNA and RNA to 5'-monophosphate ends of DNA and RNA (7,8). A double-stranded (ds) sequencing adaptor, which has both primer sequences for later PCR amplification step, is initially ligated to genomic DNA fragments as AtRNL prefers self-ligation or circularization. Alkali treatment exposes the rNMP-specific 2',3'-cyclic monophosphate or 2'-monophosphate termini. Upon ligation by AtRNL, the rNMP is captured along with its upstream DNA sequence while unligated linear single-stranded (ss) DNA is degraded with T5 exonuclease. Yeast 2'-phosphotransferase Tpt1 then removes the 2'-monophosphate at the ligation junction, allowing subsequent PCR amplification of the library.

The details given in this Example demonstrate an Illumina library to be sequenced on MiSeq with 50-cycle single-end reads.

Reagents
 1. DNase/RNase-free water
 2. Qubit dsDNA HS Assay Kit (Life Technologies)
 3. Adaptor.L oligonucleotide (PAGE-purified, 5'-PNNNNNNNNAGATCGGAAGAGCGTCGTG-TAGGGAAAGAGGGAGTTCAGACGTGTGCTCTT CCGATCTAGCCAGCGCAGACCGTGAGGT-3') (Integrated DNA Technologies) (SEQ ID NO: 7)
 4. Adaptor.S oligonucleotide (Desalted, 5'-P-CCTCACG-GTCTGCGCTGGCT-Am-3') (SEQ ID NO: 8) (Integrated DNA Technologies)
 5. Annealing Buffer (500 mM Tris-HCl, pH 7.5, 2.5 M NaCl, 50 mM EDTA)
 6. illustra MicroSpin G-25 Column (GE Healthcare Life Sciences)
 7. 10×NEBuffer 2 (New England Biolabs)
 8. 20U/μL DraI (New England Biolabs)
 9. 20U/μL EcoRV (New England Biolabs)
 10. 5U/μL SspI (New England Biolabs)
 11. PCR Purification Kit (QIAGEN)
 12. Experion DNA 12K Analysis Kit (BIO-RAD)
 13. 10 mM dATP (Sigma-Aldrich)
 14. 5U/μL Klenow Fragment (3'→5' exo−) (New England Biolabs)
 15. 400U/μL T4 DNA Ligase with 10×T4 DNA Ligase Reaction Buffer (New England Biolabs)
 16. Agencourt RNAClean XP (Beckman Coulter)
 17. 2 M NaOH
 18. 2 M HCl
 19. pH Litmus Paper
 20. 3.75 uM purified AtRNL protein
 21. 10×AtRNL Reaction Buffer (500 mM Tris-HCl, pH 7.5, 400 mM NaCl, 50 mM MgCl2, 10 mM DTT, 300 μM ATP)
 22. 10U/μL T5 Exonuclease with 10×NEBuffer 4 (New England Biolabs)
 23. 37 uM purified Tpt1 protein
 24. 10×Tpt1 Reaction Buffer (200 mM Tris-HCl, pH 7.5, 50 mM MgCl2, 1 mM DTT, 4% Triton X-100)
 25. 50 mM NAD+(Sigma-Aldrich)
 26. PCR.1.Index oligonucleotide (Desalted, 5'-CAAGCAGAAGACGGCATACGAGATcgtgatGT-GACTGGAGTTCAGACGTGTGCTCTTCCGAT C-3') (Eurofins MWG Operon) (SEQ ID NO: 9)
 27. PCR.2 oligonucleotide (Desalted, 5'-AATGATACG-GCGACCACCGAGATCTACACTCTTTCCCTACAC-GACGCTCTTCCGATCT-3') (SEQ ID NO: 10)
 28. 2U/uL Phusion DNA Polymerase with 5×HF Buffer, 100% DMSO, and 10 mM dNTPs (New England Biolabs)
 29. 6% Non-denaturing Polyacrylamide (29:1) Mini-Gel
 30. 1×TBE Buffer
 31. SYBR Gold Nucleic Acid Stain (Life Technologies)

Equipment
 1. Qubit 2.0 (Life Technologies)
 2. Experion Automated Electrophoresis System (BIO-RAD)
 3. NanoDrop Spectrophotometer (Thermo Scientific)
 4. Thermal Cycler for PCR
 5. Mini-PROTEAN Tetra Cell (BIO-RAD)
 6. Gel Imaging System (UV-light)

Procedure

Preparation of rNMPs-Embedded in Genomic DNA

1. Extract a minimum of 10 ug of genomic DNA from the cells. Various methods of genomic DNA extraction could be used. Koh et al. (1) used *S. cerevisiae* cells and the protocol "Preparation of Yeast Samples" in the QIAGEN Genomic DNA Handbook.

3. Use Qubit 2.0 (dsDNA HS) to quantify the amount of extracted genomic DNA.

Preparation of Ds Sequencing Adaptor

1. Each of oligonucleotides (oligos) Adaptor.L and Adaptor.S can be resuspended in DNase/RNase-free water to a concentration of 50 µM and 500 µM, respectively. (All subsequent steps of the protocol use DNase/RNase-free water).

2. Set up the mixture for annealing Adaptor.L/Adaptor.S as follows:

Annealing Buffer: 3 µL
50 µM Adaptor. L: 25 µL
500 µM Adaptor.S: 12.5 µL
$H_2O$: 9.5 µL
Total: 50 µL 5-fold excess of Adaptor.S was added to the mixture to ensure that all Adaptor.L molecules are annealed to Adaptor.S. The remaining single-stranded Adaptor.S will be removed in subsequent purification steps.

3. Perform annealing by heating the mixture to about 95-100° C. and gradually cooling to room temperature. The resulting ds Adaptor.L/Adaptor.S is at a concentration of 25 uM.

4. Desalt the mixture by using a spin column. Koh et al. 1 used illustra MicroSpin G-25 Column.

5. Use NanoDrop to quantify the amount of desalted ds Adaptor.L/Adaptor.S. Typically, the yielded concentration ranges from 10 to 13 µM. A concentration of 10 µM will be assumed for subsequent steps of the protocol.

Fragmentation of rNMPs-Embedded in Genomic DNA

1. Set up 2 identical reactions of restriction enzyme digestion of genomic DNA as follows (for *S. cerevisiae* genomic DNA as an example):

10×NEBuffer 2: 12 µL
Genomic DNA: 5 ug (x µL)
20U/µL DraI: 4 µL
20U/µL EcoRV: 4 µL
5U/µL SspI: 4 µL
$H_2O$: 96-x µL
Total: 120 µL Genomic DNA can be digested with a different set of blunt-end resulting restriction enzymes. It can be preferable that the restriction sites are well-distributed in the genome and that the digestion results in a population of fragments with an average size of 800-1,500 bp.

2. Incubate at 37° C. overnight.

3. Purify the fragmented DNA by using a spin column. Koh et al. (1) used the QIAGEN spin column from their PCR Purification Kit. Both reactions can be purified using a single column with elution volume of 30 µL.

4. Use Qubit 2.0 (dsDNA HS) to quantify the amount of fragmented DNA. Typically, the concentration of the resulting DNA is ~200 ng/µL, following the reaction conditions listed above. A concentration of 200 ng/µL will be assumed for subsequent steps of the protocol.

5. Check the size range of the fragmented DNA by using the Experion DNA 12K Analysis Kit. Typically, with the reaction conditions listed above, the fragmentation results in an average size of about 1,500 bp.

dA-Tailing and Ds Sequencing Adaptor-Ligation of Fragmented rNMPs-Embedded DNA

1. Set up a dA-tailing reaction as follows:
10×NEBuffer 2: 5 µL
10 mM dATP: 1 µL
200 ng/µL Fragmented DNA: 25 µL (5 µg)
5U/µL Klenow Fragment (3'→5' exo-): 3 µL
$H_2O$: 16 µL
Total: 50 µL 2. Incubate at 37° C. for 30 min.

3. Purify using a spin column. Koh et al. (1) used the QIAGEN spin column from their PCR Purification Kit, with elution volume of about 30 µL.

4. Set up a sequencing adaptor-ligation reaction as follows:

10×T4 DNA Ligase Buffer: 5 µL
10 uM Adaptor.L/Adaptor.S: 5 µL
dA-tailed DNA: 30 µL
400U/uL T4 DNA Ligase: 5 µL
$H_2O$: 5 µL
Total: 50 µL 5. Incubate at 15° C. overnight.

6. Purify using Agencourt RNAClean XP with elution volume of 30 µL.

Alkali treatment of adaptor-ligated rNMPs-embedded DNA

1. Set up an alkali-treatment reaction as follows:
2 M NaOH: 7.5 µL
Adaptor-ligated DNA: 30 µL
$H_2O$: 12.5 µL
Total: 50 µL 2. Incubate at 55° C. for 2 h.

3. Neutralize with 2 M HCl to pH 7. Use pH Litmus Paper to check the pH. Typically, 7.5-8 µL is used for neutralization.

4. Purify using Agencourt RNAClean XP with elution volume of 20 µL.

5. Heat the resulting solution at 95° C. for 3 min to ensure denaturation of dsDNA and immediately chill on ice.

Self-Ligation (Circularization) of rNMP-Terminating DNA by AtRNL

1. Set up 2 reactions, one without AtRNL (AtRNL−) and one with (AtRNL+), as follows:

AtRNL−
10×AtRNL Reaction Buffer: 2 µL
Alkali-treated DNA: 10 µL
$H_2O$: 8 µL
Total: 20 µL AtRNL+
10×AtRNL Reaction Buffer: 2 µL
Alkali-treated DNA: 10 µL
3.75 µM AtRNL: 5.4 µL
$H_2O$: 2.6 µL
Total: 20 µL Final reaction concentration of AtRNL is about 1 µM.

3. Incubate all reactions at about 30° C. for about 1 h.

4. Purify each reaction using RNAClean XP with elution volume of 30 µL.

Removal of linear ssDNA

1. Set up 4 reactions, one without (AtRNL−T5Exo−; AtRNL+T5Exo−) and one with T5 Exonuclease (AtRNL−T5Exo+; AtRNL+T5Exo+) for each of AtRNL− and AtRNL+ product, as follows:

AtRNL−T5Exo−
10×NEBuffer 4: 5 µL
AtRNL−DNA: 15 µL
$H_2O$: 30 µL

Total: 50 μL
AtRNL−T5Exo+
10×NEBuffer 4: 5 μL
AtRNL−DNA: 15 μL
10U/μL T5 Exonuclease: 5 μL
H$_2$O: 25 μL
Total: 50 μL
AtRNL+T5Exo−
10×NEBuffer 4: 5 μL
AtRNL+DNA: 15 μL
H$_2$O: 25 μL
Total: 50 μL
AtRNL+T5Exo+
10×NEBuffer 4: 5 μL
AtRNL+DNA: 15 μL
10U/uL T5 Exonuclease: 5 μL
H$_2$O: 25 μL
Total: 50 μL
T5Exo− samples are optional as dA-tailing and adaptor-ligation reactions are standard steps. They can act as positive control for the later PCR reaction.
2. Incubate all reactions about 37° C. for 2 h.
3. Purify each reaction using RNAClean XP with elution volume of 20 μL.

Removal of 2'-Phosphate at the Ligation Junction
1. Set up 4 reactions with Tpt1 for each of AtRNL−T5Exo−, AtRNL−T5Exo+, AtRNL+T5Exo−, and AtRNL+T5Exo+ products, as follows:
Tpt1+
10×Tpt1 Reaction Buffer: 4 μL
50 mM NAD+: 8 μL
DNA: 20 μL
37 uM Tpt1: 1.1 μL
H$_2$O: 6.9 μL
Total: 40 μL
Final reaction concentration of Tpt1 is 1 μM. DNA indicates either AtRNL−T5Exo−, AtRNL−T5Exo+, AtRNL+T5Exo−, or AtRNL+T5Exo+ product.
2. Incubate all reactions at about 30° C. for 1 hr.
3. Purify each reaction using RNAClean XP with elution volume of about 30 μL.

Figure 24B:
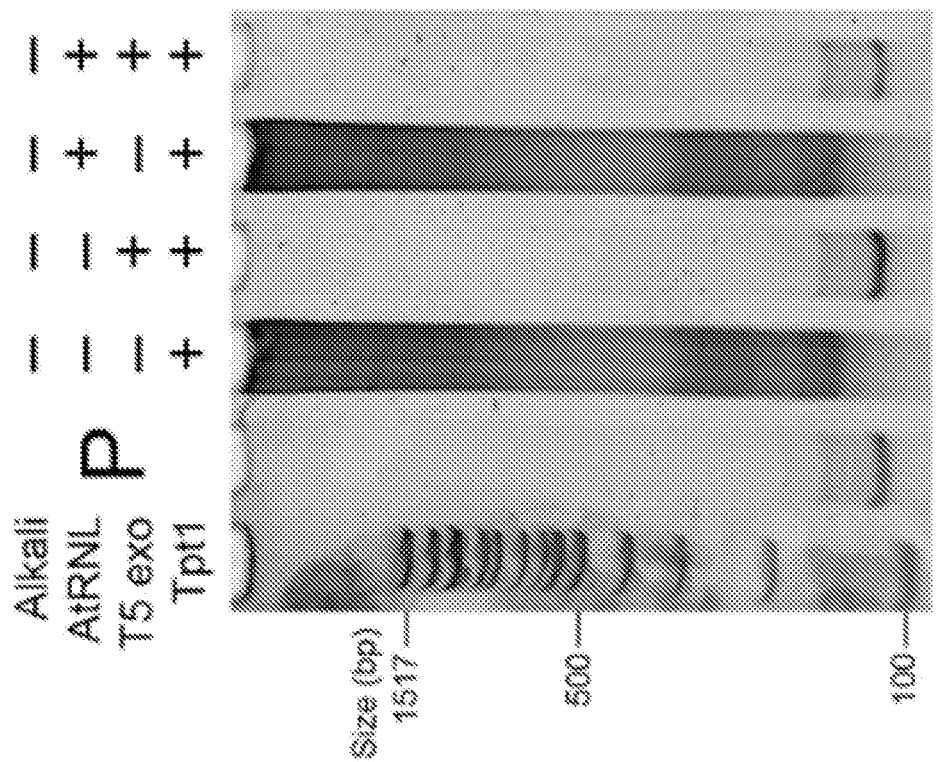
FIGS. 24A-24B show images demonstrating a Ribose-seq library from genomic DNA of S. cervisiae rnh201Δ (KK-100) cells. Appropriate PCR products were analyzed by PAGE. 'P' indicates primers-only. No amplification product was observed when either (FIG. 24A) AtRNL ligation step or (FIG. 24B) alkali treatment was omitted. Tpt1 denotes the step of 2'-phosphate removal at the ligation junction in FIGS. 1-2. First left lane, ds DNA ladder.
Figure 24A:
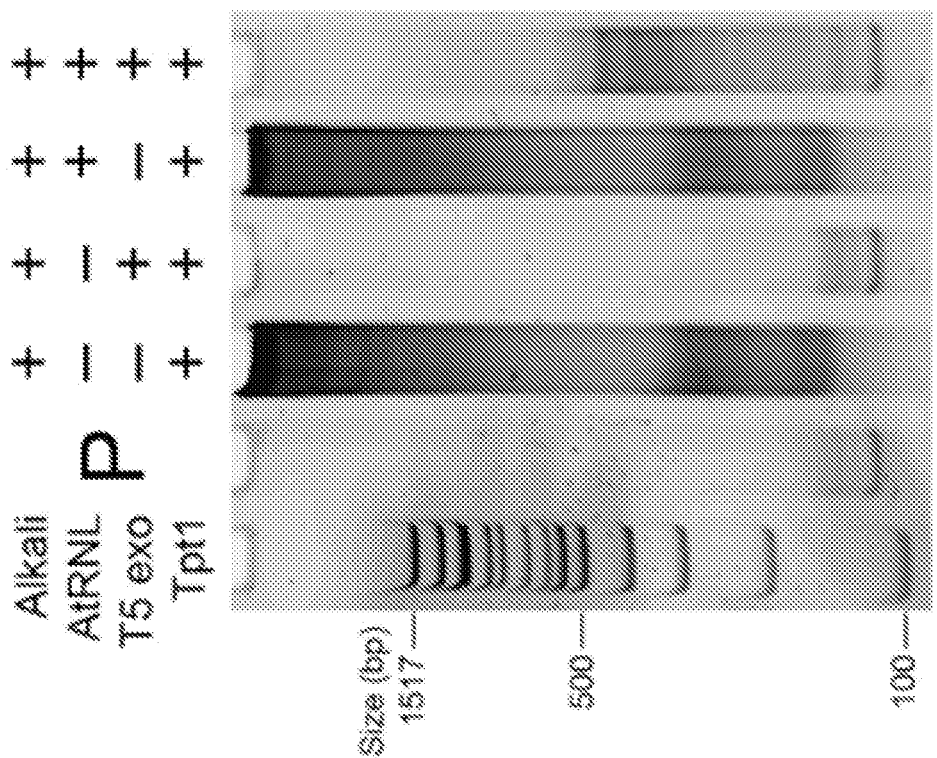

PCR Amplification and Library Verification
1. Set up 5 PCR reactions, one without any template (Primers-only) and four with each of AtRNL−T5Exo−Tpt1+, AtRNL−T5Exo+Tpt1+, AtRNL+T5Exo−Tpt1+, or AtRNL+T5Exo+Tpt1+ products, as follows:
Primers-Only
5×HF Buffer: 10 μL
10 mM dNTPs: 2 μL
100% DMSO: 0.5 μL
40 uM PCR.1.Index: 1 μL
40 uM PCR.2: 1 μL
2U/uL Phusion DNA Polymerase: 0.5 μL
H$_2$O: 35 μL
Total: 50 μL
Template+
5×HF Buffer: 10 μL
10 mM dNTPs: 2 μL
100% DMSO: 0.5 μL
40 μM PCR.1.Index: 1 μL
40 μM PCR.2: 1 μL
DNA: 20 μL
2U/μL Phusion DNA Polymerase: 0.5 μL
H$_2$O: 15 μL
Total: 50 μL
DNA indicates either AtRNL−T5Exo−Tpt1+, AtRNL−T5Exo+Tpt1+, AtRNL+T5Exo−Tpt1+, or AtRNL+T5Exo+Tpt1+ product. 5-30 μL of each product could be used as template for PCR. Koh et al. (1) used 20 μL. For products which were not treated with T5 Exonuclease (AtRNL−T5Exo−Tpt1+ and AtRNL+T5Exo−Tpt1+), 5 μL is sufficient to visualize non-specific amplification.
2. Run PCR with the following settings:
98° C. for 30 s
98° C. for 10 s, 65° C. for 20 s, and 72° C. for 30 s (repeated for 30 cycles)
72° C. for 5 m
4° C.
PCR can be run for 26-32 cycles. Koh et al. used 30 cycles.
3. Run 6% Non-denaturing PAGE with 10 uL aliquot of each sample. Koh et al. used 100 by DNA
Ladder (NEB) as the ladder.
4. Stain the gel in 1×SYBR Gold (Life Technologies) for 30-40 m.
5. Visualize under UV light. An exemplary gel image is shown in FIGS. 24A-24B
2. AtRNL+T5Exo+Tpt1+ sample will be the ribose-seq library while Primers-only and AtRNL−T5Exo+Tpt1+ samples will be the controls where no amplification should be observed (only primer dimers).
6. Purify PCR mixtures from Primers-only, AtRNL−T5Exo+Tpt1+, and AtRNL+T5Exo+Tpt1+ using RNAClean XP with elution volume of 15 μL. Controls Primers-only and AtRNL−T5Exo+Tpt1+ are also purified so that the amount of actual ribose-seq library can be determined and quantitatively confirmed.
7. Use Qubit 2.0 (dsDNA HS) or other suitable protocol to quantify the amount of ribose-seq library. Confirm that the amount of purified Primers-only product is similar to the amount of AtRNL−T5Exo+Tpt1+. The amount of the actual ribose-seq library can be calculated by subtracting the amount of AtRNL−T5Exo+Tpt1+(which should be just primer dimers) from AtRNL+T5Exo+Tpt1+. Typically, about 25 nM of the ribose-seq library is resulted.

References for Example 2

1 Koh, K. D., Balachander, S., Hesselberth, J. R. & Storici, F. Ribose-seq: global mapping of ribonucleotides embedded in genomic DNA. Nat. Methods 12, 251-257 (2015).
2 Williams, J. S. & Kunkel, T. A. Ribonucleotides in DNA: origins, repair and consequences. DNA Repair (Amst.) 19, 27-37 (2014).
3 Potenski, C. J. & Klein, H. L. How the misincorporation of ribonucleotides into genomic DNA can be both harmful and helpful to cells. Nucleic Acids Res. 42, 10226-10234 (2014).
4 Lujan, S. A., Williams, J. S., Clausen, A. R., Clark, A. B. & Kunkel, T. A. Ribonucleotides are signals for mismatch repair of leading-strand replication errors. Mol. Cell 50, 437-443 (2013).
5 Reijns, M. A. et al. Lagging-strand replication shapes the mutational landscape of the genome. Nature 518, 502-506 (2015).
6 Reijns, M. A. et al. Enzymatic removal of ribonucleotides from DNA is essential for mammalian genome integrity and development. Cell 149, 1008-1022 (2012).
7 Schutz, K., Hesselberth, J. R. & Fields, S. Capture and sequence analysis of RNAs with terminal 2',3'-cyclic phosphates. RNA 16, 621-631 (2010).

8 Remus, B. S. & Shuman, S. Distinctive kinetics and substrate specificities of plant and fungal tRNA ligases. RNA 20, 462-473 (2014).

Example 3

Computational Analysis of "ribo-seq" Libraries
Introduction rNMPs embedded in DNA are the most prevalent nonstandard nucleotide found in DNA. They can be incorporated into DNA during DNA replication and repair and/or formed during DNA damage. rNMPs in DNA can distort the double helix, which can result in genome instability and disease. rNMPs may therefore have clinical signification for a variety of disease (e.g. Aicardi-Goutieres syndrome, systemic Lupus erythematosus, and various types of cancer). FIG. 3 demonstrates an embodiment of a method to detect embedded rNMPs in DNA. Profiling of rNMPs embedded in DNA can facilitate identification, inter alia, of biomarkers for disease and drug targets and facilitate, inter alia, an understanding of diseases and normal and abnormal function of DNA.

Generally, libraries were created using the ribose-seq method described elsewhere herein. The libraries generated were sequenced using Illumina Mi-Seq. The reads were aligned to the reference genome of interest. Then a computational analysis of the ribose-seq libraries was conducted. During computational analysis the coordinates of the rNMPs were determined, nucleotide (rNMP and dTNP) frequencies were calculated, and distribution of rNMPs in the genome and any hotspots of rNMPs were identified.

Figure 41:
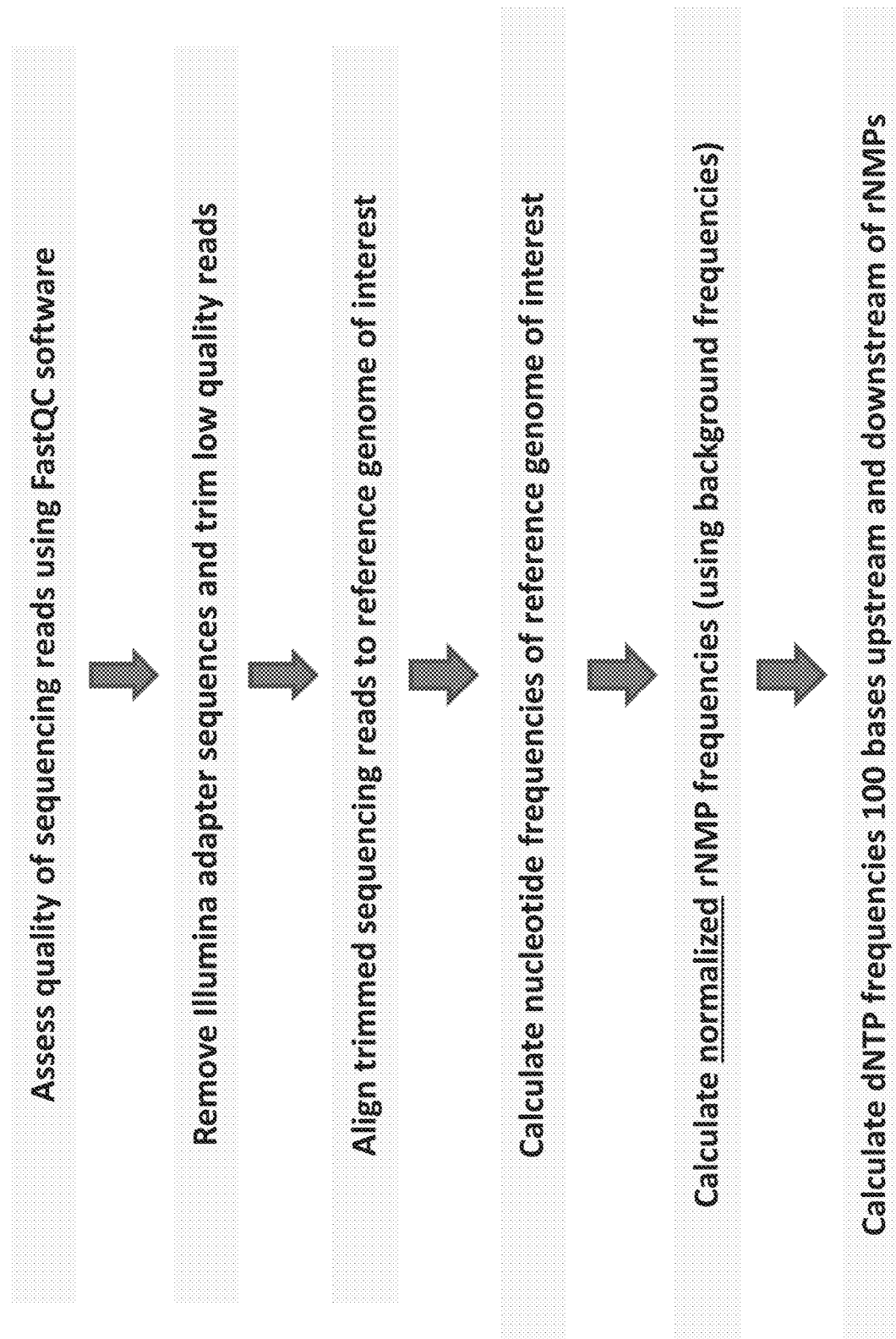
FIG. 41 shows steps in an embodiment of a computational analysis of libraries generated by ribose-seq.
Figure 42A:
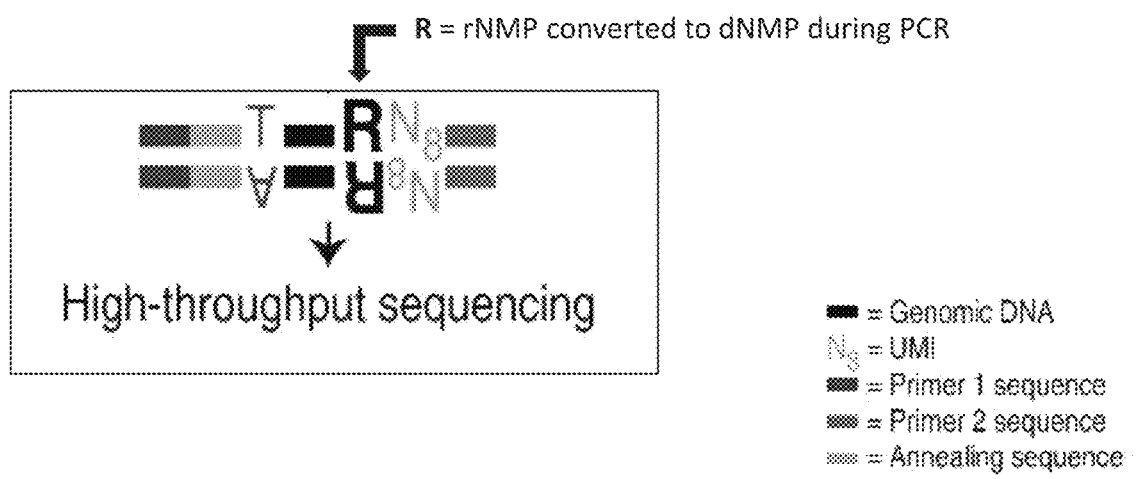
Figure 43:
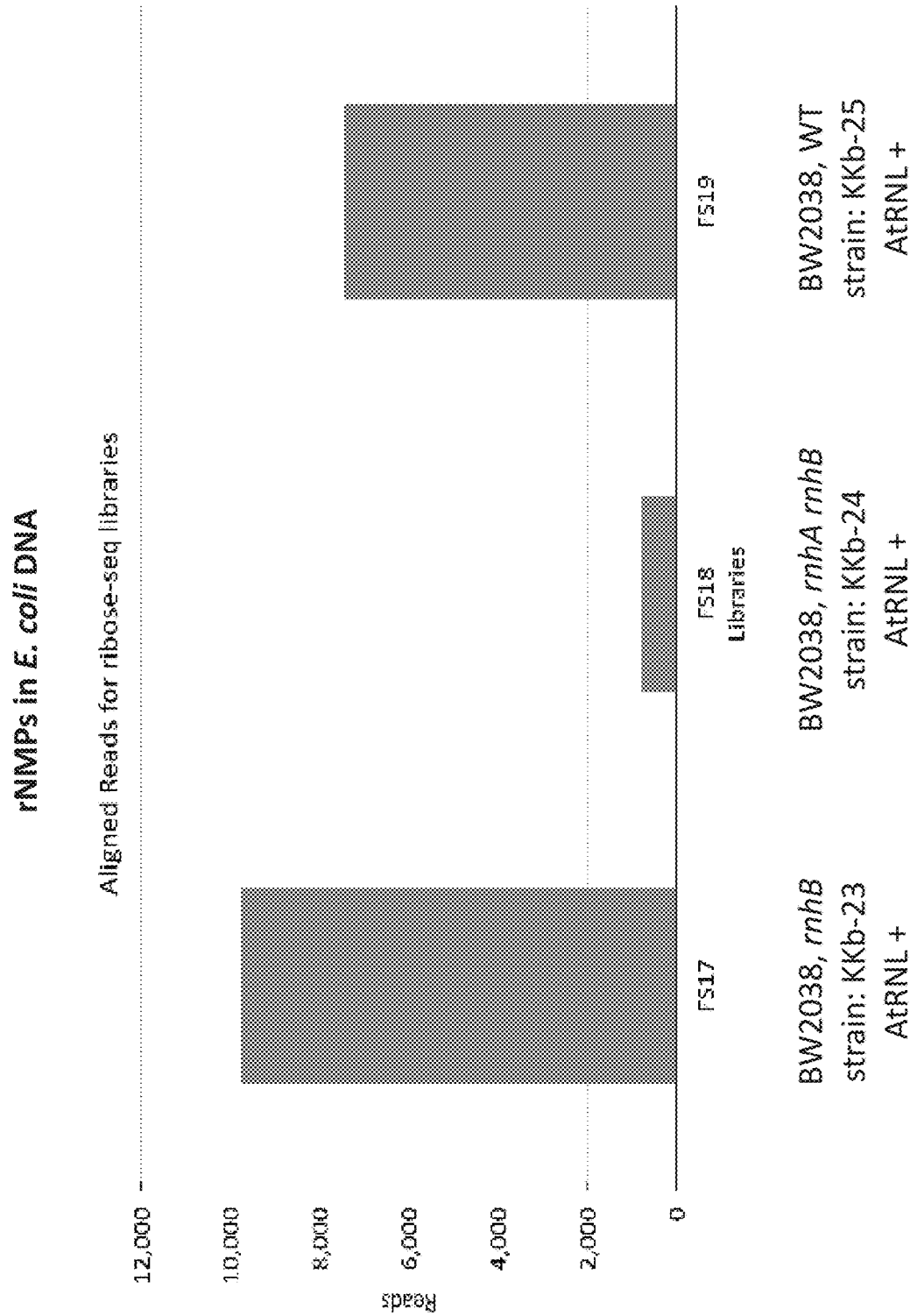
FIG. 43 shows a graph demonstrating aligned reads for ribose-seq libraries for detecting rNMPs in *E. coli* DNA.
Figure 44:
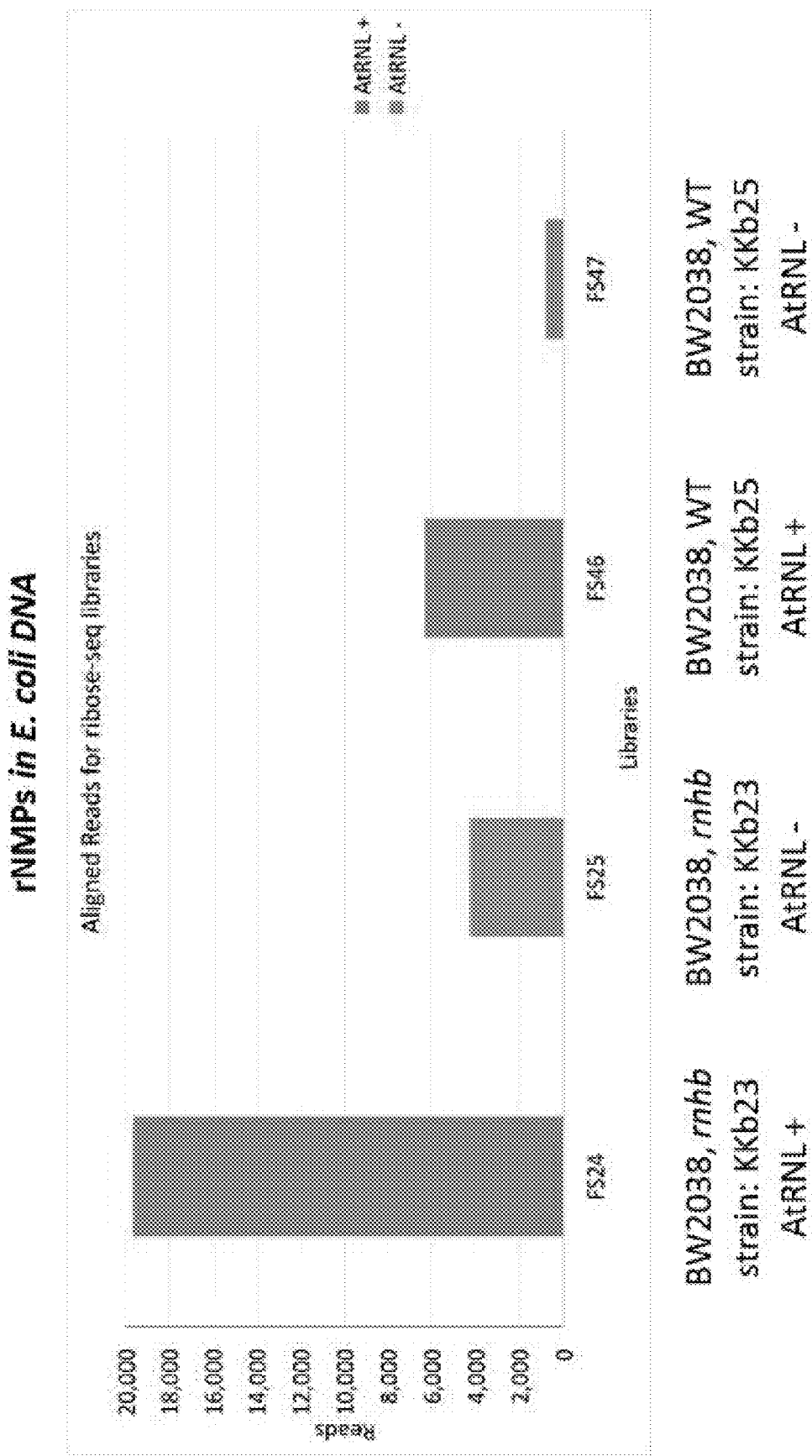
FIG. 44 shows a graph demonstrating aligned reads for ribose-seq libraries for detecting rNMPs in *E. coli* DNA generated with and without AtRNL.
Figure 45:
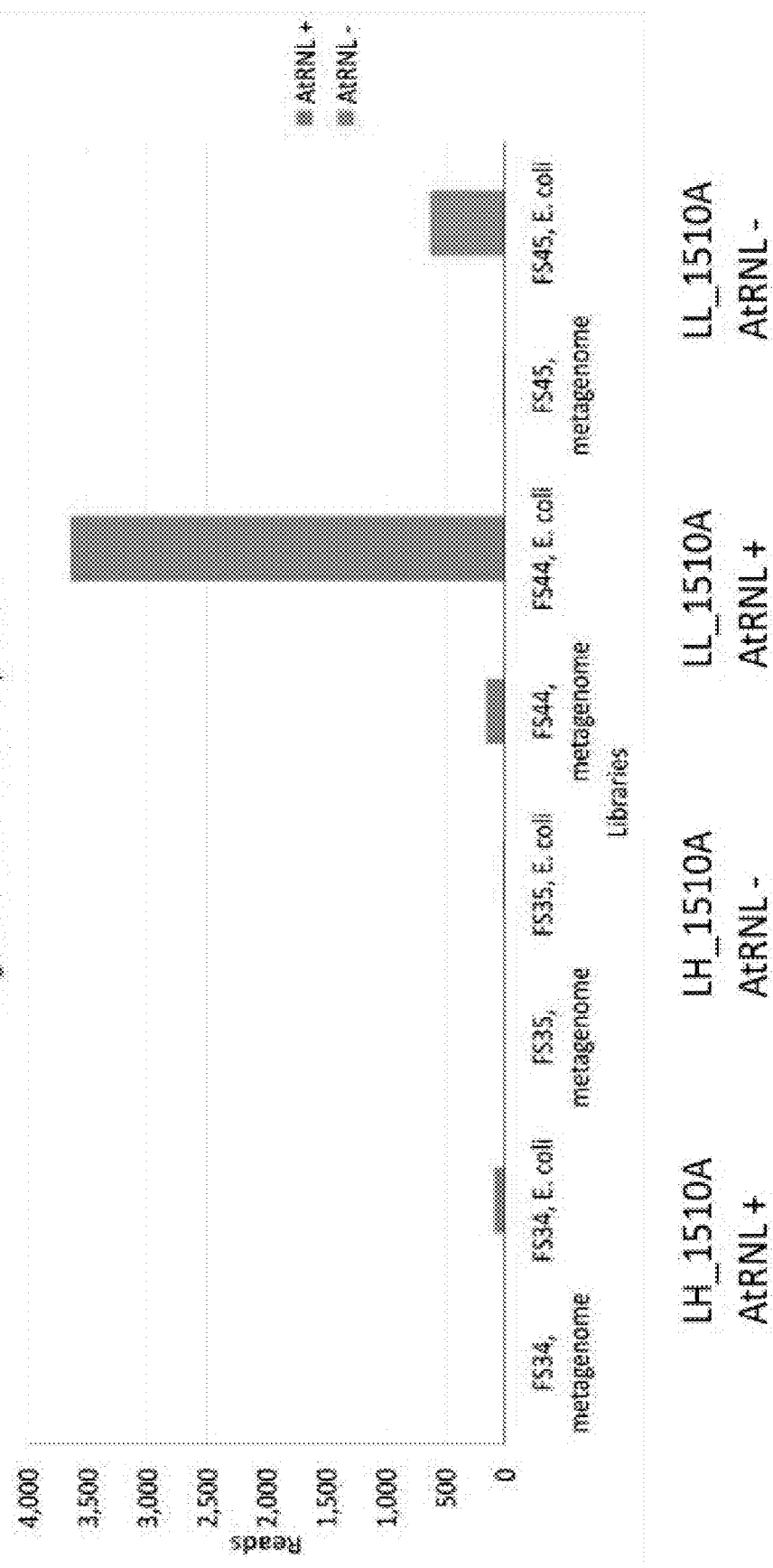
FIG. 45 shows a graph demonstrating aligned reads for ribose-seq libraries for examining rNMPs in a metagenome.
Figure 46:
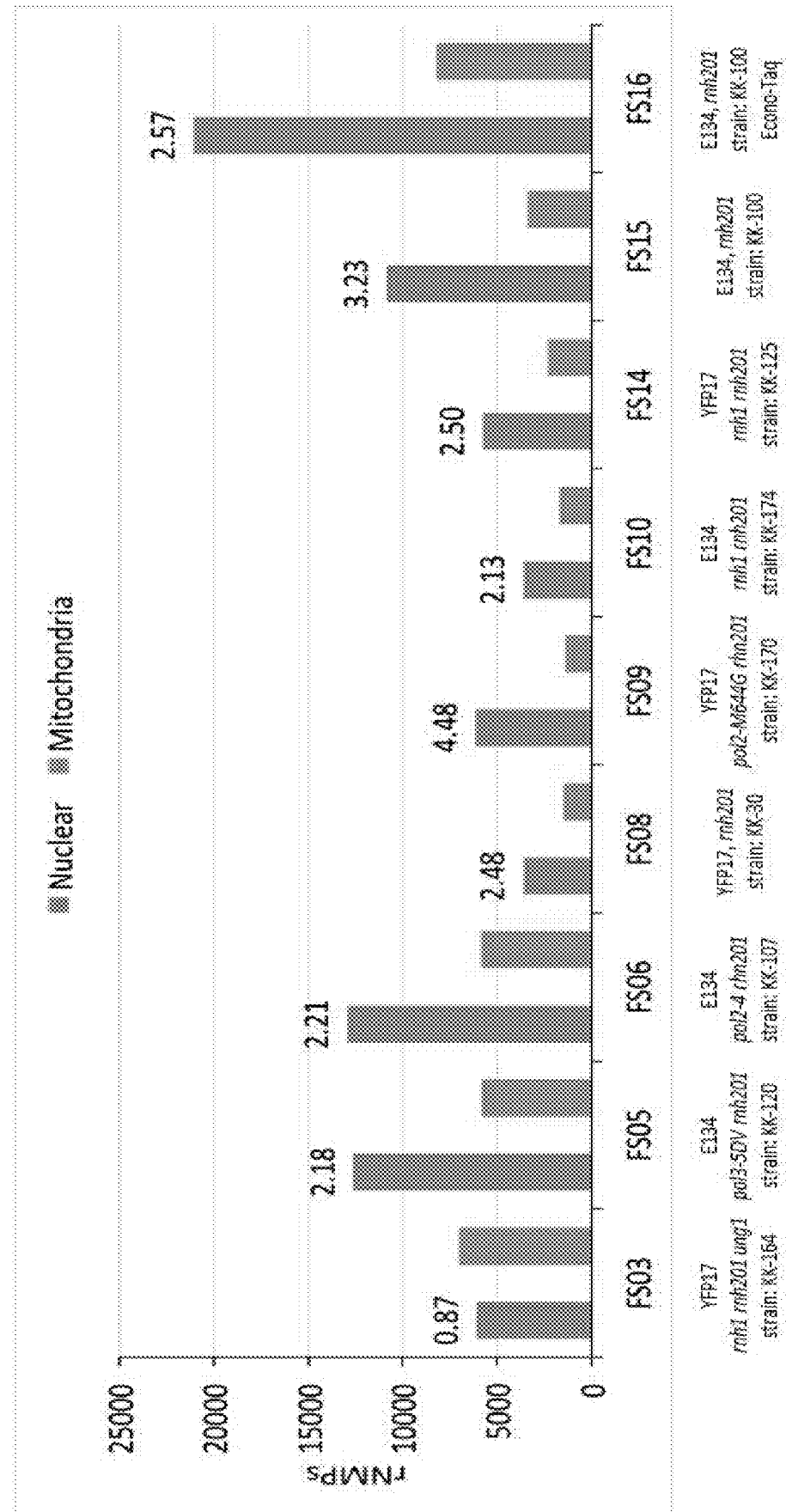
FIG. 46 shows a graph demonstrating rNMPs in *S. cerevisiae* nuclear and mitochondria genomic DNA in ribose-seq libraries.
Figure 47:
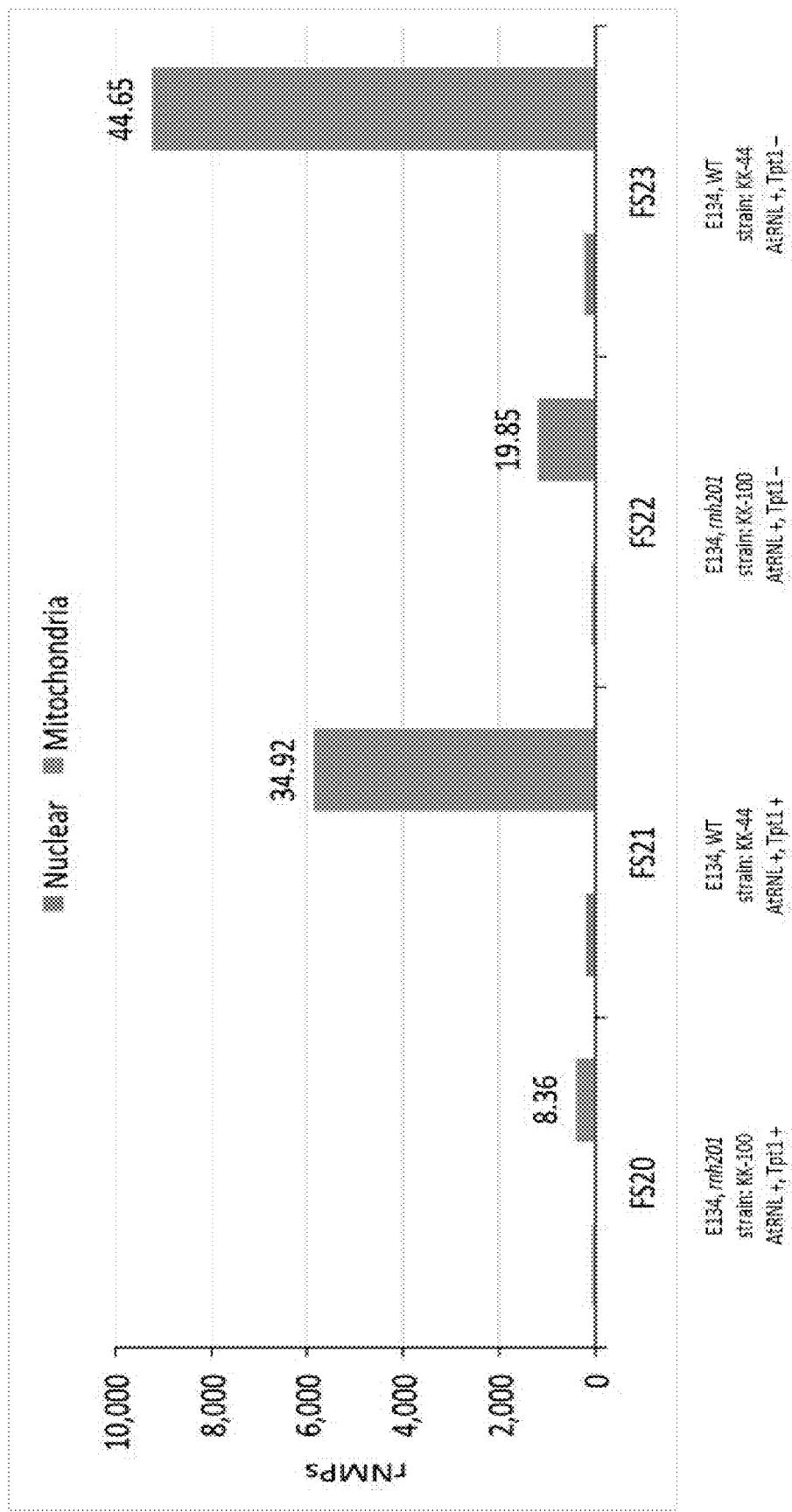
FIG. 47 shows a graph demonstrating rNMPs in *S. cerevisiae* nuclear and mitochondria genomic DNA in ribose-seq libraries.
Figure 48:
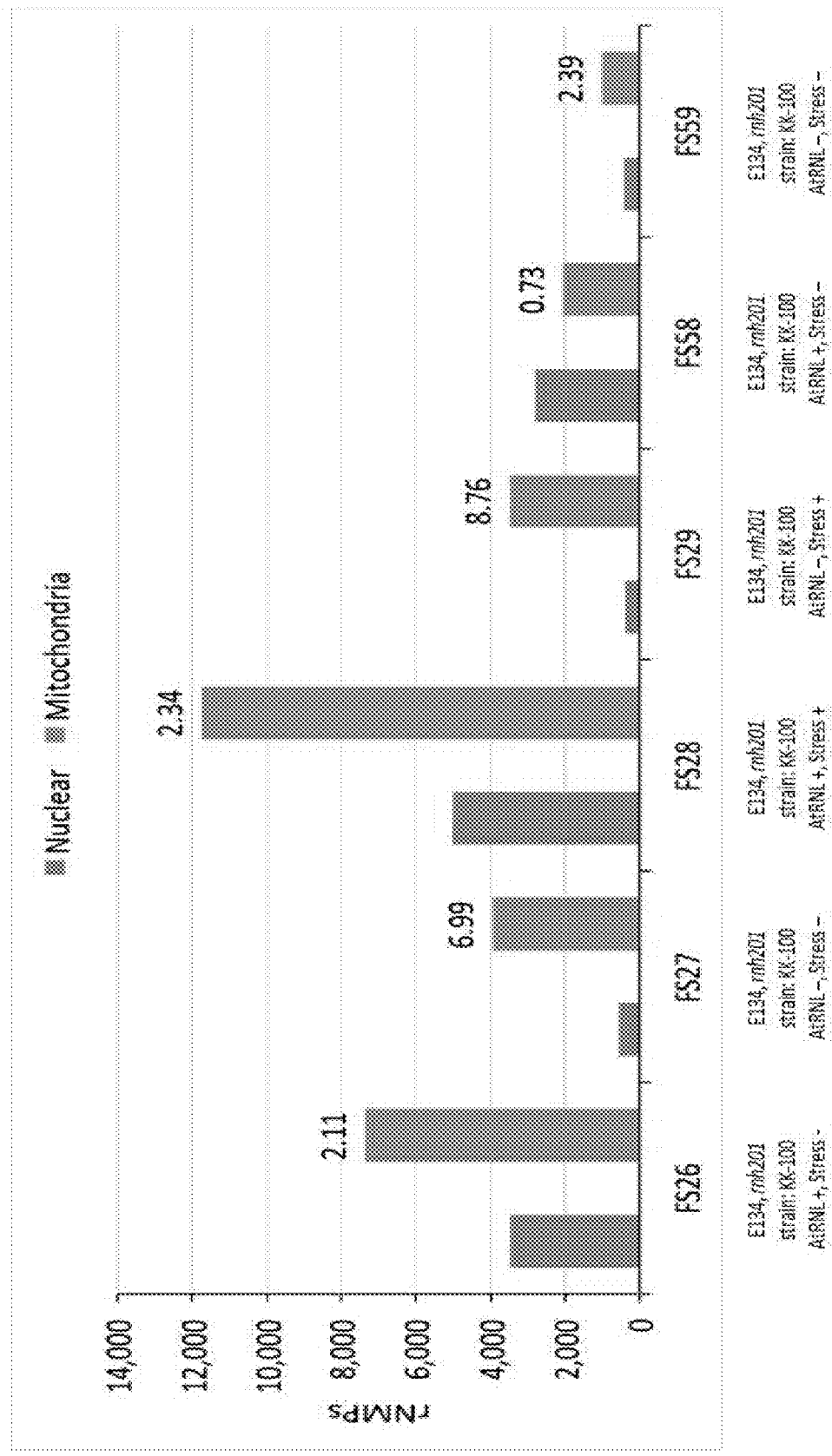
FIG. 48 shows a graph demonstrating rNMPs in *S. cerevisiae* nuclear and mitochondria genomic DNA.
Figure 49:
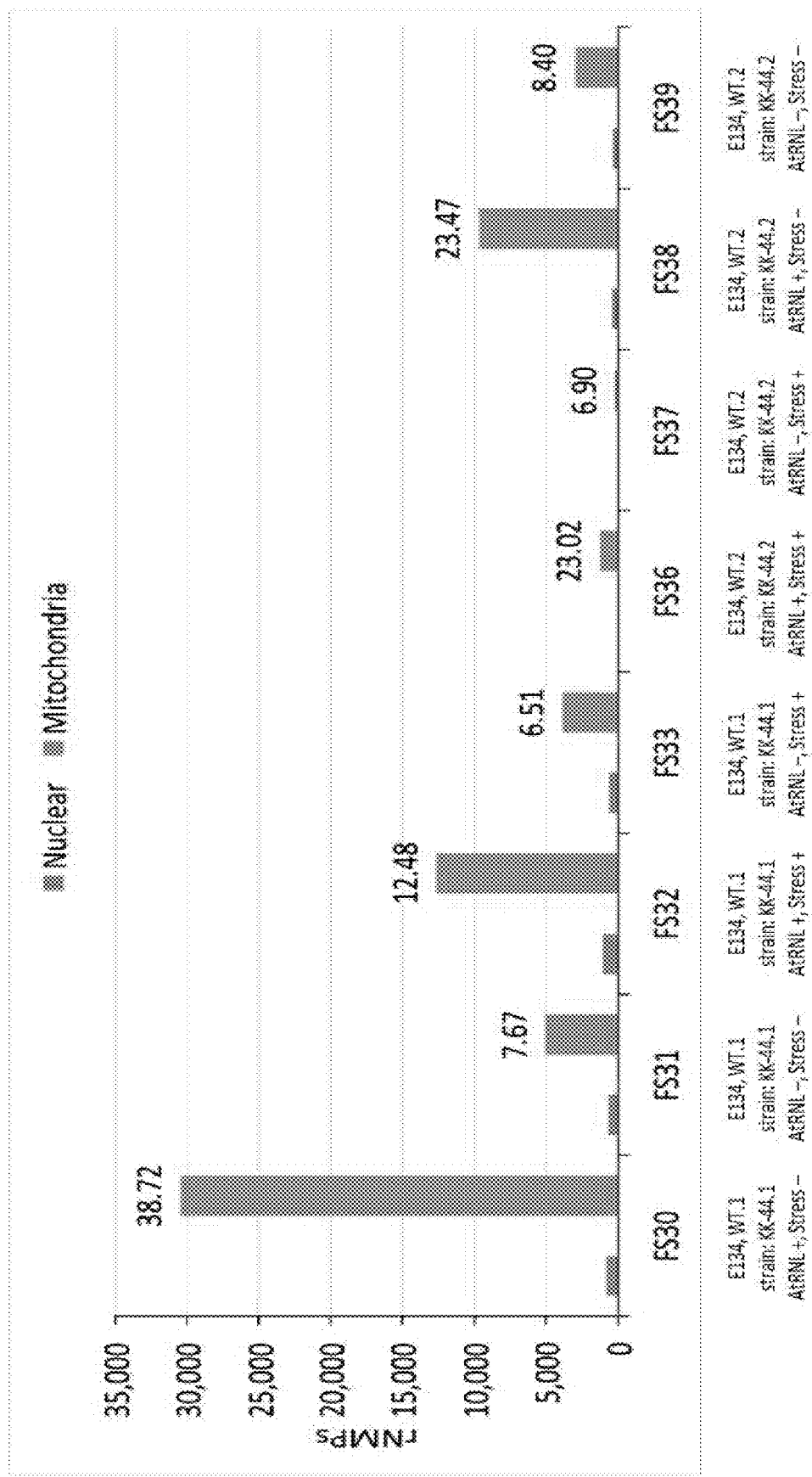
FIG. 49 shows a graph demonstrating rNMPs in *S. cerevisiae* nuclear and mitochondria genomic DNA.
Figure 50:
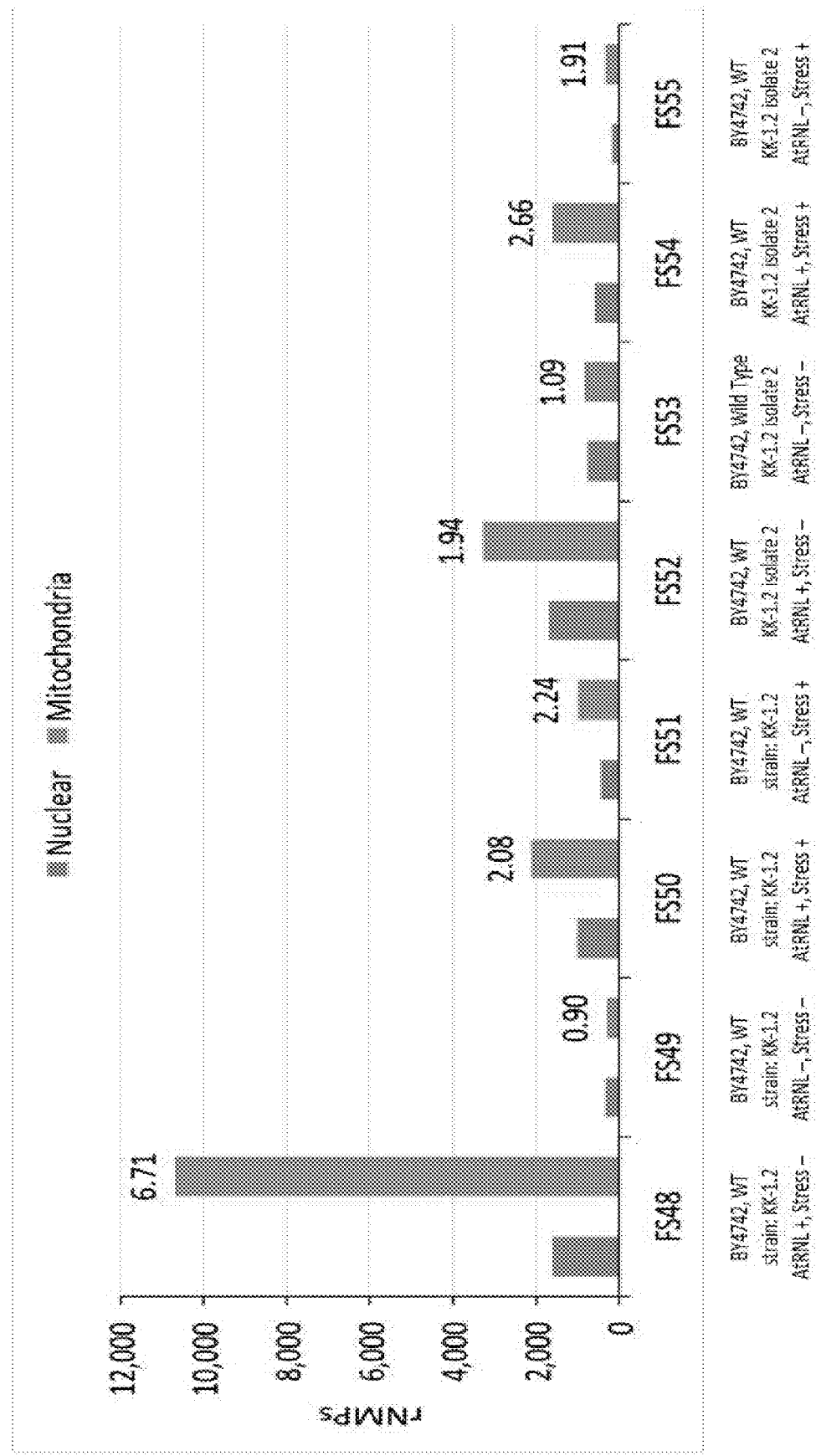
FIG. 50 shows a graph demonstrating rNMPs in *S. cerevisiae* nuclear and mitochondria genomic DNA.
Figure 51:
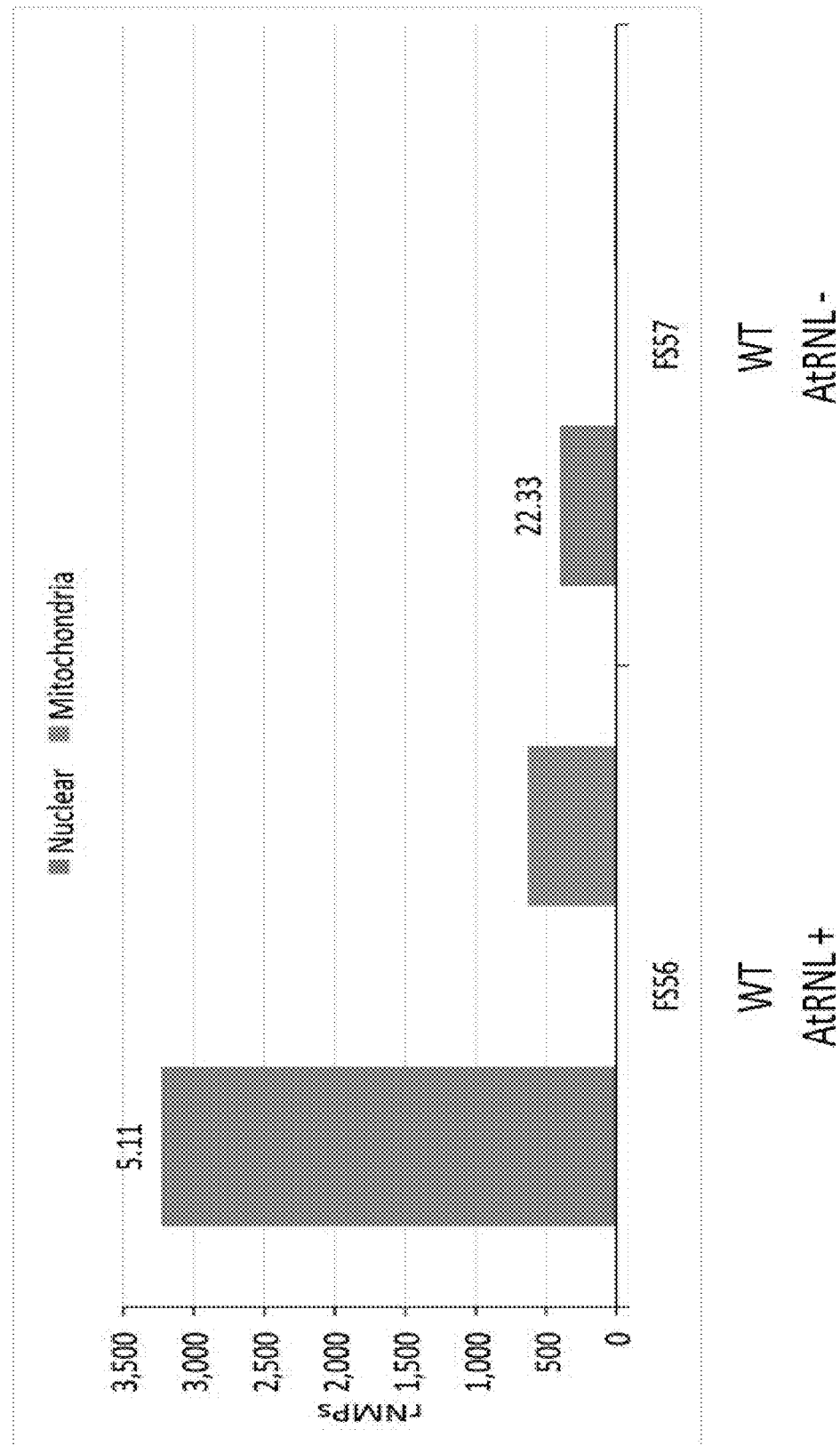
FIG. 51 shows a graph demonstrating rNMPs in HeLa cell nuclear and mitochondria genomic DNA.
Figure 52:
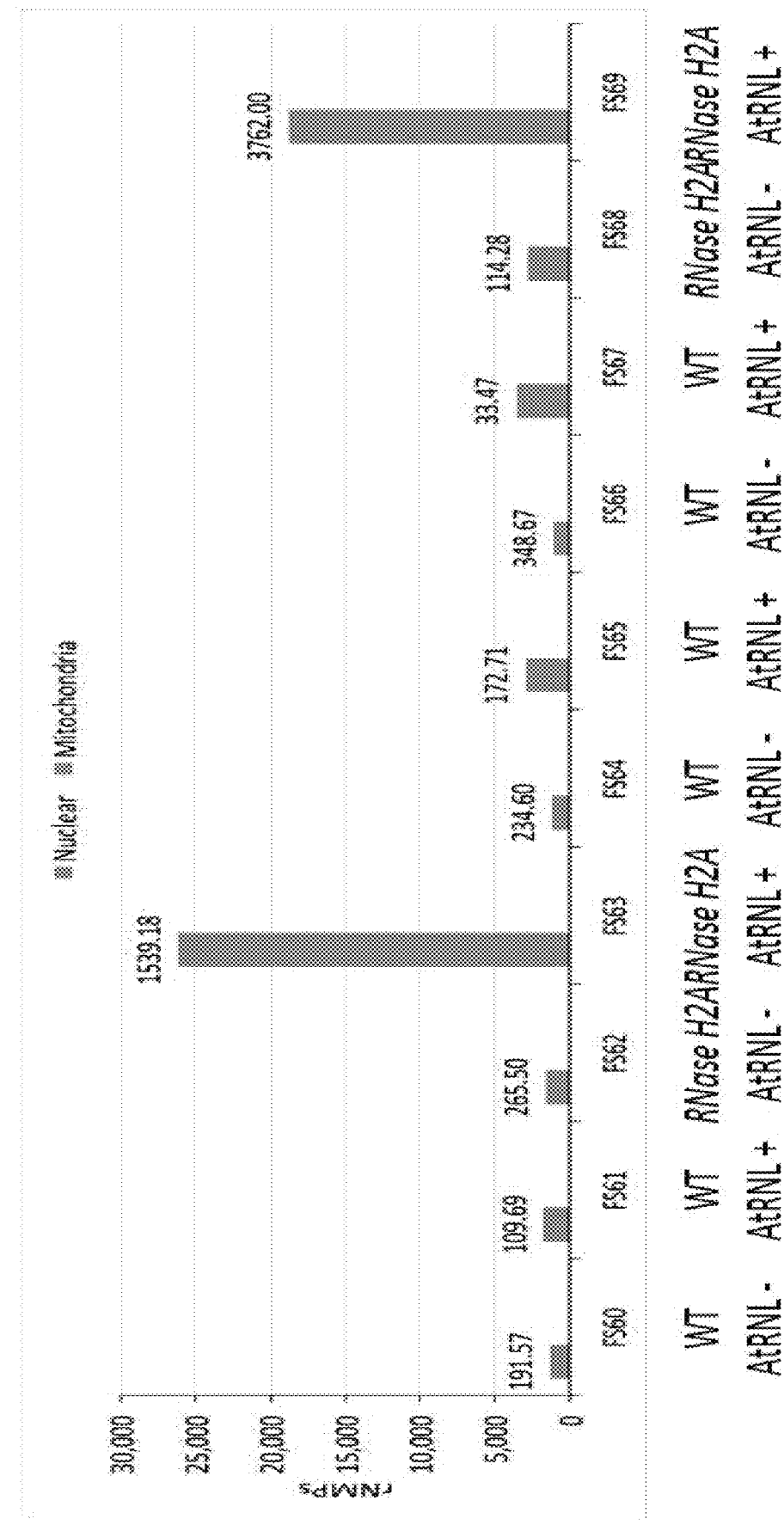
FIG. 52 shows a graph demonstrating rNMPs in mouse embryonic fibroblast cell (MEF) nuclear and mitochondria genomic DNA.
Figure 53:
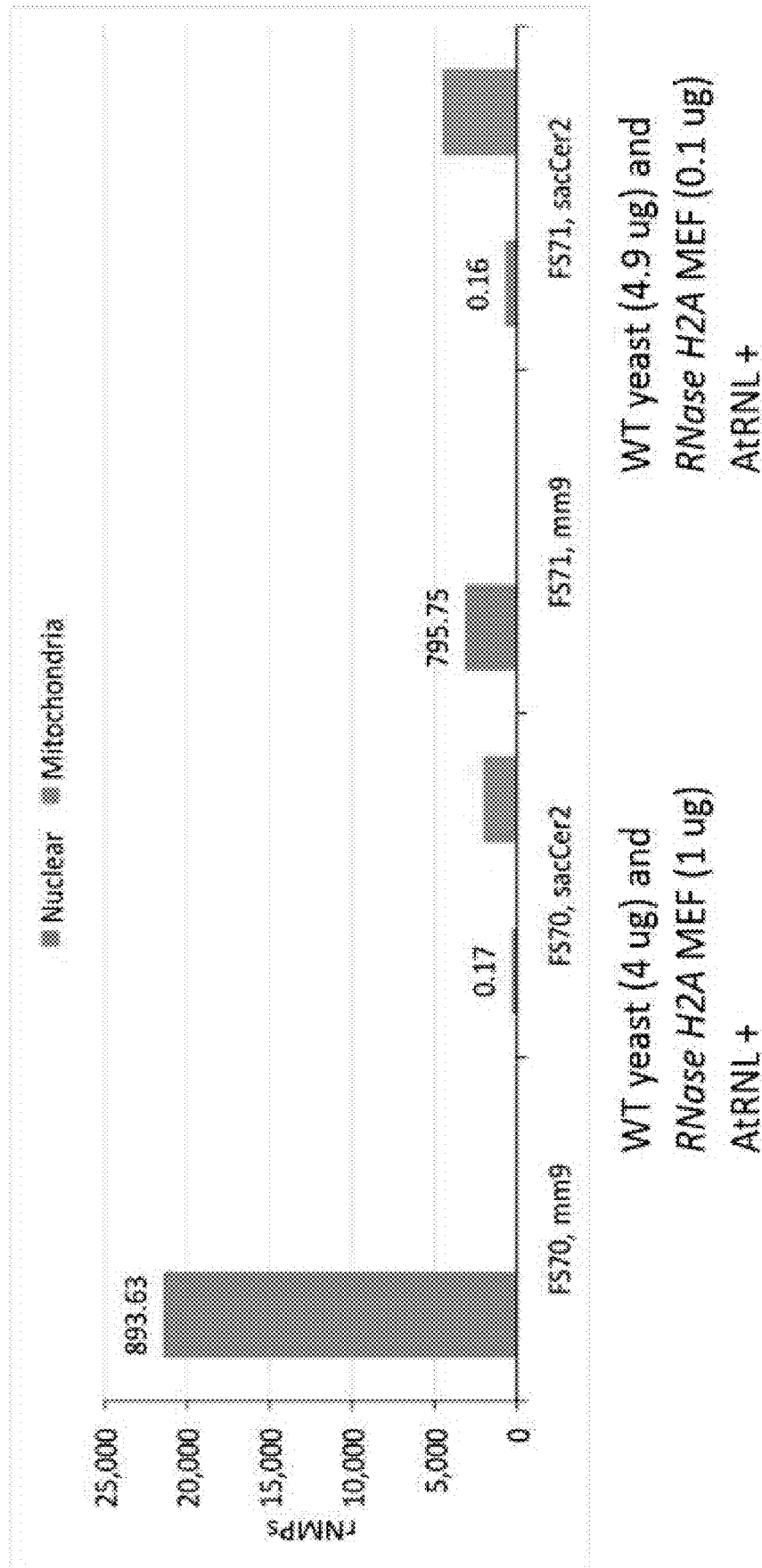
FIG. 53 shows rNMPs in *S. cerevisiae*/MEF nuclear and mitochondria genomic DNA.
Figure 54A:
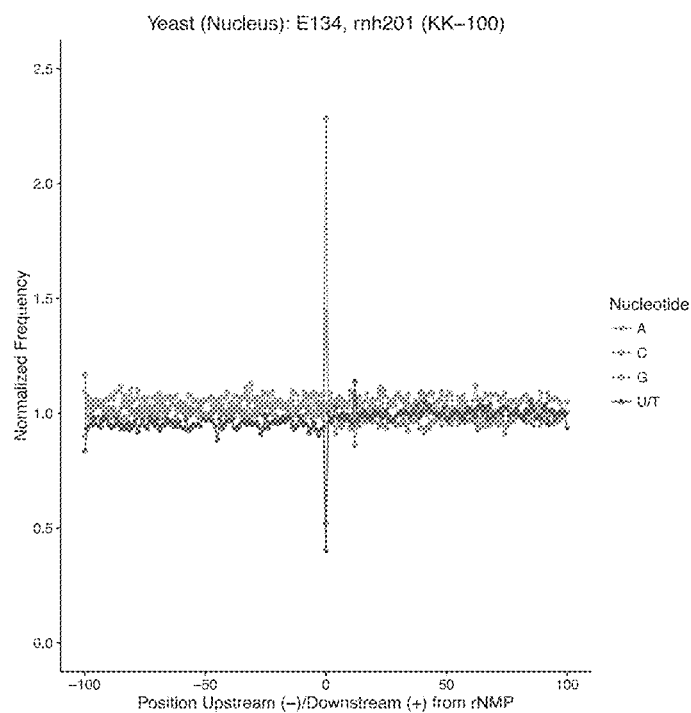
FIGS. 54A-54XX shows nucleotide frequencies for embedded rNMPs determined via an embodiment of a computational analyses.
Figure 54B:
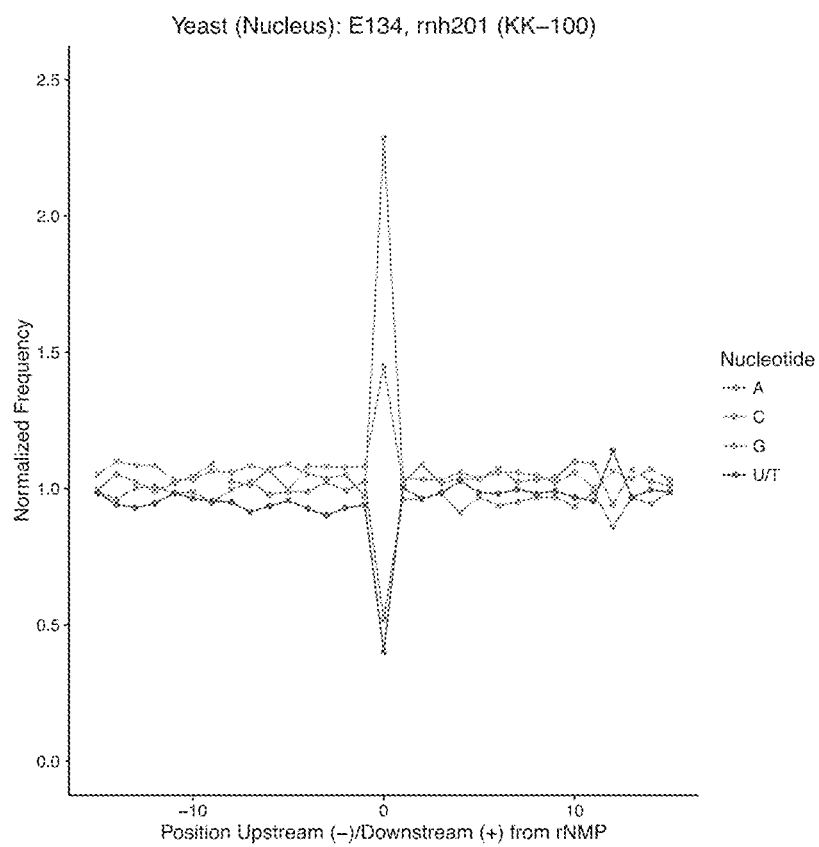
Figure 54C:
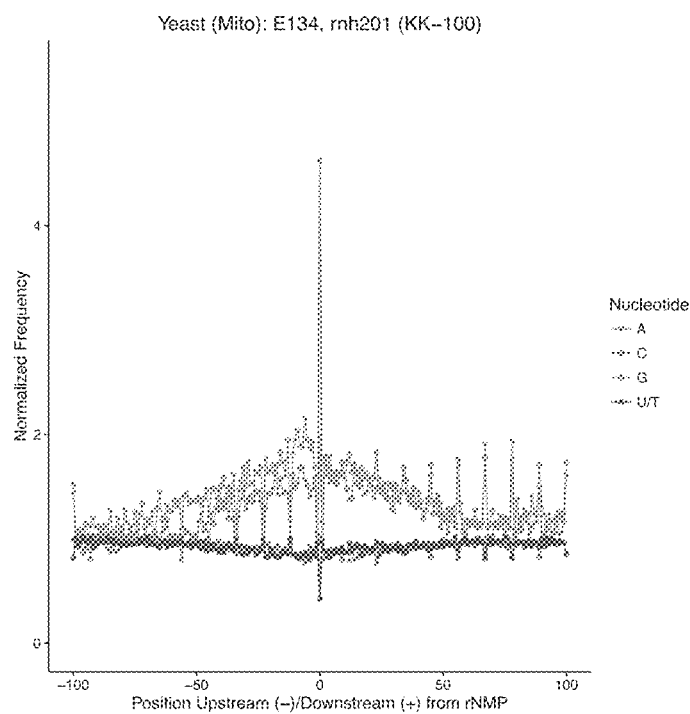
Figure 54D:
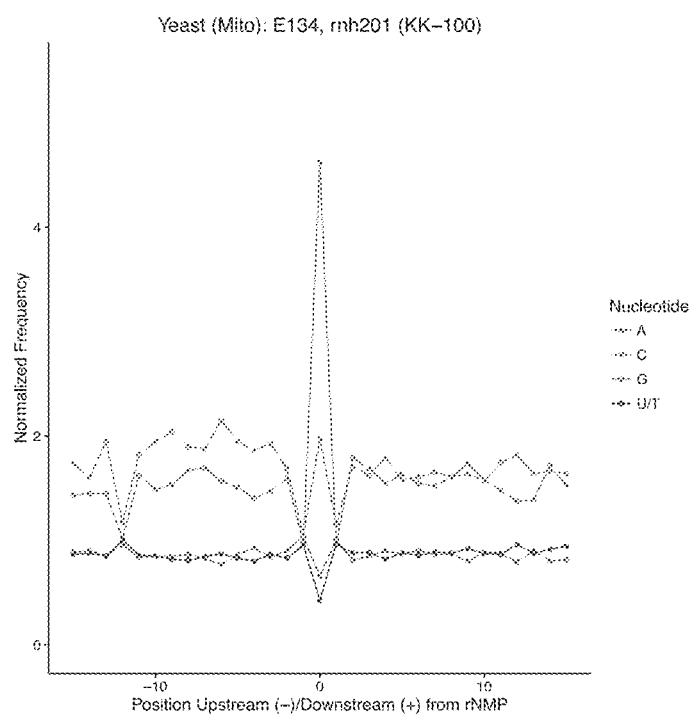
Figure 54E:
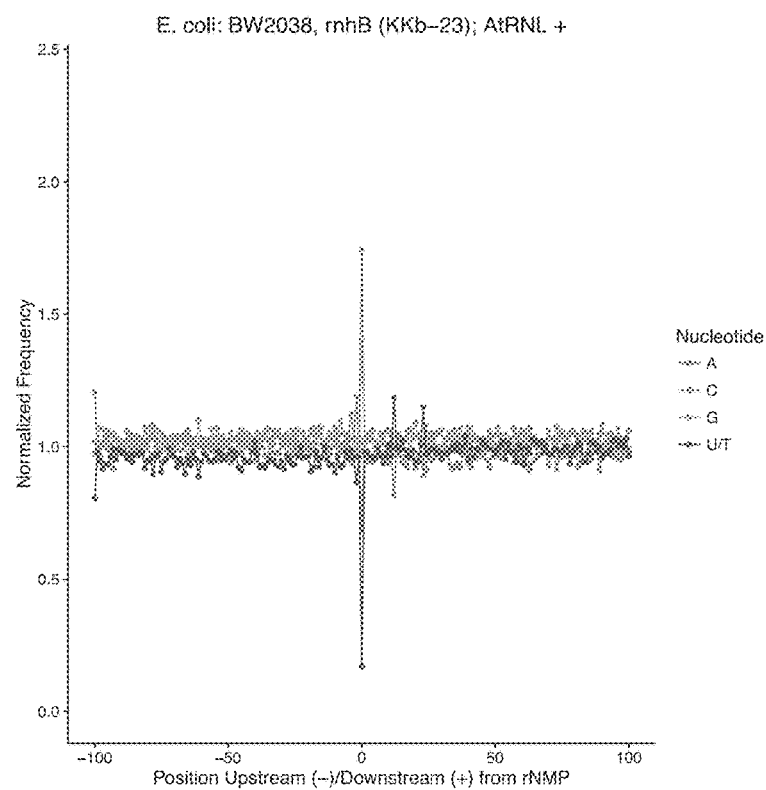
Figure 54F:
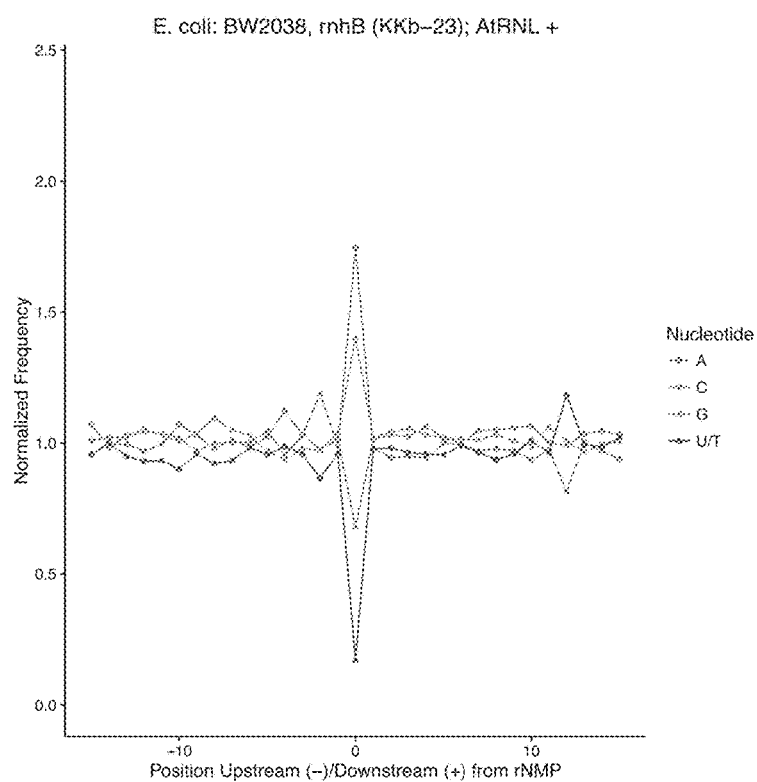
Figure 54G:
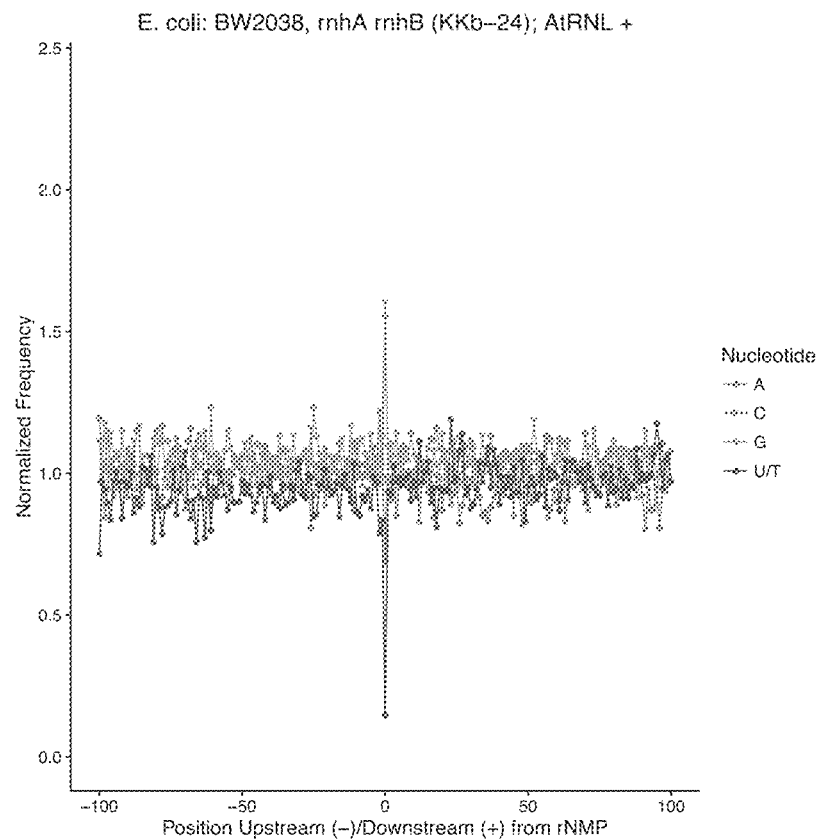
Figure 54H:
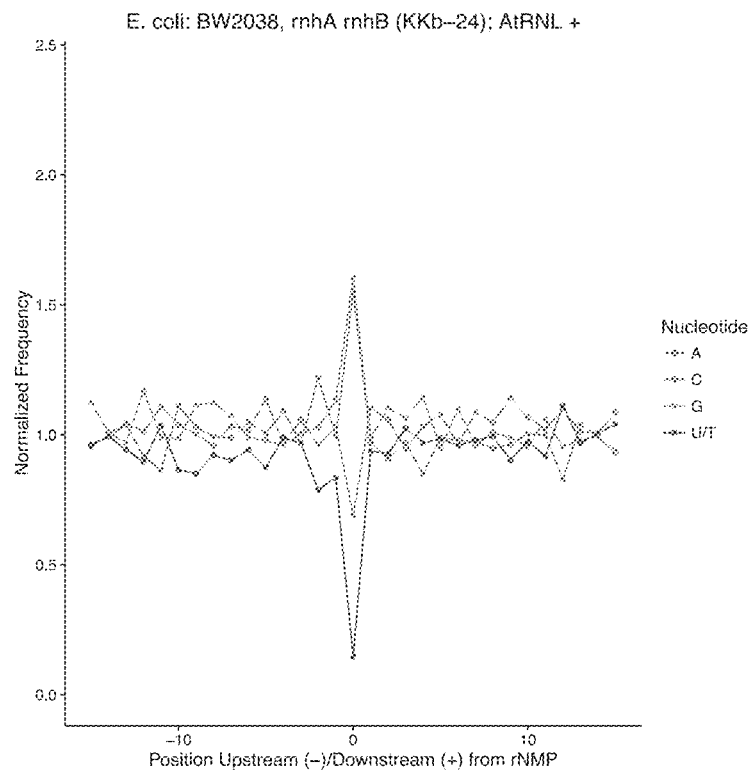
Figure 54I:
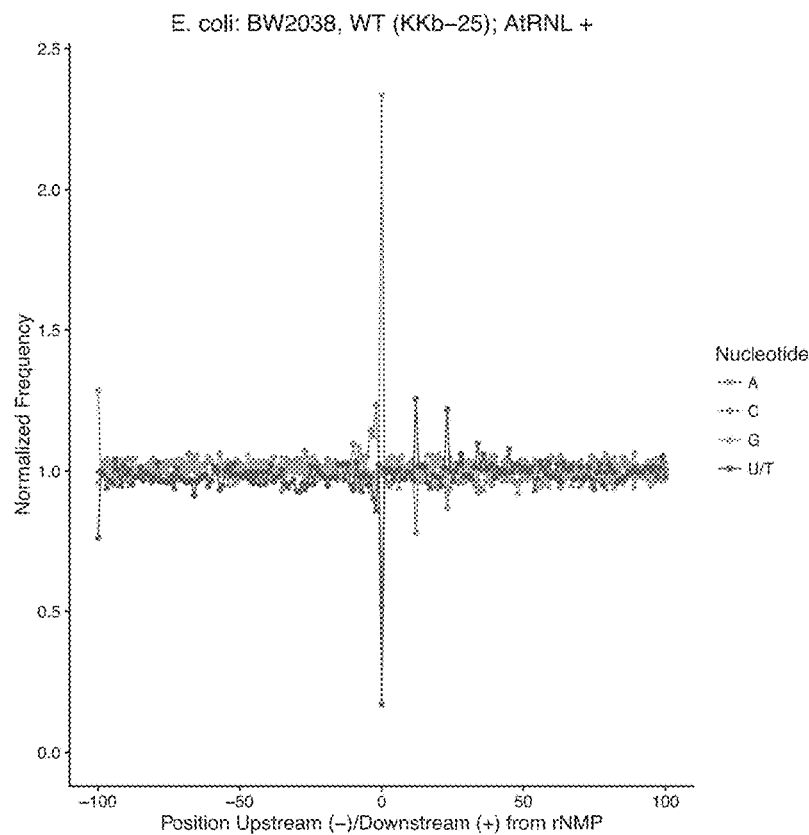
Figure 54J:
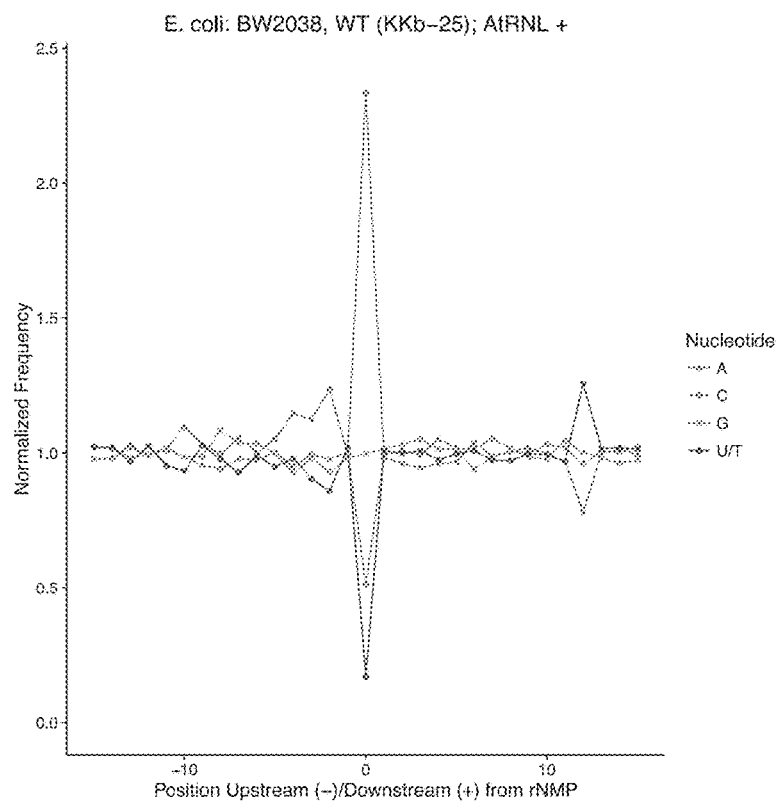
Figure 54K:
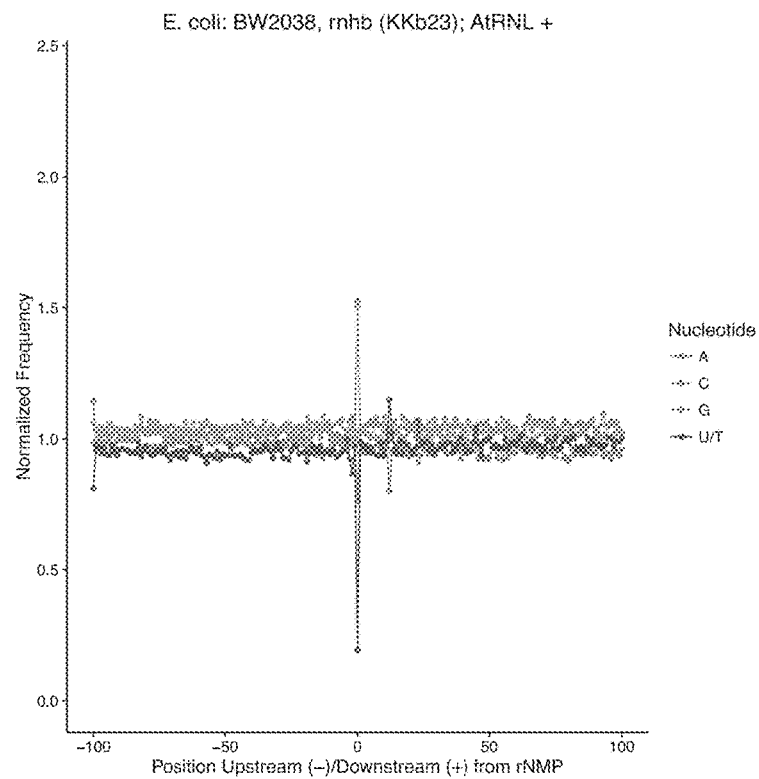
Figure 54L:
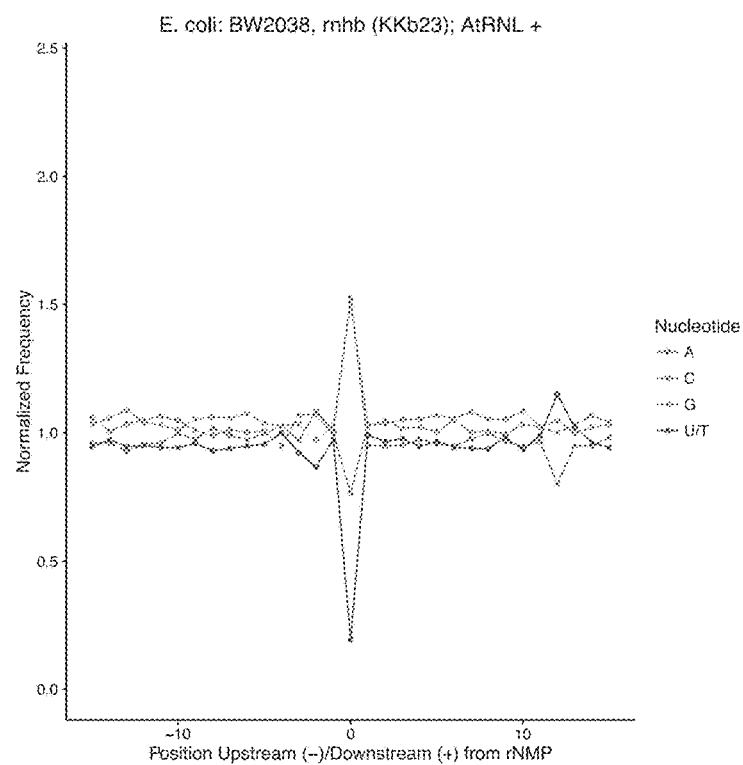
Figure 54M:
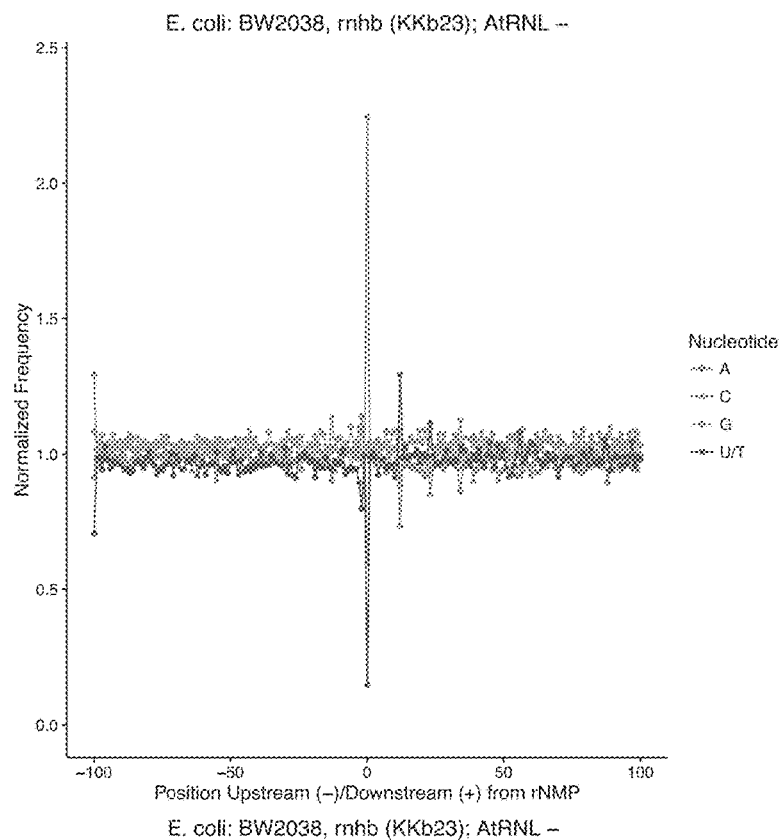
Figure 54N:
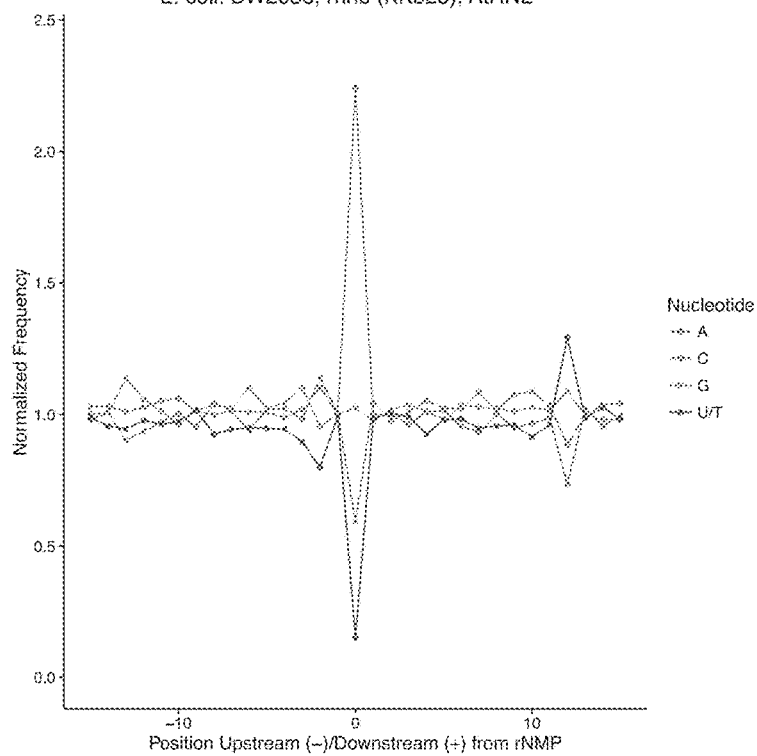
Figure 54O:
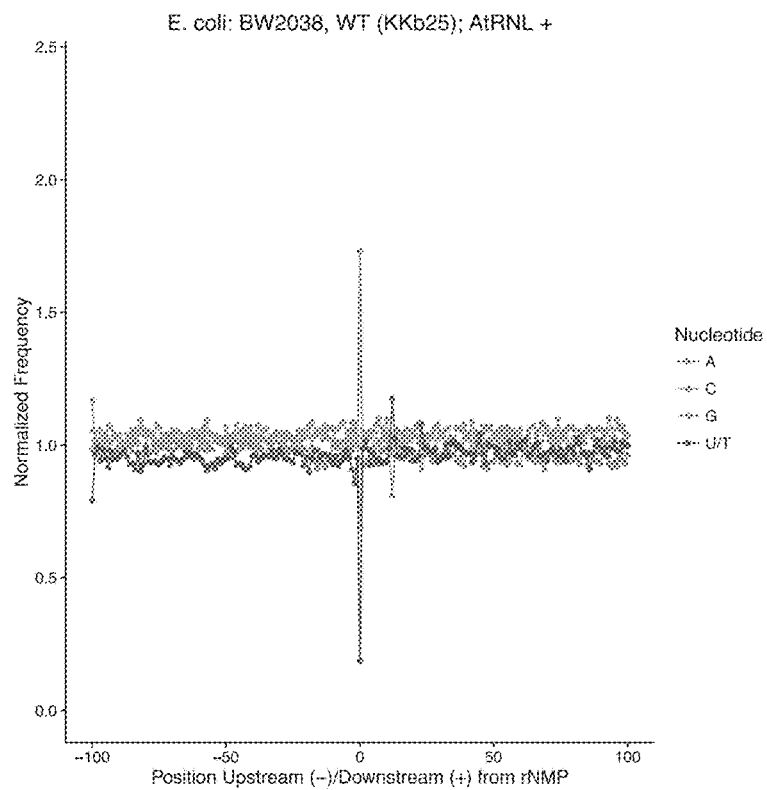
Figure 54P:
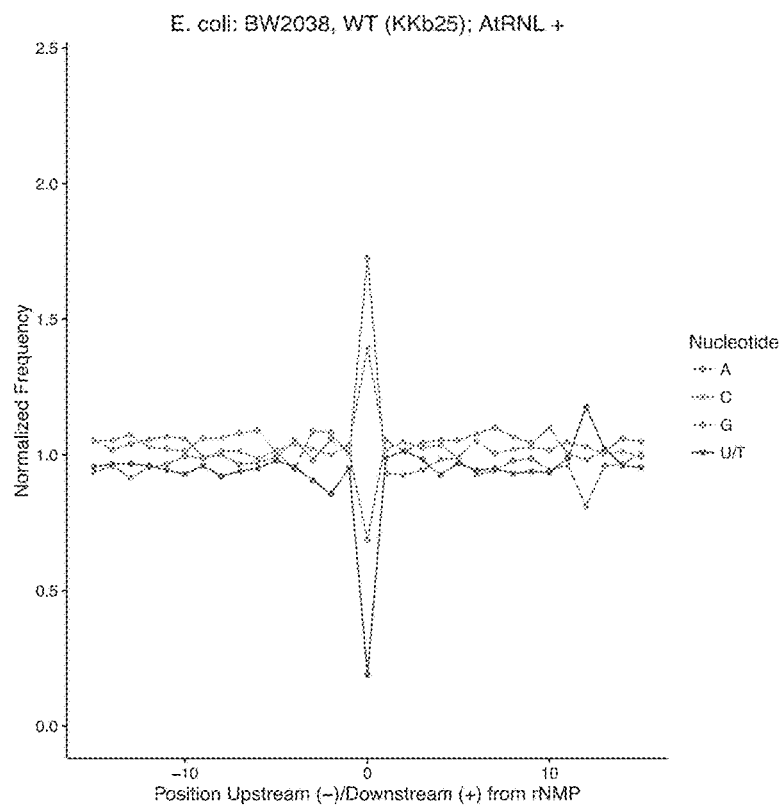
Figure 54Q:
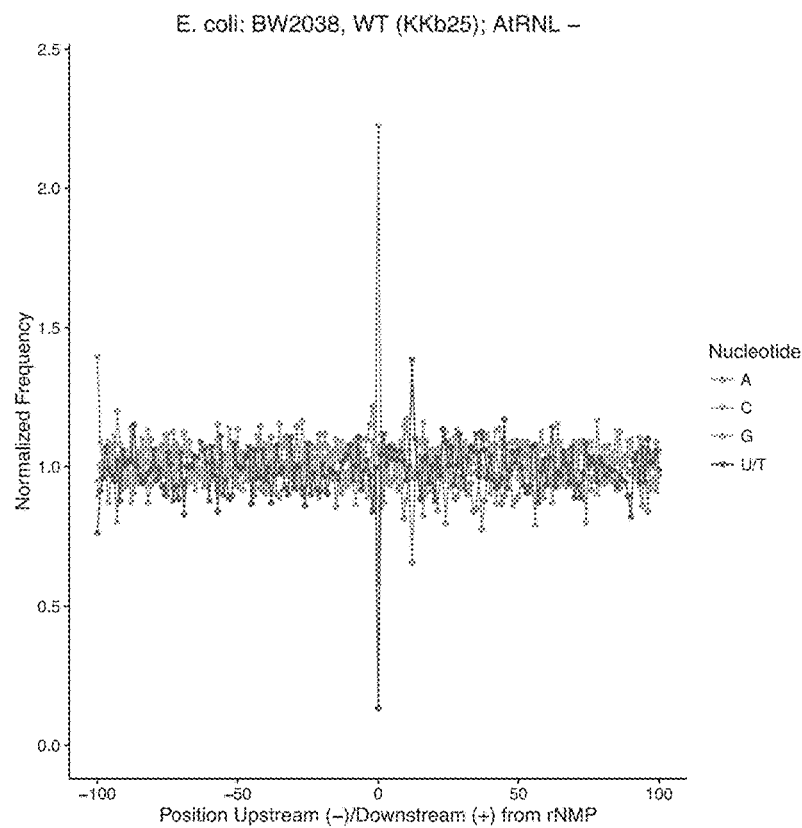
Figure 54R:
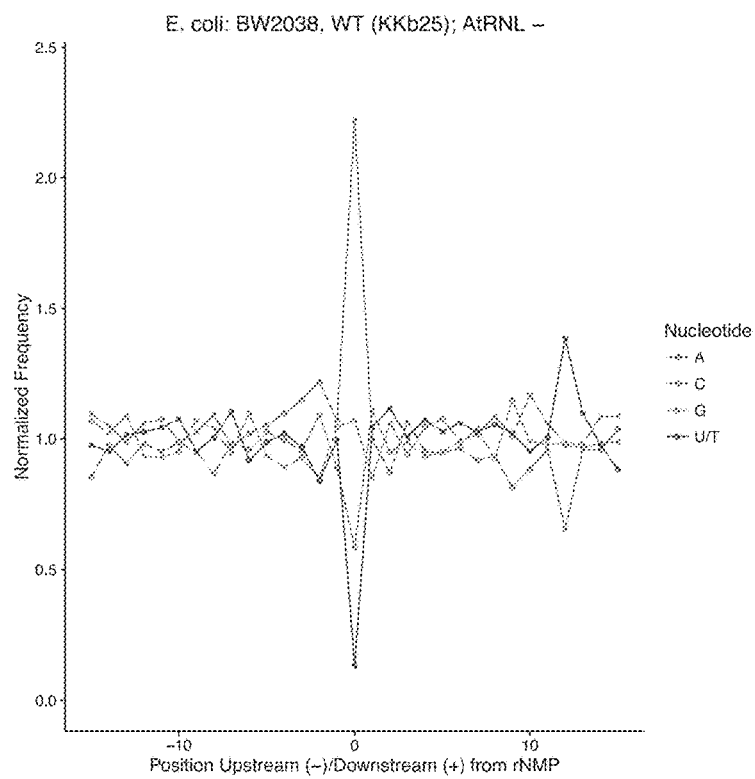
Figure 54S:
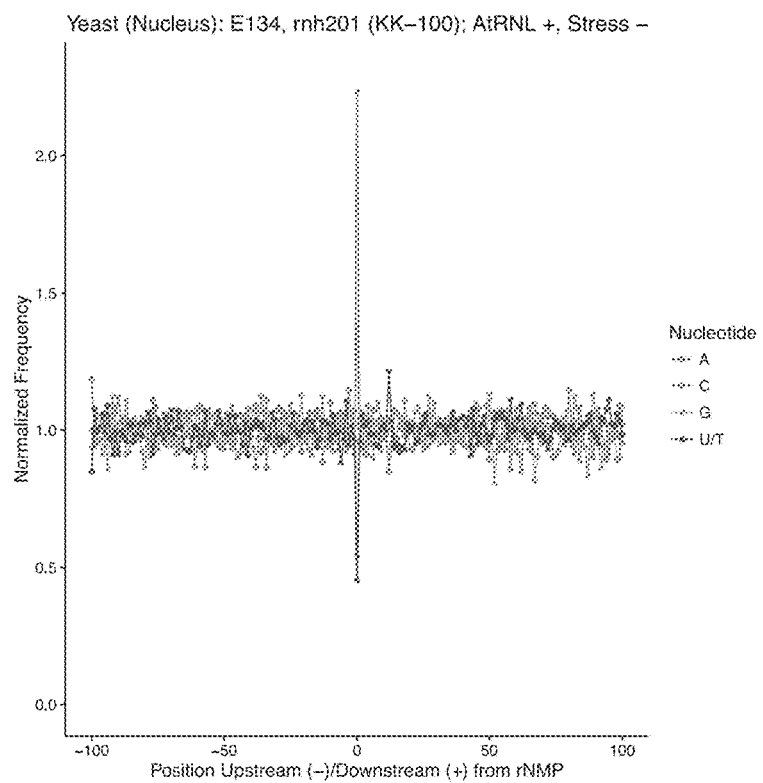
Figure 54T:
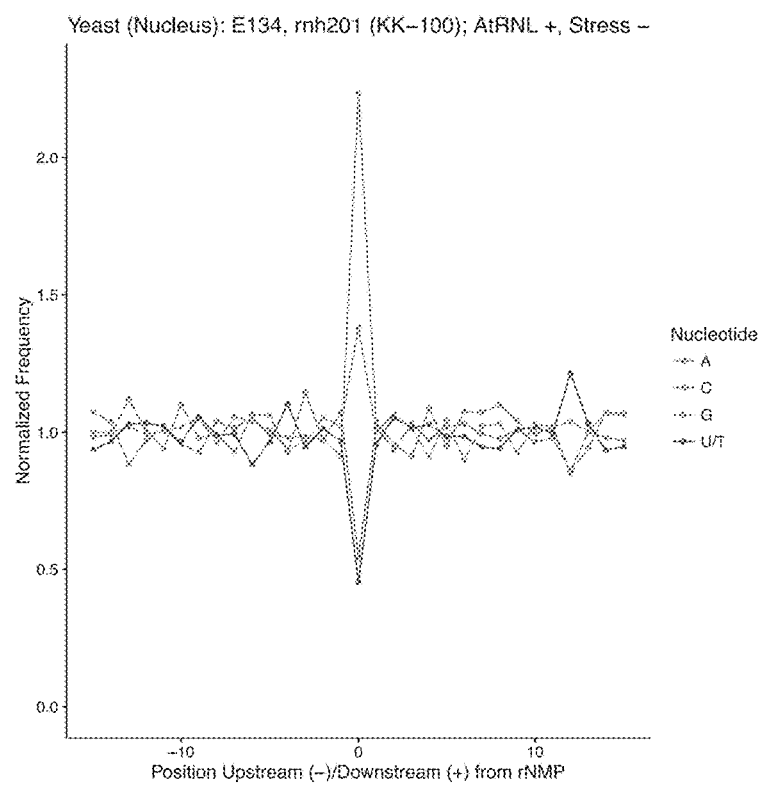
Figure 54U:
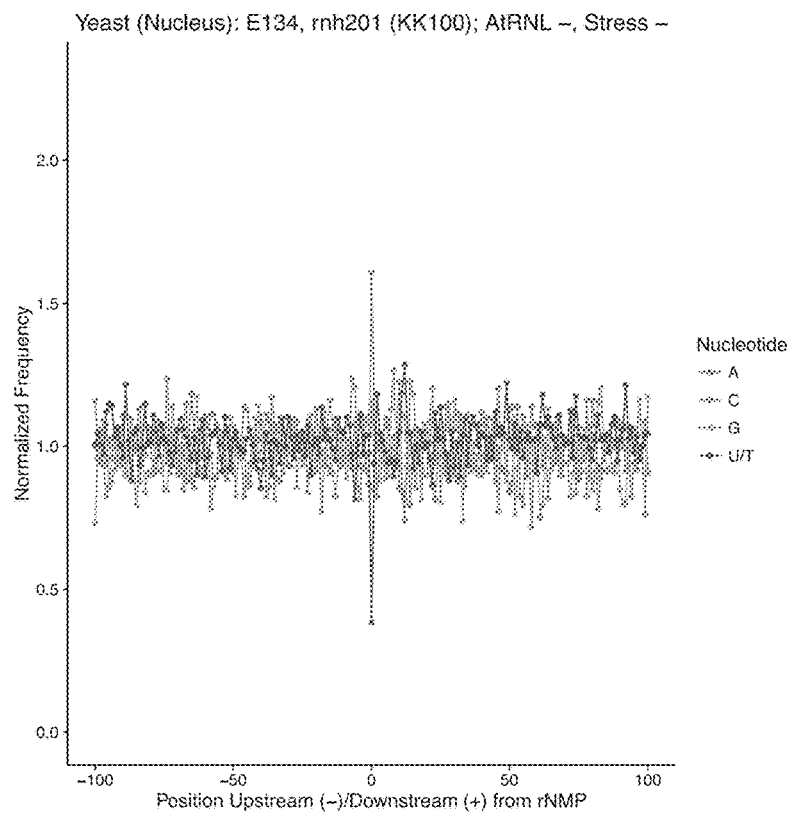
Figure 54V:
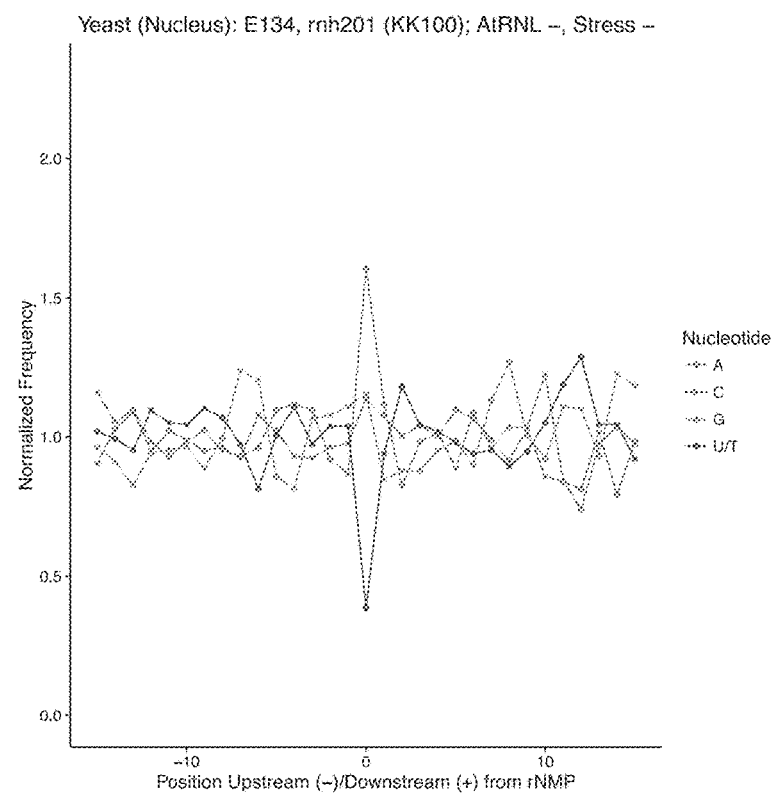
Figure 54W:
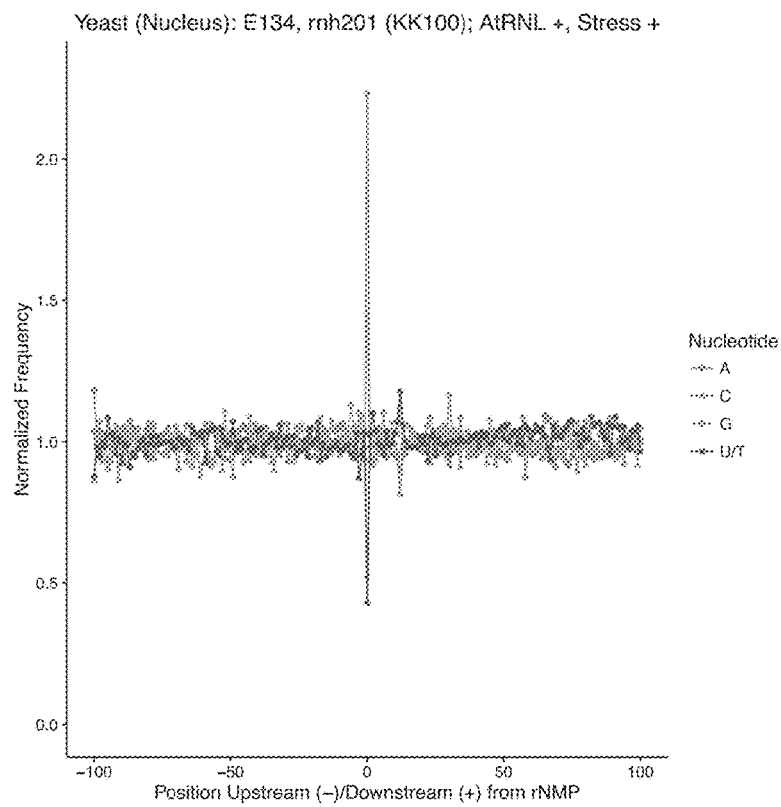
Figure 54X:
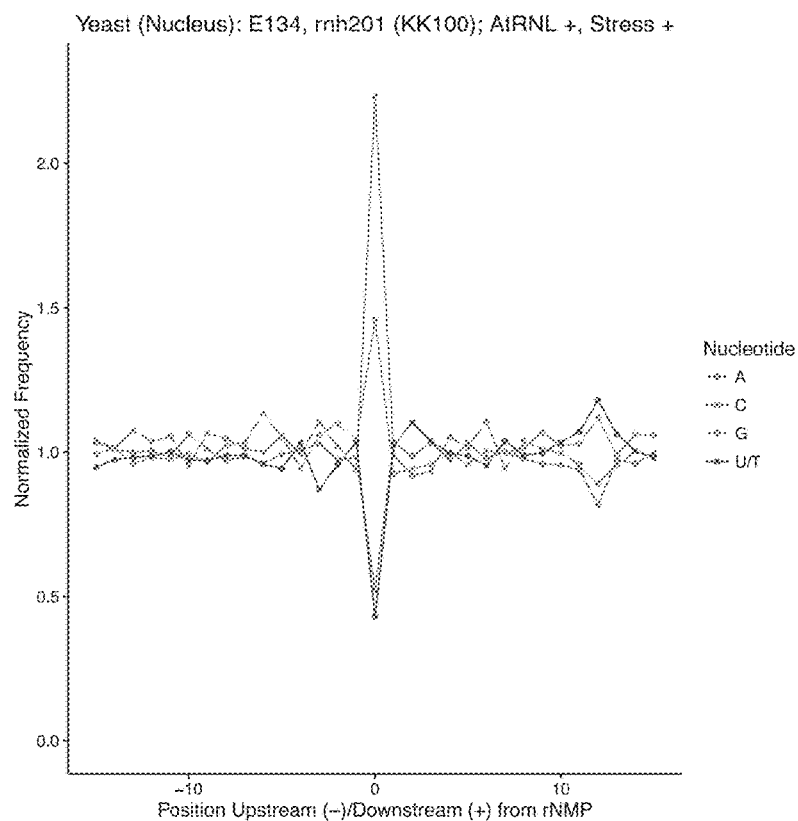
Figure 54Y:
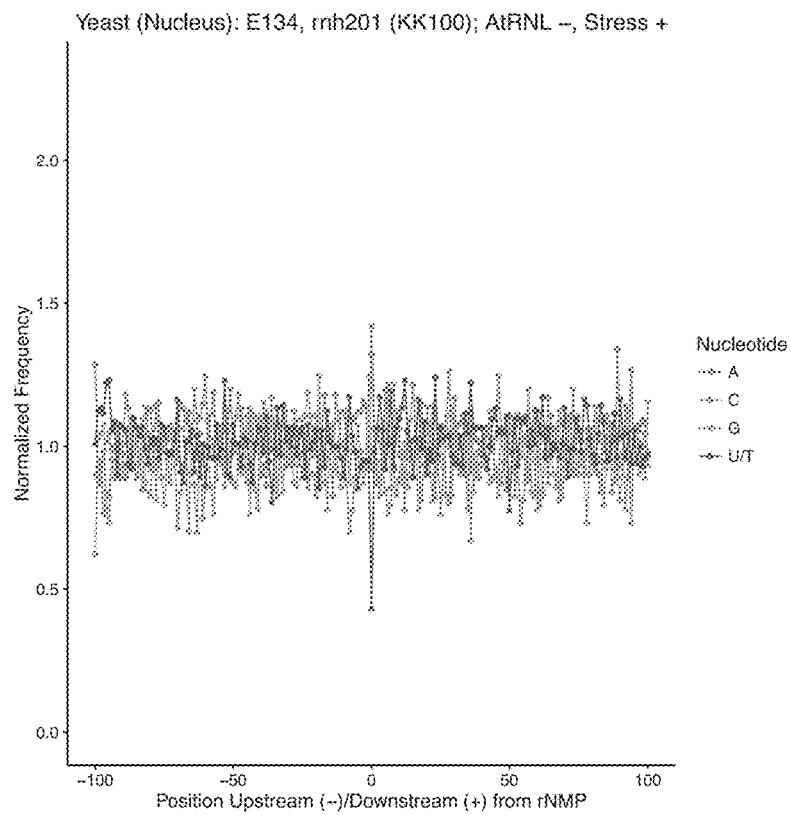
Figure 54Z:
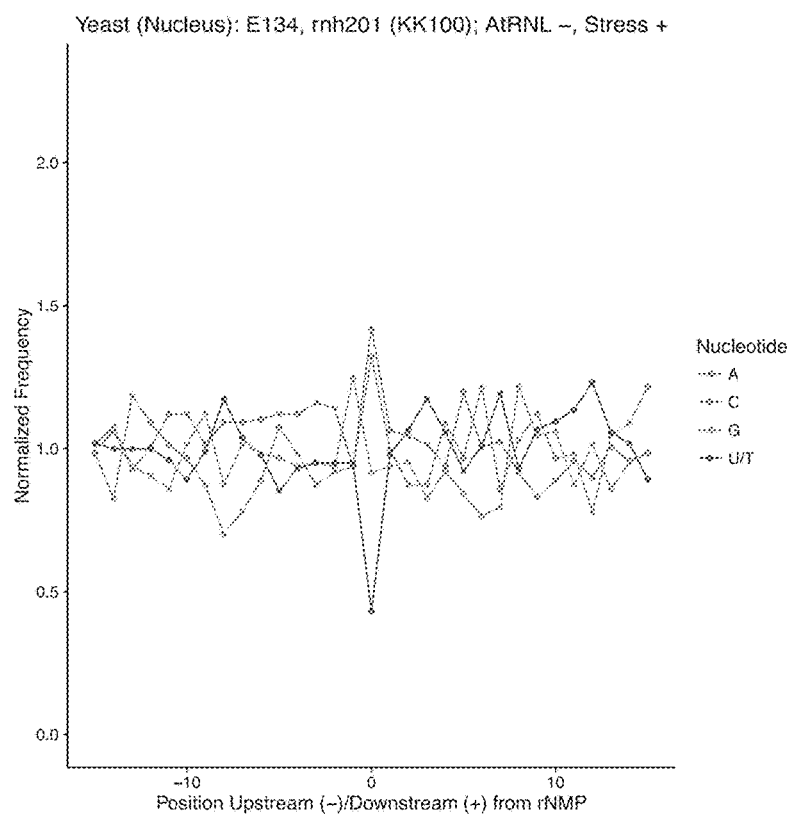
Figure 54A:
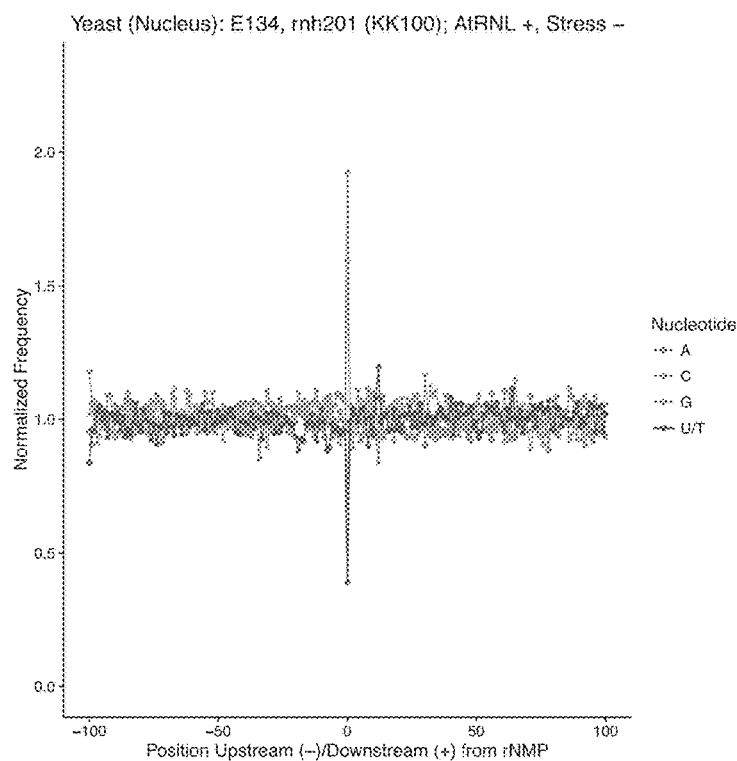
Figure 54B:
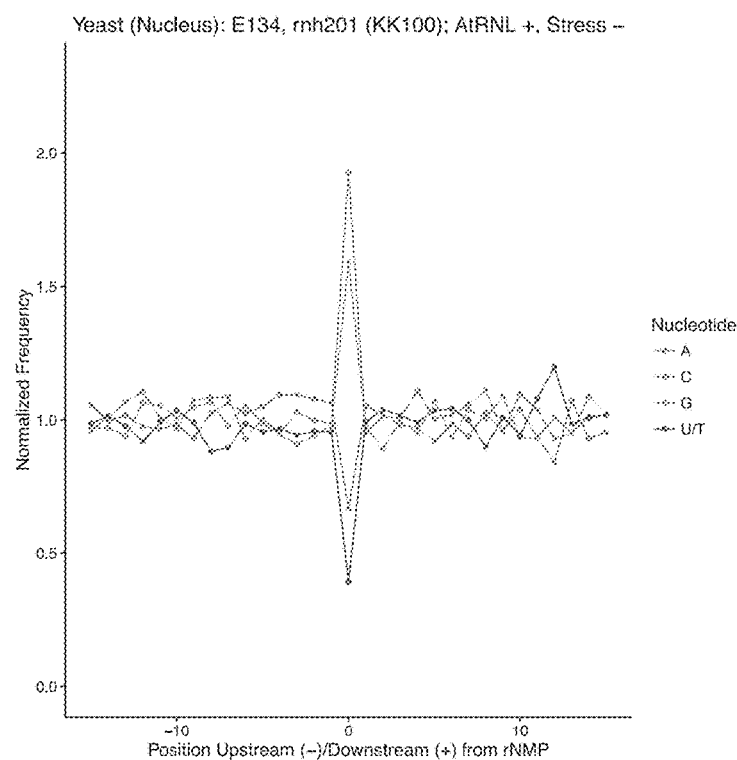
Figure 54C:
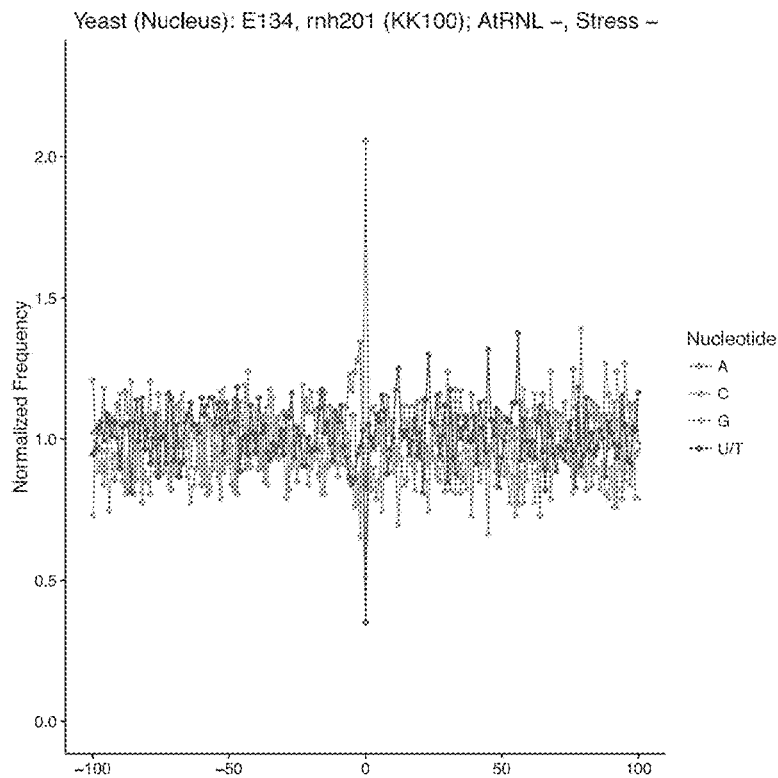
Figure 54D:
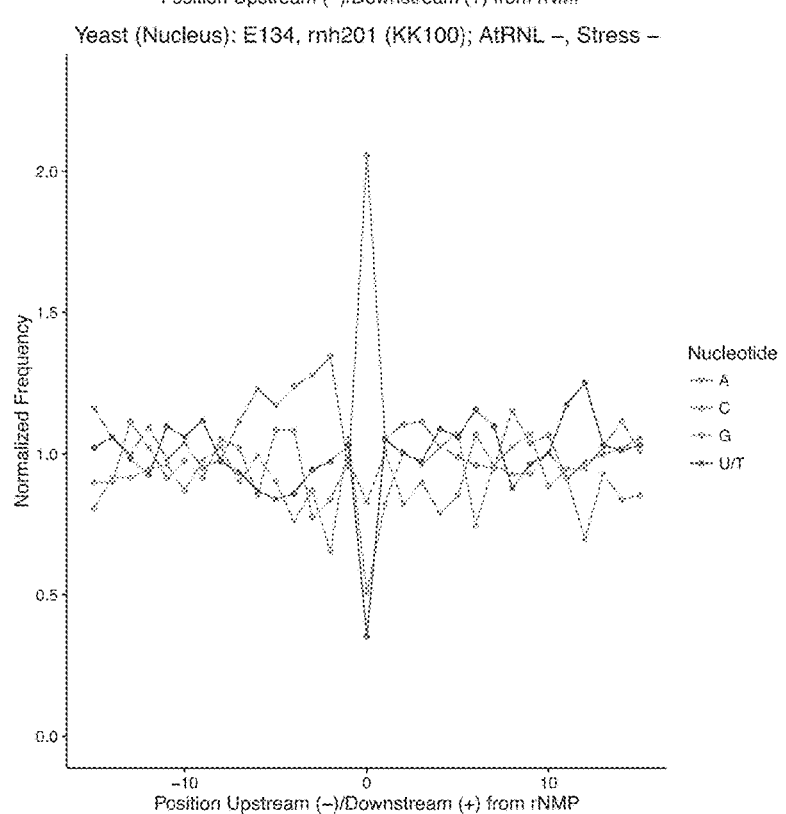
Figure 54E:
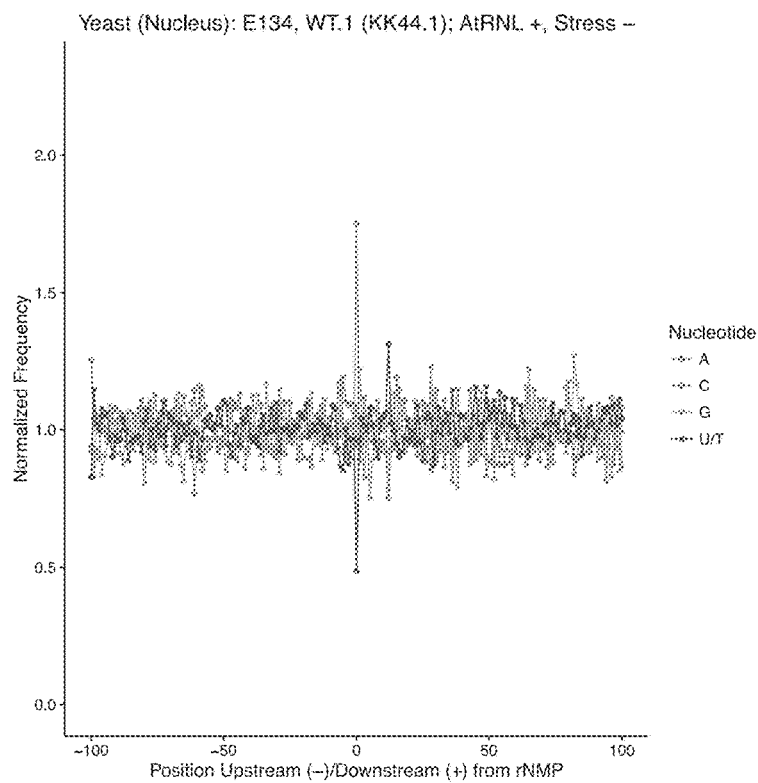
Figure 54F:
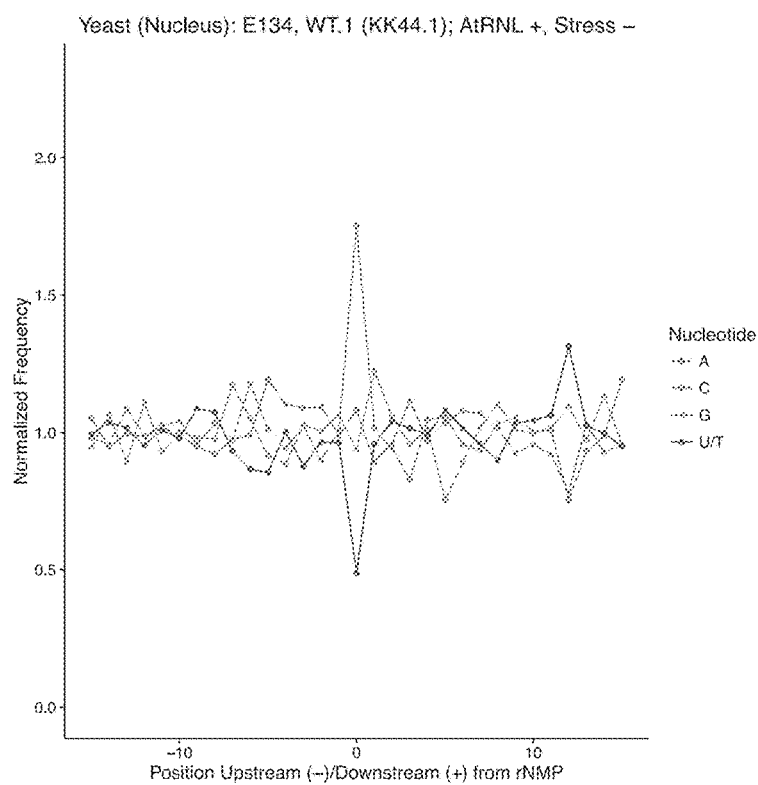
Figure 54G:
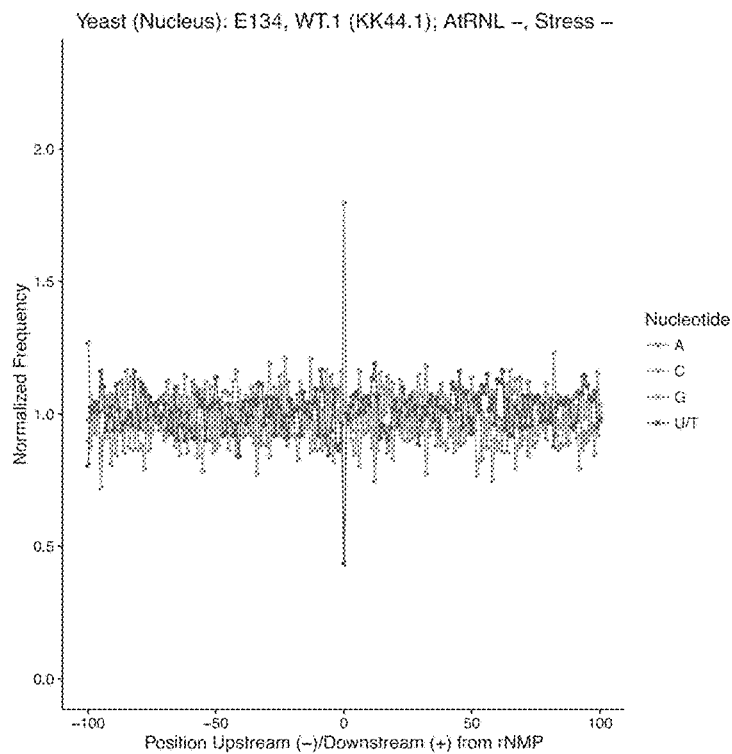
Figure 54H:
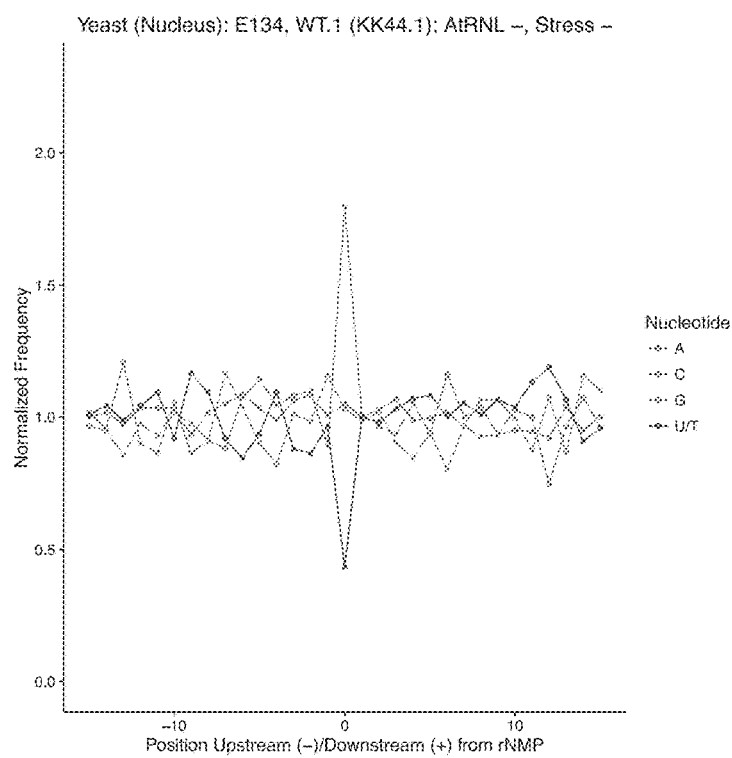
Figure 54I:
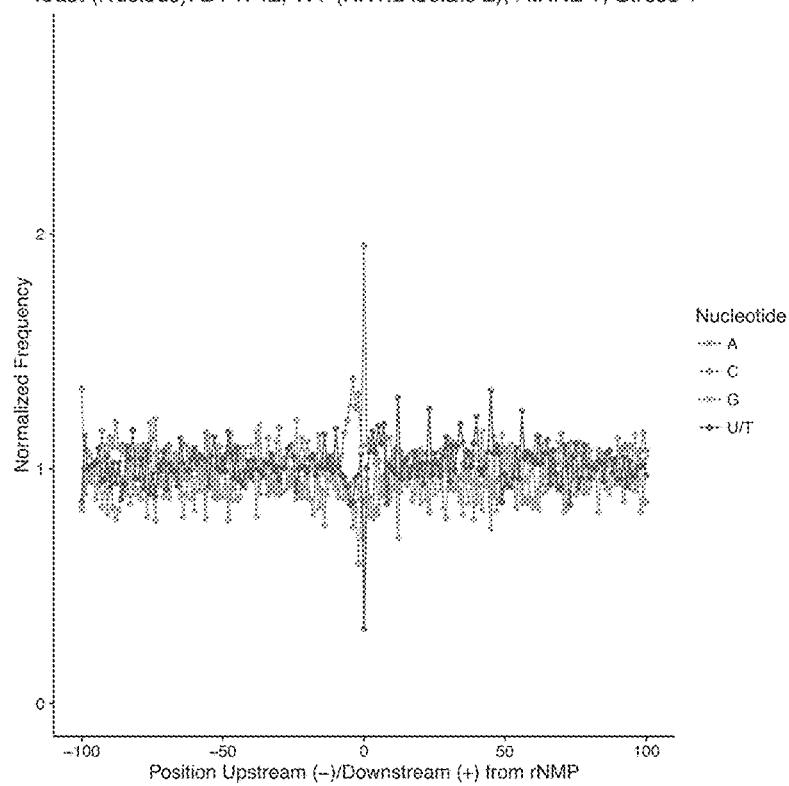
Figure 54J:
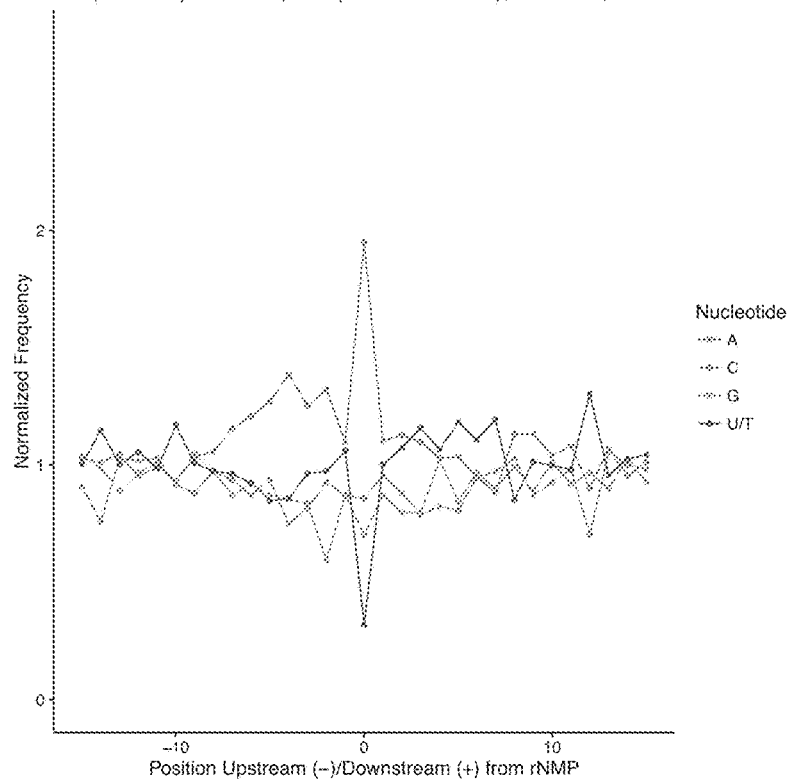
Figure 54K:
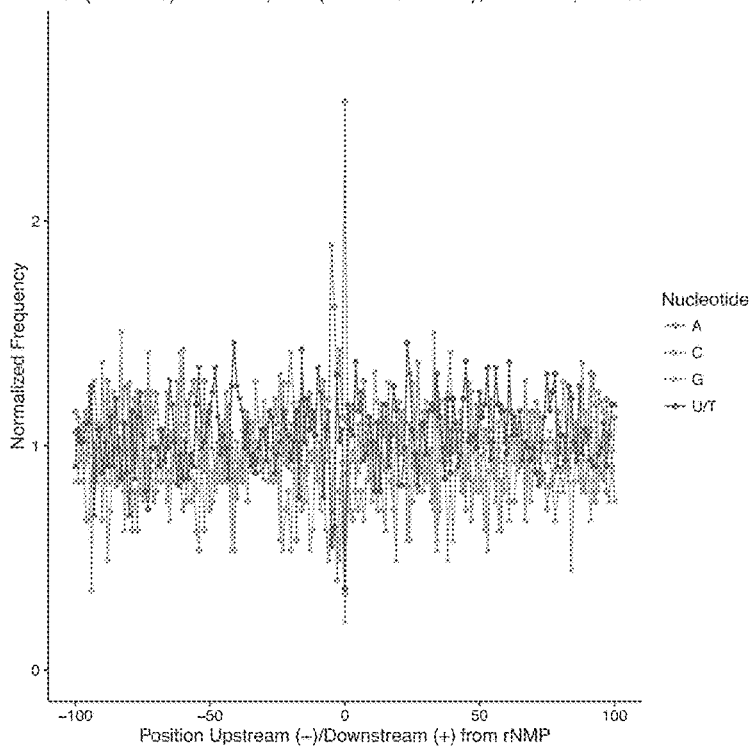
Figure 54L:
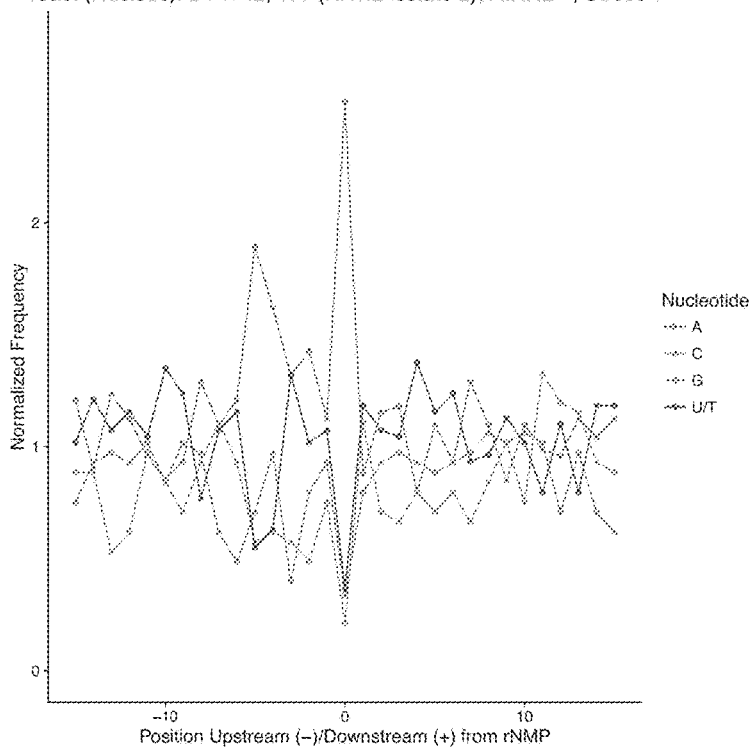
Figure 54M:
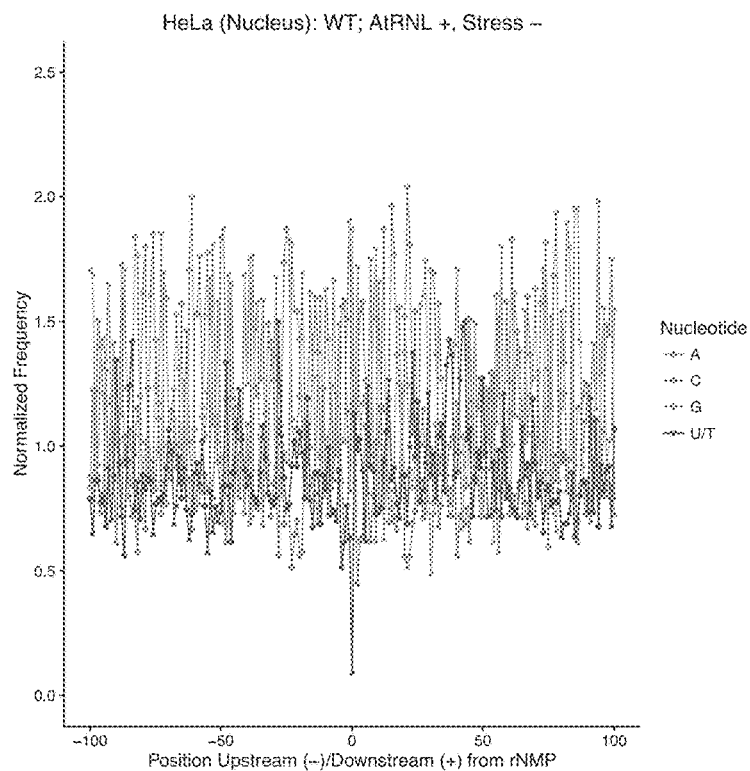
Figure 54N:
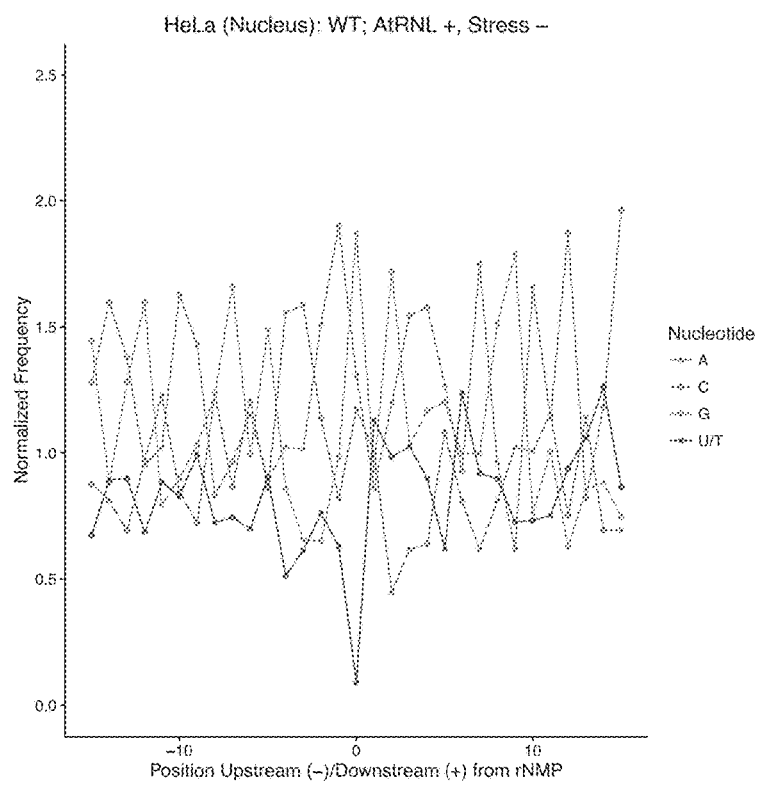
Figure 54O:
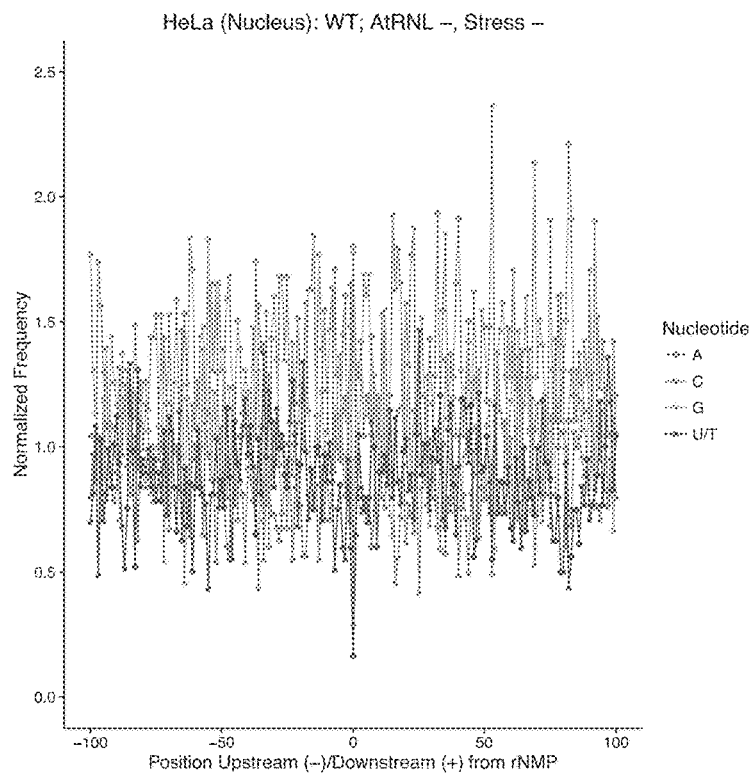
Figure 54P:
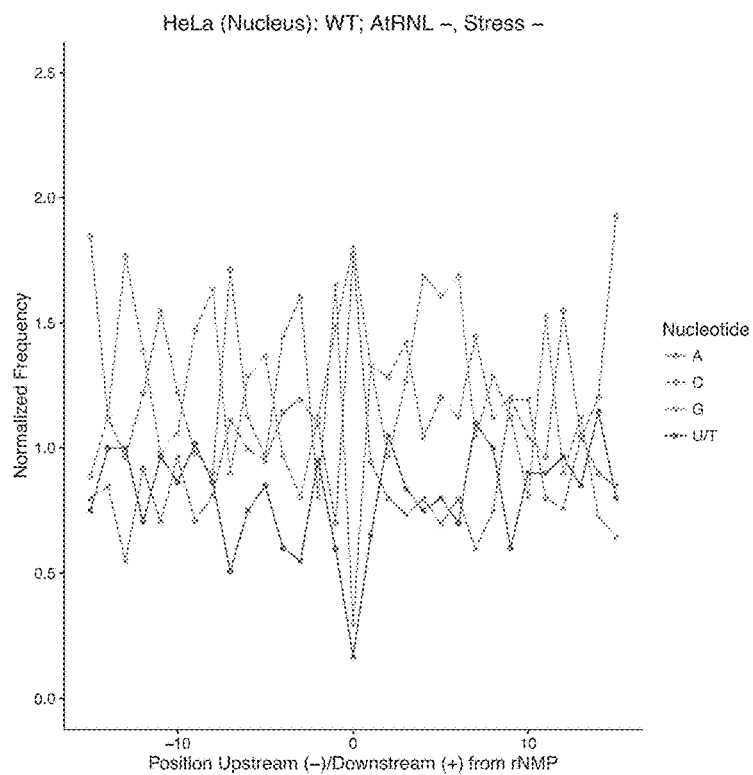
Figure 54Q:
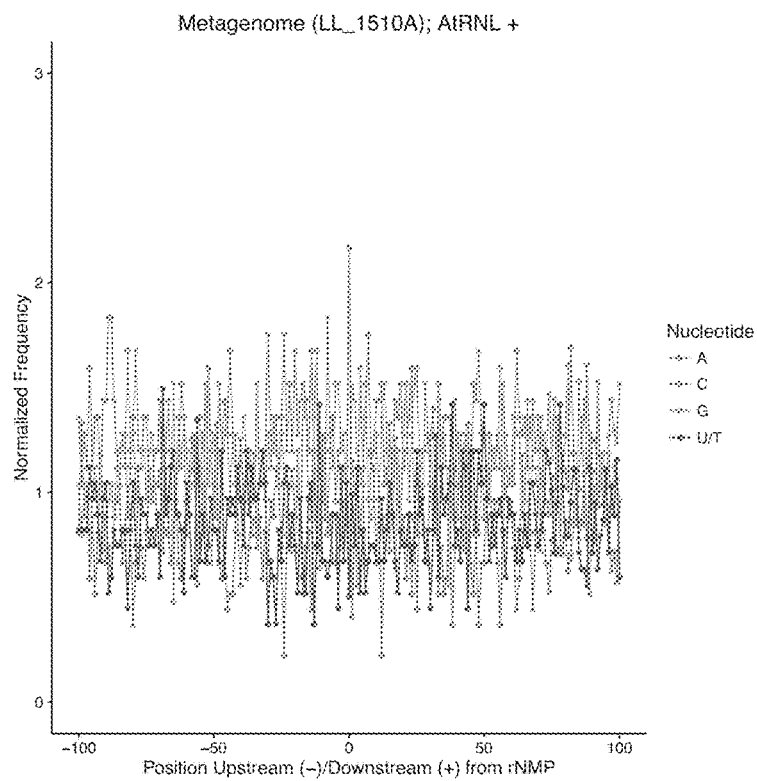
Figure 54R:
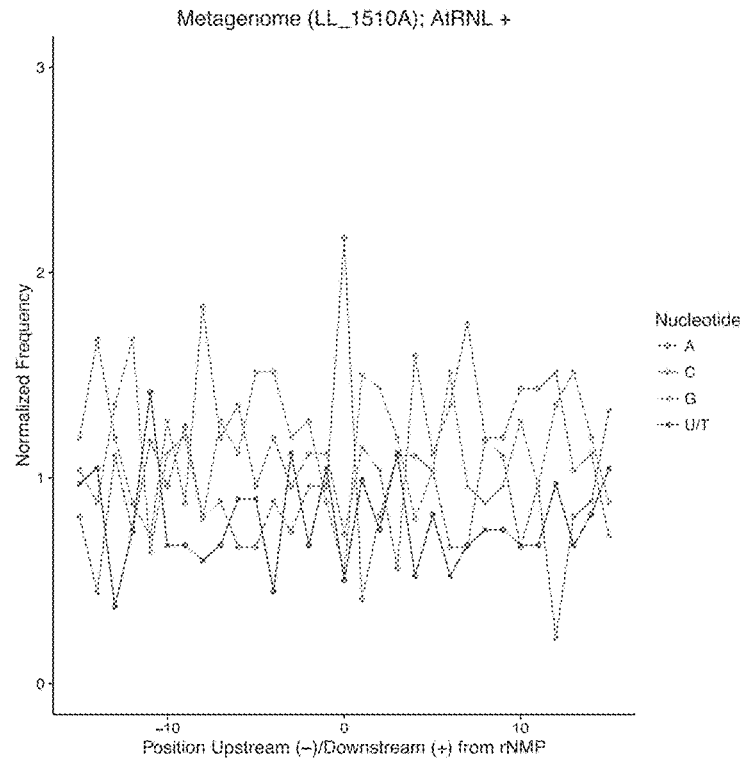
Figure 54S:
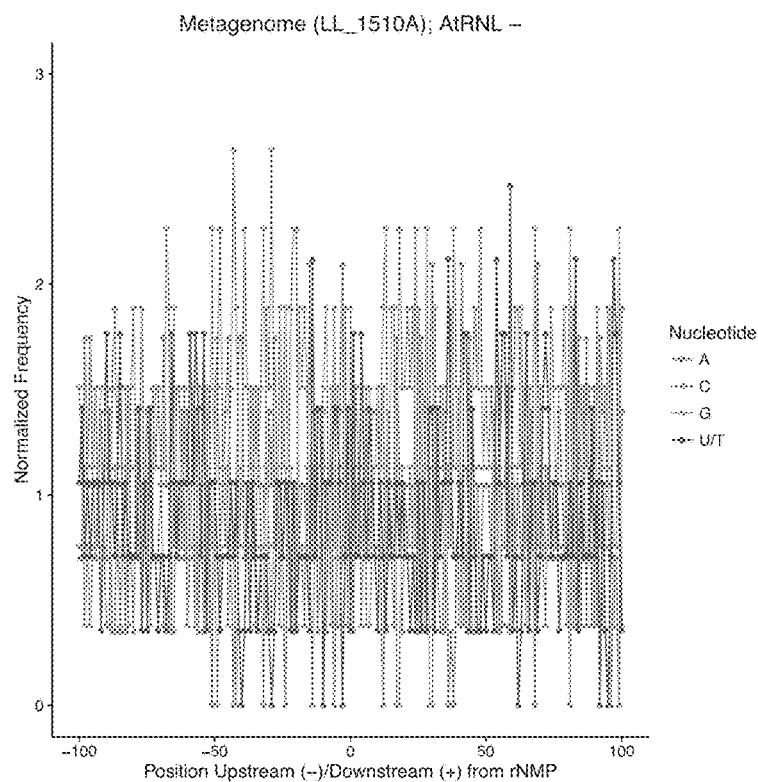
Figure 54T:
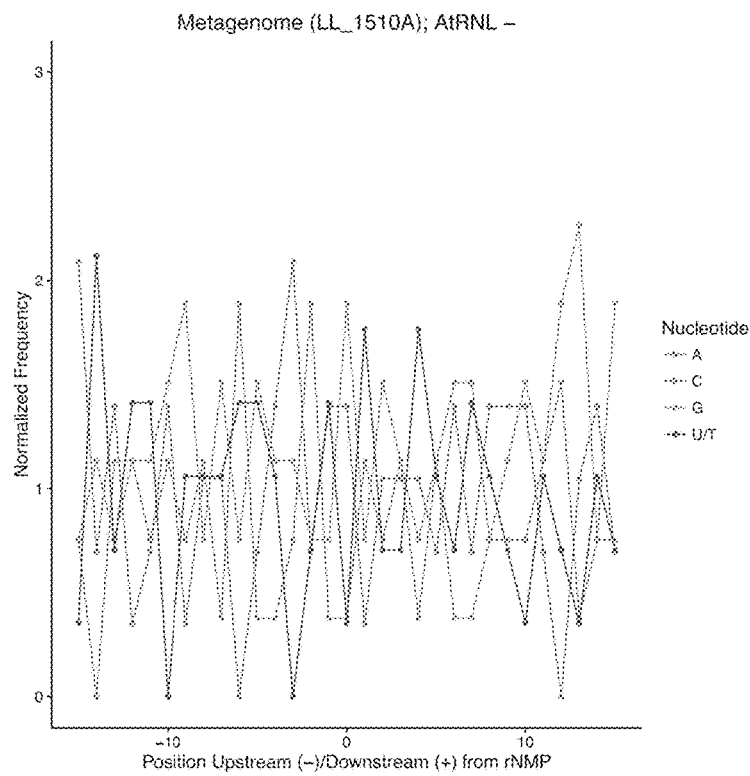
Figure 54U:
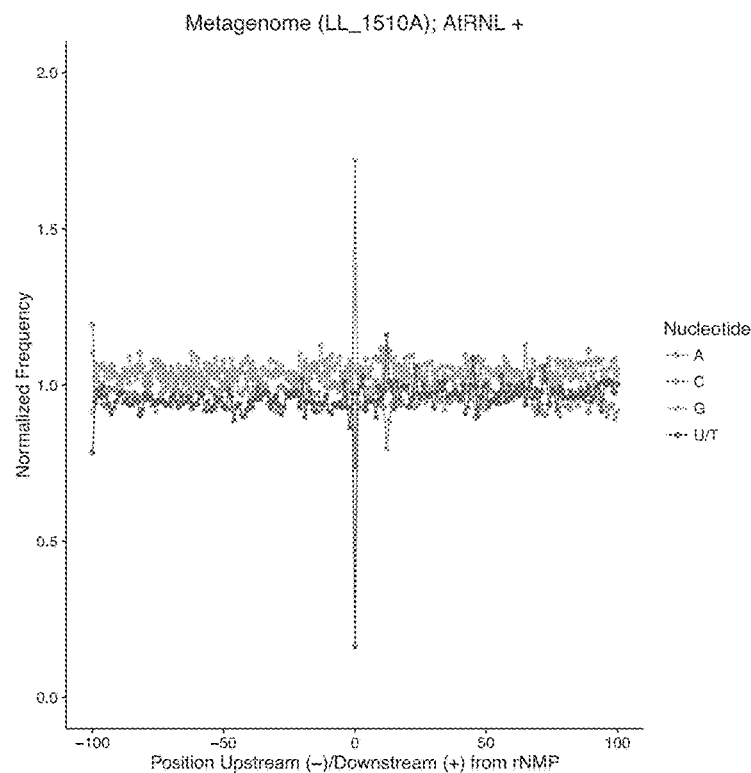
Figure 54V:
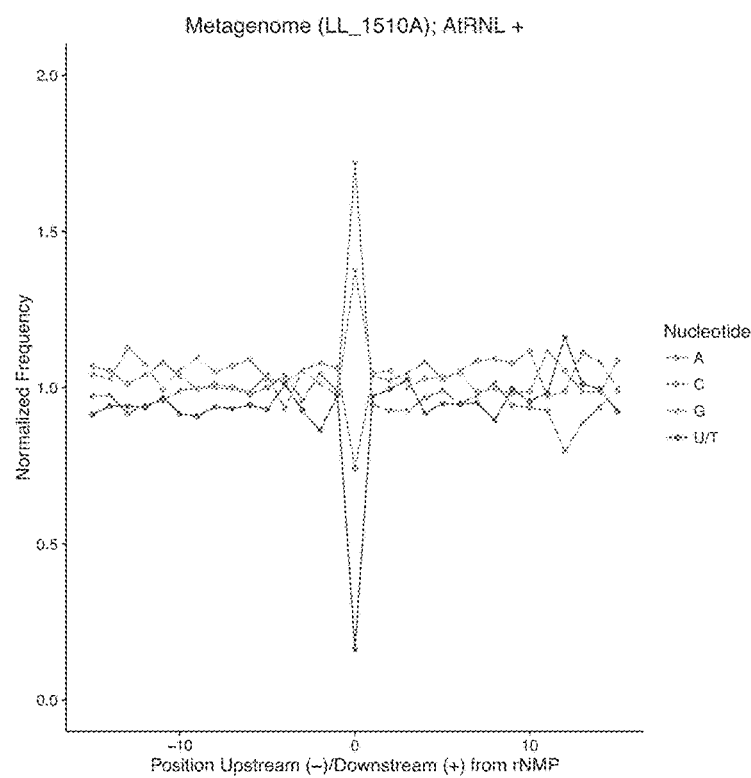

In some analyses, computational analysis was performed as shown in FIG. 41. The analysis can begin by assessing the quality of the sequencing reads using a suitable software program including, but not limited to, Fast QC software. Other suitable programs will be appreciated by those of ordinary skill in the art. The Illumina adapter sequences can be removed and the low quality reads can be trimmed. The trimmed sequencing reads can be aligned to a reference genome of interest. After alignment, the nucleotide frequencies of the reference genome of interest can be calculated. The normalized rNMP frequencies (using background frequencies) can be calculated. The dNTP frequencies about 100 bases upstream and downstream of the rNMPs can be analyzed. FIGS. 42A-42B describes a process of aligning the trimmed reads to the reference genome of interest and calculation and plotting of nucleotide frequencies. FIGS. 43-53 show graphs demonstrating various results for the computational analyses. FIGS. 54A-54XX show graphs demonstrating nucleotide frequencies for the computational analyses.

References for Example 3

1. Shen, Y., K. D. Koh, B. Weiss, and F. Storici. Mispaired rNMPs in DNA are mutagenic and are targets of mismatch repair and RNases H. Nature: Structural and Molecular Biology 19.1 (2011): 98-105.
2. Williams, J. S., S. A. Lujan, and T. A. Kunkel. Processing ribonucleotides incorporated during eukaryotic DNA replication. Nature Reviews 17, 350-363 (2016).
3. Koh, K. D., S. Balachander, J. R. Hesselberth, and F. Storici. Ribose-seq: global mapping of ribonucleotides embedded in genomic DNA. Nature Methods 12(3) (2015): 251-257.
4. Sparks, J. L., H. Chon, S. M. Cerritelli, T. A. Kunkel, E. Johansson, R. J. Crouch, and P. M. Burgers. RNase H2-Initiated Ribonucleotide Excision Repair. Molecular Cell 47, 980-986 (2012).
5. Aicardi-Goutieres syndrome. Genetics Home Reference. National Institutes of Health. 9 Aug. 2016<http://ghr.nlm.nih.gov/condition/aicardi-goutieres-syndrome>.
6. Systemic Lupus Erythematosus. Genetics Home Reference. National Institutes of Health. 9 Aug. 2016<https://ghr.nlm.nih.gov/condition/systemic-lupus-erythematosus>.

We claim:

1. A method of detecting a ribonucleotide in a molecule of deoxyribonucleic acid (DNA), the method comprising:
   ligating a first adaptor to a fragment of genomic DNA, wherein the adaptor comprises: a first primer-binding sequence;
   a first annealing sequence, wherein the first annealing sequence is coupled to the first primer-binding sequence;
   and a unique molecular identifier (UMI) sequence, wherein the UMI sequence is coupled to the first primer-binding sequence;
   cleaving the fragment of genomic DNA via an alkali treatment;
   ligating the cleaved fragment of genomic DNA using an *Arabidopsis thaliana* tRNA ligase (AtRNL) to produce a circular single stranded DNA fragment;
   amplifying the circular single stranded DNA fragment using polymerase chain reaction (PCR) to produce a PCR product using a first primer that is capable of specifically binding the first primer-binding sequence and a second primer that is capable of specifically binding a second primer-binding sequence; and
   sequencing the PCR product.

2. The method of claim 1, further comprising the step of removing a 2'-phosphate from the circular single stranded DNA fragment prior to amplifying the circular single stranded DNA fragment.

3. The method of claim 1, wherein the AtRNL has an amino acid sequence that is 90-100% identical to SEQ ID NO: 1 or SEQ ID NO: 2.

4. The method of claim 3, wherein the AtRNL has blunt-end ligase activity.

5. The method of claim 1, wherein the molecule of DNA is obtained from a cell.

6. The method of claim 5, wherein the cell is a eukaryotic cell or a prokaryotic cell.

7. The method of claim 6, further comprising ligating a second adaptor to the cleaved fragment of genomic DNA on the end opposite of where the first adaptor is ligated, wherein the second adaptor comprises a second annealing sequence and wherein the second annealing sequence is identical to the first annealing sequence.

8. The method of claim 1, wherein the fragment of genomic DNA has blunt ends.

9. The method of claim 1, further comprising the step of fragmenting genomic DNA prior to the step of ligating the adaptor to the fragment of genomic DNA.

10. The method of claim 1, further comprising the step of dA-tailing the fragment of genomic DNA prior to the step of ligating the adaptor to the fragment of genomic DNA.

11. The method of claim 1, further comprising the step of removing a linear single stranded DNA after the step of ligating the cleaved fragment of genomic DNA.

12. The method of claim 1, wherein the adaptor further comprises a second primer-binding sequence.

13. A method of detecting a ribonucleotide in a molecule of deoxyribonucleic acid (DNA), the method comprising:
ligating an adaptor to a fragment of genomic DNA, wherein the adaptor comprises:
a first primer-binding sequence;
a second primer-binding sequence, wherein the second primer-binding sequence is coupled to the first primer-binding sequence;
a first annealing sequence, wherein the first annealing sequence is coupled to the first primer-binding sequence; and
a unique molecular identifier (UMI) sequence, wherein the UMI sequence is coupled to the first primer-binding sequence;
cleaving the fragment of genomic DNA via an alkali treatment;
ligating the cleaved fragment of genomic DNA using an *Arabidopsis thaliana* tRNA ligase (AtRNL) to produce a circular single stranded DNA fragment;
amplifying the circular single stranded DNA fragment using polymerase chain reaction (PCR) to produce a PCR product, using a first primer that is capable of specifically binding the first primer-binding sequence and a second primer that is capable of specifically binding the second primer-binding sequence; and
sequencing the PCR product.

14. The method of claim 13, further comprising the step of removing a 2'-phosphate from the circular single stranded DNA fragment prior to amplifying the circular single stranded DNA fragment.

15. The method of claim 13, wherein the fragment of genomic DNA has blunt ends.

16. The method of claim 13, further comprising the step of fragmenting genomic DNA prior to the step of ligating the adaptor to the fragment of genomic DNA.

17. The method of claim 13, further comprising the step of dA-tailing the fragment of genomic DNA prior to the step of ligating the adaptor to the fragment of genomic DNA.

18. The method of claim 13, further comprising the step of removing a linear single stranded DNA after the step of ligating the cleaved fragment of genomic DNA.

19. The method of claim 13, further comprising ligating a second adaptor to the cleaved fragment of genomic DNA on the end opposite of where the first adaptor is ligated, wherein the second adaptor comprises a second annealing sequence and wherein the second annealing sequence is identical to the first annealing sequence.

20. A method of detecting a ribonucleotide in a molecule of deoxyribonucleic acid (DNA), the method comprising:
ligating an adaptor to a fragment of genomic DNA, wherein the adaptor comprises: a first primer-binding sequence;
a first annealing sequence, wherein the first annealing sequence is coupled to the first primer-binding sequence; and a unique molecular identifier (UMI) sequence, wherein the UMI sequence is coupled to the first primer-binding sequence;
cleaving the fragment of genomic DNA via an alkali treatment;
ligating the cleaved fragment of genomic DNA using a ligase capable of coupling a 2',3'-cyclic phosphate to a 5'-phosphate to produce a circular single stranded DNA fragment;
amplifying the circular single stranded DNA fragment using polymerase chain reaction (PCR) to produce a PCR product; and
sequencing the PCR product using a first primer that is capable of specifically binding the first primer-binding sequence.

21. The method of claim 20, wherein the ligase is an *Arabidopsis thaliana* tRNA ligase (AtRNL).

22. The method of claim 21, wherein the AtRNL has an amino acid sequence that is 90-100% identical to SEQ ID NO: 1 or SEQ ID NO: 2.

23. The method of claim 20, wherein the ligase is an RtcB ligase.

24. The method of claim 23, wherein the RtcB ligase has an amino acid sequence that is 90-100% identical to SEQ ID NO: 3.

25. The method of claim 21, further comprising the step of removing a 2'-phosphate from the circular single stranded DNA fragment prior to amplifying the circular single stranded DNA fragment.

26. The method of claim 21, wherein the fragment of genomic DNA has blunt ends.

27. The method of claim 21, further comprising the step of fragmenting genomic DNA prior to the step of ligating the adaptor to the fragment of genomic DNA.

28. The method of claim 21, further comprising the step of dA-tailing the fragment of genomic DNA prior to the step of ligating the adaptor to the fragment of genomic DNA.

29. The method of claim 21, further comprising the step of removing a linear single stranded DNA after the step of ligating the cleaved fragment of genomic DNA.

30. The method of claim 21, wherein the adaptor further comprises a second primer-binding sequence.

31. The method of claim 30, further comprising the step of sequencing the PCR product using a second primer that is capable of specifically binding the second primer-binding sequence, wherein the step of sequencing the PCR product using the second primer is performed simultaneously or sequentially with the step of sequencing the PCR product using the first primer that is capable of specifically binding the first primer-binding sequence.

32. The method of claim 31, wherein the ligase has blunt-end ligase activity.

33. The method of claim 31, wherein the molecule of DNA is obtained from a cell.

34. The method of claim 33, wherein the cell is a eukaryotic cell or a prokaryotic cell.

35. The method of claim 20, further comprising ligating a second adaptor to the cleaved fragment of genomic DNA on the end opposite of where the first adaptor is ligated, wherein the second adaptor comprises a second annealing sequence and wherein the second annealing sequence is identical to the first annealing sequence.

* * * * *

SEQUENCE LISTING

<160> NUMBER OF SEQ ID NOS: 43

<210> SEQ ID NO 1
<211> LENGTH: 1104
<212> TYPE: PRT
<213> ORGANISM: Arabidopsis thaliana

<400> SEQUENCE: 1

```
Met Asp Ala Pro Phe Glu Ser Gly Asp Ser Ser Ala Thr Val Val Ala
1               5                   10                  15

Glu Ala Val Asn Asn Gln Phe Gly Gly Leu Ser Leu Lys Glu Ser Asn
            20                  25                  30

Thr Asn Ala Pro Val Leu Pro Ser Gln Thr Thr Ser Asn His Arg Val
        35                  40                  45

Gln Asn Leu Val Trp Lys Pro Lys Ser Tyr Gly Thr Val Ser Gly Ser
    50                  55                  60

Ser Ser Ala Thr Glu Val Gly Lys Thr Ser Ala Val Ser Gln Ile Gly
65                  70                  75                  80

Ser Ser Gly Asp Thr Lys Val Gly Leu Asn Leu Ser Lys Ile Phe Gly
                85                  90                  95

Gly Asn Leu Leu Glu Lys Phe Ser Val Asp Lys Ser Thr Tyr Cys His
            100                 105                 110
```

-continued

```
Ala Gln Ile Arg Ala Thr Phe Tyr Pro Lys Phe Glu Asn Glu Lys Thr
            115                 120                 125

Asp Gln Glu Ile Arg Thr Arg Met Ile Glu Met Val Ser Lys Gly Leu
130                 135                 140

Ala Thr Leu Glu Val Ser Leu Lys His Ser Gly Ser Leu Phe Met Tyr
145                 150                 155                 160

Ala Gly His Lys Gly Ala Tyr Ala Lys Asn Ser Phe Gly Asn Ile
                165                 170                 175

Tyr Thr Ala Val Gly Val Phe Val Leu Ser Arg Met Phe Arg Glu Ala
            180                 185                 190

Trp Gly Thr Lys Ala Pro Lys Lys Glu Ala Glu Phe Asn Asp Phe Leu
        195                 200                 205

Glu Lys Asn Arg Met Cys Ile Ser Met Glu Leu Val Thr Ala Val Leu
    210                 215                 220

Gly Asp His Gly Gln Arg Pro Leu Asp Asp Tyr Val Val Thr Ala
225                 230                 235                 240

Val Thr Glu Leu Gly Asn Gly Lys Pro Gln Phe Tyr Ser Thr Ser Glu
            245                 250                 255

Ile Ile Ser Phe Cys Arg Lys Trp Arg Leu Pro Thr Asn His Val Trp
            260                 265                 270

Leu Phe Ser Thr Arg Lys Ser Val Thr Ser Phe Phe Ala Ala Phe Asp
        275                 280                 285

Ala Leu Cys Glu Glu Gly Ile Ala Thr Ser Val Cys Arg Ala Leu Asp
    290                 295                 300

Glu Val Ala Asp Ile Ser Val Pro Ala Ser Lys Asp His Val Lys Val
305                 310                 315                 320

Gln Gly Glu Ile Leu Glu Gly Leu Val Ala Arg Ile Val Ser Ser Gln
            325                 330                 335

Ser Ser Arg Asp Met Glu Asn Val Leu Arg Asp His Pro Pro Pro
                340                 345                 350

Cys Asp Gly Ala Asn Leu Asp Leu Gly Leu Ser Leu Arg Glu Ile Cys
            355                 360                 365

Ala Ala His Arg Ser Asn Glu Lys Gln Gln Met Arg Ala Leu Leu Arg
    370                 375                 380

Ser Val Gly Pro Ser Phe Cys Pro Ser Asp Val Glu Trp Phe Gly Asp
385                 390                 395                 400

Glu Ser His Pro Lys Ser Ala Asp Lys Ser Val Ile Thr Lys Phe Leu
                405                 410                 415

Gln Ser Gln Pro Ala Asp Tyr Ser Thr Ser Lys Leu Gln Glu Met Val
            420                 425                 430

Arg Leu Met Lys Glu Lys Arg Leu Pro Ala Ala Phe Lys Cys Tyr His
        435                 440                 445

Asn Phe His Arg Ala Glu Asp Ile Ser Pro Asp Asn Leu Phe Tyr Lys
    450                 455                 460

Leu Val Val His Val His Ser Asp Ser Gly Phe Arg Arg Tyr His Lys
465                 470                 475                 480

Glu Met Arg His Met Pro Ser Leu Trp Pro Leu Tyr Arg Gly Phe Phe
                485                 490                 495

Val Asp Ile Asn Leu Phe Lys Ser Asn Lys Gly Arg Asp Leu Met Ala
            500                 505                 510

Leu Lys Ser Ile Asp Asn Ala Ser Glu Asn Asp Gly Arg Gly Glu Lys
        515                 520                 525

Asp Gly Leu Ala Asp Asp Asp Ala Asn Leu Met Ile Lys Met Lys Phe
```

```
                530               535               540
Leu Thr Tyr Lys Leu Arg Thr Phe Leu Ile Arg Asn Gly Leu Ser Ile
545                 550               555               560

Leu Phe Lys Asp Gly Ala Ala Tyr Lys Thr Tyr Leu Arg Gln
                565               570               575

Met Lys Ile Trp Gly Thr Ser Asp Gly Lys Gln Lys Glu Leu Cys Lys
                580               585               590

Met Leu Asp Glu Trp Ala Ala Tyr Ile Arg Arg Lys Cys Gly Asn Asp
                595               600               605

Gln Leu Ser Ser Thr Tyr Leu Ser Glu Ala Glu Pro Phe Leu Glu
                610               615               620

Gln Tyr Ala Lys Arg Ser Pro Lys Asn His Ile Leu Ile Gly Ser Ala
625                 630               635               640

Gly Asn Leu Val Arg Thr Glu Asp Phe Leu Ala Ile Val Asp Gly Asp
                645               650               655

Leu Asp Glu Glu Gly Asp Leu Val Lys Lys Gln Gly Val Thr Pro Ala
                660               665               670

Thr Pro Glu Pro Ala Val Lys Glu Ala Val Gln Lys Asp Glu Gly Leu
                675               680               685

Ile Val Phe Phe Pro Gly Ile Pro Gly Ser Ala Lys Ser Ala Leu Cys
                690               695               700

Lys Glu Leu Leu Asn Ala Pro Gly Gly Phe Gly Asp Asp Arg Pro Val
705                 710               715               720

His Thr Leu Met Gly Asp Leu Val Lys Gly Lys Tyr Trp Pro Lys Val
                725               730               735

Ala Asp Glu Arg Arg Lys Lys Pro Gln Ser Ile Met Leu Ala Asp Lys
                740               745               750

Asn Ala Pro Asn Glu Asp Val Trp Arg Gln Ile Glu Asp Met Cys Arg
                755               760               765

Arg Thr Arg Ala Ser Ala Val Pro Ile Val Ala Asp Ser Glu Gly Thr
                770               775               780

Asp Thr Asn Pro Tyr Ser Leu Asp Ala Leu Ala Val Phe Met Phe Arg
785                 790               795               800

Val Leu Gln Arg Val Asn His Pro Gly Lys Leu Asp Lys Glu Ser Ser
                805               810               815

Asn Ala Gly Tyr Val Leu Leu Met Phe Tyr His Leu Tyr Glu Gly Lys
                820               825               830

Asn Arg Asn Glu Phe Glu Ser Glu Leu Ile Glu Arg Phe Gly Ser Leu
                835               840               845

Ile Lys Met Pro Leu Leu Lys Ser Asp Arg Thr Pro Leu Pro Asp Pro
850                 855               860

Val Lys Ser Val Leu Glu Gly Ile Asp Leu Phe Asn Leu His Ser
865                 870               875               880

Arg Arg His Gly Arg Leu Glu Ser Thr Lys Gly Thr Tyr Ala Ala Glu
                885               890               895

Trp Thr Lys Trp Glu Lys Gln Leu Arg Asp Thr Leu Val Ala Asn Ser
                900               905               910

Glu Tyr Leu Ser Ser Ile Gln Val Pro Phe Glu Ser Met Val His Gln
                915               920               925

Val Arg Glu Glu Leu Lys Thr Ile Ala Lys Gly Asp Tyr Lys Pro Pro
930                 935               940

Ser Ser Glu Lys Arg Lys His Gly Ser Ile Val Phe Ala Ala Ile Asn
945                 950               955               960
```

```
Leu Pro Ala Thr Gln Val His Ser Leu Leu Glu Lys Leu Ala Ala
                965                 970                 975

Asn Pro Thr Met Arg Ser Phe Leu Glu Gly Lys Lys Ser Ile Gln
                980                 985                 990

Glu Lys Leu Glu Arg Ser His Val Thr Leu Ala His Lys Arg Ser His
        995                 1000                1005

Gly Val Ala Thr Val Ala Ser Tyr Ser Gln His Leu Asn Arg Glu
        1010                1015                1020

Val Pro Val Glu Leu Thr Glu Leu Ile Tyr Asn Asp Lys Met Ala
        1025                1030                1035

Ala Leu Thr Ala His Val Gly Ser Val Asp Gly Glu Thr Val Val
        1040                1045                1050

Ser Lys Asn Glu Trp Pro His Val Thr Leu Trp Thr Ala Glu Gly
        1055                1060                1065

Val Thr Ala Lys Glu Ala Asn Thr Leu Pro Gln Leu Tyr Leu Glu
        1070                1075                1080

Gly Lys Ala Ser Arg Leu Val Ile Asp Pro Pro Val Ser Ile Ser
        1085                1090                1095

Gly Pro Leu Glu Phe Phe
        1100

<210> SEQ ID NO 2
<211> LENGTH: 1177
<212> TYPE: PRT
<213> ORGANISM: Arabidopsis thaliana

<400> SEQUENCE: 2

Met Ser Leu Ile Pro His Thr Thr His Phe Ala Phe Ser Ile Asn Ile
1               5                   10                  15

His Leu Ser Ala Thr Ser Arg Thr Ser Ser Leu Leu Arg Ser Ser Ser
                20                  25                  30

Pro Tyr Phe Thr Leu Ala Arg Ser Leu Cys Phe Asn Ser Ser Ile Arg
            35                  40                  45

Phe Leu Ser Ser Asp Met Pro Lys Lys Gln Lys Lys Arg Asp His Ala
    50                  55                  60

Glu Gln Lys Trp Gln Val Lys Pro Lys Met Asp Ala Pro Phe Glu Ser
65                  70                  75                  80

Gly Asp Ser Ser Ala Thr Val Val Ala Glu Ala Val Asn Asn Gln Phe
                85                  90                  95

Gly Gly Leu Ser Leu Lys Glu Ser Asn Thr Asn Ala Pro Val Leu Pro
            100                 105                 110

Ser Gln Thr Thr Ser Asn His Arg Val Gln Asn Leu Val Trp Lys Pro
        115                 120                 125

Lys Ser Tyr Gly Thr Val Ser Gly Ser Ser Ala Thr Glu Val Gly
    130                 135                 140

Lys Thr Ser Ala Val Ser Gln Ile Gly Ser Ser Gly Asp Thr Lys Val
145                 150                 155                 160

Gly Leu Asn Leu Ser Lys Ile Phe Gly Gly Asn Leu Leu Glu Lys Phe
                165                 170                 175

Ser Val Asp Lys Ser Thr Tyr Cys His Ala Gln Ile Arg Ala Thr Phe
            180                 185                 190

Tyr Pro Lys Phe Glu Asn Glu Lys Thr Asp Gln Glu Ile Arg Thr Arg
        195                 200                 205

Met Ile Glu Met Val Ser Lys Gly Leu Ala Thr Leu Glu Val Ser Leu
```

```
                210                 215                 220
Lys His Ser Gly Ser Leu Phe Met Tyr Ala Gly His Lys Gly Gly Ala
225                 230                 235                 240

Tyr Ala Lys Asn Ser Phe Gly Asn Ile Tyr Thr Ala Val Gly Val Phe
            245                 250                 255

Val Leu Ser Arg Met Phe Arg Glu Ala Trp Gly Thr Lys Ala Pro Lys
                260                 265                 270

Lys Glu Ala Glu Phe Asn Asp Phe Leu Glu Lys Asn Arg Met Cys Ile
            275                 280                 285

Ser Met Glu Leu Val Thr Ala Val Leu Gly Asp His Gly Gln Arg Pro
290                 295                 300

Leu Asp Asp Tyr Val Val Val Thr Ala Val Thr Glu Leu Gly Asn Gly
305                 310                 315                 320

Lys Pro Gln Phe Tyr Ser Thr Ser Glu Ile Ile Ser Phe Cys Arg Lys
                325                 330                 335

Trp Arg Leu Pro Thr Asn His Val Trp Leu Phe Ser Thr Arg Lys Ser
            340                 345                 350

Val Thr Ser Phe Phe Ala Ala Phe Asp Ala Leu Cys Glu Glu Gly Ile
                355                 360                 365

Ala Thr Ser Val Cys Arg Ala Leu Asp Glu Val Ala Asp Ile Ser Val
370                 375                 380

Pro Ala Ser Lys Asp His Val Lys Val Gln Gly Glu Ile Leu Glu Gly
385                 390                 395                 400

Leu Val Ala Arg Ile Val Ser Ser Gln Ser Ser Arg Asp Met Glu Asn
                405                 410                 415

Val Leu Arg Asp His Pro Pro Pro Cys Asp Gly Ala Asn Leu Asp
            420                 425                 430

Leu Gly Leu Ser Leu Arg Glu Ile Cys Ala Ala His Arg Ser Asn Glu
                435                 440                 445

Lys Gln Gln Met Arg Ala Leu Leu Arg Ser Val Gly Pro Ser Phe Cys
450                 455                 460

Pro Ser Asp Val Glu Trp Phe Gly Asp Glu Ser His Pro Lys Ser Ala
465                 470                 475                 480

Asp Lys Ser Val Ile Thr Lys Phe Leu Gln Ser Gln Pro Ala Asp Tyr
            485                 490                 495

Ser Thr Ser Lys Leu Gln Glu Met Val Arg Leu Met Lys Glu Lys Arg
                500                 505                 510

Leu Pro Ala Ala Phe Lys Cys Tyr His Asn Phe His Arg Ala Glu Asp
            515                 520                 525

Ile Ser Pro Asp Asn Leu Phe Tyr Lys Leu Val Val His Val His Ser
530                 535                 540

Asp Ser Gly Phe Arg Arg Tyr His Lys Glu Met Arg His Met Pro Ser
545                 550                 555                 560

Leu Trp Pro Leu Tyr Arg Gly Phe Phe Val Asp Ile Asn Leu Phe Lys
            565                 570                 575

Ser Asn Lys Gly Arg Asp Leu Met Ala Leu Lys Ser Ile Asp Asn Ala
                580                 585                 590

Ser Glu Asn Asp Gly Arg Gly Glu Lys Asp Gly Leu Ala Asp Asp
            595                 600                 605

Ala Asn Leu Met Ile Lys Met Lys Phe Leu Thr Tyr Lys Leu Arg Thr
610                 615                 620

Phe Leu Ile Arg Asn Gly Leu Ser Ile Leu Phe Lys Asp Gly Ala Ala
625                 630                 635                 640
```

-continued

Ala Tyr Lys Thr Tyr Tyr Leu Arg Gln Met Lys Ile Trp Gly Thr Ser
                645                 650                 655

Asp Gly Lys Gln Lys Glu Leu Cys Lys Met Leu Asp Glu Trp Ala Ala
                660                 665                 670

Tyr Ile Arg Arg Lys Cys Gly Asn Asp Gln Leu Ser Ser Ser Thr Tyr
                675                 680                 685

Leu Ser Glu Ala Glu Pro Phe Leu Glu Gln Tyr Ala Lys Arg Ser Pro
            690                 695                 700

Lys Asn His Ile Leu Ile Gly Ser Ala Gly Asn Leu Val Arg Thr Glu
705                 710                 715                 720

Asp Phe Leu Ala Ile Val Asp Gly Asp Leu Asp Glu Gly Asp Leu
                725                 730                 735

Val Lys Lys Gln Gly Val Thr Pro Ala Thr Pro Glu Pro Ala Val Lys
                740                 745                 750

Glu Ala Val Gln Lys Asp Glu Gly Leu Ile Val Phe Phe Pro Gly Ile
                755                 760                 765

Pro Gly Ser Ala Lys Ser Ala Leu Cys Lys Glu Leu Leu Asn Ala Pro
            770                 775                 780

Gly Gly Phe Gly Asp Asp Arg Pro Val His Thr Leu Met Gly Asp Leu
785                 790                 795                 800

Val Lys Gly Lys Tyr Trp Pro Lys Val Ala Asp Glu Arg Arg Lys Lys
                805                 810                 815

Pro Gln Ser Ile Met Leu Ala Asp Lys Asn Ala Pro Asn Glu Asp Val
            820                 825                 830

Trp Arg Gln Ile Glu Asp Met Cys Arg Arg Thr Arg Ala Ser Ala Val
                835                 840                 845

Pro Ile Val Ala Asp Ser Glu Gly Thr Asp Thr Asn Pro Tyr Ser Leu
            850                 855                 860

Asp Ala Leu Ala Val Phe Met Phe Arg Val Leu Gln Arg Val Asn His
865                 870                 875                 880

Pro Gly Lys Leu Asp Lys Glu Ser Ser Asn Ala Gly Tyr Val Leu Leu
                885                 890                 895

Met Phe Tyr His Leu Tyr Glu Gly Lys Asn Arg Asn Glu Phe Glu Ser
                900                 905                 910

Glu Leu Ile Glu Arg Phe Gly Ser Leu Ile Lys Met Pro Leu Leu Lys
            915                 920                 925

Ser Asp Arg Thr Pro Leu Pro Asp Pro Val Lys Ser Val Leu Glu Glu
            930                 935                 940

Gly Ile Asp Leu Phe Asn Leu His Ser Arg Arg His Gly Arg Leu Glu
945                 950                 955                 960

Ser Thr Lys Gly Thr Tyr Ala Ala Glu Trp Thr Lys Trp Glu Lys Gln
                965                 970                 975

Leu Arg Asp Thr Leu Val Ala Asn Ser Glu Tyr Leu Ser Ser Ile Gln
            980                 985                 990

Val Pro Phe Glu Ser Met Val His Gln Val Arg Glu Glu Leu Lys Thr
            995                 1000                1005

Ile Ala Lys Gly Asp Tyr Lys Pro Pro Ser Ser Glu Lys Arg Lys
            1010                1015                1020

His Gly Ser Ile Val Phe Ala Ala Ile Asn Leu Pro Ala Thr Gln
            1025                1030                1035

Val His Ser Leu Leu Glu Lys Leu Ala Ala Ala Asn Pro Thr Met
            1040                1045                1050

Arg Ser Phe Leu Glu Gly Lys Lys Ser Ile Gln Glu Lys Leu
1055                1060                1065

Glu Arg Ser His Val Thr Leu Ala His Lys Arg Ser His Gly Val
1070                1075                1080

Ala Thr Val Ala Ser Tyr Ser Gln His Leu Asn Arg Glu Val Pro
1085                1090                1095

Val Glu Leu Thr Glu Leu Ile Tyr Asn Asp Lys Met Ala Ala Leu
1100                1105                1110

Thr Ala His Val Gly Ser Val Asp Gly Glu Thr Val Val Ser Lys
1115                1120                1125

Asn Glu Trp Pro His Val Thr Leu Trp Thr Ala Glu Gly Val Thr
1130                1135                1140

Ala Lys Glu Ala Asn Thr Leu Pro Gln Leu Tyr Leu Glu Gly Lys
1145                1150                1155

Ala Ser Arg Leu Val Ile Asp Pro Pro Val Ser Ile Ser Gly Pro
1160                1165                1170

Leu Glu Phe Phe
1175

<210> SEQ ID NO 3
<211> LENGTH: 408
<212> TYPE: PRT
<213> ORGANISM: Escherichia coli

<400> SEQUENCE: 3

Met Asn Tyr Glu Leu Leu Thr Thr Glu Asn Ala Pro Val Lys Met Trp
1               5                   10                  15

Thr Lys Gly Val Pro Val Glu Ala Asp Ala Arg Gln Gln Leu Ile Asn
                20                  25                  30

Thr Ala Lys Met Pro Phe Ile Phe Lys His Ile Ala Val Met Pro Asp
            35                  40                  45

Val His Leu Gly Lys Gly Ser Thr Ile Gly Ser Val Ile Pro Thr Lys
        50                  55                  60

Gly Ala Ile Ile Pro Ala Ala Val Gly Val Asp Ile Gly Cys Gly Met
65                  70                  75                  80

Asn Ala Leu Arg Thr Ala Leu Thr Ala Glu Asp Leu Pro Glu Asn Leu
                85                  90                  95

Ala Glu Leu Arg Gln Ala Ile Glu Thr Ala Val Pro His Gly Arg Thr
            100                 105                 110

Thr Gly Arg Cys Lys Arg Asp Lys Gly Ala Trp Glu Asn Pro Pro Val
        115                 120                 125

Asn Val Asp Ala Lys Trp Ala Glu Leu Glu Ala Gly Tyr Gln Trp Leu
    130                 135                 140

Thr Gln Lys Tyr Pro Arg Phe Leu Asn Thr Asn Tyr Lys His Leu
145                 150                 155                 160

Gly Thr Leu Gly Thr Gly Asn His Phe Ile Glu Ile Cys Leu Asp Glu
                165                 170                 175

Ser Asp Gln Val Trp Ile Met Leu His Ser Gly Ser Arg Gly Ile Gly
            180                 185                 190

Asn Ala Ile Gly Thr Tyr Phe Ile Asp Leu Ala Gln Lys Glu Met Gln
        195                 200                 205

Glu Thr Leu Glu Thr Leu Pro Ser Arg Asp Leu Ala Tyr Phe Met Glu
    210                 215                 220

Gly Thr Glu Tyr Phe Asp Asp Tyr Leu Lys Ala Val Ala Trp Ala Gln
225                 230                 235                 240

```
Leu Phe Ala Ser Leu Asn Arg Asp Ala Met Met Glu Asn Val Val Thr
                245                 250                 255

Ala Leu Gln Ser Ile Thr Gln Lys Thr Val Arg Gln Pro Gln Thr Leu
            260                 265                 270

Ala Met Glu Glu Ile Asn Cys His His Asn Tyr Val Gln Lys Glu Gln
        275                 280                 285

His Phe Gly Glu Glu Ile Tyr Val Thr Arg Lys Gly Ala Val Ser Ala
    290                 295                 300

Arg Ala Gly Gln Tyr Gly Ile Ile Pro Gly Ser Met Gly Ala Lys Ser
305                 310                 315                 320

Phe Ile Val Arg Gly Leu Gly Asn Glu Glu Ser Phe Cys Ser Cys Ser
                325                 330                 335

His Gly Ala Gly Arg Val Met Ser Arg Thr Lys Ala Lys Lys Leu Phe
            340                 345                 350

Ser Val Glu Asp Gln Ile Arg Ala Thr Ala His Val Glu Cys Arg Lys
        355                 360                 365

Asp Ala Glu Val Ile Asp Glu Ile Pro Met Ala Tyr Lys Asp Ile Asp
    370                 375                 380

Ala Val Met Ala Ala Gln Ser Asp Leu Val Glu Val Ile Tyr Thr Leu
385                 390                 395                 400

Arg Gln Val Val Cys Val Lys Gly
                405

<210> SEQ ID NO 4
<211> LENGTH: 11
<212> TYPE: DNA
<213> ORGANISM: Artificial Sequence
<220> FEATURE:
<223> OTHER INFORMATION: UMI sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (8)..(11)
<223> OTHER INFORMATION: n is a, c, g, or t

<400> SEQUENCE: 4
nnnncgtnnn n                                                             11

<210> SEQ ID NO 5
<211> LENGTH: 11
<212> TYPE: DNA
<213> ORGANISM: Artificial Sequence
<220> FEATURE:
<223> OTHER INFORMATION: UMI sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (8)..(11)
<223> OTHER INFORMATION: n is a, c, g, or t

<400> SEQUENCE: 5
nnnngacnnn n                                                             11

<210> SEQ ID NO 6
<211> LENGTH: 8
<212> TYPE: DNA
<213> ORGANISM: Artificial Sequence
```

```
<220> FEATURE:
<223> OTHER INFORMATION: UMI sequence
<220> FEATURE:
<221> NAME/KEY: misc_feature
<222> LOCATION: (1)..(8)
<223> OTHER INFORMATION: n is a, c, g, or t

<400> SEQUENCE: 6 nnnnnnnn                                                                    8

<210> SEQ ID NO 7
<211> LENGTH: 87
<212> TYPE: DNA
<213> ORGANISM: Artificial Sequence
<220> FEATURE:
<223> OTHER INFORMATION: adaptor L sequence
<220> FEATURE:
<221> NAME/KEY: misc_feature
<222> LOCATION: (1)..(8)
<223> OTHER INFORMATION: n is a, c, g, or t

<400> SEQUENCE: 7
nnnnnnnnag atcggaagag cgtcgtgtag ggaaagaggg agttcagacg tgtgctcttc          60
cgatctagcc agcgcagacc gtgaggt                                              87

<210> SEQ ID NO 8
<211> LENGTH: 20
<212> TYPE: DNA
<213> ORGANISM: Artificial Sequence
<220> FEATURE:
<223> OTHER INFORMATION: adaptor S sequence

<400> SEQUENCE: 8
cctcacggtc tgcgctggct                                                      20

<210> SEQ ID NO 9
<211> LENGTH: 63
<212> TYPE: DNA
<213> ORGANISM: Artificial Sequence
<220> FEATURE:
<223> OTHER INFORMATION: PCR.1.Index  sequence

<400> SEQUENCE: 9
caagcagaag acggcatacg agatcgtgat gtgactggag ttcagacgtg tgctcttccg          60
atc                                                                       63

<210> SEQ ID NO 10
<211> LENGTH: 58
<212> TYPE: DNA
<213> ORGANISM: Artificial Sequence
<220> FEATURE:
<223> OTHER INFORMATION: PCR.2 oligonucleotide

<400> SEQUENCE: 10
aatgatacgg cgaccaccga gatctacact ctttccctac acgacgctct tccgatct           58

<210> SEQ ID NO 11
<211> LENGTH: 47
<212> TYPE: DNA
<213> ORGANISM: Artificial Sequence
<220> FEATURE:
<223> OTHER INFORMATION: Lig.47.D

<400> SEQUENCE: 11
cccgagtgtg atcatctggt cgctggggaa tgagtcaggc cacggcg                        47
```

```
<210> SEQ ID NO 12
<211> LENGTH: 47
<212> TYPE: DNA
<213> ORGANISM: Artificial Sequence
<220> FEATURE:
<223> OTHER INFORMATION: Lig.47.R  "G" at position 32 is a
      ribonucleotide

<400> SEQUENCE: 12
cccgagtgtg atcatctggt cgctggggaa tgagtcaggc cacggcg                47

<210> SEQ ID NO 13
<211> LENGTH: 30
<212> TYPE: DNA
<213> ORGANISM: Artificial Sequence
<220> FEATURE:
<223> OTHER INFORMATION: Lig.30.rA position 22 "A" is a ribonucleotide
<220> FEATURE:
<221> NAME/KEY: misc_feature
<222> LOCATION: (1)..(21)
<223> OTHER INFORMATION: n is a, c, g, t or u
<220> FEATURE:
<221> NAME/KEY: misc_feature
<222> LOCATION: (23)..(30)
<223> OTHER INFORMATION: n is a, c, g, t or u

<400> SEQUENCE: 13
nnnnnnnnnn nnnnnnnnnn nannnnnnnn                                   30

<210> SEQ ID NO 14
<211> LENGTH: 30
<212> TYPE: DNA
<213> ORGANISM: Artificial Sequence
<220> FEATURE:
<223> OTHER INFORMATION: Lig.30.rG -position 22 "G" is a ribonucleotide
<220> FEATURE:
<221> NAME/KEY: misc_feature
<222> LOCATION: (1)..(21)
<223> OTHER INFORMATION: n is a, c, g, t or u
<220> FEATURE:
<221> NAME/KEY: misc_feature
<222> LOCATION: (23)..(30)
<223> OTHER INFORMATION: n is a, c, g, t or u

<400> SEQUENCE: 14
nnnnnnnnnn nnnnnnnnnn ngnnnnnnnn                                   30

<210> SEQ ID NO 15
<211> LENGTH: 30
<212> TYPE: DNA
<213> ORGANISM: Artificial Sequence
<220> FEATURE:
<223> OTHER INFORMATION: Lig.30.rU -position 22 "U" is a ribonucleotide
<220> FEATURE:
<221> NAME/KEY: misc_feature
<222> LOCATION: (1)..(21)
<223> OTHER INFORMATION: n is a, c, g, t or u
<220> FEATURE:
<221> NAME/KEY: misc_feature
<222> LOCATION: (23)..(30)
<223> OTHER INFORMATION: n is a, c, g, t or u

<400> SEQUENCE: 15
nnnnnnnnnn nnnnnnnnnn nunnnnnnnn                                   30

<210> SEQ ID NO 16
<211> LENGTH: 30
<212> TYPE: DNA
<213> ORGANISM: Artificial Sequence
<220> FEATURE:
```

```
<223> OTHER INFORMATION: Lig.30.rC - position 22 "C" is a ribonucleotide
<220> FEATURE:
<221> NAME/KEY: misc_feature
<222> LOCATION: (1)..(21)
<223> OTHER INFORMATION: n is a, c, g, t or u
<220> FEATURE:
<221> NAME/KEY: misc_feature
<222> LOCATION: (23)..(30)
<223> OTHER INFORMATION: n is a, c, g, t or u

<400> SEQUENCE: 16
nnnnnnnnnn nnnnnnnnnn ncnnnnnnnn                                       30

<210> SEQ ID NO 17
<211> LENGTH: 63
<212> TYPE: DNA
<213> ORGANISM: Artificial Sequence
<220> FEATURE:
<223> OTHER INFORMATION: PCR.1.Index2

<400> SEQUENCE: 17
caagcagaag acggcatacg agatacatcg gtgactggag ttcagacgtg tgctcttccg      60
atc                                                                   63

<210> SEQ ID NO 18
<211> LENGTH: 63
<212> TYPE: DNA
<213> ORGANISM: Artificial Sequence
<220> FEATURE:
<223> OTHER INFORMATION: PCR.1.Index3

<400> SEQUENCE: 18
caagcagaag acggcatacg agatgcctaa gtgactggag ttcagacgtg tgctcttccg      60
atc                                                                   63

<210> SEQ ID NO 19
<211> LENGTH: 63
<212> TYPE: DNA
<213> ORGANISM: Artificial Sequence
<220> FEATURE:
<223> OTHER INFORMATION: PCR.1.Index4

<400> SEQUENCE: 19
caagcagaag acggcatacg agattggtca gtgactggag ttcagacgtg tgctcttccg      60
atc                                                                   63

<210> SEQ ID NO 20
<211> LENGTH: 46
<212> TYPE: DNA
<213> ORGANISM: Artificial Sequence
<220> FEATURE:
<223> OTHER INFORMATION: ByTemp.rC - "C" in position 8 is a
      ribonucleotide
<220> FEATURE:
<221> NAME/KEY: misc_feature
<222> LOCATION: (1)..(7)
<223> OTHER INFORMATION: n is a, c, g, t or u
<220> FEATURE:
<221> NAME/KEY: misc_feature
<222> LOCATION: (9)..(16)
<223> OTHER INFORMATION: n is a, c, g, t or u

<400> SEQUENCE: 20
nnnnnnncnn nnnnnnagat cggaagagcg tcgtgtaggg aaagag                    46

<210> SEQ ID NO 21
```

```
<211> LENGTH: 46
<212> TYPE: DNA
<213> ORGANISM: Artificial Sequence
<220> FEATURE:
<223> OTHER INFORMATION: ByTemp.rU
<220> FEATURE:
<221> NAME/KEY: misc_feature
<222> LOCATION: (1)..(7)
<223> OTHER INFORMATION: n is a, c, g, t or u
<220> FEATURE:
<221> NAME/KEY: misc_feature
<222> LOCATION: (9)..(16)
<223> OTHER INFORMATION: n is a, c, g, t or u

<400> SEQUENCE: 21
nnnnnnnunn nnnnnnagat cggaagagcg tcgtgtaggg aaagag                46

<210> SEQ ID NO 22
<211> LENGTH: 30
<212> TYPE: DNA
<213> ORGANISM: Artificial Sequence
<220> FEATURE:
<223> OTHER INFORMATION: ByPrim

<400> SEQUENCE: 22
ctctttccct acacgacgct cttccgatct                                  30

<210> SEQ ID NO 23
<211> LENGTH: 60
<212> TYPE: DNA
<213> ORGANISM: Artificial Sequence
<220> FEATURE:
<223> OTHER INFORMATION: LEU2.D

<400> SEQUENCE: 23
ttaggtgctg tgggtggtcc taaatgggga tccggtagtg ttaggcctga acaaggttta  60

<210> SEQ ID NO 24
<211> LENGTH: 60
<212> TYPE: DNA
<213> ORGANISM: Artificial Sequence
<220> FEATURE:
<223> OTHER INFORMATION: LEU2.rG-"G" in postiion 50 is a ribonucleotide

<400> SEQUENCE: 24
ttaggtgctg tgggtggtcc taaatgggga tccggtagtg ttaggcctga acaaggttta  60

<210> SEQ ID NO 25
<211> LENGTH: 60
<212> TYPE: DNA
<213> ORGANISM: Artificial Sequence
<220> FEATURE:
<223> OTHER INFORMATION: LEU2.dU

<400> SEQUENCE: 25
ttaggtgctg tgggtggtcc taaatgggga tccggtagtg utaggcctga acaaggttta  60

<210> SEQ ID NO 26
<211> LENGTH: 60
<212> TYPE: DNA
<213> ORGANISM: Artificial Sequence
<220> FEATURE:
<223> OTHER INFORMATION: LEU2.rU

<400> SEQUENCE: 26
ttaggtgctg tgggtggtcc taaatgggga tccggtagtg utaggcctga acaaggttta  60
```

```
<210> SEQ ID NO 27
<211> LENGTH: 20
<212> TYPE: DNA
<213> ORGANISM: Artificial Sequence
<220> FEATURE:
<223> OTHER INFORMATION: LEU2.3

<400> SEQUENCE: 27
atgtctgccc ctaagaagat                                                   20

<210> SEQ ID NO 28
<211> LENGTH: 20
<212> TYPE: DNA
<213> ORGANISM: Artificial Sequence
<220> FEATURE:
<223> OTHER INFORMATION: LEU2.6

<400> SEQUENCE: 28
tgccaaagaa taaggtcaac                                                   20

<210> SEQ ID NO 29
<211> LENGTH: 12
<212> TYPE: DNA
<213> ORGANISM: Artificial Sequence
<220> FEATURE:
<223> OTHER INFORMATION: product after dA tailing 5' end P-
<220> FEATURE:
<221> NAME/KEY: misc_feature
<222> LOCATION: (1)..(11)
<223> OTHER INFORMATION: n is a, c, g, t or u

<400> SEQUENCE: 29
nnnnnnnnnn na                                                           12

<210> SEQ ID NO 30
<211> LENGTH: 80
<212> TYPE: DNA
<213> ORGANISM: Artificial Sequence
<220> FEATURE:
<223> OTHER INFORMATION: product after adaptor ligation, The sixth "N"
      is a ribonucleotide, 3' and 5' ends are Am modified
<220> FEATURE:
<221> NAME/KEY: misc_feature
<222> LOCATION: (49)..(59)
<223> OTHER INFORMATION: n is a, c, g, t or u

<400> SEQUENCE: 30
ggagttcaga cgtgtgctct tccgatcagc cagcgcagac cgtgaggtnn nnnnnnnna        60 cctcactgtc tgcgctggct                                                   80

<210> SEQ ID NO 31
<211> LENGTH: 54
<212> TYPE: DNA
<213> ORGANISM: Artificial Sequence
<220> FEATURE:
<223> OTHER INFORMATION: product after alkali treatment- N at position
      54 is a ribonucleotide. This ribonucleotide has a cyclic phosphate
      (cP)
<220> FEATURE:
<221> NAME/KEY: misc_feature
<222> LOCATION: (49)..(54)
<223> OTHER INFORMATION: n is a, c, g, t or u

<400> SEQUENCE: 31
ggagttcaga cgtgtgctct tccgatcagc cagcgcagac cgtgaggtnn nnnn             54

<210> SEQ ID NO 32
<211> LENGTH: 26
```

```
<212> TYPE: DNA
<213> ORGANISM: Artificial Sequence
<220> FEATURE:
<223> OTHER INFORMATION: product after alkali treatment- no
      ribonucleotide. 3' end is Am modified, 5' end is -OH
<220> FEATURE:
<221> NAME/KEY: misc_feature
<222> LOCATION: (1)..(5)
<223> OTHER INFORMATION: n is a, c, g, or t

<400> SEQUENCE: 32
nnnnnacctc actgtctgcg ctggct                                          26

<210> SEQ ID NO 33
<211> LENGTH: 80
<212> TYPE: DNA
<213> ORGANISM: Artificial Sequence
<220> FEATURE:
<223> OTHER INFORMATION: product after alkali treatment- no
      ribonucleotides. 5' and 3' ends are Am modified
<220> FEATURE:
<221> NAME/KEY: misc_feature
<222> LOCATION: (49)..(59)
<223> OTHER INFORMATION: n is a, c, g, or t

<400> SEQUENCE: 33
ggagttcaga cgtgtgctct tccgatcagc cagcgcagac cgtgaggtnn nnnnnnnna     60 cctcactgtc tgcgctggct                                                80

<210> SEQ ID NO 34
<211> LENGTH: 38
<212> TYPE: DNA
<213> ORGANISM: Artificial Sequence
<220> FEATURE:
<223> OTHER INFORMATION: linker sequence
<220> FEATURE:
<221> NAME/KEY: misc_feature
<222> LOCATION: (1)..(8)
<223> OTHER INFORMATION: n is a, c, g, t or u

<400> SEQUENCE: 34
nnnnnnnnag aucggaagag cgucguguag ggaaagag                             38

<210> SEQ ID NO 35
<211> LENGTH: 92
<212> TYPE: DNA
<213> ORGANISM: Artificial Sequence
<220> FEATURE:
<223> OTHER INFORMATION: product after linker ligation, 3' and 5' ends
      Am modified
<220> FEATURE:
<221> NAME/KEY: misc_feature
<222> LOCATION: (49)..(62)
<223> OTHER INFORMATION: n is a, c, g, t or u

<400> SEQUENCE: 35
ggagttcaga cgtgtgctct tccgatcagc cagcgcagac cgtgaggtnn nnnnnnnnn     60 nnagaucgga agagcgucgu guagggaaag ag                                  92

<210> SEQ ID NO 36
<211> LENGTH: 92
<212> TYPE: DNA
<213> ORGANISM: Artificial Sequence
<220> FEATURE:
<223> OTHER INFORMATION: product after treatment with Tpt1, 6th N
      corresponds to a ribonucleotide, 3' and 5' ends Am modified
<220> FEATURE:
<221> NAME/KEY: misc_feature
<222> LOCATION: (49)..(62)
```

<223> OTHER INFORMATION: n is a, c, g, t or u

<400> SEQUENCE: 36
ggagttcaga cgtgtgctct tccgatcagc cagcgcagac cgtgaggtnn nnnnnnnnn    60 nnagaucgga agagcgucgu guagggaaag ag    92

<210> SEQ ID NO 37
<211> LENGTH: 92
<212> TYPE: DNA
<213> ORGANISM: Artificial Sequence
<220> FEATURE:
<223> OTHER INFORMATION: product after Reverse transcription
<220> FEATURE:
<221> NAME/KEY: misc_feature
<222> LOCATION: (49)..(62)
<223> OTHER INFORMATION: n is a, c, g, t or u

<400> SEQUENCE: 37
ggagttcaga cgtgtgctct tccgatcagc cagcgcagac cgtgaggtnn nnnnnnnnn    60 nnagaucgga agagcgucgu guagggaaag ag    92

<210> SEQ ID NO 38
<211> LENGTH: 33
<212> TYPE: DNA
<213> ORGANISM: Artificial Sequence
<220> FEATURE:
<223> OTHER INFORMATION: RT primer

<400> SEQUENCE: 38
tctagccttc tcgcagcaca tccctttctc aca    33

<210> SEQ ID NO 39
<211> LENGTH: 92
<212> TYPE: DNA
<213> ORGANISM: Artificial Sequence
<220> FEATURE:
<223> OTHER INFORMATION: PCR template strand, contains a ribonucleotide
      at 6th position N.
<220> FEATURE:
<221> NAME/KEY: misc_feature
<222> LOCATION: (49)..(62)
<223> OTHER INFORMATION: n is a, c, g, t or u

<400> SEQUENCE: 39
ggagttcaga cgtgtgctct tccgatcagc cagcgcagac cgtgaggtnn nnnnnnnnn    60 nnagaucgga agagcgucgu guagggaaag ag    92

<210> SEQ ID NO 40
<211> LENGTH: 95
<212> TYPE: DNA
<213> ORGANISM: Artificial Sequence
<220> FEATURE:
<223> OTHER INFORMATION: complementary strand to SEQ ID NO: 39. Note the
      complement to the ribonucleotide is a deoxyribonucleotide in this
      strand
<220> FEATURE:
<221> NAME/KEY: misc_feature
<222> LOCATION: (49)..(62)
<223> OTHER INFORMATION: n is a, c, g, or t

<400> SEQUENCE: 40
cctcaagtct gcacacgaga aggctagtcg gtcgcgtctg gcactccann nnnnnnnnn    60 nntctagcct tctcgcagca catccctttc tcaca    95

<210> SEQ ID NO 41

```
<211> LENGTH: 11
<212> TYPE: DNA
<213> ORGANISM: Artificial Sequence
<220> FEATURE:
<223> OTHER INFORMATION: DNA fragment containing a ribonucleotide. The
      6th position N is a ribonucleotide in this fragment
<220> FEATURE:
<221> NAME/KEY: misc_feature
<222> LOCATION: (1)..(11)
<223> OTHER INFORMATION: n is a, c, g, t or u

<400> SEQUENCE: 41
nnnnnnnnnn n                                                              11

<210> SEQ ID NO 42
<211> LENGTH: 92
<212> TYPE: DNA
<213> ORGANISM: Artificial Sequence
<220> FEATURE:
<223> OTHER INFORMATION: ligation product
<220> FEATURE:
<221> NAME/KEY: misc_feature
<222> LOCATION: (1)..(8)
<223> OTHER INFORMATION: n is a, c, g, t or u
<220> FEATURE:
<221> NAME/KEY: misc_feature
<222> LOCATION: (87)..(92)
<223> OTHER INFORMATION: n is a, c, g, t or u

<400> SEQUENCE: 42
nnnnnnnnga tcggaagagc acacgtctga actccctctt tccctacacg acgctcttcc         60
gatctagcca gcgcagaccg tgaggtnnnn nn                                       92

<210> SEQ ID NO 43
<211> LENGTH: 92
<212> TYPE: DNA
<213> ORGANISM: Artificial Sequence
<220> FEATURE:
<223> OTHER INFORMATION: product after TpT1 treatment
<220> FEATURE:
<221> NAME/KEY: misc_feature
<222> LOCATION: (1)..(8)
<223> OTHER INFORMATION: n is a, c, g, t or u
<220> FEATURE:
<221> NAME/KEY: misc_feature
<222> LOCATION: (87)..(92)
<223> OTHER INFORMATION: n is a, c, g, t or u

<400> SEQUENCE: 43
nnnnnnnnga tcggaagagc acacgtctga actccctctt tccctacacg acgctcttcc         60
gatctagcca gcgcagaccg tgaggtnnnn nn                                       92
```